United States Patent
Sui et al.

(10) Patent No.: US 10,618,893 B2
(45) Date of Patent: *Apr. 14, 2020

(54) GPR120 AGONISTS FOR THE TREATMENT OF TYPE II DIABETES

(71) Applicant: JANSSEN PHARMACEUTICA NV, Beerse (BE)

(72) Inventors: Zhihua Sui, Norristown, PA (US); Chaozhong Cai, North Wales, PA (US); Xuqing Zhang, Spring House, PA (US)

(73) Assignee: JANSSEN PHARMACEUTICALS NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/180,612

(22) Filed: Nov. 5, 2018

(65) Prior Publication Data

US 2019/0071435 A1 Mar. 7, 2019

Related U.S. Application Data

(62) Division of application No. 14/200,108, filed on Mar. 7, 2014, now Pat. No. 10,118,922.

(60) Provisional application No. 61/783,213, filed on Mar. 14, 2013.

(51) Int. Cl.
| | | |
|---|---|---|
| C07D 417/12 | (2006.01) | |
| C07D 275/02 | (2006.01) | |
| C07D 275/03 | (2006.01) | |
| C07D 333/16 | (2006.01) | |
| C07D 409/04 | (2006.01) | |
| C07D 417/04 | (2006.01) | |
| C07D 333/32 | (2006.01) | |
| C07D 275/00 | (2006.01) | |

(52) U.S. Cl.
CPC ......... *C07D 417/12* (2013.01); *C07D 275/00* (2013.01); *C07D 275/02* (2013.01); *C07D 275/03* (2013.01); *C07D 333/16* (2013.01); *C07D 333/32* (2013.01); *C07D 409/04* (2013.01); *C07D 417/04* (2013.01)

(58) Field of Classification Search
CPC .................................................... C07D 417/12
USPC .......................................................... 549/29
See application file for complete search history.

(56) References Cited

U.S. PATENT DOCUMENTS

2011/0313003 A1 12/2011 Shi et al.

FOREIGN PATENT DOCUMENTS

| EP | 1559422 | 8/2005 |
|---|---|---|
| EP | 1731505 | 12/2006 |
| EP | 2151236 | 2/2010 |
| JP | 2004-534035 | 11/2004 |
| JP | 2010519306 | 6/2010 |
| JP | 2012506386 | 3/2012 |
| WO | WO-02/092590 | 11/2002 |
| WO | WO-2004/063155 | 7/2004 |
| WO | WO-2004/063184 | 7/2004 |
| WO | WO-2005/063729 | 7/2005 |
| WO | WO-2005/066136 | 7/2005 |
| WO | WO-2008/030520 | 3/2008 |
| WO | WO-2008/030618 | 3/2008 |
| WO | WO-2008/103501 | 8/2008 |
| WO | WO-2009/117421 | 9/2009 |
| WO | WO-2010/048207 | 4/2010 |
| WO | WO-2010/080537 | 7/2010 |

(Continued)

OTHER PUBLICATIONS

Adachi et al., "Free fatty acids administered into the colon promote the secretion of glucagon-like peptide-1 and insulin.", Biochem. Biophys. Res. Commun., 2006, pp. 332-337, vol. 340.

(Continued)

*Primary Examiner* — Taofiq A Solola
(74) *Attorney, Agent, or Firm* — Arnall Golden Gregory LLP

(57) ABSTRACT

Disclosed are compounds, compositions and methods for treating of disorders that are affected by the modulation of the GPR120 receptor. Such compounds are represented by Formula (I) and Formula (II) as follows:

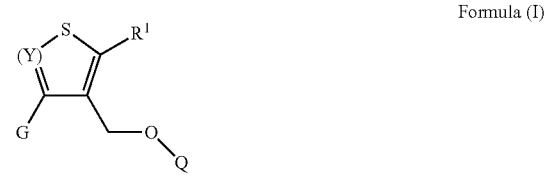

Formula (I)

wherein Y, $R^1$, G, and Q are defined herein; and

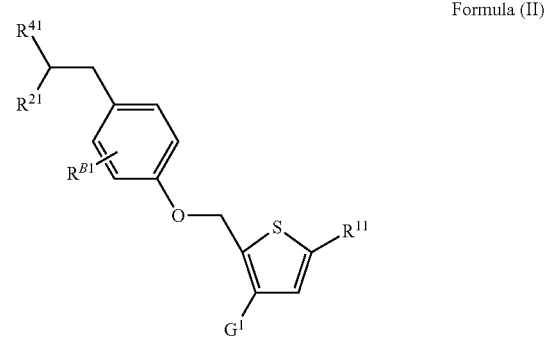

Formula (II)

wherein $R^{11}$, $R^{21}$, $R^{41}$, $R^{B1}$ and $G^1$, are defined herein.

13 Claims, No Drawings

(56) References Cited

FOREIGN PATENT DOCUMENTS

| WO | WO-2010/104195 | 9/2010 |
| WO | WO-2011/066183 | 6/2011 |
| WO | WO-2011/094890 | 8/2011 |
| WO | WO-2011/159297 | 12/2011 |

OTHER PUBLICATIONS

American Diabetes Association, "Economic Costs of Diabetes in the U.S. in 2007", Diabetes Care, 2008 ,pp. 1-20, vol. 31.

American Diabetes Association. DiabetesPro: Health Professional Resources and Statistics. Fact Sheet. 2014.

Ballatore et al., "Carboxylic Acid (Bio)Isosteres in Drug Design.", ChemMedChem, Mar. 2013, pp. 385-395, vol. 8(3).

Bell, G.I. and Polonsky, K.S., "Diabetes mellitus and genetically programmed defects in .beta. cell function", Nature, Dec. 13, 2001, pp. 788-791, vol. 414.

Bhatt et al., CoMSIA study on substituted ary l alkanoic acid analogs as GPR40 agonists, Chemical Biology & Drug Design, 2011, 77(5), 361-372.

Chen et al., "Chapter 32. The use of bioisosteric groups in lead optimization.", Annual Reports in Medicinal Chemistry—38, 2003, pp. 333-346.

Fukuda et al., "Directed Lithiation of N-Benzenesulfonyl-3-bromopyrrole. Electrophile-Controlled Regioselective Functionalization via Dynamic Equilibrium between C-2 and C-5 Lithio Species.", Organic Letters, 2010, pp. 2734-2737, vol. 12(12).

Gotoh et al., "The regulation of adipogenesis through GPR120.", Biochem. Biophys. Res. Commun., 2007, pp. 591-597, vol. 354.

Hara et al., "Novel selective ligands for free fatty acid receptors GPR120 and GPR40.", Naunyn-Schmied Arc. Pharmacol., 2009, pp. 247-255, vol. 380.

Hirasawa et al., "Free fatty acids regulate gut incretin glucagon-like peptide-1 secretion through GPR120", Nature Med, 2005, pp. 90-94, vol. 11(1).

International Search Report and Written Opinion of the International Searching Authority relating to International Patent Application No. PCT/US2014/021732, which corresponds to U.S. Appl. No. 14/200,108, dated May 20, 2014.

International Search Report and Written Opinion of the International Searching Authority relating to International Patent Application No. PCT/US2014/021740, which corresponds to U.S. Appl. No. 14/200,097, dated May 23, 2014.

International Search Report and Written Opinion of the International Searching Authority relating to International Patent Application No. PCT/US2014/021762, which corresponds to U.S. Appl. No. 14/200,114, dated May 21, 2014.

International Search Report and Written Opinion of the International Searching Authority relating to International Patent Application No. PCT/US2014/021775, which corresponds to U.S. Appl. No. 14/200,127, dated May 15, 2014.

Ishikawa et al., "Cesium Fluroide-Mediated Claisen Rearrangements of Phenyl Propargyl Esters: Effect of a Substituent on the Phenyl Ring on the Rearrangement.sup.1.", Heterocycles, 1994, pp. 371-380, vol. 39(1).

Itoh et al., "Free fatty acids regulate insulin secretion from pancreatic .beta. cells through GPR40", Nature, Mar. 13, 2003, pp. 173-176, vol. 422.

King, Med. Chem., Principle and Practice (1994), pp. 206-208.

Knop et al., "Incretin-Based Therapy of Type 2 Diabetes Mellitus.", Curr.Protein Pept. Sci., 2009, pp. 46-55, vol. 10.

Meanwell, "Synopsis of Some Recent Tactical Application of Bioisosteres in Drug Design," J. Med Chem, 2011: 54: pp. 2529-2591.

Moller, D.E., "New Drug Targets for type 2 diabetes and the metabolic syndrome.", Nature, Dec. 13, 2001, pp. 821-827, vol. 414.

Nathan, D.M., "Initial Management of Glycemia in Type 2 Diabetes Mellitus", N. Engl. J. Med., Oct. 24, 2002, pp. 1342-1349, vol. 347(17).

Partial International Search Report relating to International Patent Application No. PCT/2014/021790, dated Jun. 24, 2014.

Steneberg et al., "The FFA receptor GPR40 links hyperinsulinemia, hepatic steatosis and impaired glucose homeostasis in mouse"., Cell Metab, Apr. 2005, pp. 245-258, vol. 1.

Sun et al., "Structure-Activity Relationships of GPR120 Agonists Based on a Docking Simulation.", Molecular Pharmaceology, Nov. 1, 2010, pp. 804-810, vol. 78(5), XP0055122562.

Turner et al., "Glycemic Control With Diet, Sulfonylurea, Metformin or Insulin in Patients With Type 2 Diabetes Mellitus.", JAMA, Jun. 2, 1999, pp. 2005-2012, vol. 281(21).

Wild et al., "Global Prevalence of Diabetes", Diabetes Care, May 2004, pp. 1047-1053, vol. 27(5).

GPR120 AGONISTS FOR THE TREATMENT OF TYPE II DIABETES

CROSS-REFERENCE TO RELATED APPLICATIONS

This application is a Division of application Ser. No. 14/200,108, filed on Mar. 7, 2014, which claims priority of the benefits of the filing of U.S. Provisional Application Ser. No. 61/783,213, filed on Mar. 14, 2013. The complete disclosure of the aforementioned related U.S. patent applications are hereby incorporated herein by reference for all purposes.

FIELD OF THE INVENTION

The present invention relates to novel isothiazole and thiophene derivatives which are GPR120 agonists and are useful for the treatment of disorders that are affected by the modulation of the GPR120 receptor. The invention also relates to pharmaceutical compositions comprising such compounds, to processes to prepare such compounds and compositions, and to the use of such compounds or pharmaceutical compositions for the treatment of various diseases, syndromes and disorders, including obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

BACKGROUND OF THE INVENTION

A diabetes mellitus epidemic is unfolding across the globe with the World Health Organization (WHO) reporting a worldwide prevalence of 177 million patients with diabetes. It is estimated that the incidence of all forms of diabetes totals approximately 2.8% of the world population. The number of newly diagnosed diabetic patients is increasing by 4-5% per year. The total number of people with diabetes worldwide is projected to rise to 366 million (4.4% prevalence) in 2030. Type 2 diabetes accounts for approximately 95% of all diabetes cases. Long-term complications of Type 2 diabetes include atherosclerosis, heart disease, stroke, end-stage renal disease, retinopathy leading to blindness, nerve damage, sexual dysfunction, frequent infections, and difficult-to-treat foot ulcers, sometimes resulting in lower limb amputation. Diabetics are twice as likely to develop cardiovascular disease or have a stroke, 2 to 6 times more likely to have transient ischemic attacks, and 15 to 40 times more likely to require lower-limb amputation compared with the general population. The total estimated cost of diabetes in 2007 in the United States was $174 billion, including $116 billion in medical expenditures. The largest components of medical expenditures attributed to diabetes are hospital inpatient care (50% of total cost), diabetes medication and supplies (12%), retail prescriptions to treat complications of diabetes (11%), and physician office visits (9%). This may be related to the lack of durable efficacy of current drug therapies for Type 2 diabetes (>50% Type 2 patients are not reaching the targeted blood glucose control with current oral medications after 5 years of treatment). There is a general consensus that a considerable need exists for improved awareness, diagnosis and new, more effective, drug therapies for diabetes.

GLP-1 is secreted from specific cells in the colon following a meal and is a key regulator of glucose homeostasis, linking the gut, brain and pancreas. GLP-1 potentiates insulin secretion, reduces glucagon secretion and preserves β-cell function whilst also improving satiety. Levels of post-prandial GLP-1 are reduced in Type 2 diabetics and dramatically elevated following gastric by-pass surgery, contributing to the amelioration of Type 2 diabetes in these patients. Approaches that prolong the half-life of GLP-1 (JANUVIA (Merck), GALVUS (Novartis)) or activate the GLP-1 receptor (BYETTA (Amylin)) have been recently approved for use in Type 2 diabetes.

Hyperinsulinemia in patients with Type 2 diabetes mellitus results from peripheral insulin resistance, coupled with inadequate pancreatic insulin secretion and elevated glucagon levels. There is a strong correlation between obesity and peripheral insulin resistance and hyperinsulinemia. Accumulation of free fatty acids in insulin responsive tissues other than fat (i.e. muscle and liver) results in tissue insulin resistance. Additionally, free fatty acids have a direct effect on the pancreas and in the colon and further stimulate glucose-dependent insulin secretion and GLP-1 release with acute exposure whereas chronic exposure of free fatty acids impairs insulin secretion and becomes toxic to the β-cell. In the liver, hyperinsulinemia per se has been linked to exacerbating insulin resistance by increasing liver fatty acid accumulation and hepatic glucose output creating a vicious cycle of disease progression. Current therapeutic strategies only partially address the complex pathology of free fatty acids in the exacerbation of diabetes. Agents that target both liver and pancreas function, directly or indirectly via GLP-1 release, either individually or in combination with current treatment, could significantly improve blood glucose control while maintaining β-cell function. Agents that potentiate GLP-1 release also have the ability to reduce weight, providing additional benefits.

GPR120 is a seven transmembrane g-protein coupled receptor (GPCR) that is predominantly expressed in the intestine and adipose. GPR120 functions as a receptor for long chain free fatty acids (FFAs). Acute FFA stimulation of GPR120 in GLP-1 expressing cell-lines amplifies GLP-1 release. Administration of α-linolenic acid into the colon of mice increases GLP-1 and potentiates insulin release following a glucose challenge. In contrast to agonists of GPR40, the existing literature suggests that a GPR120 agonist would potentiate insulin secretion and reduce glucagon indirectly via GLP-1 release. GPR120 is also expressed in adipose, with expression induced during differentiation. Inhibition of GPR120 expression in 3T3-L1 adipocytes has been shown to reduce adipocyte differentiation. The role of the receptor in the adipose or in the taste cells of the tongue, where it has also been found, remains unclear.

GPR120 is a Gq coupled GPCR that acts a receptor for long chain fatty acids. It belongs to a family of lipid binding GPCRs that include GPR 40, 41, 43. Functionally, GPR120s closest homolog is GPR40. The cloned rat and mouse GPR120 receptors have been cloned and have >85% homology with the human receptor. GPR120 signals through Gq to elevate intracellular $Ca^{2+}$ levels as well as activate MAP kinase signal transduction cascades. GPR120's activation of calcium flux and PKC activation is most likely how FFAs contribute to the release GLP-1 in the L-cell.

Although relatively little is known about GPR120 due to a lack of potent, selective pharmacological tools or a documented metabolic phenotype of GPR120 knockout mice, the potential to elevate GLP-1 from a small-molecule perspective is attractive as a novel approach to an unmet medical need in the treatment of Type 2 diabetes mellitus and related disorders. The beneficial effects of elevating GLP-1 are already well validated in the clinic and in addition to improved glucose homeostasis, offer the potential of weight loss. Thus GPR120 agonists may be complementary to existing diabetes therapies that affect liver insulin sensitivity and those that preserve β-cell function.

SUMMARY OF THE INVENTION

The present invention is directed to compounds of Formula (I)

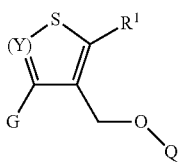

Formula (I)

wherein
Y is C(R³) or N; wherein R³ is hydrogen or methyl;
R¹ is selected from the group consisting of hydrogen, $C_{1-4}$alkyl, fluoro, chloro, cyclopropyl, 1,1-difluoroethyl, perfluoroethyl, trifluoromethyl, and phenyl; wherein phenyl is optionally independently substituted with one or two substituents that are $C_{1-2}$alkyl, methoxy, chloro, fluoro, or trifluoromethyl;
Q is selected from the group consisting of q1 to q6 q1

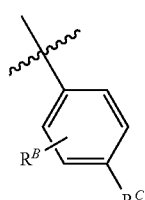

q2

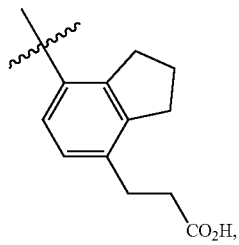

q3

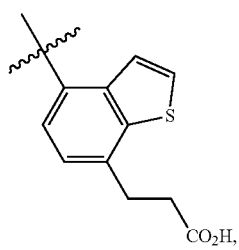

q4

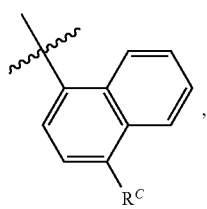

q5

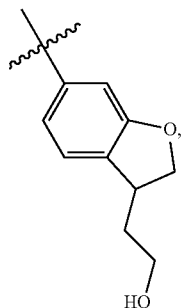

q6

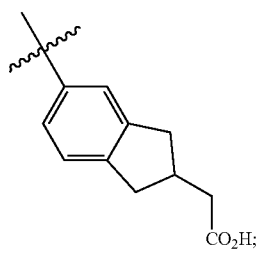

wherein
$R^B$ is one to four substituents independently selected from the group consisting of methyl, ethyl, methoxy, fluoro, chloro, bromo, trifluoromethyl, and trifluoromethoxy; provided that $R^B$ is no more than one of ethyl, methoxy, bromo, trifluoromethyl, or trifluoromethoxy;
$R^C$ is
i)

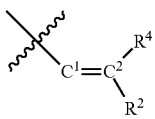

wherein the bond between $C^1$ and $C^2$ is a single bond or double bond;
$R^2$ is hydroxymethyl or carboxy;
$R^4$ is hydrogen or methyl;
ii) hydroxymethylethynyl;
iii) carboxycyclopropyl; or
iv) hydroxymethylcyclopropyl;
G is
i) hydrogen;
ii) $C_{1-4}$alkyl;
iii) methoxy;
iv) chloro;
v) trifluoromethyl;
vi) cyclopentyl or cyclopentenyl;
vii) pyridinyl optionally independently substituted with one or two substituents selected from the group consisting of $C_{1-2}$alkyl, $C_{1-2}$alkoxy, chloro, and fluoro;
viii) thiophenyl optionally substituted with one chloro substituent;
ix) a benzofused heterocyclyl that is benzo[d][1,3]dioxol-5-yl or 2,3-dihydrobenzofuran-5-yl;
x) tetrahydrofuranyl;
xi) 3,3-difluorocyclobut-1-yl;
xii) 3,3-difluorocyclopent-1-yl; or
xiii) 4-($R^A$)phenyl, wherein $R^A$ is selected from the group consisting of hydrogen, ethynyl, $C_{1-3}$alkyl, $C_{1-2}$alkoxy, fluoro, chloro, bromo, 1-fluoroethyl, 1,1-difluoroethyl, trifluoromethyl, methylcarbonyl, and cyclopropyl;
wherein said phenyl of group xiii) is optionally independently further substituted with one or two additional fluoro or methoxy substituents;
or an enantiomer, diastereomer, or pharmaceutically acceptable salt form thereof.

The present invention is also directed to compounds of Formula (II)

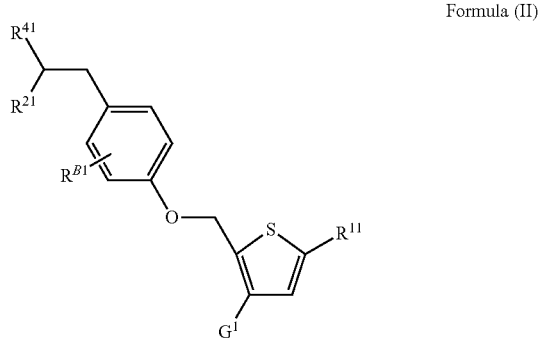

Formula (II)

wherein
R$^{11}$ is selected from the group consisting of hydrogen, methyl, fluoro, chloro, and trifluoromethyl;
R$^{B1}$ is one to four substituents independently selected from the group consisting of fluoro and methyl;
R$^{21}$ is hydroxymethyl or carboxy;
R$^{41}$ is hydrogen or methyl;
G$^{1}$ is
i) C$_{1-4}$alkoxy;
ii) chloro; or
iii) 4-(R$^{41}$)phenyl, wherein R$^{41}$ is selected from the group consisting of C$_{1-2}$alkyl and chloro;
or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or Formula (II), or a pharmaceutically acceptable salt form thereof.

Also provided are processes for making a pharmaceutical composition comprising, consisting of, and/or consisting essentially of admixing a compound of Formula (I) or Formula (II), and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the agonism of GPR120, such as Type II diabetes, using a compound of Formula (I) or Formula (II).

The present invention also is also directed to the use of any of the compounds described herein in the preparation of a medicament wherein the medicament is prepared for treating a disease or condition that is affected by the agonism of GPR120, selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders, in a subject in need thereof.

The present invention is also directed to the preparation of substituted isothiazole and thiophene derivatives that act as selective agonists of the GPR120 receptor.

Exemplifying the invention are methods of treating a disorder modulated by GPR120 selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders, comprising administering to a subject in need thereof a therapeutically effective amount of any of the compounds or pharmaceutical compositions described above.

In another embodiment, the present invention is directed to a compound of Formula (I) or Formula (II) for use in the treatment of a disorder affected by the agonism of GPR120 selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

In another embodiment, the present invention is directed to a composition comprising a compound of Formula (I) or Formula (II) for the treatment of a disorder affected by the agonism of GPR120 selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., C$_{1-8}$) refer independently to the number of carbon atoms in an alkyl moiety or to the alkyl portion of a larger alkyl-containing substituent. In substituent groups with multiple alkyl groups such as, (C$_{1-6}$alkyl)$_2$amino-, the C$_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(═O)OH.

The term "formyl" refers to the group —C(═O)H.

The term "oxo" refers to the group (═O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

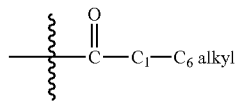

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "GPR120 agonist" is intended to encompass a compound that interacts with GPR120 to substantially increase its catalytic activity, thereby increasing the concentrations of its substrate(s).

The term "GPR120-modulated" is used to refer to the condition of being affected by the modulation of the GPR120 receptor, including but not limited to, the state of being mediated by the GPR120 receptor, for the treatment of a disease or condition such as obesity or Type II diabetes.

As used herein, unless otherwise noted, the term "disorder modulated by the GPR120 receptor" shall mean any disease, disorder or condition characterized in that at least one of its characteristic symptoms is alleviated or eliminated upon treatment with a GPR120 receptor agonist. Suitably examples include, but are not limited to obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus, dyslipidemia or metabolic syndrome X; more preferably, Type II diabetes mellitus or dyslipidemia.

As used herein unless otherwise noted, the term "obesity related cardiovascular disorders" shall mean any cardiovascular disease, disorder or condition in which obesity or diabetes (preferably, Type II Diabetes) has a role in the initiation or exacerbation of said disorder or condition. Suitable examples include, but are not limited to, hypertension, atherosclerosis and cardiac fibrosis.

As used herein, unless otherwise noted, the term "affect" or "affected" (when referring to a disease, syndrome, condition or disorder that is affected by agonism of GPR120) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the agonism of GPR120 receptor. Such methods comprise, consist of and/or consist essentially of administering to a subject, including an animal, a mammal, and a human in need of such treatment, amelioration and/or prevention, a therapeutically effective amount of a compound of Formula (I) or Formula (II), or an enantiomer, diastereomer, solvate or pharmaceutically acceptable salt thereof.

In particular, the compounds of Formula (I) or Formula (II), or an enantiomer, diastereomer, solvate or pharmaceutically acceptable salt thereof are useful for treating or ameliorating diseases, syndromes, conditions, or disorders such as obesity and type II diabetes.

More particularly, the compounds of Formula (I) or Formula (II), or an enantiomer, diastereomer, solvate or pharmaceutically acceptable salt thereof are useful for treating or ameliorating type II diabetes, comprising administering to a subject in need thereof a therapeutically effective amount of a compound of Formula (I) or Formula (II), or an enantiomer, diastereomer, solvate or pharmaceutically acceptable salt thereof as herein defined.

Embodiments of the present invention include a compound of Formula (I)

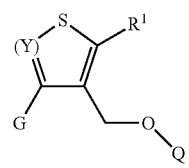

Formula (I)

wherein
a) Y is C($R^3$) wherein $R^3$ is hydrogen or methyl;
b) Y is N;
c) $R^1$ is selected from the group consisting of hydrogen, $C_{1-2}$alkyl, fluoro, chloro, cyclopropyl, perfluoroethyl, trifluoromethyl, and phenyl; wherein phenyl is optionally independently substituted with one or two substituents that are $C_{1-2}$alkyl, methoxy, chloro, or fluoro.
d) $R^1$ is selected from the group consisting of hydrogen, methyl, trifluoromethyl, and phenyl; wherein phenyl is optionally independently substituted with one or two substituents that are methyl, methoxy, chloro, or fluoro.
e) Q is selected from the group consisting of q1 to q4

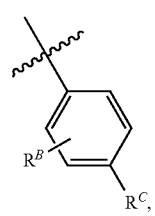

q1

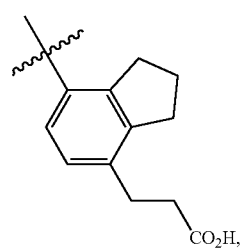

q2

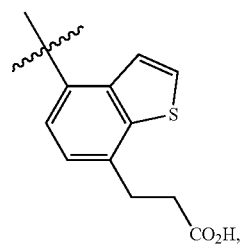

q3

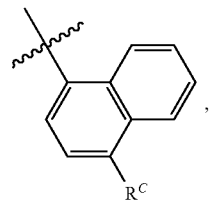

q4 wherein
$R^B$ is one to four substituents independently selected from the group consisting of methyl, ethyl, fluoro, chloro, bromo, trifluoromethyl, and trifluoromethoxy; provided that $R^B$ is no more than one of ethyl, bromo, trifluoromethyl, or trifluoromethoxy;

$R^C$ is i)

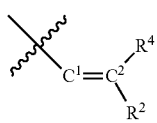

wherein the bond between $C^1$ and $C^2$ is a single bond or double bond;
$R^2$ is hydroxymethyl or carboxy;
$R^4$ is hydrogen or methyl; or ii) carboxycyclopropyl.

f) Q is selected from the group consisting of q1 to q4

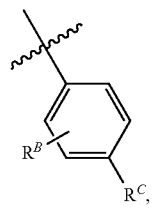
q1

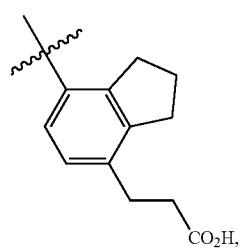
q2

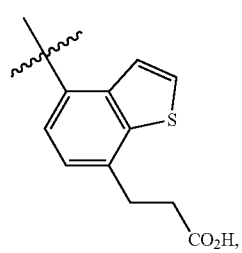
q3

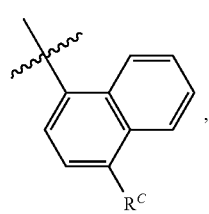
q4 wherein
$R^B$ is one to four substituents independently selected from the group consisting of methyl, fluoro, and bromo; provided that $R^B$ is no more than one of bromo;
$R^C$ is

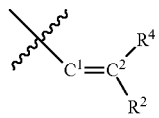

wherein the bond between $C^1$ and $C^2$ is a single bond;
$R^2$ is hydroxymethyl or carboxy; and
$R^4$ is hydrogen or methyl.

g) Q is q1

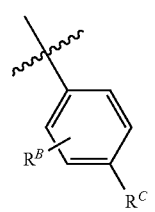
q1 wherein
$R^B$ is one to four substituents independently selected from the group consisting of methyl, fluoro, and bromo; provided that $R^B$ is no more than one of bromo;
$R^C$ is

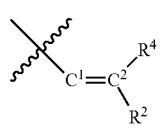

wherein the bond between $C^1$ and $C^2$ is a single bond;
$R^2$ is hydroxymethyl or carboxy; and
$R^4$ is hydrogen or methyl.

h) $R^C$ is

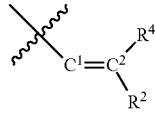

wherein the bond between $C^1$ and $C^2$ is a single bond;
$R^2$ is carboxy; and
$R^4$ is hydrogen.

i) G is
  i) hydrogen;
  ii) $C_{1-2}$alkyl;
  iii) methoxy;
  iv) chloro;
  v) trifluoromethyl;
  vi) cyclopentyl or cyclopentenyl;
  vii) pyridinyl optionally independently substituted with one or two substituents selected from the group consisting of $C_{1-2}$alkyl, $C_{1-2}$alkoxy, chloro, and fluoro;
  viii) a benzofused heterocyclyl that is benzo[d][1,3]dioxol-5-yl or 2,3-dihydrobenzofuran-5-yl;
  ix) 3,3-difluorocyclobut-1-yl;
  x) 3,3-difluorocyclopent-1-yl; or
  xi) 4-($R^A$)phenyl, wherein $R^A$ is selected from the group consisting of hydrogen, ethynyl, $C_{1-2}$alkyl, $C_{1-2}$alkoxy, fluoro, chloro, bromo, 1-fluoroethyl, 1,1-difluoroethyl, trifluoromethyl, methylcarbonyl, and cyclopropyl;

wherein said phenyl of group xi) is optionally independently further substituted with one or two additional fluoro or methoxy substituents.

j) G is
  i) methyl;
  ii) methoxy;
  iii) chloro;
  iv) trifluoromethyl;
  v) cyclopentyl or cyclopentenyl;
  vi) pyridinyl optionally independently substituted with one substituent selected from the group consisting of methyl and methoxy;
  vii) a benzofused heterocyclyl that is benzo[d][1,3]dioxol-5-yl;
  viii) 3,3-difluorocyclobut-1-yl; or
  ix) 4-($R^A$)phenyl, wherein $R^A$ is selected from the group consisting of hydrogen, $C_{1-2}$alkyl, methoxy, chloro, trifluoromethyl, and methylcarbonyl;
    wherein said phenyl of group ix) is optionally independently further substituted with one or two additional fluoro substituents;

and any combination of embodiments a) through j) above, provided that it is understood that combinations in which different embodiments of the same substituent would be combined are excluded;

or an enantiomer, diastereomer, or pharmaceutically acceptable salt form thereof.

An embodiment of the present invention includes a compound of Formula (I)

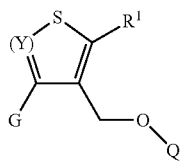

Formula (I)

wherein

Y is N or C($R^3$), wherein $R^3$ is hydrogen or methyl;

$R^1$ is selected from the group consisting of hydrogen, $C_{1-2}$alkyl, fluoro, chloro, cyclopropyl, perfluoroethyl, trifluoromethyl, and phenyl; wherein phenyl is optionally independently substituted with one or two substituents that are $C_{1-2}$alkyl, methoxy, chloro, or fluoro;

Q is selected from the group consisting of q1 to q4

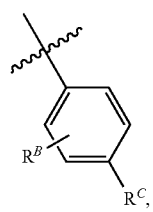

q1

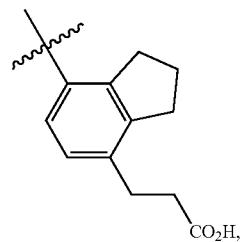

q2

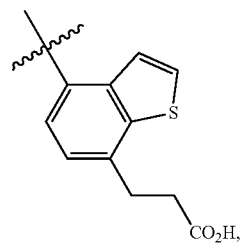

q3

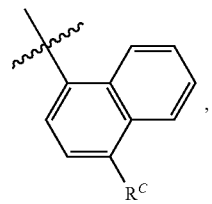

q4 wherein $R^B$ is one to four substituents independently selected from the group consisting of methyl, ethyl, fluoro, chloro, bromo, trifluoromethyl, and trifluoromethoxy; provided that $R^B$ is no more than one of ethyl, bromo, trifluoromethyl, or trifluoromethoxy;

$R^C$ is
i)

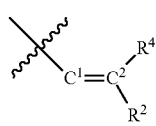

wherein the bond between $C^1$ and $C^2$ is a single bond or double bond;
$R^2$ is hydroxymethyl or carboxy;
$R^4$ is hydrogen or methyl; or
ii) carboxycyclopropyl;

G is
  i) hydrogen;
  ii) $C_{1-3}$alkyl;
  iii) methoxy;
  iv) chloro;
  v) trifluoromethyl;
  vi) cyclopentyl or cyclopentenyl;
  vii) pyridinyl optionally independently substituted with one or two substituents selected from the group consisting of $C_{1-2}$alkyl, $C_{1-2}$alkoxy, chloro, and fluoro;
  viii) a benzofused heterocyclyl that is benzo[d][1,3]dioxol-5-yl or 2,3-dihydrobenzofuran-5-yl;
  ix) 3,3-difluorocyclobut-1-yl;
  x) 3,3-difluorocyclopent-1-yl; or
  xi) 4-($R^A$)phenyl, wherein $R^A$ is selected from the group consisting of hydrogen, ethynyl, $C_{1-2}$alkyl, $C_{1-2}$alkoxy, fluoro, chloro, bromo, 1-fluoroethyl, 1,1-difluoroethyl, trifluoromethyl, methylcarbonyl, and cyclopropyl;

wherein said phenyl of group xi) is optionally independently further substituted with one or two additional fluoro or methoxy substituents;

or an enantiomer, diastereomer, or pharmaceutically acceptable salt form thereof.

An embodiment of the present invention includes a compound of Formula (I)

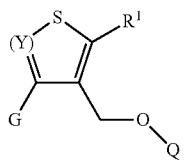

Formula (I)

wherein

Y is N or C(R$^3$), wherein R$^3$ is hydrogen or methyl;

R$^1$ is selected from the group consisting of hydrogen, methyl, trifluoromethyl, and phenyl; wherein phenyl is optionally independently substituted with one or two substituents that are methyl, methoxy, chloro, or fluoro;

Q is selected from the group consisting of q1 to q4

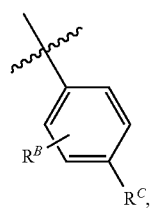

q1

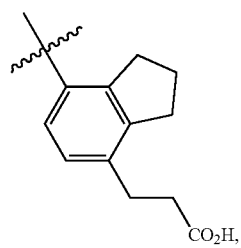

q2

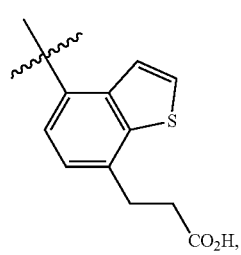

q3

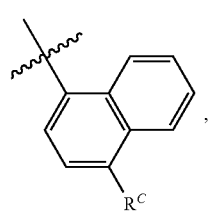

q4 wherein

R$^B$ is one to four substituents independently selected from the group consisting of methyl, fluoro, and bromo; provided that R$^B$ is no more than one of bromo;

R$^C$ is

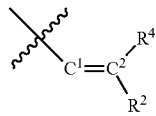

wherein the bond between C$^1$ and C$^2$ is a single bond;

R$^2$ is hydroxymethyl or carboxy;

R$^4$ is hydrogen or methyl;

G is i) methyl;
ii) methoxy;
iii) chloro;
iv) trifluoromethyl;
v) cyclopentyl or cyclopentenyl;
vi) pyridinyl optionally independently substituted with one substituent selected from the group consisting of methyl and methoxy;
vii) a benzofused heterocyclyl that is benzo[d][1,3]dioxol-5-yl;
viii) 3,3-difluorocyclobut-1-yl; or
ix) 4-(R$^A$)phenyl, wherein R$^A$ is selected from the group consisting of hydrogen, C$_{1-2}$alkyl, methoxy, chloro, trifluoromethyl, and methylcarbonyl;

wherein said phenyl of group ix) is optionally independently further substituted with one or two additional fluoro substituents;

or an enantiomer, diastereomer, or pharmaceutically acceptable salt form thereof.

An embodiment of the present invention includes a compound of Formula (I)

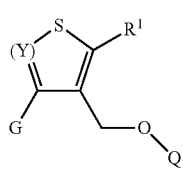

Formula (I)

wherein

Y is N or C(R$^3$), wherein R$^3$ is hydrogen or methyl;

R$^1$ is selected from the group consisting of hydrogen, methyl, trifluoromethyl, and phenyl; wherein phenyl is optionally independently substituted with one or two substituents that are methyl, methoxy, chloro, or fluoro;

Q is q1

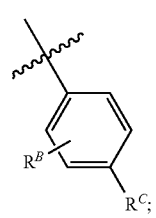

q1 wherein
R$^B$ is one to four substituents independently selected from the group consisting of methyl and fluoro;
R$^C$ is

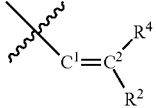

wherein the bond between C$^1$ and C$^2$ is a single bond;
R$^2$ is hydroxymethyl or carboxy;
R$^4$ is hydrogen or methyl;
G is
i) methyl;
ii) methoxy;
iii) chloro;
iv) trifluoromethyl;
v) cyclopentyl or cyclopentenyl;
vi) pyridinyl optionally independently substituted with one substituent selected from the group consisting of methyl and methoxy;
vii) a benzofused heterocyclyl that is benzo[d][1,3]dioxol-5-yl;
viii) 3,3-difluorocyclobut-1-yl; or
ix) 4-(R$^A$)phenyl, wherein R$^A$ is selected from the group consisting of hydrogen, C$_{1-2}$alkyl, methoxy, chloro, trifluoromethyl, and methylcarbonyl;
wherein said phenyl of group ix) is optionally independently further substituted with one or two additional fluoro substituents;
or an enantiomer, diastereomer, or pharmaceutically acceptable salt form thereof.

An embodiment of the present invention includes a compound of Formula (I)

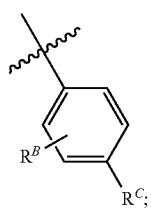

Formula (I)

wherein
Y is N;
R$^1$ is selected from the group consisting of hydrogen, methyl, trifluoromethyl, and phenyl; wherein phenyl is optionally independently substituted with one or two substituents that are methyl, methoxy, chloro, or fluoro;
Q is q1

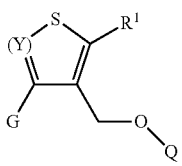

q1 wherein
R$^B$ is one to four substituents independently selected from the group consisting of methyl and fluoro;
R$^C$ is

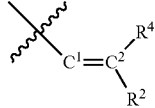

wherein the bond between C$^1$ and C$^2$ is a single bond;
R$^2$ is hydroxymethyl or carboxy;
R$^4$ is hydrogen or methyl;
G is
i) methyl;
ii) methoxy;
iii) chloro;
iv) trifluoromethyl;
v) cyclopentyl or cyclopentenyl;
vi) pyridinyl optionally independently substituted with one substituent selected from the group consisting of methyl and methoxy;
vii) a benzofused heterocyclyl that is benzo[d][1,3]dioxol-5-yl;
viii) 3,3-difluorocyclobut-1-yl; or
ix) 4-(R$^A$)phenyl, wherein R$^A$ is selected from the group consisting of hydrogen, C$_{1-2}$alkyl, methoxy, chloro, trifluoromethyl, and methylcarbonyl;
wherein said phenyl of group ix) is optionally independently further substituted with one or two additional fluoro substituents;
or an enantiomer, diastereomer, or pharmaceutically acceptable salt form thereof.

In a further embodiment of the present invention includes compounds of Formula (I)

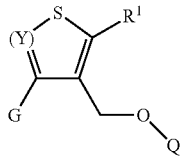

Formula (I)

selected from the group consisting of
Cpd 31, 3-(4-{[4-Cyclopent-1-en-1-yl-2-(trifluoromethyl)thiophen-3-yl]methoxy}-3,5-difluorophenyl)propanoic acid;
Cpd 32, 3-(4-{[2-(4-Ethylphenyl)-5-methyl-4-(trifluoromethyl)thiophen-3-yl]methoxy}-3,5-difluorophenyl)propan-1-ol;
Cpd 33, 3-(2,3-Dimethyl-4-{[5-methyl-2-phenyl-4-(trifluoromethyl)thiophen-3-yl]methoxy}phenyl)propanoic acid;
Cpd 34, 3-(3,5-Difluoro-4-{[4-(4-methoxyphenyl)-2-(trifluoromethyl)thiophen-3-yl]methoxy}phenyl)propanoic acid;
Cpd 35, 3-(4-{[4-(4-Chlorophenyl)-2-(trifluoromethyl)thiophen-3-yl]methoxy}-3,5-difluorophenyl)propanoic acid;
Cpd 36, 3-(3,5-Difluoro-4-{[4-(6-methylpyridin-3-yl)-2-(trifluoromethyl)thiophen-3-yl]methoxy}phenyl)propan-1-ol;
Cpd 37, 3-(4-{[4-(1,3-Benzodioxol-5-yl)-2-(trifluoromethyl)thiophen-3-yl]methoxy}-3,5-difluorophenyl)propan-1-ol;

Cpd 38, 3-(3,5-Difluoro-4-{[4-(6-methoxypyridin-3-yl)-2-(trifluoromethyl)thiophen-3-yl]methoxy}phenyl)propan-1-ol;

Cpd 39, 3-(4-{[2-(4-Ethylphenyl)-5-methyl-4-(trifluoromethyl)thiophen-3-yl]methoxy}-3,5-difluorophenyl)propanoic acid;

Cpd 40, 3-(4-{[2-(4-Chlorophenyl)-5-methyl-4-(trifluoromethyl)thiophen-3-yl]methoxy}-3,5-difluorophenyl)propanoic acid;

Cpd 41, 3-(4-{[4-(4-Ethylphenyl)thiophen-3-yl]methoxy}-2,3-dimethylphenyl)propanoic acid;

Cpd 42, 3-(3,5-Difluoro-4-{[4-(6-methoxypyridin-3-yl)-2-(trifluoromethyl)thiophen-3-yl]methoxy}phenyl)propanoic acid;

Cpd 43, 3-(4-{[4-(4-Ethylphenyl)thiophen-3-yl]methoxy}-2,3-difluorophenyl)propanoic acid;

Cpd 44, 3-(4-{[4-(1,3-Benzodioxol-5-yl)-2-(trifluoromethyl)thiophen-3-yl]methoxy}-3,5-difluorophenyl)propanoic acid;

Cpd 45, 3-(3,5-Difluoro-4-{[4-(4-methoxyphenyl)-2-(trifluoromethyl)thiophen-3-yl]methoxy}phenyl)propan-1-ol;

Cpd 46, 3-(4-{[4-(4-Chlorophenyl)-2-(trifluoromethyl)thiophen-3-yl]methoxy}-3,5-difluorophenyl)propan-1-ol;

Cpd 47, 3-(4-{[4-(4-Chlorophenyl)-2-(trifluoromethyl)thiophen-3-yl]methoxy}-2,3-difluorophenyl)propanoic acid;

Cpd 48, 3-(4-{[2-(4-Ethylphenyl)thiophen-3-yl]methoxy}-2,3-difluorophenyl)propanoic acid;

Cpd 49, 3-(4-{[2-(4-Ethylphenyl)thiophen-3-yl]methoxy}-2,3-dimethylphenyl)propanoic acid;

Cpd 50, 3-(4-{[4-(4-Chlorophenyl)-2-(trifluoromethyl)thiophen-3-yl]methoxy}-2,3,5-trifluorophenyl)propanoic acid;

Cpd 51, 3-(4-{[4-(2,3-Dihydro-1-benzofuran-5-yl)-2-(trifluoromethyl)thiophen-3-yl]methoxy}-3,5-difluorophenyl)propanoic acid;

Cpd 52, 3-(4-{[2-(4-Ethylphenyl)thiophen-3-yl]methoxy}-3,5-difluorophenyl)propanoic acid;

Cpd 53, 3-(4-{[4-(4-Ethylphenyl)thiophen-3-yl]methoxy}-3,5-difluorophenyl)propanoic acid;

Cpd 54, 3-(4-{[4-(4-Ethylphenyl)-2-(trifluoromethyl)thiophen-3-yl]methoxy}-2,3-dimethylphenyl)propanoic acid;

Cpd 55, 3-(4-{[4-(2,3-Dihydro-1-benzofuran-5-yl)-2-(trifluoromethyl)thiophen-3-yl]methoxy}-3,5-difluorophenyl)propan-1-ol;

Cpd 56, 3-(4-{[4-(4-Chlorophenyl)-2-(trifluoromethyl)thiophen-3-yl]methoxy}-2,3,5-trifluorophenyl)propan-1-ol;

Cpd 57, 3-(4-{[4-(4-Chlorophenyl)-2-(trifluoromethyl)thiophen-3-yl]methoxy}-2,3-dimethylphenyl)propanoic acid;

Cpd 58, 3-(4-{[4-(4-Fluorophenyl)-2-(trifluoromethyl)thiophen-3-yl]methoxy}-2,3-dimethylphenyl)propanoic acid;

Cpd 59, 3-(4-{[4-(4-Chloro-2-fluorophenyl)-2-(trifluoromethyl)thiophen-3-yl]methoxy}-2,3-dimethylphenyl)propanoic acid;

Cpd 60, 3-(4-{[4-(4-Methoxyphenyl)-2-(trifluoromethyl)thiophen-3-yl]methoxy}-2,3-dimethylphenyl)propanoic acid;

Cpd 61, 3-(4-{[2-(4-Ethylphenyl)-5-methyl-4-(trifluoromethyl)thiophen-3-yl]methoxy}-2,3-dimethylphenyl)propanoic acid;

Cpd 62, 3-(3,5-Difluoro-4-{[4-(6-methylpyridin-3-yl)-2-(trifluoromethyl)thiophen-3-yl]methoxy}phenyl)propanoic acid;

Cpd 63, 3-(4-{[5-(4-Chlorophenyl)-3-(trifluoromethyl)isothiazol-4-yl]methoxy}-5-fluoro-2-methylphenyl)propan-1-ol;

Cpd 64, 3-(4-{[3-(4-Ethylphenyl)-5-(1-methylethyl)isothiazol-4-yl]methoxy}-2,3-dimethylphenyl)propanoic acid;

Cpd 65, 3-(3,5-Difluoro-4-{[3-(2-fluoro-4-methylphenyl)-5-(trifluoromethyl)isothiazol-4-yl]methoxy}phenyl)propanoic acid;

Cpd 66, 3-(4-{[3-Chloro-5-(4-ethylphenyl)isothiazol-4-yl]methoxy}-2,3-difluorophenyl)propanoic acid;

Cpd 67, 3-(4-{[3-(4-Chloro-3-fluorophenyl)-5-(trifluoromethyl)isothiazol-4-yl]methoxy}-3,5-difluorophenyl)propanoic acid;

Cpd 68, 3-(4-{[3-(4-Chlorophenyl)-5-(trifluoromethyl)isothiazol-4-yl]methoxy}-3-fluorophenyl)propanoic acid;

Cpd 69, 3-(3-Bromo-4-{[3-(4-chlorophenyl)-5-(trifluoromethyl)isothiazol-4-yl]methoxy}phenyl)propanoic acid;

Cpd 70, 3-(4-{[3-(4-Ethylphenyl)-5-(trifluoromethyl)isothiazol-4-yl]methoxy}-3,5-difluorophenyl)propanoic acid;

Cpd 71, 3-(4-{[3-Cyclopentyl-5-(trifluoromethyl)isothiazol-4-yl]methoxy}-3,5-difluorophenyl)propanoic acid;

Cpd 72, 3-(4-{[3-Chloro-5-(4-chlorophenyl)isothiazol-4-yl]methoxy}-2,3-difluorophenyl)propanoic acid;

Cpd 73, 3-(4-{[3-(4-Ethylphenyl)-5-(trifluoromethyl)isothiazol-4-yl]methoxy}-2,3-difluorophenyl)propanoic acid;

Cpd 74, 3-(4-{[3-(4-Chloro-2-fluorophenyl)-5-(trifluoromethyl)isothiazol-4-yl]methoxy}-3,5-difluorophenyl)propanoic acid Cpd 75, 3-(4-{[3-Chloro-5-(4-chlorophenyl)isothiazol-4-yl]methoxy}-3,5-difluorophenyl)propanoic acid;

Cpd 76, 3-(3,5-Difluoro-4-{[3-(2-fluoro-4-methylphenyl)-5-(trifluoromethyl)isothiazol-4-yl]methoxy}phenyl)-2-methylpropanoic acid;

Cpd 77, 3-(4-{[3-Chloro-5-(2-fluoro-4-methylphenyl)isothiazol-4-yl]methoxy}-3,5-difluorophenyl)propanoic acid;

Cpd 78, 3-(4-{[3-Chloro-5-(4-chlorophenyl)isothiazol-4-yl]methoxy}-3,5-difluorophenyl)propan-1-ol;

Cpd 79, 3-(4-{[3-(4-Chlorophenyl)-5-(trifluoromethyl)isothiazol-4-yl]methoxy}-3,5-difluorophenyl)propanoic acid;

Cpd 80, 3-(4-{[3-(4-Ethylphenyl)-5-(trifluoromethyl)isothiazol-4-yl]methoxy}-3,5-difluorophenyl)-2-methylpropanoic acid;

Cpd 81, 3-(3,5-Difluoro-4-{[3-(6-methoxypyridin-3-yl)-5-(trifluoromethyl)isothiazol-4-yl]methoxy}phenyl)propan-1-ol;

Cpd 82, 3-(4-{[3-(4-Chloro-3-fluorophenyl)-5-(trifluoromethyl)isothiazol-4-yl]methoxy}-2,3-dimethylphenyl)propanoic acid;

Cpd 83, 3-(4-{[3-Chloro-5-(4-ethylphenyl)isothiazol-4-yl]methoxy}-2,3-difluorophenyl)propan-1-ol;

Cpd 84, 3-(3,5-Difluoro-4-{[5-(2-fluoro-4-methylphenyl)-3-methylisothiazol-4-yl]methoxy}phenyl)propanoic acid;

Cpd 85, 3-(4-{[3-Chloro-5-(4-ethylphenyl)isothiazol-4-yl]methoxy}-2,3-dimethylphenyl)propanoic acid;

Cpd 86, 3-(4-{[3-(4-Methoxyphenyl)-5-(trifluoromethyl)isothiazol-4-yl]methoxy}-2,3-dimethylphenyl)propanoic acid;

Cpd 87, 3-(4-{[3-(1,3-Benzodioxol-5-yl)-5-(trifluoromethyl)isothiazol-4-yl]methoxy}-3,5-difluorophenyl)propanoic acid;

Cpd 88, 3-(4-{[3-Chloro-5-(4-chlorophenyl)isothiazol-4-yl]methoxy}-2,3-dimethylphenyl)propanoic acid;

Cpd 89, 3-(4-{[3-(2-Fluoro-4-methylphenyl)-5-(trifluoromethyl)isothiazol-4-yl]methoxy}-2,3-dimethylphenyl)propanoic acid;

Cpd 90, 3-(4-{[3-(4-Chloro-3-fluorophenyl)-5-(trifluoromethyl)isothiazol-4-yl]methoxy}-3,5-difluorophenyl)-2-methylpropanoic acid;

Cpd 91, 3-(3,5-Difluoro-4-{[3-(3-fluoro-4-methylphenyl)-5-(trifluoromethyl)isothiazol-4-yl]methoxy}phenyl)propanoic acid;

Cpd 92, 3-(4-{[3-(4-Ethylphenyl)-5-(trifluoromethyl)isothiazol-4-yl]methoxy}-1-benzothiophen-7-yl)propanoic acid;

Cpd 93, 3-(4-{[3-(1,3-Benzodioxol-5-yl)-5-(trifluoromethyl)isothiazol-4-yl]methoxy}-3,5-difluorophenyl)propan-1-ol;

Cpd 94, 3-(3,5-Difluoro-4-{[3-(3-methoxyphenyl)-5-(trifluoromethyl)isothiazol-4-yl]methoxy}phenyl)propanoic acid;

Cpd 95, 3-(3,5-Difluoro-4-{[5-(2-fluoro-4-methylphenyl)-3-(trifluoromethyl)isothiazol-4-yl]methoxy}phenyl)propanoic acid;

Cpd 96, 3-(4-{[3-(4-Chloro-2,6-difluorophenyl)-5-(trifluoromethyl)isothiazol-4-yl]methoxy}-3,5-difluorophenyl)propanoic acid;

Cpd 97, 3-(4-{[3-Chloro-5-(4-methoxyphenyl)isothiazol-4-yl]methoxy}-3,5-difluorophenyl)propanoic acid;

Cpd 98, 3-(3,5-Difluoro-4-{[3-(6-methoxypyridin-3-yl)-5-(trifluoromethyl)isothiazol-4-yl]methoxy}phenyl)propanoic acid;

Cpd 99, 3-(3,5-Difluoro-4-{[3-(4-methoxyphenyl)-5-(trifluoromethyl)isothiazol-4-yl]methoxy}phenyl)propanoic acid;

Cpd 100, 3-(4-{[3-(4-Chlorophenyl)-5-(trifluoromethyl)isothiazol-4-yl]methoxy}-3,5-difluorophenyl)propan-1-ol;

Cpd 101, 3-{4-[(3-Chloro-5-phenylisothiazol-4-yl)methoxy]-2,3-dimethylphenyl}propanoic acid;

Cpd 102, 3-(4-{[3-Chloro-5-(4-chlorophenyl)isothiazol-4-yl]methoxy}-2,3-difluorophenyl)propan-1-ol;

Cpd 103, 3-(7-{[3-(4-Ethylphenyl)-5-(trifluoromethyl)isothiazol-4-yl]methoxy}-2,3-dihydro-1H-inden-4-yl)propanoic acid;

Cpd 104, 3-(4-{[3-Chloro-5-(2-chlorophenyl)isothiazol-4-yl]methoxy}-2,3-dimethylphenyl)propanoic acid;

Cpd 105, 3-(4-{[3-(4-Ethylphenyl)-5-(trifluoromethyl)isothiazol-4-yl]methoxy}-3-fluorophenyl)-2-methylpropanoic acid;

Cpd 106, 3-(4-{[3-(4-Chlorophenyl)-5-(trifluoromethyl)isothiazol-4-yl]methoxy}-2,3-difluorophenyl)propanoic acid;

Cpd 107, 3-(4-{[3-Chloro-5-(2-fluoro-4-methylphenyl)isothiazol-4-yl]methoxy}-2,3,5-trifluorophenyl)propanoic acid;

Cpd 108, 3-(4-{[3-(4-Chlorophenyl)-5-(trifluoromethyl)isothiazol-4-yl]methoxy}-3,5-difluorophenyl)-2-methylpropanoic acid;

Cpd 109, 3-(4-{[3-(3-Fluoro-4-methylphenyl)-5-(trifluoromethyl)isothiazol-4-yl]methoxy}-2,3-dimethylphenyl)propanoic acid;

Cpd 110, 3-(4-{[5-(4-Chloro-3-fluorophenyl)-3-(trifluoromethyl)isothiazol-4-yl]methoxy}-3,5-difluorophenyl)propanoic acid;

Cpd 111, 3-(4-{[3-Chloro-5-(4-ethylphenyl)isothiazol-4-yl]methoxy}-2,3,5-trifluorophenyl)propanoic acid;

Cpd 112, 3-[4-({3-Chloro-5-[4-(trifluoromethyl)phenyl]isothiazol-4-yl}methoxy)-2,3-dimethylphenyl]propanoic acid;

Cpd 113, 3-(4-{[3-(4-Chlorophenyl)-5-(trifluoromethyl)isothiazol-4-yl]methoxy}-3,5-difluoro-2-methylphenyl)propanoic acid;

Cpd 114, 3-(4-{[3-Chloro-5-(4-chloro-2-fluorophenyl)isothiazol-4-yl]methoxy}-3,5-difluorophenyl)propanoic acid;

Cpd 115, 3-(3,5-Difluoro-4-{[3-(4-methylphenyl)-5-(trifluoromethyl)isothiazol-4-yl]methoxy}phenyl)propanoic acid;

Cpd 116, 3-(4-{[3-(4-Chlorophenyl)-5-(trifluoromethyl)isothiazol-4-yl]methoxy}-2,3,5-trifluorophenyl)propanoic acid;

Cpd 117, 3-(4-{[3-(4-Ethylphenyl)-5-(trifluoromethyl)isothiazol-4-yl]methoxy}-2,3,5-trifluorophenyl)propanoic acid;

Cpd 118, 3-(4-{[3-(4-Ethylphenyl)-5-(trifluoromethyl)isothiazol-4-yl]methoxy}-2,3,5,6-tetrafluorophenyl)propanoic acid;

Cpd 119, 3-(4-{[3-(4-Chlorophenyl)-5-methylisothiazol-4-yl]methoxy}-2,3-difluorophenyl)propanoic acid;

Cpd 120, 3-(4-{[3-(2-Fluoro-4-methoxyphenyl)-5-(trifluoromethyl)isothiazol-4-yl]methoxy}-2,3-dimethylphenyl)propanoic acid;

Cpd 121, 3-[3,5-Difluoro-4-({5-(trifluoromethyl)-3-[4-(trifluoromethyl)phenyl]isothiazol-4-yl}methoxy)phenyl]propanoic acid;

Cpd 122, 3-(4-{[3-Chloro-5-(4-chloro-2-fluorophenyl)isothiazol-4-yl]methoxy}-2,3-dimethylphenyl)propanoic acid;

Cpd 123, 3-(3,5-Difluoro-4-{[5-(2-fluoro-4-methylphenyl)-3-methoxyisothiazol-4-yl]methoxy}phenyl)propanoic acid;

Cpd 124, 3-(4-{[3-Chloro-5-(4-ethylphenyl)isothiazol-4-yl]methoxy}-3,5-difluorophenyl)propanoic acid;

Cpd 125, 3-(4-{[3-(4-Chlorophenyl)-5-(trifluoromethyl)isothiazol-4-yl]methoxy}-5-fluoro-2-methylphenyl)propanoic acid;

Cpd 126, 3-(4-{[3-(3-Methoxyphenyl)-5-(trifluoromethyl)isothiazol-4-yl]methoxy}-2,3-dimethylphenyl)propanoic acid;

Cpd 127, 3-(4-{[3-(4-Ethylphenyl)-5-(trifluoromethyl)isothiazol-4-yl]methoxy}-2,3-dimethylphenyl)propanoic acid;

Cpd 128, 3-(4-{[3-(4-Ethyl-2-fluorophenyl)-5-(trifluoromethyl)isothiazol-4-yl]methoxy}-3,5-difluorophenyl)propanoic acid;

Cpd 129, 3-(4-{[5-(3,4-Difluorophenyl)-3-(trifluoromethyl)isothiazol-4-yl]methoxy}-3,5-difluorophenyl)propanoic acid;

Cpd 130, 3-(4-{[3-(4-Ethylphenyl)-5-(trifluoromethyl)isothiazol-4-yl]methoxy}naphthalen-1-yl)propanoic acid;

Cpd 131, 3-(4-{[3-(4-Acetylphenyl)-5-(trifluoromethyl)isothiazol-4-yl]methoxy}-3,5-difluorophenyl)propanoic acid;

Cpd 132, 3-(4-{[3-(4-Chlorophenyl)-5-(trifluoromethyl)isothiazol-4-yl]methoxy}-2,3-difluorophenyl)propan-1-ol;

Cpd 133, 3-(4-{[3-(4-Chloro-2,6-difluorophenyl)-5-(trifluoromethyl)isothiazol-4-yl]methoxy}-2,3-dimethylphenyl)propanoic acid;

Cpd 134, 3-(2,3-Dimethyl-4-{[3-phenyl-5-(trifluoromethyl)isothiazol-4-yl]methoxy}phenyl)propanoic acid;

Cpd 135, 3-(4-{[3-(4-Ethylphenyl)-5-(trifluoromethyl)isothiazol-4-yl]methoxy}-3,5-difluorophenyl)propan-1-ol;

Cpd 136, 3-(4-{[5-(4-Chloro-3-fluorophenyl)-3-(trifluoromethyl)isothiazol-4-yl]methoxy}-2,3-dimethylphenyl)propanoic acid;

Cpd 137, 3-(4-{[3-(3,3-Difluorocyclobutyl)-5-(trifluoromethyl)isothiazol-4-yl]methoxy}-2,3-dimethylphenyl)propanoic acid;

Cpd 138, 3-(4-{[3-(4-Chloro-3-fluorophenyl)-5-(trifluoromethyl)isothiazol-4-yl]methoxy}-2,3,5-trifluorophenyl)propanoic acid;

Cpd 139, 3-(4-{[3-(4-Ethylphenyl)-5-(trifluoromethyl)isothiazol-4-yl]methoxy}-2,3-difluorophenyl)propan-1-ol;

Cpd 140, 3-(4-{[3-Chloro-5-(4-ethylphenyl)isothiazol-4-yl]methoxy}-2,3,5-trifluorophenyl)propan-1-ol;

Cpd 141, 3-(4-{[3-Cyclopentyl-5-(trifluoromethyl)isothiazol-4-yl]methoxy}-3,5-difluorophenyl)propan-1-ol;

Cpd 142, 3-(4-{[3-(4-Chlorophenyl)-5-(trifluoromethyl)isothiazol-4-yl]methoxy}-2,3-dimethylphenyl)propanoic acid;

Cpd 143, 3-(4-{[5-(3,4-Difluorophenyl)-3-(trifluoromethyl)isothiazol-4-yl]methoxy}-2,3-dimethylphenyl)propanoic acid;

Cpd 144, 3-(4-{[3-(4-Chloro-3-methoxyphenyl)-5-(trifluoromethyl)isothiazol-4-yl]methoxy}-2,3-dimethylphenyl)propanoic acid;

Cpd 145, 3-(3,5-Difluoro-4-{[3-phenyl-5-(trifluoromethyl)isothiazol-4-yl]methoxy}phenyl)propanoic acid;

Cpd 146, 3-[4-({3-[4-(1-Fluoroethyl)phenyl]-5-(trifluoromethyl)isothiazol-4-yl}methoxy)-2,3-dimethylphenyl]propanoic acid;

Cpd 147, 3-(4-{[3-(3,3-Difluorocyclobutyl)-5-(trifluoromethyl)isothiazol-4-yl]methoxy}-3,5-difluorophenyl)propanoic acid;

Cpd 148, 3-(4-{[3-(4-Chloro-3-fluorophenyl)-5-(trifluoromethyl)isothiazol-4-yl]methoxy}-5-fluoro-2-methylphenyl)propanoic acid;

Cpd 149, 3-(4-{[5-Cyclopropyl-3-(4-ethylphenyl)isothiazol-4-yl]methoxy}-2,3-dimethylphenyl)propanoic acid;

Cpd 150, 3-(4-{[3-Ethyl-5-(2-fluoro-4-methylphenyl)isothiazol-4-yl]methoxy}-3,5-difluorophenyl)propanoic acid;

Cpd 151, 3-(3,5-Difluoro-4-{[3-(2-fluoro-4-methoxyphenyl)-5-(trifluoromethyl)isothiazol-4-yl]methoxy}phenyl)propanoic acid;

Cpd 152, 3-(4-{[3-(4-Chlorophenyl)-5-(trifluoromethyl)isothiazol-4-yl]methoxy}-2,3,5,6-tetrafluorophenyl)propanoic acid;

Cpd 153, 3-(4-{[3-(5-Chloro-3-fluoropyridin-2-yl)-5-(trifluoromethyl)isothiazol-4-yl]methoxy}-3,5-difluorophenyl)propanoic acid;

Cpd 154, 3-(4-{[3-Chloro-5-(4-fluorophenyl)isothiazol-4-yl]methoxy}-2,3-dimethylphenyl)propanoic acid;

Cpd 155, 3-(4-{[5-(2-Fluoro-4-methylphenyl)-3-(trifluoromethyl)isothiazol-4-yl]methoxy}-2,3-dimethylphenyl)propanoic acid;

Cpd 156, 3-(4-{[3-Chloro-5-(3-chlorophenyl)isothiazol-4-yl]methoxy}-2,3-dimethylphenyl)propanoic acid;

Cpd 157, 3-[4-{[3-(4-Ethylphenyl)-5-(trifluoromethyl)isothiazol-4-yl]methoxy}-2-fluoro-3-(trifluoromethyl)phenyl]propanoic acid;

Cpd 158, 3-(4-{[5-(4-Ethylphenyl)isothiazol-4-yl]methoxy}-2,3-dimethylphenyl)propanoic acid;

Cpd 159, 3-[4-{[5-(4-Chlorophenyl)-3-(trifluoromethyl)isothiazol-4-yl]methoxy}-2-(trifluoromethoxy)phenyl]propanoic acid;

Cpd 160, 3-(4-{[3-(4-Cyclopropylphenyl)-5-(trifluoromethyl)isothiazol-4-yl]methoxy}-3,5-difluorophenyl)propanoic acid;

Cpd 161, 3-(4-{[3-(4-Ethynylphenyl)isothiazol-4-yl]methoxy}-2,3-dimethylphenyl)propanoic acid;

Cpd 162, 3-(4-{[3-(4-Chlorophenyl)-5-(trifluoromethyl)isothiazol-4-yl]methoxy}-3-ethylphenyl)propanoic acid;

Cpd 163, (1R,2R)-2-(4-{[3-(4-Ethylphenyl)-5-(trifluoromethyl)isothiazol-4-yl]methoxy}-3,5-difluorophenyl)cyclopropanecarboxylic acid;

Cpd 164, 3-(4-{[3-(3,3-Difluorocyclopentyl)-5-(trifluoromethyl)isothiazol-4-yl]methoxy}-3,5-difluorophenyl)propanoic acid;

Cpd 165, 3-(4-{[3-(4-Chloro-3-fluorophenyl)-5-(trifluoromethyl)isothiazol-4-yl]methoxy}phenyl)-2-methylpropanoic acid;

Cpd 166, 3-(4-{[3-(4-Chlorophenyl)isothiazol-4-yl]methoxy}-2,3-dimethylphenyl)propanoic acid;

Cpd 167, 3-(4-{[3-(6-Methoxypyridin-3-yl)-5-(trifluoromethyl)isothiazol-4-yl]methoxy}-2,3-dimethylphenyl)propanoic acid;

Cpd 168, 3-(4-{[3-Chloro-5-(4-methoxyphenyl)isothiazol-4-yl]methoxy}-2,3-difluorophenyl)propan-1-ol;

Cpd 169, 3-(4-{[3-(4-Bromophenyl)isothiazol-4-yl]methoxy}-3,5-difluorophenyl)propanoic acid;

Cpd 170, 3-(4-{[3-(4-Bromophenyl)isothiazol-4-yl]methoxy}-2,3-dimethylphenyl)propanoic acid;

Cpd 171, 3-[4-{[3-(2-Fluoro-4-methylphenyl)-5-(trifluoromethyl)isothiazol-4-yl]methoxy}-2-(trifluoromethyl)phenyl]propanoic acid;

Cpd 172, 3-(4-{[3-(3-Fluoro-4-methoxyphenyl)-5-(trifluoromethyl)isothiazol-4-yl]methoxy}-2,3-dimethylphenyl)propanoic acid;

Cpd 173, 3-[4-{[3-(4-Chlorophenyl)-5-(trifluoromethyl)isothiazol-4-yl]methoxy}-2-(trifluoromethyl)phenyl]propanoic acid;

Cpd 174, 3-(4-{[3-(2,4-Difluorophenyl)-5-(trifluoromethyl)isothiazol-4-yl]methoxy}-3,5-difluorophenyl)propanoic acid;

Cpd 175, 3-[4-{[3-Chloro-5-(2-fluoro-4-methylphenyl)isothiazol-4-yl]methoxy}-2-(trifluoromethyl)phenyl]propanoic acid;

Cpd 176, (5-{[3-(4-Ethylphenyl)-5-(trifluoromethyl)isothiazol-4-yl]methoxy}-2,3-dihydro-1H-inden-1-yl)acetic acid;

Cpd 177, 3-(4-{[3-(4-Chloro-3-methoxyphenyl)-5-(trifluoromethyl)isothiazol-4-yl]methoxy}-3,5-difluorophenyl)propanoic acid;

Cpd 178, 3-[4-({3-[4-(1,1-Difluoroethyl)phenyl]-5-(trifluoromethyl)isothiazol-4-yl}methoxy)-2,3-dimethylphenyl]propanoic acid;

Cpd 179, 3-(4-{[3-(4-Chlorophenyl)isothiazol-4-yl]methoxy}-3,5-difluorophenyl)propanoic acid;

Cpd 180, 3-(4-{[3-(5-Chloro-3-fluoropyridin-2-yl)-5-(trifluoromethyl)isothiazol-4-yl]methoxy}-2,3-dimethylphenyl)propanoic acid;

Cpd 181, 3-(2,3-Dichloro-4-{[5-(4-chlorophenyl)-3-(trifluoromethyl)isothiazol-4-yl]methoxy}phenyl)propanoic acid;

Cpd 182, 3-(3,5-Difluoro-4-{[3-methoxy-5-(4-methoxyphenyl)isothiazol-4-yl]methoxy}phenyl)propanoic acid;

Cpd 183, 3-(4-{[3-Chloro-5-(4-ethylphenyl)isothiazol-4-yl]methoxy}-3,5-difluorophenyl)propan-1-ol;

Cpd 184, 3-(4-{[5-(2,4-Dimethylphenyl)-3-(trifluoromethyl)isothiazol-4-yl]methoxy}-2,3-dimethylphenyl)propanoic acid;

Cpd 185, (2E)-3-(4-{[3-Chloro-5-(4-chlorophenyl)isothiazol-4-yl]methoxy}-2,3-difluorophenyl)prop-2-enoic acid;

Cpd 186, 3-(4-{[3-Chloro-5-(4-methoxyphenyl)isothiazol-4-yl]methoxy}-2,3-dimethylphenyl)propanoic acid;

Cpd 187, 3-(4-{[3-(4-Bromophenyl)isothiazol-4-yl]methoxy}-2,3-difluorophenyl)propanoic acid;

Cpd 188, 3-(4-{[3-(4-Ethyl-2-fluorophenyl)-5-(trifluoromethyl)isothiazol-4-yl]methoxy}-3,5-difluorophenyl)-2-methylpropanoic acid;

Cpd 189, 3-(4-{[3-(4-Chlorophenyl)isothiazol-4-yl]methoxy}-2,3-difluorophenyl)propanoic acid;

Cpd 190, 3-(4-{[3-(4-Cyclopropylphenyl)-5-(trifluoromethyl)isothiazol-4-yl]methoxy}-2,3-dimethylphenyl)propanoic acid;

Cpd 191, 3-(3,5-Difluoro-4-{[5-(2-fluoro-4-methylphenyl)-3-(1-methylethyl)isothiazol-4-yl]methoxy}phenyl)propanoic acid;

Cpd 192, 3-(4-{[3-(4-Ethylphenyl)-5-(pentafluoroethyl)isothiazol-4-yl]methoxy}-2,3-dimethylphenyl)propanoic acid;

Cpd 193, 3-(4-{[3-Chloro-5-(2-methylphenyl)isothiazol-4-yl]methoxy}-3,5-difluorophenyl)propanoic acid;

Cpd 194, 3-(4-{[3-(4-Ethyl-3-fluorophenyl)-5-(trifluoromethyl)isothiazol-4-yl]methoxy}-3,5-difluorophenyl)propanoic acid;

Cpd 195, 3-(4-{[3-(4-Chlorophenyl)-5-(trifluoromethyl)isothiazol-4-yl]methoxy}phenyl)-2-methylpropanoic acid;

Cpd 196, 3-(4-{[3-(2,4-Difluorophenyl)-5-(trifluoromethyl)isothiazol-4-yl]methoxy}-3,5-difluorophenyl)-2-methylpropanoic acid;

Cpd 197, 3-(4-{[3-(2,6-Difluoro-4-methoxyphenyl)-5-(trifluoromethyl)isothiazol-4-yl]methoxy}-3,5-difluorophenyl)propanoic acid;

Cpd 198, 3-(4-{[3-tert-Butyl-5-(trifluoromethyl)isothiazol-4-yl]methoxy}-2,3-dimethylphenyl)propanoic acid;

Cpd 199, 3-(4-{[3-(3,3-Difluorocyclopentyl)-5-(trifluoromethyl)isothiazol-4-yl]methoxy}-2,3-dimethylphenyl)propanoic acid;

Cpd 200, 3-(4-{[5-(1,1-Difluoroethyl)-3-(4-ethylphenyl)isothiazol-4-yl]methoxy}-2,3-dimethylphenyl)propanoic acid;

Cpd 201, (2E)-3-(4-{[3-(4-Chlorophenyl)-5-(trifluoromethyl)isothiazol-4-yl]methoxy}-3,5-difluorophenyl)prop-2-enoic acid;

Cpd 202, 3-(4-{[3-(5-Chlorothiophen-2-yl)isothiazol-4-yl]methoxy}-3,5-difluorophenyl)propanoic acid;

Cpd 203, 3-[4-{[5-(2-Methylphenyl)-3-(trifluoromethyl)isothiazol-4-yl]methoxy}-2-(trifluoromethyl)phenyl]propanoic acid;

Cpd 204, 3-(4-{[3-(5-Chlorothiophen-2-yl)isothiazol-4-yl]methoxy}-2,3-dimethylphenyl)propanoic acid;

Cpd 205, (1R,2S)-2-(4-{[3-(4-chlorophenyl)-5-(trifluoromethyl)isothiazol-4-yl]methoxy}phenyl)cyclopropanecarboxylic acid;

Cpd 206, 3-(4-{[3-(5-Chloro-3-fluoropyridin-2-yl)-5-(trifluoromethyl)isothiazol-4-yl]methoxy}-5-fluoro-2-methylphenyl)propanoic acid;

Cpd 207, 3-(4-{[3-(4-Chloro-2,6-difluorophenyl)-5-(trifluoromethyl)isothiazol-4-yl]methoxy}-5-fluoro-2-methylphenyl)propanoic acid;

Cpd 208, 3-(2-Chloro-4-{[5-(4-chlorophenyl)-3-(trifluoromethyl)isothiazol-4-yl]methoxy}phenyl)propanoic acid;

Cpd 209, 3-(4-{[3-Chloro-5-(4-ethylphenyl)isothiazol-4-yl]methoxy}-2,3-dimethylphenyl)propan-1-ol;

Cpd 210, 3-[4-{[3-Chloro-5-(2-methylphenyl)isothiazol-4-yl]methoxy}-5-methyl-2-(trifluoromethyl)phenyl]propanoic acid;

Cpd 211, 3-(3,5-Difluoro-4-{[5-(2-fluoro-4-methylphenyl)-3-phenylisothiazol-4-yl]methoxy}phenyl)propanoic acid;

Cpd 212, 3-(4-{[3-(4-Ethyl-3-fluorophenyl)-5-(trifluoromethyl)isothiazol-4-yl]methoxy}-3,5-difluorophenyl)-2-methylpropanoic acid;

Cpd 213, 3-(4-{[3-(4-Chlorophenyl)-5-(trifluoromethyl)isothiazol-4-yl]methoxy}-3,5-difluorophenyl)prop-2-yn-1-ol;

Cpd 214, 3-(3,5-Difluoro-4-{[3-(tetrahydrofuran-3-yl)-5-(trifluoromethyl)isothiazol-4-yl]methoxy}phenyl)propanoic acid;

Cpd 215, 3-[4-{[3-Chloro-5-(2-methylphenyl)isothiazol-4-yl]methoxy}-5-ethyl-2-(trifluoromethyl)phenyl]propanoic acid;

Cpd 216, 3-(4-{[3-(4-Ethylphenyl)-5-(trifluoromethyl)isothiazol-4-yl]methoxy}-3,5-difluorophenyl)-2-methylpropan-1-ol;

Cpd 217, 3-(4-{[5-Ethyl-3-(4-ethylphenyl)isothiazol-4-yl]methoxy}-2,3-dimethylphenyl)propanoic acid;

Cpd 218, 3-(4-{[3-Chloro-5-(4-propylphenyl)isothiazol-4-yl]methoxy}-2,3-dimethylphenyl)propanoic acid;

Cpd 219, [(1R,2R)-2-(4-{[3-(4-Ethylphenyl)-5-(trifluoromethyl)isothiazol-4-yl]methoxy}-3,5-difluorophenyl)cyclopropyl]methanol;

Cpd 220, 2-(6-{[3-(4-Ethylphenyl)-5-(trifluoromethyl)isothiazol-4-yl]methoxy}-2,3-dihydro-1-benzofuran-3-yl)ethanol;

Cpd 221, 3-[4-{[5-(2-Fluoro-4-methylphenyl)-3-(trifluoromethyl)isothiazol-4-yl]methoxy}-2-(trifluoromethyl)phenyl]propanoic acid;

Cpd 222, 3-(4-{[3-Chloro-5-(2-methylphenyl)isothiazol-4-yl]methoxy}-2-methoxyphenyl)propanoic acid;

Cpd 223, 3-(4-{[3-(4-Chlorophenyl)-5-(trifluoromethyl)isothiazol-4-yl]methoxy}-3,5-difluoro-2-methylphenyl)propan-1-ol;

Cpd 224, 3-[2,3-Dimethyl-4-({5-(trifluoromethyl)-3-[4-(trifluoromethyl)phenyl]isothiazol-4-yl}methoxy)phenyl]propanoic acid;

Cpd 225, 3-(4-{[3-(4-Ethyl-2-fluorophenyl)-5-(trifluoromethyl)isothiazol-4-yl]methoxy}-2,3-dimethylphenyl)propanoic acid;

Cpd 226, 3-(4-{[3-(5-Chlorothiophen-2-yl)isothiazol-4-yl]methoxy}-2,3-difluorophenyl)propanoic acid;

Cpd 227, 3-(4-{[3-Chloro-5-(2-methylphenyl)isothiazol-4-yl]methoxy}-2-ethylphenyl)propanoic acid;

Cpd 228, 3-(4-{[3-(4-Ethylphenyl)-5-methoxyisothiazol-4-yl]methoxy}-2,3-dimethylphenyl)propanoic acid;

Cpd 229, 3-(4-{[3-(2,6-Difluoro-4-methoxyphenyl)-5-(trifluoromethyl)isothiazol-4-yl]methoxy}-2,3-dimethylphenyl)propanoic acid;

Cpd 230, 3-(4-{[3-(4-Chlorophenyl)-5-(trifluoromethyl)isothiazol-4-yl]methoxy}-3,5-difluorophenyl)-2-methylpropan-1-ol;

Cpd 231, 3-(4-{[3-(4-Chlorophenyl)isothiazol-4-yl]methoxy}-3,5-difluoro-2-methylphenyl)propanoic acid;

Cpd 232, 3-[4-{[5-(2,4-Dimethylphenyl)-3-(trifluoromethyl)isothiazol-4-yl]methoxy}-2-(trifluoromethyl)phenyl]propanoic acid;

Cpd 233, 3-(4-{[3-(4-Ethylphenyl)-5-phenylisothiazol-4-yl]methoxy}-2,3-dimethylphenyl)propanoic acid;

Cpd 234, 3-(3,5-Difluoro-4-{[3-(4-methoxyphenyl)-5-(trifluoromethyl)isothiazol-4-yl]methoxy}phenyl)propan-1-ol;

Cpd 235, 3-(4-{[3-(4-Chlorophenyl)-5-(trifluoromethyl)isothiazol-4-yl]methoxy}-3-methylphenyl)propanoic acid;

Cpd 236, 3-(4-{[3-Chloro-5-(2,4-dimethylphenyl)isothiazol-4-yl]methoxy}-3,5-difluorophenyl)propanoic acid;

Cpd 237, 3-(3,5-Difluoro-4-{[3-(3-fluoro-4-methoxyphenyl)-5-(trifluoromethyl)isothiazol-4-yl]methoxy}phenyl)propanoic acid;

Cpd 238, 3-(4-{[3-(4-Ethylphenyl)-5-(trifluoromethyl)isothiazol-4-yl]methoxy}-2,3,5-trifluorophenyl)propan-1-ol;

Cpd 239, 3-(4-{[3-(4-Ethylphenyl)-5-(trifluoromethyl)isothiazol-4-yl]methoxy}-3,5-dimethylphenyl)propanoic acid;

Cpd 240, (2E)-3-(4-{[3-(4-Chlorophenyl)-5-(trifluoromethyl)isothiazol-4-yl]methoxy}-2,3-difluorophenyl)prop-2-enoic acid;

Cpd 241, 3-(3,5-Dibromo-4-{[3-(4-chlorophenyl)-5-(trifluoromethyl)isothiazol-4-yl]methoxy}phenyl)propanoic acid;

Cpd 242, 3-(4-{[3-Chloro-5-(4-methoxyphenyl)isothiazol-4-yl]methoxy}-2,3-difluorophenyl)propanoic acid;

Cpd 243, 3-(4-{[3-Chloro-5-(4-methoxyphenyl)isothiazol-4-yl]methoxy}-3,5-difluorophenyl)propan-1-ol;

Cpd 244, 3-(4-{[3-Chloro-5-(4-methoxyphenyl)isothiazol-4-yl]methoxy}-2,3-dimethylphenyl)propan-1-ol;

Cpd 245, 3-(4-{[3-Chloro-5-(4-methoxyphenyl)isothiazol-4-yl]methoxy}-2,3-difluorophenyl)propanoic acid;

Cpd 246, 3-[4-{[3-Chloro-5-(2-methylphenyl)isothiazol-4-yl]methoxy}-5-fluoro-2-(trifluoromethyl)phenyl]propanoic acid;

Cpd 247, 3-(4-{[3-Chloro-5-(4-methoxyphenyl)isothiazol-4-yl]methoxy}-2,3-dimethylphenyl)propan-1-ol;

Cpd 248, 2-(4-{[3-(4-Chlorophenyl)-5-(trifluoromethyl)isothiazol-4-yl]methoxy}-3,5-difluorophenyl)ethanol;

Cpd 249, 3-(4-{[3-Chloro-5-(4-methoxyphenyl)isothiazol-4-yl]methoxy}-3,5-difluorophenyl)propan-1-ol;

Cpd 250, 3-(4-{[3-(4-Ethylphenyl)-5-(trifluoromethyl)thiophen-2-yl]methoxy}-2,3-dimethylphenyl)propanoic acid;

Cpd 251, 3-(3-{[3-(4-Ethylphenyl)-5-(trifluoromethyl)isothiazol-4-yl]methoxy}-2,4-difluorophenyl)-2-methylpropan-1-ol;

or a pharmaceutically acceptable salt form thereof.

Embodiments of the present invention includes a compound of Formula (II)

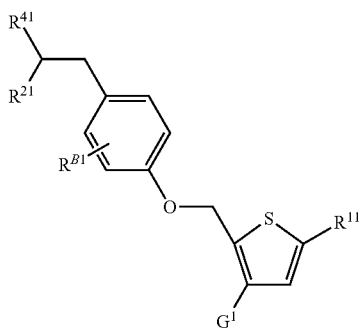

Formula (II)

wherein $R^{B1}$, $R^{21}$, and $R^{41}$ are as defined herein, and $R^{11}$ is selected from the group consisting of hydrogen, fluoro, and chloro;

$G^1$ is chloro or 4-($R^{A1}$)phenyl; wherein $R^{A1}$ is selected from the group consisting of $C_{1-2}$alkyl and chloro;

and any combination of embodiments as defined hereinabove, provided that it is understood that combinations in which different embodiments of the same substituent would be combined are excluded;

or an enantiomer, diastereomer, or pharmaceutically acceptable salt form thereof.

An embodiment of the present invention includes a compound of Formula (II)

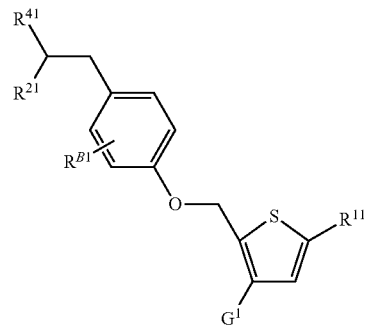

Formula (II)

wherein $R^{11}$ is selected from the group consisting of hydrogen, fluoro, and chloro;

$R^{B1}$ is one to four substituents independently selected from the group consisting of fluoro and methyl;

$R^{21}$ is hydroxymethyl or carboxy;

$R^{41}$ is hydrogen or methyl;

$G^1$ is chloro or 4-($R^{A1}$)phenyl, wherein $R^{A1}$ is selected from the group consisting of $C_{1-2}$alkyl and chloro;

or an enantiomer, diastereomer, or pharmaceutically acceptable salt form thereof.

In a further embodiment of the present invention includes compounds of Formula (II)

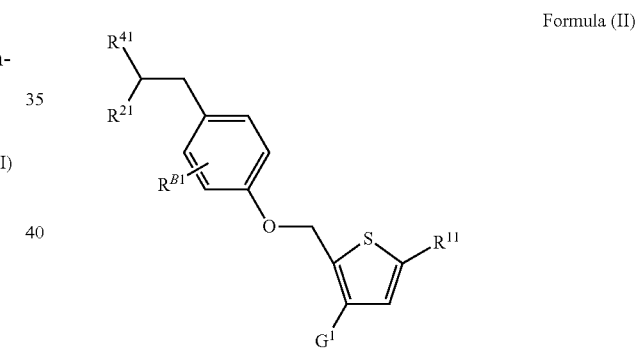

Formula (II)

selected from the group consisting of

Cpd 1, 3-(4-{[3-(4-Ethylphenyl)-5-fluorothiophen-2-yl]methoxy}-2,3-dimethylphenyl)propanoic acid;

Cpd 2, 3-(4-{[5-Chloro-3-(4-chlorophenyl)thiophen-2-yl]methoxy}-3,5-difluorophenyl)propanoic acid;

Cpd 3, 3-(4-{[3-(4-Chlorophenyl)-5-fluorothiophen-2-yl]methoxy}-2,3-dimethylphenyl)propanoic acid;

Cpd 4, 3-(4-{[3-(4-Ethylphenyl)thiophen-2-yl]methoxy}-2,3-difluorophenyl)propan-1-ol;

Cpd 5, 3-(4-{[5-Chloro-3-(4-ethylphenyl)thiophen-2-yl]methoxy}-2,3-dimethylphenyl)propanoic acid;

Cpd 6, 3-(4-{[5-Chloro-3-(4-chlorophenyl)thiophen-2-yl]methoxy}-2,3-dimethylphenyl)propanoic acid;

Cpd 7, 3-(4-{[3-(4-Ethylphenyl)-5-fluorothiophen-2-yl]methoxy}-3,5-difluorophenyl)propanoic acid;

Cpd 8, 3-(4-{[5-Chloro-3-(4-ethylphenyl)thiophen-2-yl]methoxy}-3,5-difluorophenyl)propanoic acid;

Cpd 9, 3-(4-{[5-Chloro-3-(4-ethylphenyl)thiophen-2-yl]methoxy}-3,5-difluorophenyl)propan-1-ol;

Cpd 10, 3-(4-{[3-(4-Chlorophenyl)-5-fluorothiophen-2-yl]methoxy}-3,5-difluorophenyl)propanoic acid;

Cpd 11, 3-(4-{[5-Chloro-3-(4-ethylphenyl)thiophen-2-yl]methoxy}-2,3-difluorophenyl)propanoic acid;
Cpd 12, 3-(4-{[3-(4-Ethylphenyl)-5-fluorothiophen-2-yl]methoxy}-2,3-difluorophenyl)propanoic acid;
Cpd 13, 3-(4-{[3-(4-Ethylphenyl)-5-methylthiophen-2-yl]methoxy}-2,3-dimethylphenyl)propanoic acid;
Cpd 14, 3-(4-{[5-Chloro-3-(4-ethylphenyl)thiophen-2-yl]methoxy}-2,3-difluorophenyl)propan-1-ol;
Cpd 15, 3-(4-{[5-Chloro-3-(4-chlorophenyl)thiophen-2-yl]methoxy}-2,3-dimethylphenyl)propan-1-ol;
Cpd 16, 3-(3,5-Difluoro-4-{[3-(1-methylethoxy)-5-(trifluoromethyl)thiophen-2-yl]methoxy}phenyl)propanoic acid;
Cpd 17, 3-(4-{[3-(4-Ethylphenyl)-5-fluorothiophen-2-yl]methoxy}-2,3-difluorophenyl)propan-1-ol;
Cpd 18, 3-(4-{[3-(4-Chlorophenyl)-5-fluorothiophen-2-yl]methoxy}-3,5-difluorophenyl)propan-1-ol;
Cpd 19, 3-(4-{[5-Chloro-3-(4-chlorophenyl)thiophen-2-yl]methoxy}-3,5-difluorophenyl)propan-1-ol;
Cpd 20, 3-(4-{[3-(4-Ethylphenyl)thiophen-2-yl]methoxy}-3,5-difluorophenyl)propan-1-ol;
Cpd 21, 3-(4-{[3-(4-Ethylphenyl)-5-(trifluoromethyl)thiophen-2-yl]methoxy}-2,3-difluorophenyl)propanoic acid;
Cpd 22, 3-(4-{[3-(4-Ethylphenyl)-5-(trifluoromethyl)thiophen-2-yl]methoxy}-3,5-difluorophenyl)propanoic acid;
Cpd 23, 3-(4-{[3-(4-Ethylphenyl)-5-methylthiophen-2-yl]methoxy}-2,3-difluorophenyl)propan-1-ol;
Cpd 24, 3-(4-{[3-(4-Ethylphenyl)-5-methylthiophen-2-yl]methoxy}-3,5-difluorophenyl)propan-1-ol;
Cpd 25, 3-(4-{[3-(4-Ethylphenyl)-5-methylthiophen-2-yl]methoxy}-3,5-difluorophenyl)propanoic acid;
Cpd 26, 3-(4-{[3-(4-Ethylphenyl)-5-methylthiophen-2-yl]methoxy}-2,3-difluorophenyl)propanoic acid;
Cpd 27, 3-(4-{[3-(4-Ethylphenyl)-5-fluorothiophen-2-yl]methoxy}-3,5-difluorophenyl)propan-1-ol;
Cpd 28, 3-(4-{[5-Chloro-3-(4-chlorophenyl)thiophen-2-yl]methoxy}-2,3-difluorophenyl)propanoic acid;
Cpd 29, 3-(4-{[5-Chloro-3-(4-chlorophenyl)thiophen-2-yl]methoxy}-2,3-difluorophenyl)propan-1-ol;
Cpd 30, 3-(4-{[3-(4-Chlorophenyl)-5-fluorothiophen-2-yl]methoxy}-2,3-dimethylphenyl)propan-1-ol;
or a pharmaceutically acceptable salt form thereof.

In a further embodiment, the present invention is directed to a compound of Formula (I) or Formula (II), wherein the compound of Formula (I) or Formula (II) has a measured $EC_{50}$ according to the β-arrestin A procedure taught in Biological Example 1, (which follows herein) of less than about 1.0 µM, preferably less than about 0.500 µM, more preferably less than about 0.200 µM, more preferably less than about 0.100 µM, more preferably less than about 0.050 µM.

In an embodiment, the present invention is directed to a compound of Formula (I) or Formula (II), wherein the compound of Formula (I) or Formula (II) has a measured $EC_{50}$ according to the Calcium A procedure taught in Biological Example 2, (which follows herein) of less than about 1.0 µM, preferably less than about 0.500 µM, more preferably less than about 0.200 µM, more preferably less than about 0.100 µM, more preferably less than about 0.050 µM.

For use in medicine, salts of compounds of Formula (I) or Formula (II) refer to non-toxic "pharmaceutically acceptable salts." Other salts may, however, be useful in the preparation of compounds of Formula (I) or Formula (II) or of their pharmaceutically acceptable salt forms thereof. Suitable pharmaceutically acceptable salts of compounds of Formula (I) or Formula (II) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) or Formula (II) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I) or Formula (II). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I) or Formula (II).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) or Formula (II) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+) - \text{enantiomer} = \frac{(\text{mass}(+) - \text{enantiomer})}{(\text{mass}(+) - \text{enantiomer}) + (\text{mass}(-) - \text{enantiomer})} \times 100.$$

Another embodiment of the present invention is a composition, including a pharmaceutical composition, comprising, consisting of, and consisting essentially of the (−)-enantiomer of a compound of Formula (I) or Formula (II) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-) - \text{enantiomer} = \frac{(\text{mass}(-) - \text{enantiomer})}{(\text{mass}(+) - \text{enantiomer}) + (\text{mass}(-) - \text{enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) or Formula (II) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) or Formula (II) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) or Formula (II) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) or Formula (II) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or Formula (II) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) or Formula (II) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I) or Formula (II).

Advantageously, a compound of Formula (I) or Formula (II) may be administered in a single daily dose, or the total daily dosage may be administered in divided doses of two, three and four times daily.

Optimal dosages of a compound of Formula (I) or Formula (II) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) or Formula (II) may be administered in any of the foregoing compositions and dosage regimens or by means of those compositions and dosage regimens established in the art whenever use of a compound of Formula (I) or Formula (II) is required for a subject in need thereof.

As GPR120 agonists, the compounds of Formula (I) and Formula (II) are useful in methods for treating or preventing a disease, a syndrome, a condition or a disorder in a subject, including an animal, a mammal and a human in which the disease, the syndrome, the condition or the disorder is affected by the modulation, including agonism, of the GPR120 receptor. Such methods comprise, consist of and/or consist essentially of administering to a subject, including an animal, a mammal, and a human, in need of such treatment or prevention, a therapeutically effective amount of a compound, salt or solvate of Formula (I) or Formula (II).

In another embodiment, the present invention is directed to a compound of Formula (I) or Formula (II) for use in the treatment of a disorder affected by the agonism of GPR120 receptor selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus, dyslipidemia or metabolic syndrome X; more preferably, Type II diabetes mellitus or dyslipidemia.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
ADDP azodicarboxylic dipiperidide
aq. aqueous
Bn or Bzl benzyl
BINAP 2,2'-bis(diphenylphosphino)-1,1'-binaphthyl
Boc tert-butyloxycarbonyl
conc. concentrated
dba dibenzylideneacetone
DBU 1,8-diazabicyclo[5.4.0]undec-7-ene
DCC N,N'-dicyclohexyl-carbodiimide
DCE 1,2-dichloroethane
DCM dichloromethane
DEAD diethyl azodicarboxylate
DIBAL diisobutylaluminum hydride
DIPEA or DIEA diisopropyl-ethyl amine
DMA dimethylaniline
DMAP 4-dimethylaminopyridine
DMF N,N-dimethylformamide
DMSO dimethylsulfoxide
DPPA diphenylphosphoryl azide dppf 1,1'-bis(diphenylphosphino)ferrocene
EA ethyl acetate
EDCl 1-ethyl-3-(3-dimethylaminopropyl) carbodiimide
ESI electrospray ionization
EtOAc or EA ethyl acetate
EtOH ethanol
GCMS gas chromatography-mass spectrometry
h or hr(s) hour or hours
HEK human embryonic kidney
HPLC high performance liquid chromatography
LAH lithium aluminum hydride
LDA lithium diisopropylamide
LHMDS lithium bis(trimethylsilyl)amide
MEK methyl ethyl ketone
MeOH methanol
MHz megahertz
min minute or minutes
MS mass spectrometry
Ms methanesulfonyl
NBS N-bromosuccinimide
NMM N-methylmorpholine
NMP N-methylpyrrolidone
NMR nuclear magnetic resonance
PCC pyridinium chlorochromate
PE petroleum ether
RP reverse-phase
rt or RT room temperature
$R_t$ retention time
Sec second or seconds
SEM-Cl 2-(trimethylsilyl)ethoxymethyl chloride
TBAF tetrabutylammonium fluoride
TBDMS t-butyldimethylsilyl
TBP tributyl phosphate
TEA or $Et_3N$ triethylamine
TFA trifluoroacetic acid
THF tetrahydrofuran
TIPS triisopropylsilyl
TLC thin layer chromatography
TMS tetramethylsilane
Ts 4-toluenesulfonyl General Schemes Compounds of formula (Ia) may be prepared according to the process as described in the Scheme 1, below.

Scheme 1

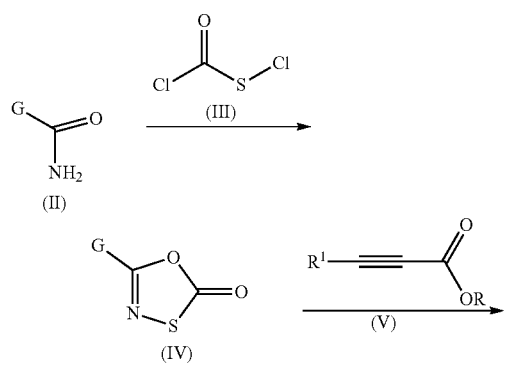

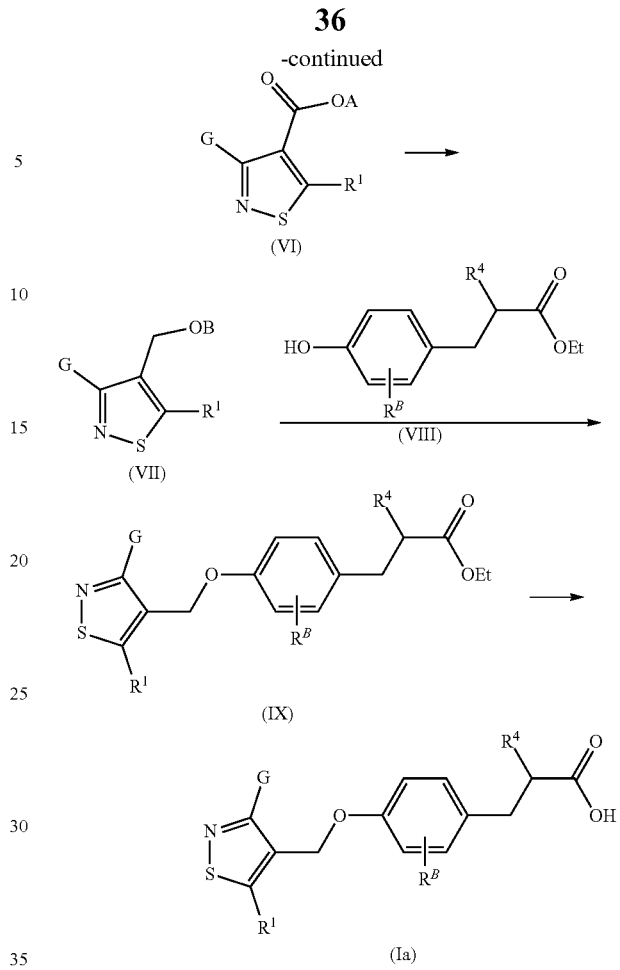

Accordingly, a suitably substituted amide compound of formula (II), a commercially available compound or compound prepared by the corresponding acid through known methods, is reacted with a commercially available reagent of formula (III), in an organic solvent such as toluene, xylene, chlorobenzene and the like, at a temperature in the range from 100° C. to about 160° C., to yield the corresponding compound of formula (IV).

The compound of formula (IV) is reacted with a suitably substituted compound of formula (V), a commercially available compound or compound prepared by known methods, in an organic solvent such as toluene, chlorobenzene, 1,3-dichlorobenzene, and the like, at a temperature in the range from 150° C. to about 200° C., to yield the corresponding compound of formula (VI).

The compound of formula (VI) is reacted with a commercially available reducing agent such as LAH, DIBAL, borane/THF complex and the like, in an organic solvent such as THF, ether, dioxane and the like, at a temperature in the range from about −20° C. to room temperature, to yield the corresponding compound of formula (VII) wherein B is hydrogen.

The compound of formula (VII) wherein B is hydrogen is reacted with a suitably substituted compound of formula (VIII), a compound prepared by known methods, with a commercially available coupling agents such as DEAD/$Ph_3P$, ADDP/TBP and the like, in an organic solvent such as toluene, THF, dioxane and the like, in the range from 0° C. to about 80° C., to yield the corresponding compound of formula (IX).

Alternatively, the compound of formula (VII), wherein B is hydrogen, is reacted with a commercially available reagent such as TsCl, MsCl, CCl$_4$/Ph$_3$P, NBS/Ph$_3$P and the like, either in the presence or in the absence of an organic base such as TEA, DIPEA and the like, in an organic solvent such as THF, DCM, Ether and the like, at a temperature in the range from 0® C. to room temperature, to yield the corresponding compound of formula (VII), wherein —OB is a suitably leaving group such as OTs, OMs or Cl, Br, and the like, which is then reacted with a suitably substituted compound of formula (VIII), a compound prepared by known methods, in the presence of an inorganic base such as Cs$_2$CO$_3$, K$_2$CO$_3$, NaH and the like, in an organic solvent such as THF, acetone, DMF and the like, at a temperature in the range from room temperature to 100° C., to yield the corresponding compound of formula (IX).

The compound of formula (IX) is reacted with a commercially available inorganic base such as LiOH, NaOH, KOH and the like in a mixed solvent of THF, MeOH and water and the like, at a temperature in the range from 0° C. to about 50° C., to yield the corresponding compound of formula (Ia).

Compounds of formula (Ib) may be prepared according to the process as described in the Scheme 2, below.

Scheme 2

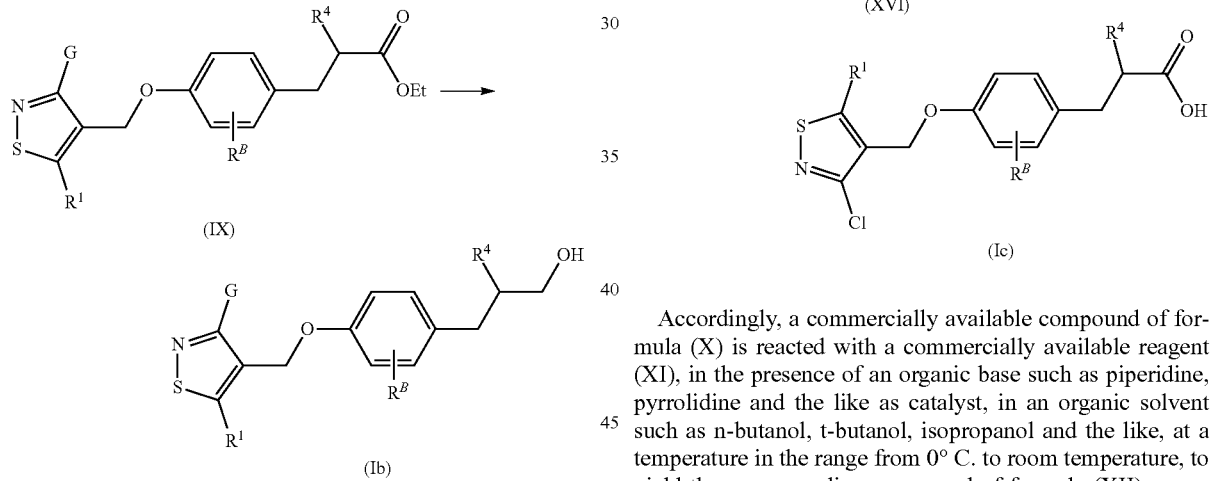

Accordingly, a suitably substituted compound of formula (IX) is reacted with a commercially available reducing agent such as LAH, DIBAL, borane/THF complex and the like, in an organic solvent such as THF, ether, dioxane and the like, at a temperature in the range from about −20° C. to room temperature, to yield the corresponding compound of formula (Ib).

Compounds of formula (Ic) may be prepared according to the process as described in the Scheme 3, below.

Scheme 3

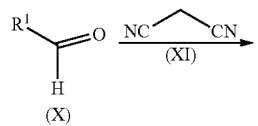

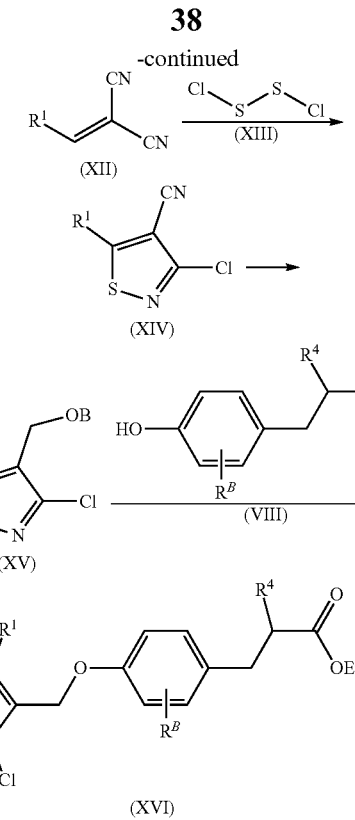

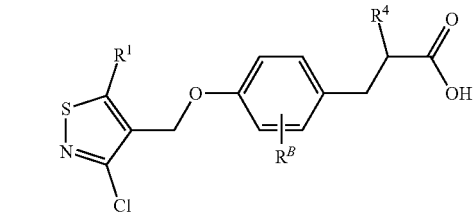

Accordingly, a commercially available compound of formula (X) is reacted with a commercially available reagent (XI), in the presence of an organic base such as piperidine, pyrrolidine and the like as catalyst, in an organic solvent such as n-butanol, t-butanol, isopropanol and the like, at a temperature in the range from 0° C. to room temperature, to yield the corresponding compound of formula (XII).

The suitably substituted compound of formula (XII) is reacted with the commercially available reagent (XIII) in an organic solvent such as pyridine, xylene and the like, at a temperature in the range from 120° C. to 180° C., to yield the corresponding compound of formula (XIV).

The suitably substituted compound of formula (XIV) is reacted with a strong acid such as sulfuric acid and the like, in aqueous solution at a temperature in the range from 100° C. to 120° C., to yield the corresponding amide intermediate, which is then reacted with an inorganic reducing reagent such as borane, LAH, DIBAL and the like, in an organic solvent such as THF, dioxane, ether and the like, at a temperature in the range from −20° C. to room temperature, to yield the corresponding compound of formula (XV) wherein B is hydrogen.

The compound of formula (XV) wherein B is hydrogen is reacted with a suitably substituted compound of formula (VIII), a compound prepared by known methods, with a commercially available coupling agents such as DEAD/

Ph₃P, ADDP/TBP and the like, in an organic solvent such as toluene, THF, dioxane and the like, at a temperature in the range from 0° C. to about 80° C., to yield the corresponding compound of formula (XVI).

Alternatively, the compound of formula (XV), wherein B is hydrogen, is reacted with a commercially available reagent such as TsCl, MsCl, CCl₄/Ph₃P, NBS/Ph₃P and the like, either in the presence or in the absence of an organic base such as TEA, DIPEA and the like, in an organic solvent such as THF, DCM, Ether and the like, at a temperature in the range from 0° C. to room temperature, to yield the corresponding compound of formula (XV), wherein —OB is a suitably leaving group such as OTs, OMs or Cl, Br, and the like, which is then reacted with a suitably substituted compound of formula (VIII), a compound prepared by known methods, in the presence of an inorganic base such as Cs₂CO₃, K₂CO₃, NaH and the like, in an organic solvent such as THF, acetone, DMF and the like, at a temperature in the range from room temperature to 100° C., to yield the corresponding compound of formula (XVI).

The compound of formula (XVI) is reacted with a commercially available inorganic base such as LiOH, NaOH, KOH and the like in a mixed solvent of THF, MeOH and water and the like, at a temperature in the range from 0° C. to about 50° C., to yield the corresponding compound of formula (Ic).

Compounds of formula (Id) may be prepared according to the process as described in the Scheme 4, below.

Scheme 4

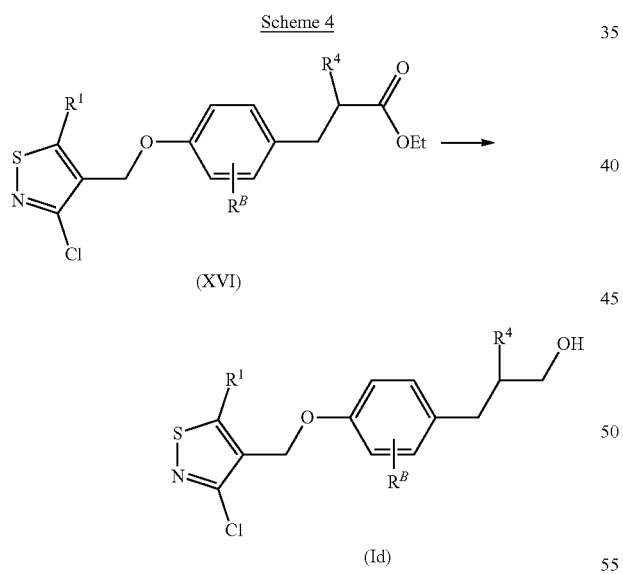

(XVI)

(Id)

Accordingly, a suitably substituted compound of formula (XVI) is reacted with a commercially available reducing agent such as LAH, DIBAL, borane/THF complex and the like, in an organic solvent such as THF, ether, dioxane and the like, at a temperature in the range from about −20° C. to room temperature, to yield the corresponding compound of formula (Id).

Compounds of formula (Ie) may alternatively be prepared according to the process outlined in Scheme 5, below.

Scheme 5

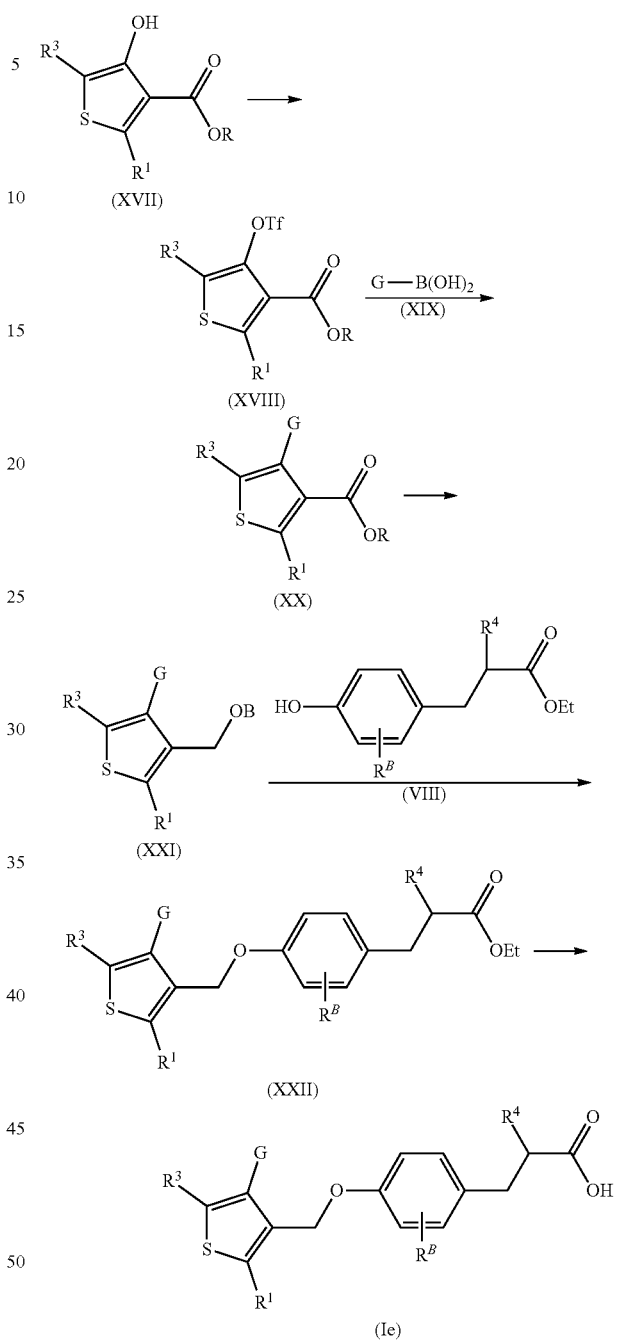

(XVII)

(XVIII)

(XX)

(XXI)

(XXII)

(Ie)

Accordingly, a commercially available or a compound prepared by known methods of formula (XVII) is reacted with a commercially available trifluoromethanesulfonic anhydride, in the presence of an organic base such as pyridine, TEA, DIPEA and the like, in an organic solvent such as DCM, 1,2-dichloroethane, THF and the like, at a temperature in the range from 0° C. to room temperature, to yield the corresponding compound of formula (XVIII).

The suitably substituted compound of formula (XVIII) is reacted with a suitably substituted compound of formula (XIX), a commercially available compound or compound prepared by known methods, in the presence of an inorganic base such as Na₂CO₃, K₂CO₃, K₃PO₄, and the like, in the presence of a suitably selected an Pd containing reagent such Pd(OAc)$_2$, Pd(Ph$_3$P)$_4$, Pd(Ph$_3$P)$_2$Cl$_2$, and the like, in the presence of a suitably selected ligand such as Ph$_3$P, BINAP, dppf, and the like, in a mixture of a suitably selected organic solvent such as toluene, ethanol, 1,4-dioxane, and the like, and water, to yield the corresponding compound of formula (XX).

The suitably substituted compound of formula (XX) is reacted an inorganic reducing reagent such as borane, LAH, DIBAL and the like, in an organic solvent such as THF, dioxane, ether and the like, at a temperature in the range from −20° C. to room temperature, to yield the corresponding compound of formula (XXI) wherein B is hydrogen.

The compound of formula (XXI) wherein B is hydrogen is reacted with a suitably substituted compound of formula (VIII), a compound prepared by known methods, with a commercially available coupling agents such as DEAD/Ph$_3$P, ADDP/TBP and the like, in an organic solvent such as toluene, THF, dioxane and the like, at a temperature in the range from 0° C. to about 80° C., to yield the corresponding compound of formula (XXII).

Alternatively, the compound of formula (XXI), wherein B is hydrogen, is reacted with a commercially available reagent such as TsCl, MsCl, CCl$_4$/Ph$_3$P, NBS/Ph$_3$P and the like, either in the presence or in the absence of an organic base such as TEA, DIPEA and the like, in an organic solvent such as THF, DCM, Ether and the like, at a temperature in the range from 0° C. to room temperature, to yield the corresponding compound of formula (XXI), wherein OB is a suitably leaving group such as OTs, OMs or Cl, Br, and the like, which is then reacted with a suitably substituted compound of formula (VIII), a compound prepared by known methods, in the presence of an inorganic base such as Cs$_2$CO$_3$, K$_2$CO$_3$, NaH and the like, in an organic solvent such as THF, acetone, DMF and the like, at a temperature in the range from room temperature to 100° C., to yield the corresponding compound of formula (XXII).

The compound of formula (XXII) is reacted with a commercially available inorganic base such as LiOH, NaOH, KOH and the like in a mixed solvent of THF, MeOH and water and the like, at a temperature in the range from 0° C. to about 50° C., to yield the corresponding compound of formula (Ie).

Compounds of formula (If) may be prepared according to the process as described in the Scheme 6, below.

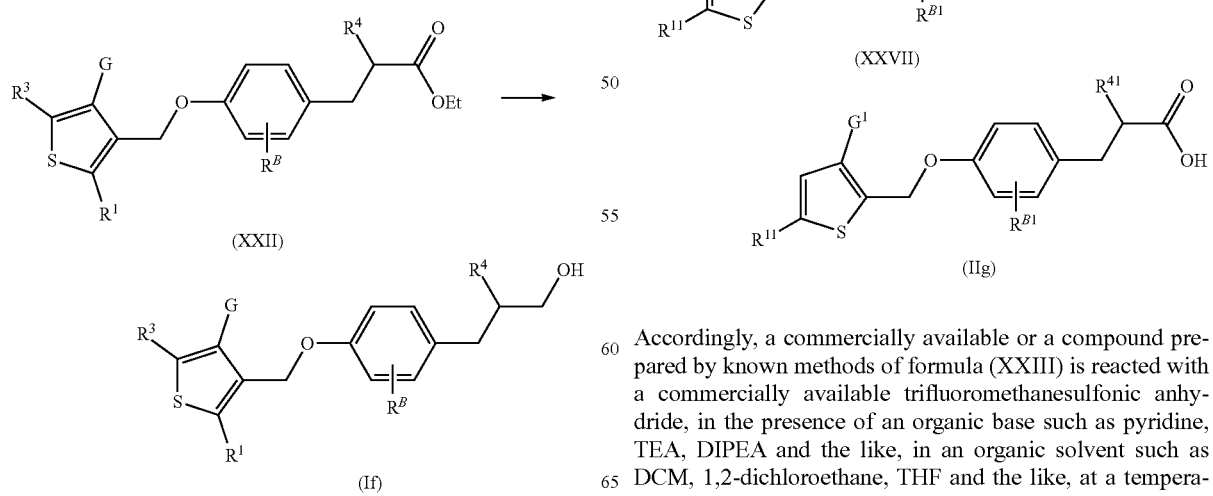

Accordingly, a suitably substituted compound of formula (XXII) is reacted with a commercially available reducing agent such as LAH, DIBAL, borane/THF complex and the like, in an organic solvent such as THF, ether, dioxane and the like, at a temperature in the range from about −20° C. to room temperature, to yield the corresponding compound of formula (If).

Compounds of formula (IIg) may be prepared according to the process as described in the Scheme 7, below.

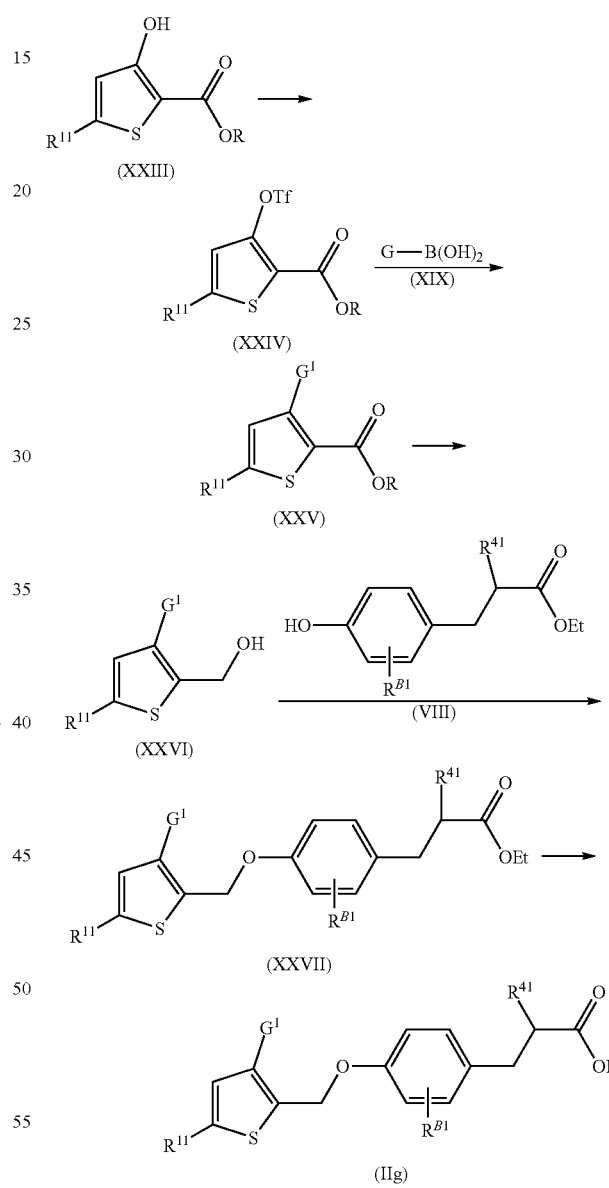

Accordingly, a commercially available or a compound prepared by known methods of formula (XXIII) is reacted with a commercially available trifluoromethanesulfonic anhydride, in the presence of an organic base such as pyridine, TEA, DIPEA and the like, in an organic solvent such as DCM, 1,2-dichloroethane, THF and the like, at a temperature in the range from 0° C. to room temperature, to yield the corresponding compound of formula (XXIV).

The suitably substituted compound of formula (XXIV) is reacted with a suitably substituted compound of formula (XIX), a commercially available compound or compound prepared by known methods, in the presence of an inorganic base such as Na$_2$CO$_3$, K$_2$CO$_3$, K$_3$PO$_4$, and the like, in the presence of a suitably selected an Pd containing reagent such Pd(OAc)$_2$, Pd(Ph$_3$P)$_4$, Pd(Ph$_3$P)$_2$Cl$_2$, and the like, in the presence of a suitably selected ligand such as Ph$_3$P, BINAP, dppf, and the like, in a mixture of a suitably selected organic solvent such as toluene, ethanol, 1,4-dioxane, and the like, and water, to yield the corresponding compound of formula (XXV).

The suitably substituted compound of formula (XXV) is reacted an inorganic reducing reagent such as borane, LAH, DIBAL and the like, in an organic solvent such as THF, dioxane, ether and the like, at a temperature in the range from –20° C. to room temperature, to yield the corresponding compound of formula (XXVI) wherein B is hydrogen.

The compound of formula (XXVI) wherein B is hydrogen is reacted with a suitably substituted compound of formula (VIII), a compound prepared by known methods, with a commercially available coupling agents such as DEAD/Ph$_3$P, ADDP/TBP and the like, in an organic solvent such as toluene, THF, dioxane and the like, at a temperature in the range from 0° C. to about 80° C., to yield the corresponding compound of formula (XXVII).

Alternatively, the compound of formula (XXVI), wherein B is hydrogen, is reacted with a commercially available reagent such as TsCl, MsCl, CCl$_4$/Ph$_3$P, NBS/Ph$_3$P and the like, either in the presence or in the absence of an organic base such as TEA, DIPEA and the like, in an organic solvent such as THF, DCM, Ether and the like, at a temperature in the range from 0° C. to room temperature, to yield the corresponding compound of formula (XXVI), wherein —OB is a suitably leaving group such as OTs, OMs or Cl, Br, and the like, which is then reacted with a suitably substituted compound of formula (VIII), a compound prepared by known methods, in the presence of an inorganic base such as Cs$_2$CO$_3$, K$_2$CO$_3$, NaH and the like, in an organic solvent such as THF, acetone, DMF and the like, at a temperature in the range from room temperature to 100° C., to yield the corresponding compound of formula (XXVII).

The compound of formula (XXVII) is reacted with a commercially available inorganic base such as LiOH, NaOH, KOH and the like in a mixed solvent of THF, MeOH and water and the like, at a temperature in the range from 0° C. to about 50° C., to yield the corresponding compound of formula (IIg).

Compounds of formula (Ih) may be prepared according to the process as described in the Scheme 8, below.

Scheme 8

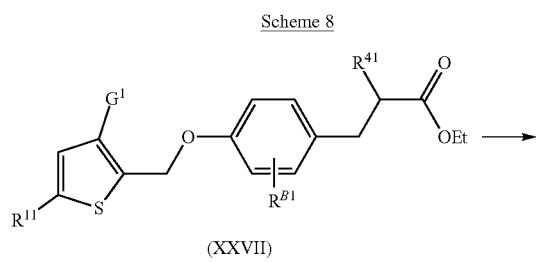

(XXVII)

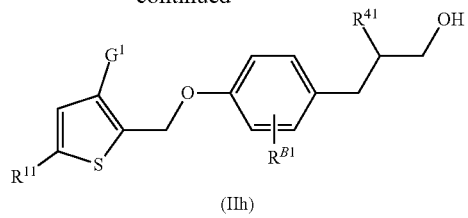

(IIh)

Accordingly, a suitably substituted compound of formula (XXVII) is reacted with a commercially available reducing agent such as LAH, DIBAL, borane/THF complex and the like, in an organic solvent such as THF, ether, dioxane and the like, at a temperature in the range from about –20° C. to room temperature, to yield the corresponding compound of formula (IIh).

SPECIFIC EXAMPLES

Example 1

3-(4-[[3-(4-chlorophenyl)-5-(trifluoromethyl)-1,2-thiazol-4-yl]methoxy]-2,3-difluorophenyl)propanoic Acid, Cpd 106

Step 1:
5-(4-chlorophenyl)-2H-1,3,4-oxathiazol-2-one

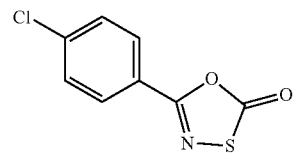 [SMILES: O=c1oc(-c2ccc(Cl)cc2)ns1]

Into a 100-mL round-bottom flask, was placed 4-chlorobenzamide (3.0 g, 19.28 mmol, 1.00 equiv), chloro(chlorosulfanyl)methanone (5.03 g, 38.40 mmol, 1.99 equiv), toluene (30 mL). The resulting solution was stirred overnight at 100° C. in an oil bath. The reaction progress was monitored by GCMS/TLC/LCMS (ethyl acetate/petroleum ether=1:20). The resulting mixture was concentrated under vacuum. The residue was applied onto a silica gel column with petroleum ether. This resulted in 3.8 g (92%) of 5-(4-chlorophenyl)-2H-1,3,4-oxathiazol-2-one as a white solid.

Step 2: Ethyl 3-(4-chlorophenyl)-5-(trifluoromethyl)-1,2-thiazole-4-carboxylate

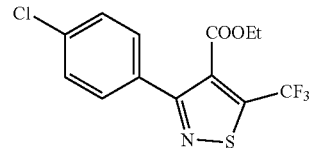 [SMILES: CCOC(=O)c1c(-c2ccc(Cl)cc2)nsc1C(F)(F)F]

Into a 50-mL sealed tube, was placed 5-(4-chlorophenyl)-2H-1,3,4-oxathiazol-2-one (2.2 g, 10.30 mmol, 1.00 equiv), ethyl 4,4,4-trifluorobut-2-ynoate (2.5 g, 15.05 mmol, 1.46 equiv), 1,3-dichlorobenzene (20 mL). The resulting solution was stirred for 18 h at 150° C. in an oil bath. The reaction progress was monitored by LCMS/GCMS/TLC (ethyl acetate/petroleum ether=1:20). The resulting mixture was concentrated under vacuum. The residue was applied onto a silica gel column with petroleum ether. This resulted in 2.8 g (81%) of ethyl 3-(4-chlorophenyl)-5-(trifluoromethyl)-1, 2-thiazole-4-carboxylate as a yellow solid. Mass spectrum (ESI, m/z): Calcd. for $C_{13}H_9ClF_3NO_2S$, 336.0 (M+H), found 336.0.

Step 3: [3-(4-chlorophenyl)-5-(trifluoromethyl)-1,2-thiazol-4-yl]methanol

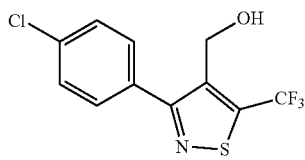 [SMILES: OCc1c(-c2ccc(Cl)cc2)nsc1C(F)(F)F]

Into a 50-mL round-bottom flask (1 atm) purged and maintained with an inert atmosphere of nitrogen, was placed ethyl 3-(4-chlorophenyl)-5-(trifluoromethyl)-1,2-thiazole-4-carboxylate (1.0 g, 2.98 mmol, 1.00 equiv), toluene (5.0 mL). This was followed by the addition of DIBAL-H (20% in toluene) (4.23 g, 29.79 mmol, 2.00 equiv) dropwise with stirring at −78° C. The resulting solution was warmed to room temperature and stirred for 1 h at 30° C. The reaction progress was monitored by LCMS. The reaction was then quenched by the addition of 10 mL of water and 10 mL $NH_4Cl$. The resulting solution was extracted with 3×20 mL of dichloromethane and the organic layers combined and dried over anhydrous sodium sulfate and concentrated under vacuum. The residue was applied onto a silica gel column with ethyl acetate/petroleum ether (1:10). This resulted in 0.72 g (82%) of [3-(4-chlorophenyl)-5-(trifluoromethyl)-1, 2-thiazol-4-yl]methanol as a yellow solid. Mass spectrum (ESI, m/z): Calcd. for $C_{11}H_7ClF_3NOS$, 294.0 (M+H), found 294.0.

Step 4: [3-(4-chlorophenyl)-5-(trifluoromethyl)-1,2-thiazol-4-yl]methyl methanesulfonate

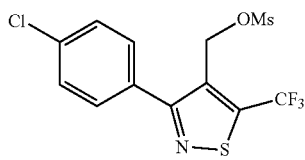 [SMILES: CS(=O)(=O)OCc1c(-c2ccc(Cl)cc2)nsc1C(F)(F)F]

Into a 50-mL round-bottom flask, was placed [3-(4-chlorophenyl)-5-(trifluoromethyl)-1,2-thiazol-4-yl]methanol (80 mg, 0.27 mmol, 1.00 equiv), dichloromethane (2.0 mL), triethylamine (83 mg, 0.82 mmol, 3.01 equiv). This was followed by the addition of MsCl (62 mg, 0.54 mmol, 2.00 equiv) dropwise with stirring at 0° C. The resulting solution was stirred for 1 h at 30° C. The reaction progress was monitored by LCMS. The reaction was then quenched by the addition of 10 mL of water. The resulting solution was extracted with 3×10 mL of dichloromethane and the organic layers combined. The resulting mixture was washed with 2×20 mL of sodium chloride. The mixture was dried over anhydrous sodium sulfate and concentrated under vacuum. This resulted in 0.12 g of [3-(4-chlorophenyl)-5-(trifluoromethyl)-1,2-thiazol-4-yl]methyl methanesulfonate as a yellow solid. This crude could be used for the next step directly. Mass spectrum (ESI, m/z): Calcd. for $C_{12}H_9ClF_3NO_3S_2$, 372.0 (M+H), found 372.0.

Step 5: Ethyl 3-(4-[[3-(4-chlorophenyl)-5-(trifluoromethyl)-1,2-thiazol-4-yl]methoxy]-2,3-difluorophenyl)propanoate

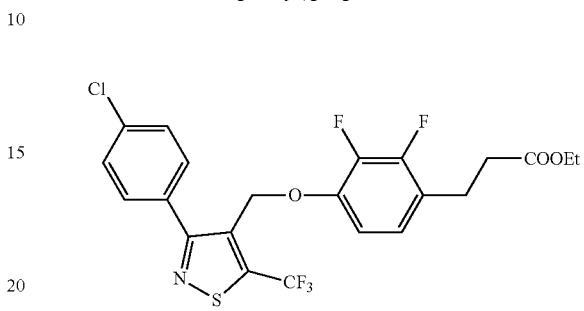

Into a 50-mL round-bottom flask, was placed [3-(4-chlorophenyl)-5-(trifluoromethyl)-1,2-thiazol-4-yl]methyl methanesulfonate (101 mg, 0.27 mmol, 1.00 equiv), ethyl 3-(2,3-difluoro-4-hydroxyphenyl)propanoate (prepared according to PCT Application WO2010/048207A2) (81 mg, 0.35 mmol, 1.30 equiv), N,N-dimethyl formamide (3.0 mL), potassium carbonate (113 mg, 0.82 mmol, 3.01 equiv). The resulting solution was stirred overnight at 30° C. The reaction progress was monitored by LCMS. The reaction was then quenched by the addition of 10 mL of water. The resulting solution was extracted with 3×10 mL of ethyl acetate and the organic layers combined and dried over anhydrous sodium sulfate and concentrated under vacuum. The residue was purified by TLC-Plate with Petroleum ether/EtOAc=6:1. This resulted in 0.10 g (73%) of ethyl 3-(4-[[3-(4-chlorophenyl)-5-(trifluoromethyl)-1,2-thiazol-4-yl]methoxy]-2,3-difluorophenyl)propanoate as a light yellow solid. Mass spectrum (ESI, m/z): Calcd. for $C_{22}H_{17}ClF_5NO_3S$, 506.1 (M+H), found 506.1.

Step 6: 3-(4-[[3-(4-chlorophenyl)-5-(trifluoromethyl)-1,2-thiazol-4-yl]methoxy]-2,3-difluorophenyl) propanoic Acid

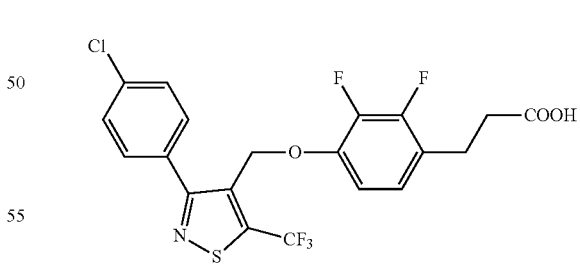

Into a 50-mL round-bottom flask, was placed ethyl 3-(4-[[3-(4-chlorophenyl)-5-(trifluoromethyl)-1, 2-thiazol-4-yl]methoxy]-2,3-difluorophenyl)propanoate (101 mg, 0.20 mmol, 1.00 equiv), tetrahydrofuran (2.0 mL), a solution of LiOH (100 mg, 4.18 mmol, 20.91 equiv) in water (2.0 mL). The resulting solution was stirred overnight at 30° C. The reaction progress was monitored by LCMS. The pH value of the solution was adjusted to 1 with aqueous HCl (2 N). The resulting mixture was concentrated under vacuum. The solids were collected by filtration and washed by hexane and EtOAc. Then the solid was dried under vacuum. This resulted in 85 mg (89%) of 3-(4-[[3-(4-chlorophenyl)-5-(trifluoromethyl)-1,2-thiazol-4-yl]methoxy]-2,3-difluorophenyl)propanoic acid as a white solid. $^1$H-NMR (300 MHz, CD$_3$OD) δ 7.69 (d, J=8.4 Hz, 2H), 7.51 (d, J=8.4 Hz, 2H), 7.01 (t, J=7.5 Hz, 1H), 6.85 (t, J=7.5 Hz, 1H), 5.19 (s, 2H), 2.94 (t, J=7.8 Hz, 2H), 2.61 (t, J=7.8 Hz, 2H). Mass spectrum (ESI, m/z): Calcd. for $C_{20}H_{13}ClF_5NO_3S$, 478.0 (M+H), found 478.1.

Example 2

3-(4-[[3-(4-ethylphenyl)-5-(trifluoromethyl)-1,2-thiazol-4-yl]methoxy]-3,5-difluorophenyl)propanoic Acid, Cpd 70

Step 1: 5-(4-ethylphenyl)-1,3,4-oxathiazol-2-one

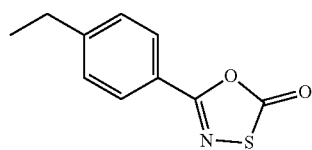

The title compound was prepared according to the procedure describe in Step 1 of Example 1 using 4-ethylbenzamide as starting material to afford the desired product as yellow solid.

Step 2: Ethyl 3-(4-ethylphenyl)-5-(trifluoromethyl)-1,2-thiazole-4-carboxylate

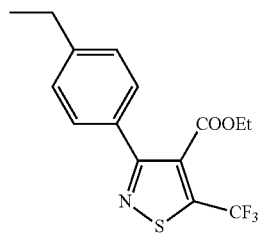 [SMILES: CCOC(=O)c1c(-c2ccc(CC)cc2)nsc1C(F)(F)F]

Into a 50-mL sealed tube, was placed ethyl 4,4,4-trifluorobut-2-ynoate (1.25 g, 7.53 mmol, 1.56 equiv), 5-(4-ethylphenyl)-2H-1,3,4-oxathiazol-2-one (1.0 g, 4.83 mmol, 1.00 equiv), 1,3-dichlorobenzene (8 mL). The resulting solution was stirred for 16 h at 150° C. The reaction progress was monitored by LCMS. The resulting mixture was concentrated under vacuum. The residue was applied onto a silica gel column with petroleum ether (100). This resulted in 1.068 g (67%) of ethyl 3-(4-ethylphenyl)-5-(trifluoromethyl)-1,2-thiazole-4-carboxylate as yellow oil.

Step 3: [3-(4-ethylphenyl)-5-(trifluoromethyl)-1,2-thiazol-4-yl]methanol

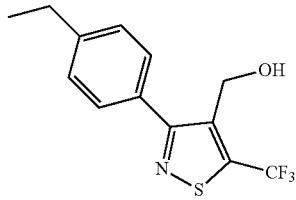 [SMILES: CCc1ccc(-c2nsc(C(F)(F)F)c2CO)cc1]

Into a 25-mL 3-necked round-bottom flask (1 atm) purged and maintained with an inert atmosphere of nitrogen, was placed ethyl 3-(4-ethylphenyl)-5-(trifluoromethyl)-1,2-thiazole-4-carboxylate (80 mg, 0.24 mmol, 1.00 equiv), toluene (2 mL). This was followed by the addition of DIBAL-H (25% in toluene) (0.690 g, 5.00 equiv) dropwise with stirring at −60° C. The resulting solution was stirred for 2 h at 28° C. The reaction progress was monitored by LCMS. The reaction mixture was cooled to 0° C. with a water/ice bath. The reaction was then quenched by the addition of 20 mL of water/NH$_4$Cl. The resulting solution was extracted with 3×20 mL of ethyl acetate and the organic layers combined. The resulting mixture was washed with 2×30 mL of sodium chloride. The mixture was dried over anhydrous sodium sulfate and concentrated under vacuum. The residue was purified by TLC-plate (EA:PE=4:1). This resulted in 0.056 g (80%) of [3-(4-ethylphenyl)-5-(trifluoromethyl)-1,2-thiazol-4-yl]methanol as a yellow solid. Mass spectrum (ESI, m/z): Calcd. for $C_{13}H_{12}F_3NOS$, 288.1 (M+H), found 288.1.

Step 4: [3-(4-ethylphenyl)-5-(trifluoromethyl)-1,2-thiazol-4-yl]methyl methanesulfonate

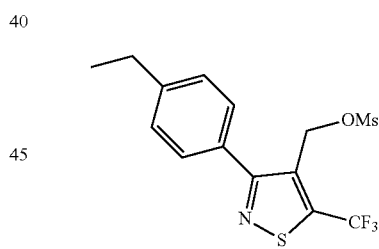

Into a 50-mL round-bottom flask, was placed [3-(4-ethylphenyl)-5-(trifluoromethyl)-1,2-thiazol-4-yl]methanol (50 mg, 0.17 mmol, 1.00 equiv), triethylamine (53 mg, 0.52 mmol, 3.01 equiv), dichloromethane (2.0 mL), MsCl (40 mg, 0.35 mmol, 2.02 equiv). The resulting solution was stirred for 0.5 h at 25° C. The reaction progress was monitored by LCMS. The reaction was then quenched by the addition of 10 mL of water. The resulting solution was extracted with 3×10 mL of dichloromethane and the organic layers combined. The resulting mixture was washed with 2×20 mL of sodium chloride. The mixture was dried over anhydrous sodium sulfate and concentrated under vacuum. This resulted in 75 mg of [3-(4-ethylphenyl)-5-(trifluoromethyl)-1,2-thiazol-4-yl]methyl methanesulfonate as a light yellow solid. The crude could be used for the next step directly. Mass spectrum (ESI, m/z): Calcd. for $C_{14}H_{14}F_3NO_3S_2$, 366.0 (M+H), found 366.0.

Step 5: Tert-butyl 3-(4-[[3-(4-ethylphenyl)-5-(trifluoromethyl)-1,2-thiazol-4-yl]methoxy]-3,5-difluorophenyl)propanoate

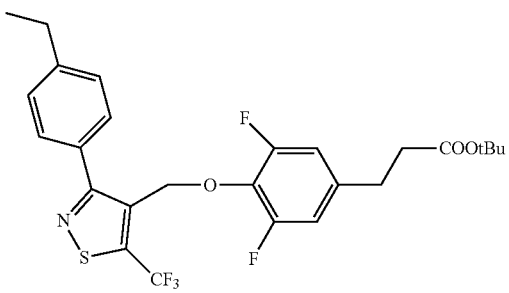

Into a 100-mL round-bottom flask, was placed [3-(4-ethylphenyl)-5-(trifluoromethyl)-1,2-thiazol-4-yl]methyl methanesulfonate (445 mg, 1.22 mmol, 1.00 equiv), tert-butyl 3-(3,5-difluoro-4-hydroxyphenyl)propanoate (prepared according to PCT Application WO2010/048207A2) (378 mg, 1.46 mmol, 1.20 equiv), potassium carbonate (542 mg, 3.92 mmol, 3.22 equiv), N,N-dimethylformamide (10.0 mL). The resulting solution was stirred overnight at 25° C. The reaction progress was monitored by LCMS. The reaction was then quenched by the addition of 10 mL of water. The resulting solution was extracted with 3×15 mL of ethyl acetate and the organic layers combined. The resulting mixture was washed with 2×15 mL of H$_2$O. The mixture was dried over anhydrous sodium sulfate and concentrated under vacuum. The residue was applied onto a silica gel column with ethyl acetate/petroleum ether (1:6). This resulted in 0.52 g (81%) of tert-butyl 3-(4-[[3-(4-ethylphenyl)-5-(trifluoromethyl)-1,2-thiazol-4-yl]methoxy]-3,5-difluorophenyl)propanoate as light yellow oil. Mass spectrum (ESI, m/z): Calcd. for C$_{21}$H$_{17}$F$_5$NOS$_3$, 427.1 (M+H), found 427.1.

Step 6: 3-(4-[[3-(4-ethylphenyl)-5-(trifluoromethyl)-1,2-thiazol-4-yl]methoxy]-3,5-difluorophenyl)propanoic Acid

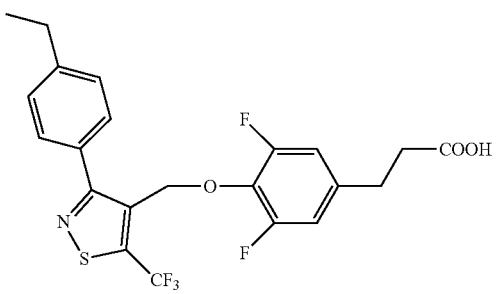 [SMILES: CCc1ccc(-c2nsc(C(F)(F)F)c2COc2c(F)cc(CCC(=O)O)cc2F)cc1]

Into a 50-mL round-bottom flask, was placed tert-butyl 3-(4-[[3-(4-ethylphenyl)-5-(trifluoromethyl)-1,2-thiazol-4-yl]methoxy]-3,5-difluorophenyl)propanoate (520 mg, 0.99 mmol, 1.00 equiv), CF$_3$COOH (2.0 mL), dichloromethane (8.0 mL). The resulting solution was stirred overnight at 25° C. The reaction progress was monitored by LCMS. The resulting mixture was concentrated under vacuum. The solid was washed by EtOAc and hexane. The mixture was filtered and the solid was dried under vacuum. This resulted in 0.37 g (80%) of 3-(4-[[3-(4-ethylphenyl)-5-(trifluoromethyl)-1,2-thiazol-4-yl]methoxy]-3,5-difluorophenyl) propanoic acid as a white solid. $^1$H-NMR (300 Hz, CD$_3$OD): δ 7.67 (d, J=8.4 Hz, 2H), 7.34 (d, J=8.4 Hz, 2H), 6.86 (d, J=9.6 Hz, 2H), 5.21 (s, 2H), 2.87 (t, J=7.5 Hz, 2H), 2.74 (q, J$_1$=7.5 Hz, J$_2$=15.2 Hz, 2H), 2.61 (t, J=7.8 Hz, 2H), 1.30 (t, J=7.5 Hz, 3H). Mass spectrum (ESI, m/z): Calcd. for C$_{22}$H$_{18}$F$_5$NO$_3$S, 472.1 (M+H), found 472.1.

Example 3

3-(4-[[3-(4-chlorophenyl)-5-(trifluoromethyl)-1,2-thiazol-4-yl]methoxy]-3,5-difluorophenyl)propanoic Acid, Cpd 79

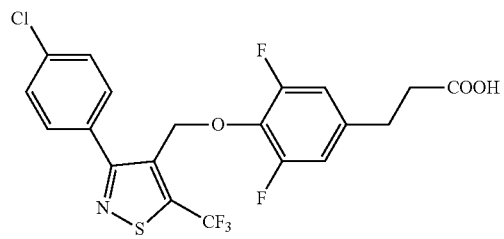 [SMILES: O=C(O)CCc1cc(F)c(OCc2c(-c3ccc(Cl)cc3)nsc2C(F)(F)F)c(F)c1]

The title compound was prepared according to the procedure described in Example 2 starting from (3-(4-ethylphenyl)-5-(trifluoromethyl)isothiazol-4-yl)methyl methanesulfonate following Step 5 and 6 using tert-butyl 3-(3,5-difluoro-4-hydroxyphenyl)propanoate as coupling agent to afford the desired product as an off-white solid. $^1$H NMR (300 MHz, CD$_3$OD) δ 7.77 (d, J=8.7 Hz, 2H), 7.51 (d, J=8.4 Hz, 2H), 6.86 (d, J=9.6 Hz, 2H), 5.20 (s, 2H), 2.87 (t, J=7.5 Hz, 2H), 2.59 (t, J=7.5 Hz, 2H). Mass spectrum (ESI, m/z): Calcd. for C$_{20}$H$_{13}$ClF$_5$NO$_3$S, 478.0 (M+H), found 478.0.

Example 4

3-(4-((3-(4-ethylphenyl)-5-(trifluoromethyl)isothiazol-4-yl)methoxy)-2,3-difluorophenyl)propanoic Acid, Cpd 73

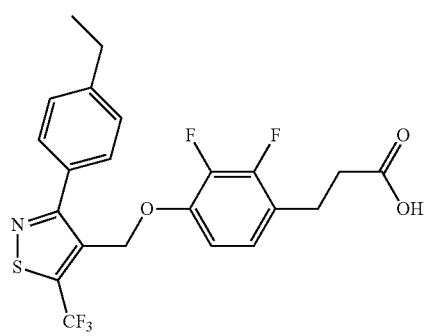

The title compound was prepared according to the procedure described in Example 1 starting from 4-ethylbenzamide following Step 1-6 using ethyl 3-(2,3-difluoro-4-hydroxyphenyl)propanoate as coupling agent followed by hydrolysis to afford the desired product as an off-white solid. $^1$H NMR (400 MHz, CDCl$_3$) δ 7.63 (d, J=7.5 Hz, 2H), 7.30

(d, J=7.5 Hz, 2H), 6.92 (t, J=6.5 Hz, 1H), 6.72 (t, J=6.5 Hz, 1H), 5.10 (s, 2H), 2.98 (t, J=6.0 Hz, 2H), 2.73 (m, 4H), 1.28 (t, J=7.0 Hz, 3H).

Example 5

3-(4-((3-(4-chlorophenyl)-5-(trifluoromethyl)isothiazol-4-yl)methoxy)-2,3-dimethylphenyl)propanoic Acid, Cpd 142

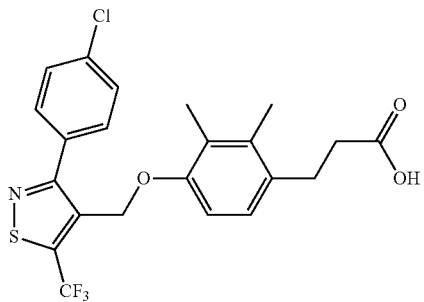 [SMILES: Cc1c(CCC(=O)O)ccc(OCc2c(-c3ccc(Cl)cc3)nsc2C(F)(F)F)c1C]

The title compound was prepared according to the procedure described in Example 1 starting from 4-chlorobenzamide following Step 1-6 using ethyl 3-(2,3-dimethyl-4-hydroxyphenyl)propanoate (prepared according to PCT Application WO2010/048207A2) as coupling agent followed by hydrolysis to afford the desired product as an off-white solid. $^1$H NMR (400 MHz, CDCl$_3$) δ 7.65 (d, J=7.5 Hz, 2H), 7.42 (d, J=7.8 Hz, 2H), 6.95 (d, J=5.5 Hz, 1H), 6.62 (d, J=6.0 Hz, 1H), 5.01 (s, 2H), 2.98 (t, J=7.5 Hz, 2H), 2.66 (t, J=7.8 Hz, 2H), 2.25 (s, 3H), 2.12 (s, 3H). LCMS (ESI, M/Z) for C$_{22}$H$_{19}$ClF$_3$NO$_3$S: 469.1, 471.1.

Example 6

3-(4-((3-(4-ethylphenyl)-5-(trifluoromethyl)isothiazol-4-yl)methoxy)-2,3-dimethylphenyl)propanoic Acid, Cpd 127

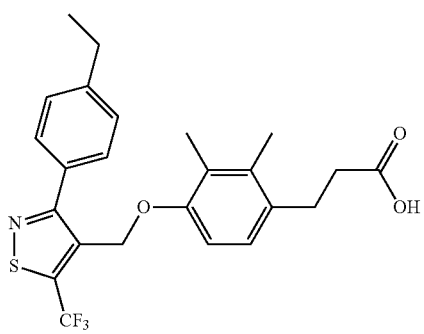 [SMILES: CCc1ccc(-c2nsc(C(F)(F)F)c2COc2ccc(CCC(=O)O)c(C)c2C)cc1]

The title compound was prepared according to the procedure described in Example 1 starting from 4-ethylbenzamide following Step 1-6 using ethyl 3-(2,3-dimethyl-4-hydroxyphenyl)propanoate as coupling agent followed by hydrolysis to afford the desired product as an off-white solid. $^1$H NMR (400 MHz, CDCl$_3$) δ 7.63 (d, J=7.0 Hz, 2H), 7.28 (d, J=7.0 Hz, 2H), 6.98 (d, J=6.5 Hz, 1H), 6.70 (d, J=6.5 Hz, 1H), 5.03 (s, 2H), 2.98 (t, J=5.5 Hz, 2H), 2.68 (q, J=7.5 Hz, 2H), 2.60 (t, J=6.0 Hz, 2H), 2.25 (s, 3H), 2.12 (s, 3H), 1.28 (t, J=7.0 Hz, 3H).

Example 7

3-(4-((3-(4-chloro-2-fluorophenyl)-5-(trifluoromethyl)isothiazol-4-yl)methoxy)-3,5-difluorophenyl)propanoic Acid, Cpd 74

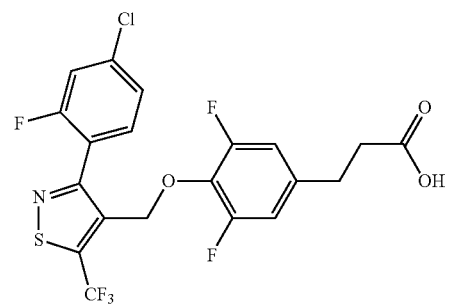 [SMILES: O=C(O)CCc1cc(F)c(OCc2c(-c3ccc(Cl)cc3F)nsc2C(F)(F)F)c(F)c1]

The title compound was prepared according to the procedure described in Example 1 starting from 2-fluoro-4-chlorobenzamide following Step 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.06 (d, J=6.0 Hz, 2H), 6.68 (d, J=7.8 Hz, 2H), 5.11 (s, 2H), 2.88 (t, J=5.8 Hz, 2H), 2.65 (t, J=6.2 Hz, 2H).

Example 8

3-(4-((3-(4-chloro-2,6-difluorophenyl)-5-(trifluoromethyl)isothiazol-4-yl)methoxy)-2,3-dimethylphenyl)propanoic Acid, Cpd 133

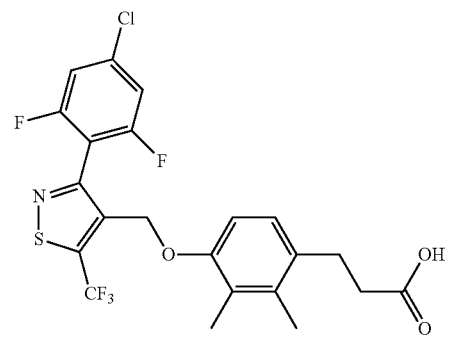 [SMILES: Cc1c(CCC(=O)O)ccc(OCc2c(-c3c(F)cc(Cl)cc3F)nsc2C(F)(F)F)c1C]

The title compound was prepared according to the procedure described in Example 1 starting from 4-chloro-2,6-dichloro-benzamide following Step 1-6 using ethyl 3-(2,3-dimethyl-4-hydroxyphenyl)propanoate as coupling agent to afford the desired product as an off-white solid. $^1$H NMR (400 MHz, CDCl$_3$) δ 7.05 (d, J=6.2 Hz, 2H), 6.96 (d, J=7.5 Hz, 1H), 6.53 (d, J=7.5 Hz, 1H), 5.02 (s, 2H), 2.94 (m, J=7.0 Hz, 2H), 2.58 (m, J=7.0 Hz, 2H), 2.21 (s, 3H), 1.86 (s, 3H).

Example 9

3-(4-((3-(4-chloro-3-methoxyphenyl)-5-(trifluoromethyl)isothiazol-4-yl)methoxy)-2,3-dimethylphenyl)propanoic Acid, Cpd 144

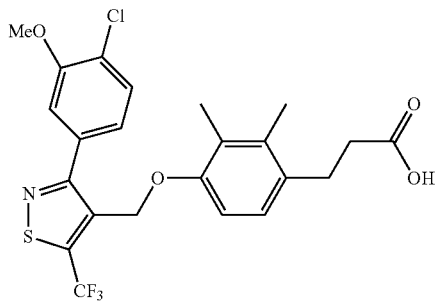 [SMILES: COc1cc(-c2nsc(C(F)(F)F)c2COc2ccc(CCC(=O)O)c(C)c2C)ccc1Cl]

The title compound was prepared according to the procedure described in Example 1 starting from 4-chloro-3-methoxy-benzamide following Step 1-6 using ethyl 3-(2,3-dimethyl-4-hydroxyphenyl)propanoate as coupling agent followed by hydrolysis to afford the desired product as an off-white solid. $^1$H NMR (400 MHz, CDCl$_3$) δ 7.42 (d, J=7.0 Hz, 1H), 7.28 (d, J=7.0 Hz, 1H), 7.26 (s, 1H), 7.01 (d, J=7.5 Hz, 1H), 6.58 (d, J=7.5 Hz, 1H), 5.01 (s, 2H), 3.68 (s, 3H), 2.98 (t, J=8.8 Hz, 2H), 2.52 (t, J=8.8 Hz, 2H), 2.21 (s, 3H), 2.12 (s, 3H).

Example 10

3-(4-((3-(3,4-difluorophenyl)-5-(trifluoromethyl)isothiazol-4-yl)methoxy)-2,3-dimethylphenyl)propanoic Acid, Cpd 143

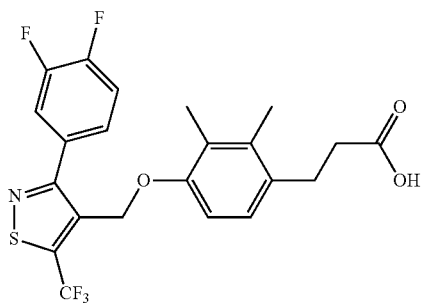 [SMILES: Cc1c(CCC(=O)O)ccc(OCc2c(-c3ccc(F)c(F)c3)nsc2C(F)(F)F)c1C]

The title compound was prepared according to the procedure described in Example 1 starting from 3,4-difluorobenzamide following Step 1-6 using ethyl 3-(2,3-dimethyl-4-hydroxyphenyl)propanoate as coupling agent to afford the desired product as an off-white solid. $^1$H NMR (400 MHz, CDCl$_3$) δ 7.42 (t, J=7.0 Hz, 1H), 7.30 (m, 2H), 6.95 (d, J=7.1 Hz, 1H), 6.68 (d, J=7.1 Hz, 1H), 4.98 (s, 2H), 2.95 (t, J=7.5 Hz, 2H), 2.62 (t, J=7.5 Hz, 2H), 2.25 (s, 3H), 2.12 (s, 3H).

Example 11

3-(4-((3-(3,4-difluorophenyl)-5-(trifluoromethyl)isothiazol-4-yl)methoxy)-3,5-difluorophenyl)propanoic Acid, Cpd 129

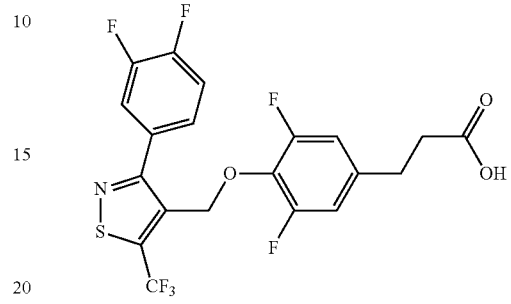

The title compound was prepared according to the procedure described in Example 1 starting from 3,4-difluorobenzamide following Step 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.58 (t, J=7.0 Hz, 1H), 7.47 (m, 1H), 7.38 (t, J=7.5 Hz, 1H), 6.82 (d, J=8.5 Hz, 2H), 5.10 (s, 2H), 2.95 (t, J=9.1 Hz, 2H), 2.68 (t, J=9.1 Hz, 2H).

Example 12

3-(4-((3-(4-chloro-3-methoxyphenyl)-5-(trifluoromethyl)isothiazol-4-yl)methoxy)-3,5-difluorophenyl)propanoic Acid, Cpd 177

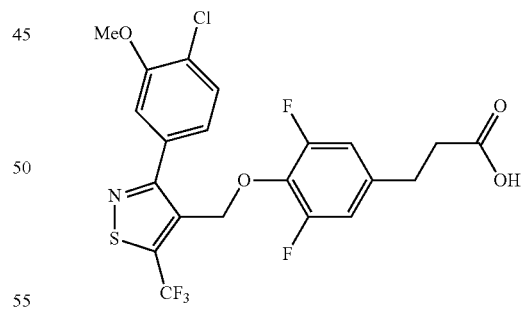

The title compound was prepared according to the procedure described in Example 1 starting from 4-chloro-3-methoxybenzamide following Steps 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.55 (d, J=6.8 Hz, 1H), 7.50 (m, 2H), 6.78 (d, J=8.1 Hz, 2H), 5.18 (s, 2H), 4.01 (s, 3H), 2.90 (t, J=7.1 Hz, 2H), 2.72 (t, J=7.5 Hz, 2H).

Example 13

3-(4-((3-(4-chloro-3-fluorophenyl)-5-(trifluoromethyl)isothiazol-4-yl)methoxy)-3,5-difluorophenyl)propanoic Acid, Cpd 67

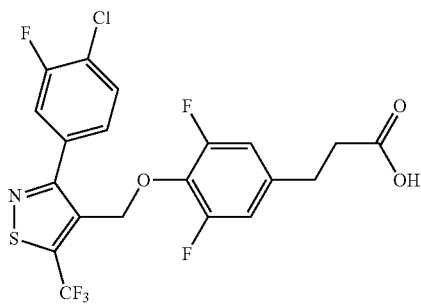 [SMILES: O=C(O)CCc1cc(F)c(OCc2c(-c3ccc(Cl)c(F)c3)nsc2C(F)(F)F)c(F)c1]

The title compound was prepared according to the procedure described in Example 1 starting from 3-fluoro-4-chlorobenzamide following Step 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.76 (dd, J=8.5, 5.5 Hz, 1H), 7.70 (d, J=7.2 Hz, 1H), 7.55 (dd, J=8.5, 7.2 Hz, 1H), 6.79 (d, J=8.8 Hz, 2H0, 8.11 (s, 2H), 2.98 (t, J=8.0 Hz, 2H), 2.70 (t, J=8.0 Hz, 2H).

Example 14

3-(4-((3-(4-chloro-2,6-difluorophenyl)-5-(trifluoromethyl)isothiazol-4-yl)methoxy)-3,5-difluorophenyl)propanoic Acid, Cpd 96

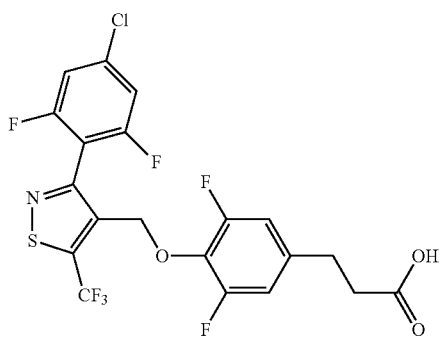 [SMILES: O=C(O)CCc1cc(F)c(OCc2c(-c3c(F)cc(Cl)cc3F)nsc2C(F)(F)F)c(F)c1]

The title compound was prepared according to the procedure described in Example 1 starting from 2,6-difluoro-4-chlorobenzamide following Steps 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.06 (d, J=6.0 Hz, 2H), 6.68 (d, J=7.8 Hz, 2H), 5.11 (s, 2H), 2.88 (t, J=5.8 Hz, 2H), 2.65 (t, J=6.2 Hz, 2H).

Example 15

3-(4-((3-(4-ethylphenyl)-5-(trifluoromethyl)isothiazol-4-yl)methoxy)-3,5-dimethylphenyl)propanoic Acid, Cpd 239

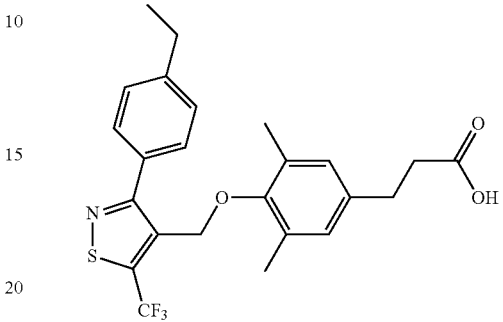

The title compound was prepared according to the procedure described in Example 1 starting from 4-ethylbenzamide following Steps 1-6 using ethyl 3-(3,5-dimethyl-4-hydroxyphenyl) propanoate (prepared according to PCT Application WO2010/048207A2) as coupling agent followed by hydrolysis to afford the desired product as an off-white solid. $^1$H NMR (400 MHz, CDCl$_3$) δ 7.58 (d, J=6.0 Hz, 2H), 7.30 (d, J=6.1 Hz, 2H), 6.76 (s, 2H), 4.98 (s, 2H), 2.82 (t, J=5.8 Hz, 2H), 2.73 (q, J=5.0 Hz, 2H), 2.63 (t, J=5.8 Hz, 2H), 1.95 (s, 6H), 1.28 (t, J=6.1 Hz, 3H).

Example 16

3-(4-((3-(2,4-difluorophenyl)-5-(trifluoromethyl)isothiazol-4-yl)methoxy)-3,5-difluorophenyl)propanoic Acid, Cpd 174

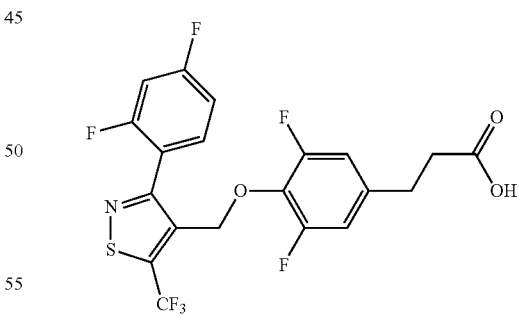

The title compound was prepared according to the procedure described in Example 1 starting from 2,4-difluorobenzamide following Steps 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.65 (dd, J=8.5, 5.5 Hz, 1H), 7.05 (d, J=5.5 Hz, 1H), 6.94 (m, J=8.0 Hz, 6.72 (d, J=8.9 Hz, 2H), 5.14 (s, 2H), 2.86 (t, J=8.0 Hz, 2H), 2.68 (t, J=8.1 Hz, 2H).

Example 17

3-(4-((3-(4-ethyl-3-fluorophenyl)-5-(trifluoromethyl) isothiazol-4-yl)methoxy)-3,5-difluorophenyl)propanoic Acid, Cpd 194

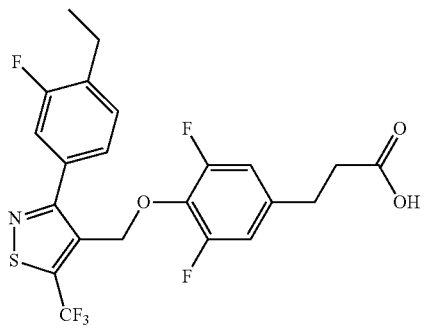 [SMILES: CCc1ccc(-c2nsc(C(F)(F)F)c2COc2c(F)cc(CCC(=O)O)cc2F)cc1F]

The title compound was prepared according to the procedure described in Example 1 starting from 3-fluoro-4-ethylbenzamide following Steps 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.66 (d, J=6.0 Hz, 1H), 7.60 (d, J=7.5 Hz, 1H), 7.37 (d, J=8.2 Hz, 1H), 6.78 (d, J=8.5 Hz, 2H), 5.17 (s, 2H), 2.89 (m, J=7.0 Hz, 2H), 2.77 (q, J=6.5 Hz, 2H), 2.70 (m, J=7.0 Hz, 2H), 1.27 (t, J=6.8 Hz, 3H).

Example 18

3-(4-((3-(4-ethyl-2-fluorophenyl)-5-(trifluoromethyl) isothiazol-4-yl)methoxy)-3,5-difluorophenyl)propanoic Acid, Cpd 128

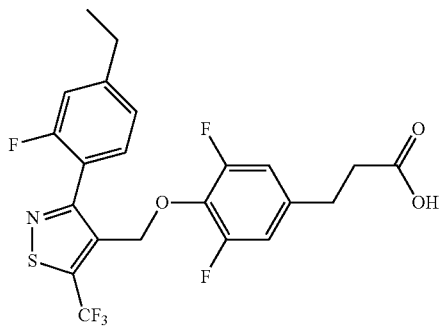 [SMILES: CCc1ccc(-c2nsc(C(F)(F)F)c2COc2c(F)cc(CCC(=O)O)cc2F)c(F)c1]

The title compound was prepared according to the procedure described in Example 1 starting from 2-fluoro-4-ethylbenzamide following Steps 1-6 using ethyl 3-(3,5-difluoro-4-hydroxyphenyl) propanoate as coupling agent followed by hydrolysis to afford the desired product as an off-white solid. $^1$H NMR (400 MHz, CDCl$_3$) δ 7.48 (t, J=7.5 Hz, 1H), 7.08 (d, J=6.5 Hz, 1H), 7.02 (d, J=8.0 Hz, 1H), 6.67 (d, J=7.9 Hz, 2H), 5.17 (s, 2H), 2.85 (t, J=7.5 Hz, 2H), 2.77 (q, J=7.0 Hz, 2H), 2.66 (t, J=7.6 Hz, 2H), 1.27 (t, J=8.0 Hz, 3H).

Example 19

3-(4-((3-(4-chloro-3-fluorophenyl)-5-(trifluoromethyl)isothiazol-4-yl)methoxy)-2,3-dimethylphenyl) propanoic Acid, Cpd 82

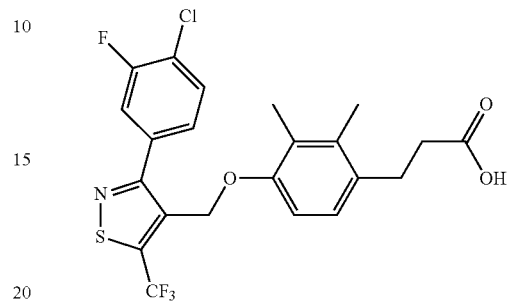

The title compound was prepared according to the procedure described in Example 1 starting from 3-fluoro-4-chloro-benzamide following Steps 1-6 using ethyl 3-(2,3-dimethyl-4-hydroxyphenyl)propanoate as coupling agent followed by hydrolysis to afford the desired product as an off-white solid. $^1$H NMR (400 MHz, CDCl$_3$) δ 7.58 (d, J=7.0 Hz, 1H), 7.49 (m, 2H), 7.02 (d, J=6.5 Hz, 1H), 6.72 (d, J=6.5 Hz, 1H), 5.02 (s, 2H), 2.98 (t, J=8.0 Hz, 2H), 2.65 (t, J=8.2 Hz, 2H), 2.25 (s, 3H), 2.13 (s, 3H).

Example 20

3-(4-((3-(4-ethyl-2-fluorophenyl)-5-(trifluoromethyl) isothiazol-4-yl)methoxy)-2,3-dimethylphenyl)propanoic Acid, Cpd 225

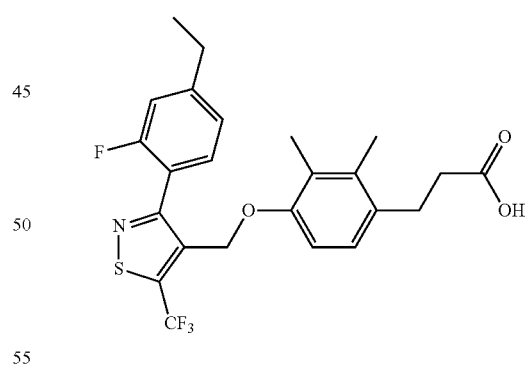

The title compound was prepared according to the procedure described in Example 1 starting from 2-fluoro-4-ethyl-benzamide following Steps 1-6 using ethyl 3-(2,3-dimethyl-4-hydroxyphenyl)propanoate as coupling agent followed by hydrolysis to afford the desired product as an off-white solid. $^1$H NMR (400 MHz, CDCl$_3$) δ 7.46 (t, J=7.8 Hz, 1H), 7.08 (d, J=7.0 Hz, 1H), 7.01 (d, J=8.2 Hz, 1H), 6.95 (d, J=7.0 Hz, 1H), 6.55 (d, J=6.7 Hz, 1H), 5.02 (s, 2H), 2.90 (m, 2H), 2.72 (q, J=8.5 Hz, 2H), 2.62 (t, J=7.9 Hz, 2H), 2.18 (s, 3H), 1.90 (s, 3H), 1.25 (t, J=8.5 Hz, 3H).

Example 21

3-(4-((3-(4-chloro-3-fluorophenyl)-5-(trifluoromethyl)isothiazol-4-yl)methoxy)-5-fluoro-2-methylphenyl)propanoic Acid, Cpd 148

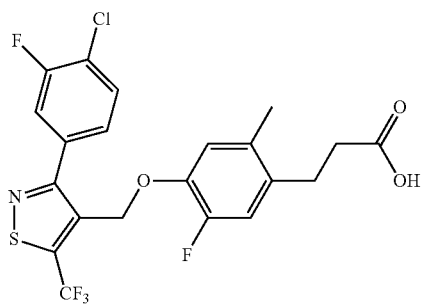 [SMILES: Cc1cc(OCc2c(-c3ccc(Cl)c(F)c3)nsc2C(F)(F)F)c(F)cc1CCC(=O)O]

The title compound was prepared according to the procedure described in Example 1 starting from 3-fluoro-4-chloro-benzamide following Steps 1-6 using ethyl 3-(5-fluoro-4-hydroxy-2-methylphenyl)propanoate as coupling agent followed by hydrolysis to afford the desired product as an off-white solid. $^1$H NMR (400 MHz, CDCl$_3$) δ 7.65 (d, J=6.0 Hz, 1H), 7.53 (dd, J=9.3, 6.8 Hz, 2H), 6.98 (d, J=8.5 Hz, 1H), 6.83 (d, J=6.5 Hz, 1H), 5.05 (s, 2H), 2.92 (t, J=6.7 Hz, 2H), 2.66 (t, J=6.7 Hz, 2H), 2.28 (s, 3H).

Example 22

3-(4-((3-(4-chloro-2,6-difluorophenyl)-5-(trifluoromethyl)isothiazol-4-yl)methoxy)-5-fluoro-2-methylphenyl)propanoic Acid, Cpd 207

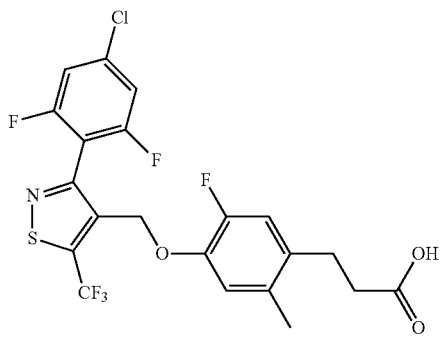 [SMILES: Cc1cc(OCc2c(-c3c(F)cc(Cl)cc3F)nsc2C(F)(F)F)c(F)cc1CCC(=O)O]

The title compound was prepared according to the procedure described in Example 1 starting from 2,6-difluoro-4-chloro-benzamide following Steps 1-6 using ethyl 3-(5-fluoro-4-hydroxy-2-methylphenyl)propanoate as coupling agent followed by hydrolysis to afford the desired product as an off-white solid. $^1$H NMR (400 MHz, CDCl$_3$) δ 7.05 (d, J=7.5 Hz, 2H), 6.82 (d, J=8.5 Hz, 1H), 6.55 (d, J=6.8 Hz, 1H), 5.11 (s, 2H), 2.90 (m, 2H), 2.62 (m, 2H), 2.22 (s, 3H).

Example 23

3-(3,5-dibromo-4-[[3-(4-chlorophenyl)-5-(trifluoromethyl)-1,2-thiazol-4-yl]methoxy]phenyl) propanoic Acid, Cpd 241

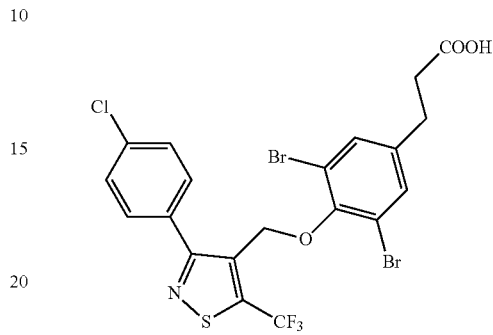

The title compound was prepared according to the procedure described in Example 1 starting from 4-difluorobenzamide following Steps 1-6 using ethyl 3-(3,5-dibromo-4-hydroxyphenyl) propanoate as coupling agent to afford the desired product as an off-white solid. $^1$H NMR (300 MHz, CD$_3$OD) δ: 7.73 (d, J=8.4 Hz, 2H), 7.47 (d, J=8.4 Hz, 2H), 5.35 (s, 2H), 2.83 (t, J=7.6 Hz, 2H), 2.58 (t, J=7.6 Hz, 2H). Mass spectrum (ESI, m/z): Calcd. for C$_{20}$H$_{13}$Br$_2$ClF$_3$NO$_3$S, 597.9 (M–H), found 598.0.

Example 24

3-(4-((3-(4-ethylphenyl)-5-(trifluoromethyl)isothiazol-4-yl)methoxy)-2,3,5-trifluorophenyl)propanoic Acid, Cpd 117

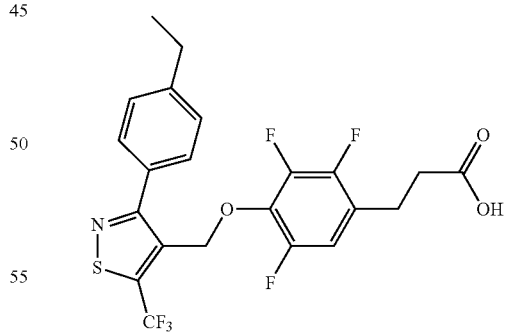

The title compound was prepared according to the procedure described in Example 1 starting from 4-ethylbenzamide following Step 1-6 using ethyl 3-(2,3,5-trifluoro-4-hydroxyphenyl) propanoate as coupling agent followed by hydrolysis to afford the desired product as an off-white solid. $^1$H NMR (400 MHz, CDCl$_3$) δ 7.74 (d, J=8.0 Hz, 2H), 7.35 (d, J=8.5 Hz, 2H), 6.80 (m, 1H), 5.20 (s, 2H), 2.96 (t, J=7.5 Hz, 2H), 2.74 (m, 4H), 1.80 (t, J=8.0 Hz, 3H).

Example 25

3-(4-((3-(4-chlorophenyl)-5-(trifluoromethyl)isothiazol-4-yl)methoxy)-3,5-difluoro-2-methylphenyl)propanoic Acid, Cpd 113

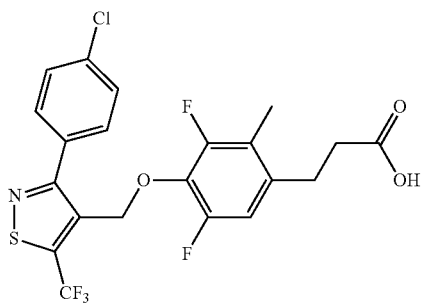 [SMILES: Cc1c(CCC(=O)O)cc(F)c(OCc2c(-c3ccc(Cl)cc3)nsc2C(F)(F)F)c1F]

The title compound was prepared according to the procedure described in Example 1 starting from 4-chlorobenzamide following Steps 1-6 using ethyl 3-(2-methyl-3,5-difluoro-4-hydroxyphenyl) propanoate as coupling agent followed by hydrolysis to afford the desired product as an off-white solid. $^1$H NMR (400 MHz, CDCl$_3$) δ 7.85 (d, J=7.1 Hz, 2H), 7.48 (d, J=7.0 Hz, 2H), 6.75 (d, J=8.3 Hz, 1H), 5.11 (s, 2H), 2.92 (t, J=8.2 Hz, 2H), 2.63 (t, J=8.1 Hz, 2H), 2.20 (s, 3H).

Example 26

3-(4-((3-(4-chlorophenyl)-5-(trifluoromethyl)isothiazol-4-yl)methoxy)-2,3,5-trifluorophenyl)propanoic Acid, Cpd 116

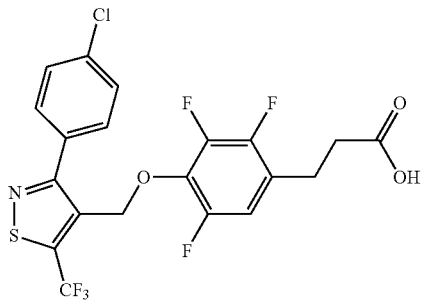 [SMILES: O=C(O)CCc1cc(F)c(OCc2c(-c3ccc(Cl)cc3)nsc2C(F)(F)F)c(F)c1F]

The title compound was prepared according to the procedure described in Example 1 starting from 4-chlorobenzamide following Steps 1-6 using ethyl 3-(2,3,5-trifluoro-4-hydroxyphenyl) propanoate as coupling agent followed by hydrolysis to afford the desired product as an off-white solid. $^1$H NMR (400 MHz, CDCl$_3$) δ 7.82 (d, J=8.1 Hz, 2H), 7.53 (d, J=8.0 Hz, 2H), 6.81 (m, 1H), 5.18 (s, 2H), 2.97 (t, J=7.5 Hz, 2H), 2.71 (t, J=7.5 Hz, 2H).

Example 27

3-(4-((3-(4-chloro-3-fluorophenyl)-5-(trifluoromethyl)isothiazol-4-yl)methoxy)-2,3,5-trifluorophenyl)propanoic Acid, Cpd 138

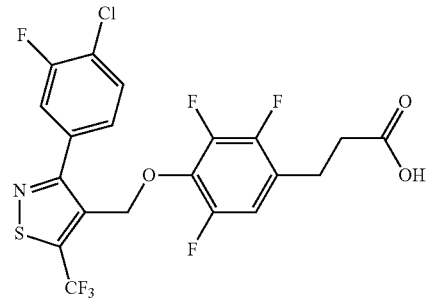 [SMILES: O=C(O)CCc1cc(F)c(OCc2c(-c3ccc(Cl)c(F)c3)nsc2C(F)(F)F)c(F)c1F]

The title compound was prepared according to the procedure described in Example 1 starting from 3-fluoro-4-chlorobenzamide following Steps 1-6 using ethyl 3-(2,3,5-trifluoro-4-hydroxyphenyl) propanoate as coupling agent followed by hydrolysis to afford the desired product as an off-white solid. $^1$H NMR (400 MHz, CDCl$_3$) δ 7.74 (dd, J=8.5, 5.3 Hz, 1H), 7.61 (dd, J=6.5 Hz, 1H), 7.55 (dd, J=8.0, 6.8 Hz, 1H), 6.82 (m, 1H), 5.15 (s, 2H), 2.98 (t, J=9.3 Hz, 2H), 2.71 (t, J=9.2 Hz, 2H).

Example 28

3-(4-((3-(4-chlorophenyl)-5-(trifluoromethyl)isothiazol-4-yl)methoxy)-2,3,5,6-tetrafluorophenyl)propanoic Acid, Cpd 152

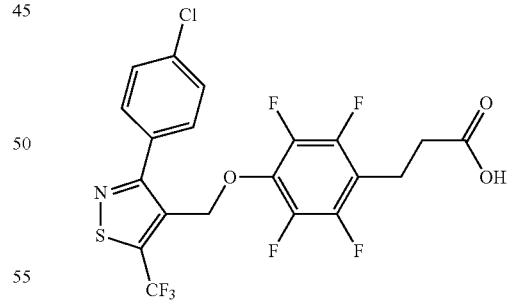

The title compound was prepared according to the procedure described in Example 1 starting from 4-chlorobenzamide following Step 1-6 using ethyl 3-(2,3,4,5-tetrafluoro-4-hydroxyphenyl) propanoate as coupling agent followed by hydrolysis to afford the desired product as an off-white solid. $^1$H NMR (400 MHz, CDCl$_3$) δ 7.81 (d, J=8.5 Hz, 2H), 7.52 (d, J=8.0 Hz, 2H), 5.21 (s, 2H), 3.05 (m, J=6.5 Hz, 2H), 2.72 (m, J=6.5 Hz, 2H).

Example 29

3-(4-((3-(4-ethylphenyl)-5-(trifluoromethyl)isothiazol-4-yl)methoxy)-2,3,5,6-tetrafluorophenyl)propanoic Acid, Cpd 118

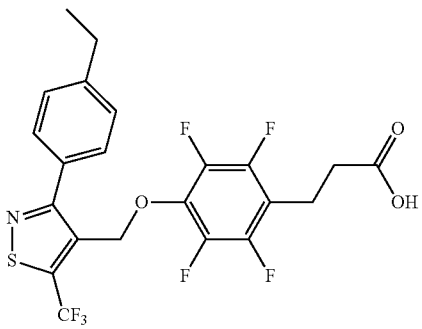 [SMILES: CCc1ccc(-c2nsc(C(F)(F)F)c2COc2c(F)c(F)c(CCC(=O)O)c(F)c2F)cc1]

The title compound was prepared according to the procedure described in Example 1 starting from 4-ethylbenzamide following Steps 1-6 using ethyl 3-(2,3,4,5-tetrafluoro-4-hydroxyphenyl) propanoate as coupling agent followed by hydrolysis to afford the desired product as an off-white solid. $^1$H NMR (400 MHz, CDCl$_3$) δ 7.72 (d, J=8.5 Hz, 2H), 7.35 (d, J=8.5 Hz, 2H), 5.24 (s, 2H), 3.06 (t, J=6.8 Hz, 2H), 2.72 (m, 4H), 1.28 (t, J=7.5 Hz, 3H).

Example 30

3-(4-((3-(4-chlorophenyl)-5-(trifluoromethyl)isothiazol-4-yl)methoxy)-5-fluoro-2-methylphenyl)propanoic Acid, Cpd 125

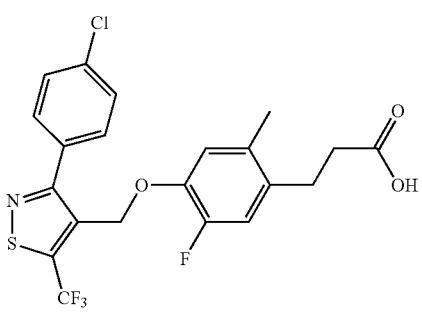 [SMILES: Cc1cc(OCc2c(-c3ccc(Cl)cc3)nsc2C(F)(F)F)c(F)cc1CCC(=O)O]

The title compound was prepared according to the procedure described in Example 1 starting from 4-chlorobenzamide following Steps 1-6 using ethyl 3-(5-fluoro-4-hydroxy-2-methylphenyl)propanoate as coupling agent followed by hydrolysis to afford the desired product as an off-white solid. $^1$H NMR (400 MHz, CDCl$_3$) δ 7.73 (d, J=8.0 Hz, 2H), 7.47 (d, J=8.1 Hz, 2H), 6.77 (d, J=8.5 Hz, 1H), 6.93 (d, J=8.5 Hz, 2H), 5.10 (s, 2H), 2.88 (t, J=8.5 Hz, 2H), 2.63 (d, J=8.2 Hz, 2H), 2.24 (s, 3H).

Example 31

3-(3,5-difluoro-4-((3-phenyl-5-(trifluoromethyl)isothiazol-4-yl)methoxy)phenyl)propanoic Acid, Cpd 145

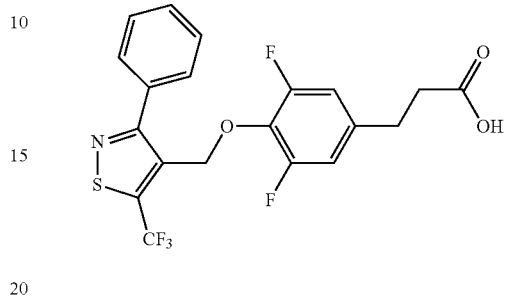

The title compound was prepared according to the procedure described in Example 1 starting from benzamide following Steps 1-6 using ethyl 3-(3,5-difluoro-4-hydroxyphenyl)propanoate as coupling agent followed by hydrolysis to afford the desired product as an off-white solid. $^1$H NMR (400 MHz, CDCl$_3$) δ 7.78 (m, 2H), 7.48 (m, 3H), 6.75 (d, J=8.2 Hz, 2H), 5.12 (s, 2H), 2.88 (t, J=7.5 Hz, 2H), 2.67 (t, J=7.5 Hz, 2H).

Example 32

3-(3, 5-difluoro-4-[[3-(4-methylphenyl)-5-(trifluoromethyl)-1,2-thiazol-4-yl]methoxy]phenyl) propanoic Acid, Cpd 115

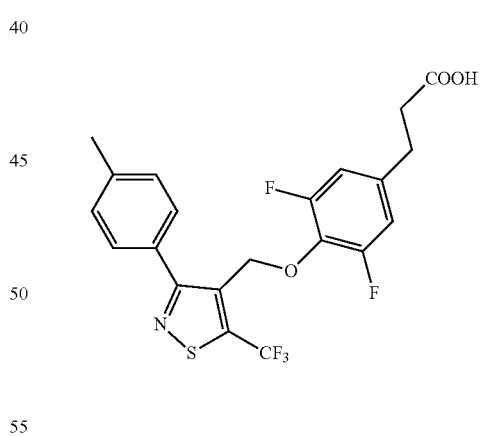

The title compound was prepared according to the procedure described in Example 1 starting from 4-methylbenzamide following Step 1-6 using ethyl 3-(3,5-difluoro-4-hydroxyphenyl)propanoate as coupling agent followed by hydrolysis to afford the desired product as an off-white solid. $^1$H NMR (300 MHz, CD$_3$OD) δ: 7.63 (d, J=8.1 Hz, 2H), 7.30 (d, J=7.8 Hz, 2H), 6.85 (d, J=9.0 Hz, 2H), 5.19 (s, 2H), 2.868 (t, J=7.5 Hz, 2H), 2.60 (t, J=7.2 Hz, 2H), 2.427 (s, 3H). Mass spectrum (ESI, m/z): Calcd. for $C_{21}H_{16}F_5NO_3S$, 456.1 (M−H), found 456.1.

Example 33

3-(4-[[3-(4-chlorophenyl)-5-(trifluoromethyl)-1,2-thiazol-4-yl]methoxy]-3-methylphenyl)propanoic Acid, Cpd 235

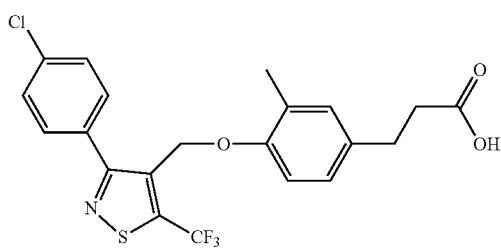 [SMILES: Cc1cc(CCC(=O)O)ccc1OCc1c(-c2ccc(Cl)cc2)nsc1C(F)(F)F]

The title compound was prepared according to the procedure described in Example 1 starting from 4-chlorobenzamide following Step 1-6 using ethyl 3-(4-hydroxy-3-methylphenyl)propanoate as coupling agent followed by hydrolysis to afford the desired product as an off-white solid. $^1$H NMR (300 MHz, CD$_3$OD) δ: 7.66 (d, J=8.4 Hz, 2H), 7.43 (d, J=8.7 Hz, 2H), 6.98 (s, 1H), 6.97 (d, J=7.8 Hz, 2H), 6.77 (d, J=7.8 Hz, 2H), 5.08 (s, 2H), 2.79 (t, J=8.1 Hz, 2H), 2.47 (t, J=7.5 Hz, 2H), 2.00 (s, 3H). Mass spectrum (ESI, m/z): Calcd. for C$_{21}$H$_{17}$ClF$_3$NO$_3$S, 454.1 (M−H), found 454.1.

Example 34

3-(4-[[3-(4-chlorophenyl)-5-(trifluoromethyl)-1,2-thiazol-4-yl]methoxy]-3-fluorophenyl)propanoic Acid, Cpd 68

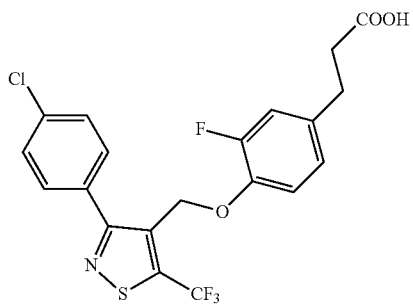 [SMILES: O=C(O)CCc1ccc(OCc2c(-c3ccc(Cl)cc3)nsc2C(F)(F)F)c(F)c1]

The title compound was prepared according to the procedure described in Example 1 starting from 4-chlorobenzamide following Step 1-6 using ethyl 3-(4-hydroxy-3-fluorophenyl)propanoate as coupling agent followed by hydrolysis to afford the desired product as an off-white solid. $^1$H NMR (400 MHz, CD$_3$OD) δ: 7.72 (d, J=8.4 Hz, 2H), 7.50 (d, J=8.4 Hz, 2H), 6.96-7.06 (m, 3H), 5.14 (s, 2H), 2.88 (t, J=7.6 Hz, 2H), 2.60 (t, J=7.6 Hz, 2H). Mass spectrum (ESI, m/z): Calcd. For C$_{20}$H$_{14}$ClF$_4$NO$_3$S, 458.0 (M−H), found 458.0.

Example 35

3-(4-((3-(4-cyclopropylphenyl)-5-(trifluoromethyl)isothiazol-4-yl)methoxy)-2,3-dimethylphenyl)propanoic Acid, Cpd 190

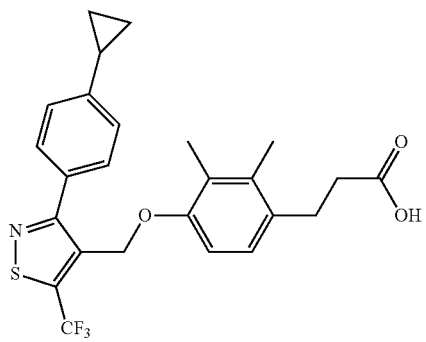 [SMILES: Cc1c(CCC(=O)O)ccc(OCc2c(-c3ccc(C4CC4)cc3)nsc2C(F)(F)F)c1C]

The title compound was prepared according to the procedure described in Example 1 starting from 4-cyclopropylbenzamide following Step 1-6 using ethyl 3-(4-hydroxy-2,3-dimethylphenyl)propanoate as coupling agent followed by hydrolysis to afford the desired product as an off-white solid. $^1$H NMR (400 MHz, CDCl$_3$) δ 7.60 (d, J=7.0 Hz, 2H), 7.12 (d, J=7.1 Hz, 2H), 6.98 (d, J=7.5 Hz, 1H), 6.70 (d, J=7.5 Hz, 1H), 5.01 (s, 2H), 2.98 (t, J=6.0 Hz, 2H), 2.65 (t, J=6.5 Hz, 2H), 2.26 (s, 3H), 2.15 (s, 3H), 1.96 (m, 1H), 1.03 (m, 2H), 0.76 (m, 2H).

Example 36

3-(3-bromo-4-[[3-(4-chlorophenyl)-5-(trifluoromethyl)-1,2-thiazol-4-yl]methoxy]phenyl)propanoic Acid, Cpd 69

Step 1: Methyl 3-(3-bromo-4-hydroxyphenyl)propanoate and Methyl 3-(3,5-dibromo-4-hydroxyphenyl)propanoate

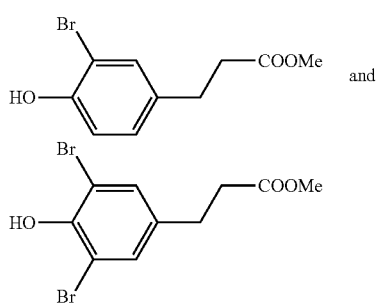

Into a 50-mL round-bottom flask, was placed methyl 3-(4-hydroxyphenyl)propanoate (1 g, 5.55 mmol, 1.00 equiv). This was followed by the addition of Br$_2$ (880 mg, 5.51 mmol, 1.00 equiv) dropwise with stirring at 0° C. To this was added methanol (25 mL). The resulting solution was stirred overnight at 0° C. in a water/ice bath. The reaction was then quenched by the addition of 5 of sodium carbonate. The resulting mixture was concentrated under vacuum. The residue was diluted with 10 mL of water, extracted with 1×20 mL of ethyl acetate and the organic layers were combained. The mixture was dried over anhydrous magnesium sulfate and concentrated. The residue was applied onto a silica gel column with ethyl acetate/petroleum ether (0-15.4%). This resulted in 1.1 g (83%) of methyl 3-(3-bromo-4-hydroxyphenyl)propanoate as a white solid and 0.3 g of methyl 3-(3,5-dibromo-4-hydroxyphenyl)propanoate as a white solid.

Step 2: 3-(3-bromo-4-[[3-(4-chlorophenyl)-5-(trifluoromethyl)-1,2-thiazol-4-yl]methoxy]phenyl)propanoic Acid

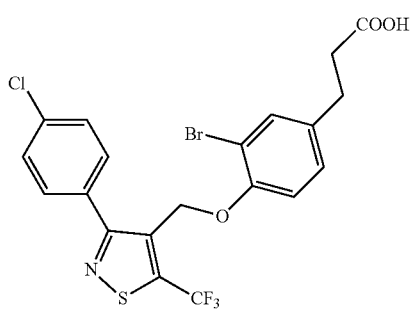 [SMILES: O=C(O)CCc1ccc(OCc2c(-c3ccc(Cl)cc3)nsc2C(F)(F)F)c(Br)c1]

The title compound was prepared according to the procedure described in Example 1 starting from 4-chlorobenzamide following Step 1-6 using ethyl 3-(4-hydroxy-3-bromophenyl) propanoate as coupling agent followed by hydrolysis to afford the desired product as an off-white solid. $^1$H NMR (400 MHz, CD$_3$OD) δ: 7.73 (d, J=8.8 Hz, 2H), 7.47 (d, J=8.8 Hz, 3H), 7.19 (d, J=8.4 Hz, 1H), 7.99 (d, J=8.4 Hz, 1H), 5.14 (s, 2H), 2.88 (t, J=7.6 Hz, 2H), 2.60 (t, J=7.6 Hz, 2H). Mass spectrum (ESI, m/z): Calcd. for C$_{20}$H$_{14}$BrClF$_3$NO$_3$S, 520.0 (M+H), found 520.0.

Example 37

3-(4-[[3-(4-chlorophenyl)-5-(trifluoromethyl)-1,2-thiazol-4-yl]methoxy]-3-ethylphenyl)propanoic Acid, Cpd 162

Step 1: Methyl 3-(3-ethyl-4-hydroxyphenyl)propanoate

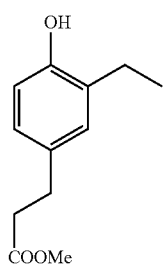

Into a 50-mL round-bottom flask purged and maintained with an inert atmosphere of nitrogen, was placed methyl 3-(3-bromo-4-hydroxyphenyl)propanoate (220 mg, 0.85 mmol, 1.00 equiv), Pd(dppf)Cl$_2$ (25.76 mg, 0.04 mmol, 0.04 equiv), Cs$_2$CO$_3$ (616.4 mg), tetrahydrofuran (5 mL), triethylborane (1.26 mL). The resulting solution was stirred overnight at 65° C. in an oil bath. The reaction was then quenched by the addition of 5 mL of water. The resulting mixture was concentrated under vacuum. The resulting solution was diluted with 20 mL of EA. The resulting mixture was washed with 3×10 mL of H$_2$O. The mixture was dried over anhydrous sodium sulfate. The residue was applied onto a silica gel column with ethylacetate/petroleum ether (10:90). This resulted in 300 mg (170%) of methyl 3-(3-ethyl-4-hydroxyphenyl)propanoate as colorless oil.

Step 2: 3-(4-[[3-(4-chlorophenyl)-5-(trifluoromethyl)-1,2-thiazol-4-yl]methoxy]-3-ethylphenyl)propanoic Acid

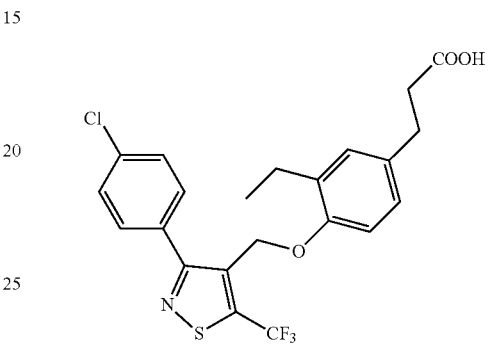

The title compound was prepared according to the procedure described in Example 1 starting from 4-chlorobenzamide following Steps 1-6 using ethyl 3-(4-hydroxy-3-ethylphenyl) propanoate as coupling agent to afford the desired product as an off-white solid. $^1$H NMR (400 MHz, CD$_3$OD) δ: 7.70 (d, J=9.2 Hz, 2H), 7.46 (d, J=8.8 Hz, 2H), 7.02 (t, J=9.6 Hz, 2H), 6.86 (d, J=8.0 Hz, 1H), 5.11 (s, 2H), 2.86 (t, J=7.6 Hz, 2H), 2.45-2.60 (m, 4H), 1.07 (t, J=7.6 Hz, 3H). Mass spectrum (ESI, m/z): Calcd. for C$_{22}$H$_{19}$ClF$_3$NO$_3$S, 468.1 (M−H), found 468.1.

Example 38

3-(4-[[3-(2H-1,3-benzodioxol-5-yl)-5-(trifluoromethyl)-1,2-thiazol-4-yl]methoxy]-3,5-difluorophenyl) propanoic Acid, Cpd 87

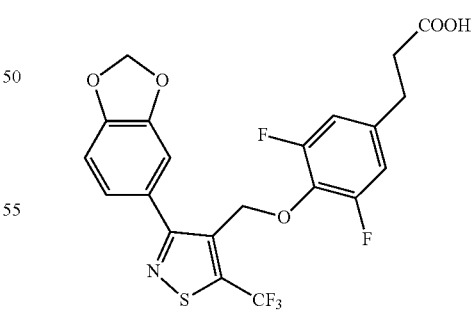

The title compound was prepared according to the procedure described in Example 1 starting from benzo[d][1,3]dioxole-5-carboxamide following Steps 1-6 using ethyl 3-(3,5-difluoro-4-hydroxyphenyl)propanoate as coupling agent followed by hydrolysis to afford the desired product as an off-white solid. $^1$H NMR (300 MHz, CD3OD) δ 7.25 (d, J=6.3 Hz, 1H), 7.17 (s, 1H), 6.84-6.88 (m, 3H), 5.16 (s, 2H), 2.83 (t, J=7.8 Hz, 2H), 2.54 (t, J=7.5 Hz, 2H). Mass spectrum (ESI, m/z): Calcd. for $C_{21}H_{14}F_5NO_5S$, 488.1 (M+H), found 488.1.

Example 39

3-(4-[[3-(4-chlorophenyl)-5-(trifluoromethyl)-4-yl]methoxy]-2-(trifluoromethyl)phenyl)propanoic Acid, Cpd 173

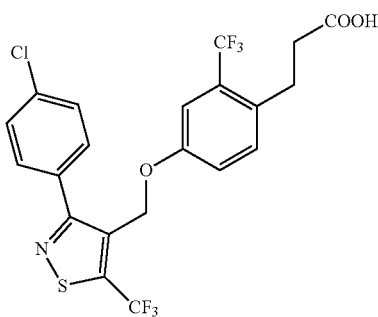 [SMILES: O=C(O)CCc1ccc(OCc2c(-c3ccc(Cl)cc3)nsc2C(F)(F)F)cc1C(F)(F)F]

The title compound was prepared according to the procedure described in Example 1 starting from 4-chlorobenzamide following Steps 1-6 using ethyl 3-(4-hydroxy-2-trifluoromethylphenyl)propanoate as coupling agent followed by hydrolysis to afford the desired product as an off-white solid. $^1$H NMR (300 MHz, $CD_3OD$) δ 7.66-7.78 (m, 2H), 7.41-7.51 (m, 3H), 7.12-7.16 (m, 2H), 5.20 (s, 2H), 3.05 (t, J=7.8 Hz, 2H), 2.58 (t, J=8.4 Hz, 2H). Mass spectrum (ESI, m/z): Calcd. for $C_{21}H_{14}ClF_6NO_3S$, 508.0 (M−H), found 508.0.

Example 40

3-(4-[[3-(4-ethylphenyl)-5-(trifluoromethyl)-1,2-thiazol-4-yl]methoxy]-3-methyl-2-(trifluoro-methyl)phenyl)propanoic Acid, Cpd 242

Step 1: [2-methoxy-6-(trifluoromethyl)phenyl]methanol

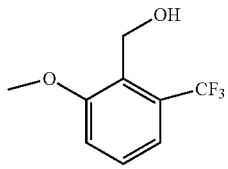

Into a 100-mL 3-necked round-bottom flask (1 atm) purged and maintained with an inert atmosphere of nitrogen, was placed 2-methoxy-6-(trifluoromethyl)benzoic acid (2.2 g, 9.99 mmol, 1.00 equiv), chlorobenzene (20 mL). This was followed by the addition of $BH_3.SMe_2$ (2M in tetrahydrofuran) (15.0 mL) dropwise with stirring at 0° C. The mixture was stirred 15 min at 0° C. Then the resulting solution was stirred for 2 h at 80° C. and continued stirring for 18 h at 130° C. in an oil bath. The reaction progress was monitored by TLC (PE:EtOAc=4:1). The reaction was then quenched by the addition of 20 mL of water, extracted with 3×20 mL of ethyl acetate and the organic layers combined and dried over anhydrous sodium sulfate and concentrated under vacuum. The residue was applied onto a silica gel column with ethyl acetate/petroleum ether (1:2). This resulted in 1.9 g (92%) of [2-methoxy-6-(trifluoromethyl)phenyl]methanol as a yellow solid.

Step 2: 2-(chloromethyl)-1-methoxy-3-(trifluoromethyl)benzene

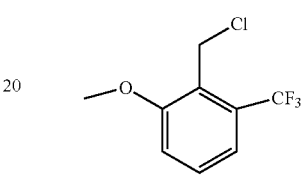

Into a 50-mL round-bottom flask, was placed [2-methoxy-6-(trifluoromethyl)phenyl] methanol (1.0 g, 4.85 mmol, 1.00 equiv), chloroform (10.0 g). This was followed by the addition of thionyl chloride (1.73 g, 14.54 mmol, 3.00 equiv) dropwise with stirring at 0° C. The resulting solution was stirred for 1 h at 30° C. The reaction progress was monitored by GCMS. The reaction was then quenched by the addition of 10 mL of water. The resulting solution was extracted with 3×15 mL of dichloromethane and the organic layers combined and dried over anhydrous sodium sulfate and concentrated under vacuum. This resulted in 1.2 g (crude) of 2-(chloromethyl)-1-methoxy-3-(trifluoromethyl)benzene as yellow oil. This residue could be used for the next step directly.

Step 3: 1-methoxy-2-methyl-3-(trifluoromethyl)benzene

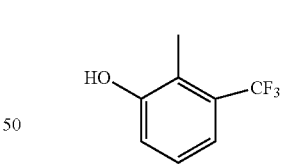

Into a 50-mL round-bottom flask, was placed 2-(chloromethyl)-1-methoxy-3-(trifluoromethyl)benzene (1.09 g, 4.85 mmol, 1.00 equiv), methanol (20 mL), Palladium carbon (1.50 g). The mixture was subjected to 2 atm of $H_2$. The resulting solution was stirred overnight at 30° C. The reaction progress was monitored by GCMS. The solids were filtered out. The 30 mL $H_2O$ was added to the solution. The resulting solution was extracted with 3×50 mL of pentane and the organic layers combined and dried over anhydrous sodium sulfate and concentrated under vacuum. This resulted in 0.74 g (80%) of 1-methoxy-2-methyl-3-(trifluoromethyl)benzene as light yellow oil. The residue could be used for the next step directly. Mass spectrum (GC, m/z): Calcd. for $C_9H_9F_3O$, 190.2 (M), found 190.2.

Step 4: 1-bromo-4-methoxy-3-methyl-2-(trifluoromethyl)benzene

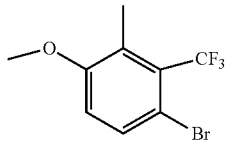

Into a 50-mL round-bottom flask, was placed 1-methoxy-2-methyl-3-(trifluoromethyl) benzene (700 mg, 3.68 mmol, 1.00 equiv), CCl$_4$ (3.0 mL). The mixture was cooled to 0° C. Br$_2$ (698 mg, 4.37 mmol, 1.19 equiv) and AcOH (0.5 mL) were added. The resulting solution was stirred for 1 h at 30° C. The reaction process was monitored by TLC (Petroleum ether). The reaction was then quenched by the addition of 10 mL of saturated sodium bicarbonate. The resulting solution was extracted with 3×10 mL of dichloromethane and the organic layers combined and dried over anhydrous sodium sulfate and concentrated under vacuum. The residue was applied onto a silica gel column with petroleum ether. This resulted in 0.7 g (71%) of 1-bromo-4-methoxy-3-methyl-2-(trifluoromethyl)benzene as yellow oil.

Step 5: Ethyl (2E)-3-[4-methoxy-3-methyl-2-(trifluoromethyl)phenyl]prop-2-enoate

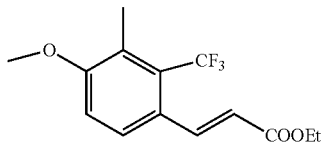 [SMILES: CCOC(=O)/C=C/c1ccc(OC)c(C)c1C(F)(F)F]

Into a 10-mL sealed tube (1 atm) purged and maintained with an inert atmosphere of nitrogen, was placed 1-bromo-4-methoxy-3-methyl-2-(trifluoromethyl)benzene (300 mg, 1.12 mmol, 1.00 equiv), ethyl prop-2-enoate (560 mg, 5.59 mmol, 5.02 equiv), P(Tol)$_3$ (61 mg, 0.20 mmol, 0.18 equiv), Pd(OAc)$_2$ (30 mg, 0.13 mmol, 0.12 equiv), triethylamine (566 mg, 5.59 mmol, 5.02 equiv), N,N-dimethylformamide (2.0 mL). The resulting solution was stirred overnight at 110° C. in an oil bath. The reaction progress was monitored by GCMS. The reaction was then quenched by the addition of 10 mL of water. The resulting solution was extracted with 3×15 mL of ethyl acetate and the organic layers combined. The resulting mixture was washed with 2×20 mL of H$_2$O. The mixture was dried over anhydrous sodium sulfate. The residue was applied onto a silica gel column with ethyl acetate/petroleum ether (1:6). This resulted in 0.16 g (50%) of ethyl (2E)-3-[4-methoxy-3-methyl-2-(trifluoromethyl)phenyl]prop-2-enoate as a yellow solid.

Step 6: Ethyl 3-[4-methoxy-3-methyl-2-(trifluoromethyl)phenyl]propanoate

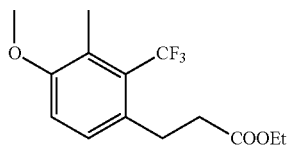 [SMILES: CCOC(=O)CCc1ccc(OC)c(C)c1C(F)(F)F]

Into a 50-mL round-bottom flask, was placed ethyl (2E)-3-[4-methoxy-3-methyl-2-(trifluoromethyl)phenyl]prop-2-enoate (230 mg, 0.80 mmol, 1.00 equiv), Palladium carbon (300 mg), methanol (15 mL). The mixture was subjected to 2 atm of H$_2$. The resulting solution was stirred overnight at 30° C. The reaction progress was monitored by LCMS. The solids were filtered out. The resulting mixture was concentrated under vacuum. This resulted in 0.22 g of ethyl 3-[4-methoxy-3-methyl-2-(trifluoromethyl)phenyl]propanoate as colorless oil. The crude could be used for the next step directly.

Step 7: Ethyl 3-[4-hydroxy-3-methyl-2-(trifluoromethyl)phenyl]propanoate

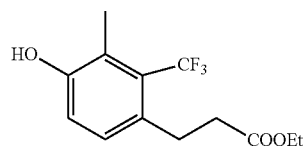 [SMILES: CCOC(=O)CCc1ccc(O)c(C)c1C(F)(F)F]

Into a 50-mL round-bottom flask (1 atm) purged and maintained with an inert atmosphere of nitrogen, was placed ethyl 3-[4-methoxy-3-methyl-2-(trifluoromethyl)phenyl]propanoate (210 mg, 0.72 mmol, 1.00 equiv), dichloromethane (2.0 mL). This was followed by the addition of BBr$_3$ (1N in dichloromethane) (1.45 mL, 2.00 equiv) dropwise with stirring at −78° C. The resulting solution was warmed to room temperature (30° C.) and stirred for 2 h. The reaction progress was monitored by LCMS. The reaction was then quenched by the addition of 10 mL of water. The resulting solution was extracted with 3×10 mL of dichloromethane and the organic layers combined and dried over anhydrous sodium sulfate and concentrated under vacuum. The residue was purified by TLC-Plate with petroleum ether/EtOAc=4:1. This resulted in 0.130 g (65%) of ethyl 3-[4-hydroxy-3-methyl-2-(trifluoromethyl)phenyl]propanoate as a yellow solid. Mass spectrum (ESI, m/z): Calcd. for C$_{13}$H$_{15}$F$_3$O$_3$, 275.1 (M−H), found 275.1.

Step 8: 3-(4-[[3-(4-ethylphenyl)-5-(trifluoromethyl)-1,2-thiazol-4-yl]methoxy]-3-methyl-2-(trifluoromethyl)phenyl)propanoic Acid

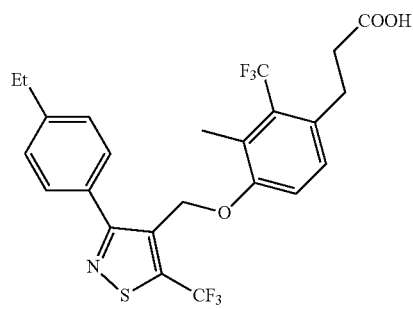 [SMILES: CCc1ccc(-c2nsc(C(F)(F)F)c2COc2ccc(CCC(=O)O)c(C(F)(F)F)c2C)cc1]

The title compound was prepared according to the procedure described in Example 1 starting following Step 5 and 6 using ethyl 3-[4-hydroxy-3-methyl-2-(trifluoromethyl)phenyl]propanoate as coupling agent to afford the desired product as an off-white solid. $^1$H-NMR (300 Hz, CD$_3$OD):

δ 7.57 (d, J=8.1 Hz, 2H), 7.30 (d, J=8.1 Hz, 2H), 7.18 (d, J=8.0 Hz, 1H), 7.11 (d, J=8.0 Hz, 1H), 5.19 (s, 2H), 3.03-3.08 (m, 2H), 2.69 (d, $J_1$=15.5 Hz. $J_2$=7.5 Hz, 2H), 2.53 (t, J=8.1 Hz, 2H), 2.15 (s, 3H), 1.25 (t, J=7.5 Hz, 3H). Mass spectrum (ESI, m/z): Calcd. for $C_{24}H_{21}F_6NO_3S$, 518.1 (M+H), found 518.1.

Example 41

3-(4-[[3-(4-ethylphenyl)-5-(trifluoromethyl)-1,2-thiazol-4-yl]methoxy]-2-fluoro-3-(trifluoromethyl)phenyl)propanoic Acid, Cpd 157

Step 1: 1-bromo-2-fluoro-4-methoxybenzene

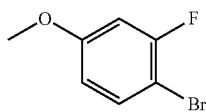

Into a 250-mL round-bottom flask, was placed 4-bromo-3-fluorophenol (5.0 g, 26.18 mmol, 1.00 equiv), tetrahydrofuran (50 mL). This was followed by the addition of potassium hydroxide (2.94 g, 52.40 mmol, 2.00 equiv) in portions. To this was added $CH_3I$ (5.6 g, 39.45 mmol, 1.51 equiv) dropwise. The resulting solution was stirred for 4 h at 30° C. TLC (Petroleum ether:EtOAc=1:4) controlled the reaction process. The reaction was then quenched by the addition of 30 mL of water. The resulting solution was extracted with 3×30 mL of ethyl acetate and the organic layers combined and dried over anhydrous sodium sulfate and concentrated under vacuum. The residue was applied onto a silica gel column with petroleum ether. This resulted in 5.2 g (97%) of 1-bromo-2-fluoro-4-methoxybenzene as yellow oil.

Step 2: 1-bromo-2-fluoro-3-iodo-4-methoxybenzene

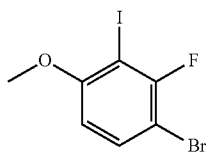

Into a 25-mL round-bottom flask (1 atm) purged and maintained with an inert atmosphere of nitrogen, was placed (i-Pr)$_2$NH (1.26 g, 12.48 mmol, 1.25 equiv), tetrahydrofuran (7 mL). This was followed by the addition of n-BuLi (2.5M in hexane) (4.8 mL) dropwise with stirring at −78° C. The mixture was stirred for 1 h at −78° C. Then this solution was added to the solution a solution of 1-bromo-2-fluoro-4-methoxybenzene (2.04 g, 9.95 mmol, 1.00 equiv) in tetrahydrofuran (5 mL) at −78 degree C. and stirred for 30 min, then I$_2$ (3.048 g, 12.00 mmol, 1.2 equiv) was added. The resulting solution was stirred for 30 min at −78° C. in a liquid nitrogen bath. The reaction progress was monitored by GCMS. The reaction was then quenched by the addition of 10 mL of water. The resulting solution was extracted with 2×20 mL of ethyl acetate and the organic layers combined and dried over anhydrous sodium sulfate and concentrated under vacuum. The residue was applied onto a silica gel column with petroleum ether. This resulted in 2.0 g (61%) of 1-bromo-2-fluoro-3-iodo-4-methoxybenzene as a light yellow solid. Mass spectrum (GC, m/z): Calcd. for $C_7H_5BrFIO$, 330.9 (M), found 330.9.

Step 3: 1-bromo-2-fluoro-4-methoxy-3-(trifluoromethyl)benzene

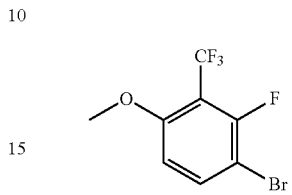

Into a 8-mL sealed tube (1 atm) purged and maintained with an inert atmosphere of nitrogen, was placed 1-bromo-2-fluoro-3-iodo-4-methoxybenzene (200 mg, 0.60 mmol, 1.00 equiv), methyl 2,2-difluoro-2-(fluorosulfonyl)acetate (930 mg, 4.84 mmol, 8.01 equiv), CuI (920 mg, 4.83 mmol, 7.99 equiv), N,N-dimethylformamide (0.7 mL), NMP (0.7 mL). The resulting solution was stirred overnight at 100° C. in an oil bath. The reaction progress was monitored by GCMS. The reaction was then quenched by the addition of 10 mL of water. The resulting solution was extracted with 6×10 mL of ethyl acetate and the organic layers combined and dried over anhydrous sodium sulfate and concentrated under vacuum. The residue was applied onto a silica gel column with petroleum ether. This resulted in 0.135 g (82%) of 1-bromo-2-fluoro-4-methoxy-3-(trifluoromethyl)benzene as a yellow solid.

Step 4: 2-fluoro-4-methoxy-3-(trifluoromethyl)benzaldehyde

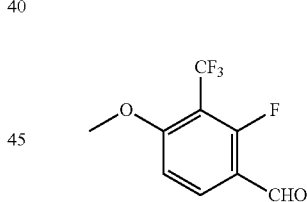

Into a 50-mL round-bottom flask purged and maintained with an inert atmosphere of nitrogen, was placed 1-bromo-2-fluoro-4-methoxy-3-(trifluoromethyl)benzene (380 mg, 1.39 mmol, 1.00 equiv), tetrahydrofuran (5.0 mL). This was followed by the addition of n-BuLi (2.5M) (0.62 mL, 1.10 equiv) dropwise with stirring at −78° C. The mixture was stirred for 1 h at −78° C. To this was added N,N-dimethylformamide (1.0 mL) and the resulting solution was stirred for 30 min at −78° C. in a liquid nitrogen bath. The reaction progress was monitored by GCMS. The reaction was then quenched by the addition of 2 mL of water. The resulting solution was extracted with 3×10 mL of ethyl acetate and the organic layers combined and dried in an oven under reduced pressure. The residue was applied onto a silica gel column with ethyl acetate/petroleum ether (1:4). This resulted in 0.140 g (45%) of 2-fluoro-4-methoxy-3-(trifluoromethyl)benzaldehyde as a light yellow solid. Mass spectrum (GC, m/z): Calcd. for $C_9H_6F_4O_2$, 222.0 (M), found 222.0.

Step 5: Ethyl (2Z)-3-[2-fluoro-4-methoxy-3-(trifluoromethyl)phenyl]prop-2-enoate

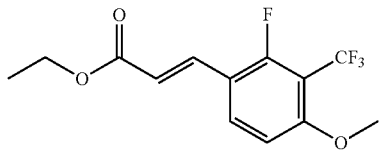 [SMILES: CCOC(=O)/C=C/c1ccc(OC)c(C(F)(F)F)c1F]

Into a 8-mL sealed tube (1 atm) purged and maintained with an inert atmosphere of nitrogen, was placed 2-fluoro-4-methoxy-3-(trifluoromethyl)benzaldehyde (143 mg, 0.64 mmol, 1.00 equiv), ethyl 2-(triphenyl-^[5]-phosphanylidene)acetate (336 mg, 0.96 mmol, 1.50 equiv), toluene (1.5 mL). The resulting solution was stirred overnight at 100° C. in an oil bath. The reaction process was monitored by TLC with petroleum ether/EtOAc=4:1. The resulting mixture was concentrated under vacuum. The residue was applied onto a silica gel column with ethyl acetate/petroleum ether (1:6). This resulted in 0.171 g (91%) of ethyl (2Z)-3-[2-fluoro-4-methoxy-3-(trifluoromethyl)phenyl]prop-2-enoate as a yellow solid.

Step 5: Ethyl 3-[2-fluoro-4-methoxy-3-(trifluoromethyl)phenyl]propanoate

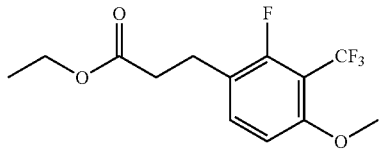 [SMILES: CCOC(=O)CCc1ccc(OC)c(C(F)(F)F)c1F]

Into a 50-mL round-bottom flask, was placed ethyl (2Z)-3-[2-fluoro-4-methoxy-3-(trifluoromethyl)phenyl]prop-2-enoate (200 mg, 0.68 mmol, 1.00 equiv), Palladium carbon (300 mg), methanol (15 mL). The solution was subjected to 2 atm of $H_2$. The resulting solution was stirred overnight at 30° C. The reaction progress was monitored by LCMS. The solids were collected by filtration. The resulting mixture was concentrated under vacuum. This resulted in 0.21 g of ethyl 3-[2-fluoro-4-methoxy-3-(trifluoromethyl)phenyl]propanoate as yellow oil. Mass spectrum (ESI, m/z): Calcd. for $C_{13}H_{14}F_4O_3$, 295.1 (M+H), found 295.1.

Step 6: Ethyl 3-[2-fluoro-4-hydroxy-3-(trifluoromethyl)phenyl]propanoate

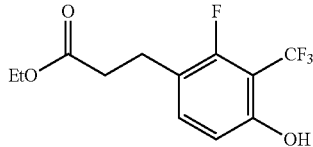 [SMILES: CCOC(=O)CCc1ccc(O)c(C(F)(F)F)c1F]

Into a 8-mL sealed tube (1 atm) purged and maintained with an inert atmosphere of nitrogen, was placed ethyl 3-[2-fluoro-4-methoxy-3-(trifluoromethyl)phenyl]propanoate (200 mg, 0.68 mmol, 1.00 equiv), dichloromethane (1.0 mL). This was followed by the addition of $BBr_3$ (1N in dichloromethane) (1.36 mL, 2.00 equiv) dropwise with stirring at −78° C. The resulting solution was warmed to room temperature and stirred for 2 h at 30° C. The reaction progress was monitored by LCMS. The reaction was then quenched by the addition of 5 mL of water. The resulting solution was extracted with 3×10 mL of dichloromethane and the organic layers combined and dried over anhydrous sodium sulfate and concentrated under vacuum. The residue was purified by TLC-Plate with petroleum ether/EtOAc=3:1. This resulted in 85 mg (45%) of ethyl 3-[2-fluoro-4-hydroxy-3-(trifluoromethyl)phenyl]propanoate as a light yellow solid. Mass spectrum (ESI, m/z): Calcd. for $C_{12}H_{12}F_4O_3$, 279.1 (M−H), found 279.1.

Step 7: 3-(4-[[3-(4-ethylphenyl)-5-(trifluoromethyl)-1,2-thiazol-4-yl]methoxy]-2-fluoro-3-(trifluoromethyl)phenyl)propanoic Acid

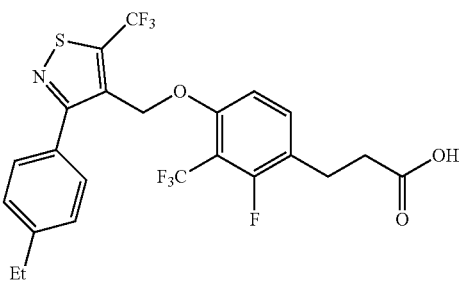 [SMILES: CCc1ccc(-c2nsc(C(F)(F)F)c2COc2ccc(CCC(=O)O)c(F)c2C(F)(F)F)cc1]

The title compound was prepared according to the procedure described in Example 1 starting following Step 5 and 6 using ethyl 3-[4-hydroxy-3-trifluoromethyl-2-(fluoro)phenyl]propanoate as coupling agent to afford the desired product as an off-white solid. $^1$H-NMR (300 Hz, $CD_3OD$): δ 7.58 (d, J=8.1 Hz, 2H), 7.50 (t, J=7.8 Hz, 1H), 7.31 (d, J=8.1 Hz, 2H), 6.97 (d, J=9.0 Hz, 1H), 5.17 (s, 2H), 2.96 (t, J=7.8 Hz, 2H), 2.73 (d, $J_1$=14.9 Hz, J=7.5 Hz, 2H), 2.62 (t, J=8.1 Hz, 2H), 1.28 (t, J=7.5 Hz, 3H). Mass spectrum (ESI, m/z): Calcd. for $C_{23}H_{18}F_7NO_3S$, 522.1 (M+H), found 522.1.

Example 42

3-(4-[[3-(4-ethylphenyl)-5-(trifluoromethyl)-1,2-thiazol-4-yl]methoxy]-3,5-bis(trifluoromethyl)phenyl)propanoic Acid, Cpd 243

Step 1: 4-methoxy-3,5-bis(trifluoromethyl)benzonitrile

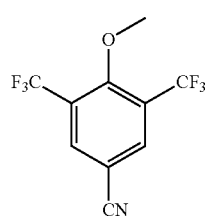 [SMILES: COc1c(C(F)(F)F)cc(C#N)cc1C(F)(F)F]

Into a 50-mL round-bottom flask, was placed methanol (10 mL) and cooled to 0° C. Na (337 mg, 14.65 mmol, 2.00 equiv) was added. When the Na was reacted completely, 4-chloro-3,5-bis(trifluoromethyl)benzonitrile (2.0 g, 7.31 mmol, 1.00 equiv) was added at 0° C. The resulting solution was stirred for 1 h at 30° C. The reaction progress was monitored by GCMS. The reaction was then quenched by the addition of 10 mL of water. The resulting solution was extracted with 3×20 mL of ethyl acetate and the organic layers combined. The resulting mixture was washed with 2×20 mL of sodium chloride. The mixture was dried over anhydrous sodium sulfate and concentrated under vacuum. The residue could been used for the next step directly. This resulted in 1.33 g of 4-methoxy-3,5-bis(trifluoromethyl) benzonitrile as yellow oil. Mass spectrum (GC, m/z): Calcd. for $C_{10}H_5F_6NO$, 269.0 (M), found 269.0.

Step 2:
4-methoxy-3,5-bis(trifluoromethyl)benzaldehyde

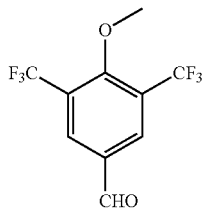

Into a 100-mL round-bottom flask, was placed 4-methoxy-3,5-bis(trifluoromethyl) benzonitrile (868 mg, 3.23 mmol, 1.00 equiv), a solution of $NaH_2PO_2 \cdot H_2O$ in water (10.0 mL), acetic acid (10.0 mL), pyridine (20.0 mL), Raney-Ni (0.9 g). The resulting solution was stirred for 3 h at 45° C. in an oil bath. The reaction progress was monitored by GCMS. The solids were filtered out. 20.0 mL EtOAc and 20.0 mL $H_2O$ were added into the mixture. The organic phase was washed by $H_2O$ with 2*20 mL and dried over $Na_2SO_4$. Ths solvent was remoned and the residue was applied onto a silica gel column with ethyl acetate/petroleum ether (1:20). This resulted in 0.43 g (49%) of 4-methoxy-3,5-bis(trifluoromethyl) benzaldehyde as yellow oil. Mass spectrum (GC, m/z): Calcd. for $C_{10}H_6F_6O_2$, 272.0 (M), found 272.0.

Step 3: Ethyl (2Z)-3-[4-methoxy-3,5-bis(trifluoromethyl)phenyl]prop-2-enoate

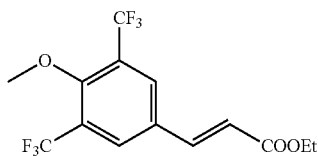 [SMILES: CCOC(=O)/C=C/c1cc(C(F)(F)F)c(OC)c(C(F)(F)F)c1]

Into a 50-mL round-bottom flask purged and maintained with an inert atmosphere of nitrogen, was placed 4-methoxy-3,5-bis(trifluoromethyl)benzaldehyde (430 mg, 1.58 mmol, 1.00 equiv), ethyl 2-(triphenyl-^[5]-phosphanylidene)acetate (825 mg, 2.37 mmol, 1.50 equiv), toluene (10.0 mL). The resulting solution was stirred overnight at 90° C. in an oil bath. The reaction progress was monitored by LCMS. The resulting mixture was concentrated under vacuum. The residue was applied onto a silica gel column with ethyl acetate/petroleum ether (1:6). This resulted in 0.28 g (52%) of ethyl (2Z)-3-[4-methoxy-3,5-bis(trifluoromethyl) phenyl]prop-2-enoate as yellow oil. Mass spectrum (ESI, m/z): Calcd. for $C_{14}H_{12}F_6O_3$, 343.1 (M+H), found 343.1.

Step 4: Ethyl 3-[4-methoxy-3,5-bis(trifluoromethyl)phenyl]propanoate

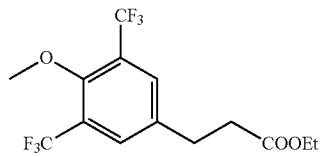 [SMILES: CCOC(=O)CCc1cc(C(F)(F)F)c(OC)c(C(F)(F)F)c1]

Into a 50-mL round-bottom flask, was placed ethyl (2Z)-3-[4-methoxy-3,5-bis(trifluoromethyl)phenyl]prop-2-enoate (280 mg, 0.82 mmol, 1.00 equiv), Palladium carbon (0.28 g), methanol (10 mL). The mixture was subjected to 2 atm of $H_2$ and stirred overnight at 25° C. The reaction progress was monitored by LCMS. The solids were filtered out. The resulting mixture was concentrated under vacuum. This resulted in 0.28 g (99%) of ethyl 3-[4-methoxy-3,5-bis(trifluoromethyl)phenyl]propanoate as yellow oil. Mass spectrum (ESI, m/z): Calcd. for $C_{14}H_{14}F_6O_3$, 345.1 (M+H), found 345.1.

Step 5: Ethyl 3-[4-hydroxy-3,5-bis(trifluoromethyl)phenyl]propanoate

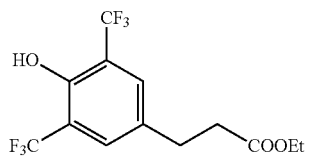

Into a 50-mL round-bottom flask (1 atm) purged and maintained with an inert atmosphere of nitrogen, was placed ethyl 3-[4-methoxy-3,5-bis(trifluoromethyl)phenyl]propanoate (270 mg, 0.78 mmol, 1.00 equiv), dichloromethane (5.0 mL). That was followed by adding $BBr_3$ (1N in dichloromethane) (1.57 mL) dropwise at −78 degree C. The resulting solution was warmed to room temperature and stirred for 2 h at 25° C. The reaction progress was monitored by LCMS. The reaction was then quenched by the addition of 5 mL of water, extracted with 3×10 mL of dichloromethane and the organic layers combined and dried over anhydrous sodium sulfate and concentrated under vacuum. The residue was applied onto a silica gel column with ethyl acetate/petroleum ether (1:4). This resulted in 0.15 g (58%) of ethyl 3-[4-hydroxy-3,5-bis(trifluoromethyl)phenyl]propanoate as yellow oil. Mass spectrum (ESI, m/z): Calcd. for $C_{13}H_{12}F_6O_3$, 329.1 (M−H), found 329.1.

Step 6: 3-(4-[[3-(4-ethylphenyl)-5-(trifluoromethyl)-1,2-thiazol-4-yl]methoxy]-3,5-bis(trifluoromethyl)phenyl)propanoic Acid

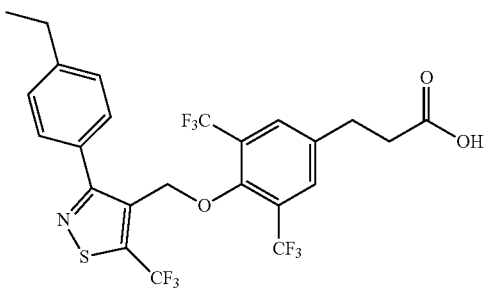 [SMILES: CCc1ccc(-c2nsc(C(F)(F)F)c2COc2c(C(F)(F)F)cc(CCC(=O)O)cc2C(F)(F)F)cc1]

The title compound was prepared according to the procedure described in Example 1 starting following Step 5 and 6 coupling (3-(4-ethylphenyl)-5-(trifluoromethyl)isothiazol-4-yl)methyl methanesulfonate and ethyl 3-(4-hydroxy-3,5-bis(trifluoromethyl)phenyl)propanoate followed by hydrolysis to afford the desired product as an off-white solid. $^1$H-NMR (300 Hz, CD$_3$OD): δ 7.75 (s, 1H), 7.69 (s, 1H), 7.46 (d, J=8.4 Hz, 2H), 7.28 (d, J=8.1 Hz, 2H), 5.36 (s, 2H), 2.67-2.74 (m, 4H), 2.45 (t, J=7.2 Hz, 2H), 1.27 (t, J=7.5 Hz, 3H). Mass spectrum (ESI, m/z): Calcd. for C$_{24}$H$_{18}$F$_9$NO$_3$S, 572.1 (M+H), found 572.1.

Example 43

3-(4-[[3-(2, 6-difluoro-4-methoxyphenyl)-5-(trifluoromethyl)-1,2-thiazol-4-yl]methoxy]-3,5-difluorophenyl)propanoic Acid, Cpd 197

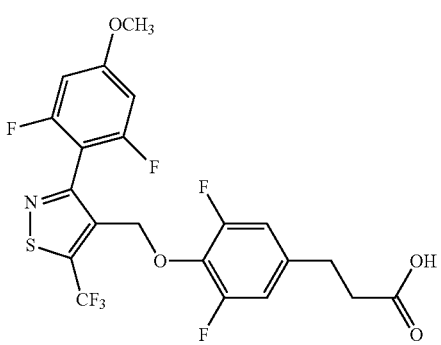 [SMILES: COc1cc(F)c(-c2nsc(C(F)(F)F)c2COc2c(F)cc(CCC(=O)O)cc2F)c(F)c1]

The title compound was prepared according to the procedure described in Example 1 starting following Step 5 and 6 coupling (3-(2,6-difluoro-4-methoxyphenyl)-5-(trifluoromethyl) isothiazol-4-yl)methyl methanesulfonate and ethyl 3-(4-hydroxy-3,5-difluoro) phenyl)propanoate followed by hydrolysis to afford the desired product as an off-white solid. $^1$H NMR (300 MHz, CD$_3$OD) δ 6.55-6.69 (m, 4H), 5.01 (s, 2H), 3.78 (s, 3H), 2.70 (t, J=7.2 Hz, 2H), 2.47 (t, J=7.5 Hz, 2H). Mass spectrum (ESI, m/z): Calcd. for C$_{21}$H$_{14}$F$_7$NO$_4$S, 508.1 (M−H), found 507.9.

Example 44

3-(3,5-difluoro-4-[[3-(4-methoxyphenyl)-5-(trifluoromethyl)-1,2-thiazol-4-yl]methoxy] phenyl)propanoic Acid, Cpd 99

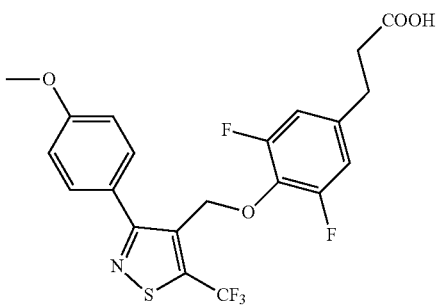 [SMILES: COc1ccc(-c2nsc(C(F)(F)F)c2COc2c(F)cc(CCC(=O)O)cc2F)cc1]

The title compound was prepared according to the procedure described in Example 1 starting following Step 5 and 6 coupling (3-(4-methoxyphenyl)-5-(trifluoromethyl) isothiazol-4-yl)methyl methanesulfonate and ethyl 3-(4-hydroxy-3,5-difluoro) phenyl)propanoate followed by hydrolysis to afford the desired product as an off-white solid. $^1$H NMR (300 MHz, CD$_3$OD) δ 7.69 (d, J=6.6 Hz, 2H), 6.99 (d, J=9.0 Hz, 2H), 6.83 (d, J=9.6 Hz, 2H), 5.15 (s, 2H), 3.84 (s, 3H), 2.83 (t, J=7.5 Hz, 2H), 2.50 (t, J=7.8 Hz, 2H). Mass spectrum (ESI, m/z): Calcd. for C$_{21}$H$_{16}$F$_5$NO$_4$S, 472.1 (M−H), found 472.1.

Example 45

3-(4-[[3-(3-fluoro-4-methoxyphenyl)-5-(trifluoromethyl)-1,2-thiazol-4-yl]methoxy]-2,3-dimethylphenyl)propanoic Acid, Cpd 172

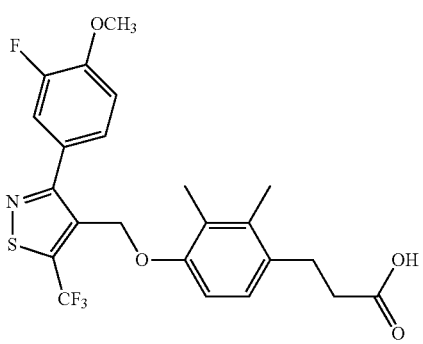 [SMILES: COc1ccc(-c2nsc(C(F)(F)F)c2COc2ccc(CCC(=O)O)c(C)c2C)cc1F]

The title compound was prepared according to the procedure described in Example 1 starting following Step 5 and 6 coupling (5-(trifluoromethyl)-3-(3-fluoro-4-methoxyphenyl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, DMSO) δ 12.12 (s, 1H), 7.48-7.58 (m, 2H), 7.31 (t, J=8.7 Hz, 1H), 6.96 (d, J=8.4 Hz, 1H), 6.80 (d, J=8.4 Hz, 1H), 5.09 (s, 2H), 3.89 (s, 3H), 2.76 (t, J=7.2 Hz, 2H), 2.41 (t, J=7.5 Hz, 2H), 2.14 (s, 3H), 1.97 (s, 3H). Mass spectrum (ESI, m/z): Calcd. for C$_{23}$H$_{21}$F$_4$NO$_4$S, 482.1 (M−H), found 482.0.

Example 46

3-(3,5-difluoro-4-[[3-(3-fluoro-4-methoxyphenyl)-5-(trifluoromethyl)-1,2-thiazol-4-yl]methoxy] phenyl)propanoic Acid, Cpd 237

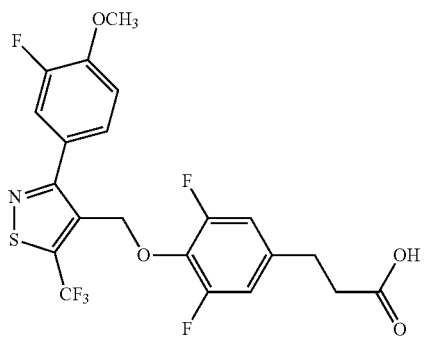 [SMILES: COc1ccc(-c2nsc(C(F)(F)F)c2COc2c(F)cc(CCC(=O)O)cc2F)cc1F]

The title compound was prepared according to the procedure described in Example 1 starting following Step 5 and 6 coupling (3-(3-fluoro-4-methoxyphenyl)-5-(trifluoromethyl)isothiazol-4-yl)methyl methanesulfonate and ethyl 3-(4-hydroxy-3,5-difluorophenyl)propanoate followed by hydrolysis to afford the desired product as an off-white solid. $^1$H NMR (400 MHz, CD$_3$OD) δ 7.55-7.63 (m, 2H), 7.22 (t, J=8.8 Hz, 2H), 6.86-6.91 (m, 2H), 5.22 (s, 2H), 3.97 (s, 3H), 2.88 (t, J=7.2 Hz, 2H), 2.60 (t, J=7.5 Hz, 2H). Mass spectrum (ESI, m/z): Calcd. for C$_{21}$H$_{15}$F$_6$NO$_4$S, 490.1 (M−H), found 489.9.

Example 47

3-(3,5-difluoro-4-[[3-(2-fluoro-4-methoxyphenyl)-5-(trifluoromethyl)-1,2-thiazol-4-yl]methoxy] phenyl)propanoic Acid, Cpd 151

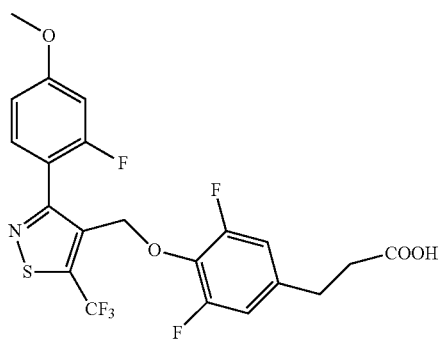 [SMILES: COc1ccc(-c2nsc(C(F)(F)F)c2COc2c(F)cc(CCC(=O)O)cc2F)c(F)c1]

The title compound was prepared according to the procedure described in Example 1 starting following Step 5 and 6 coupling (3-(2-fluoro-4-methoxyphenyl)-5-(trifluoromethyl)isothiazol-4-yl)methyl methanesulfonate and ethyl 3-(4-hydroxy-3,5-difluorophenyl)propanoate followed by hydrolysis to afford the desired product as an off-white solid. $^1$H NMR (300 MHz, CD$_3$OD) δ 7.25-7.30 (m, 1H), 6.70-6.83 (m, 4H), 5.15 (s, 2H), 3.87 (s, 3H), 2.82 (t, J=7.8 Hz, 2H), 2.57 (t, J=7.8 Hz, 2H). Mass spectrum (ESI, m/z): Calcd. for C$_{21}$H$_{17}$F$_6$NO$_4$S, 490.1 (M−H), found 489.9.

Example 48

3-(3,5-difluoro-4-[[5-(trifluoromethyl)-3-[4-(trifluoromethyl)phenyl]-1,2-thiazol-4-yl]methoxy] phenyl)propanoic Acid, Cpd 121

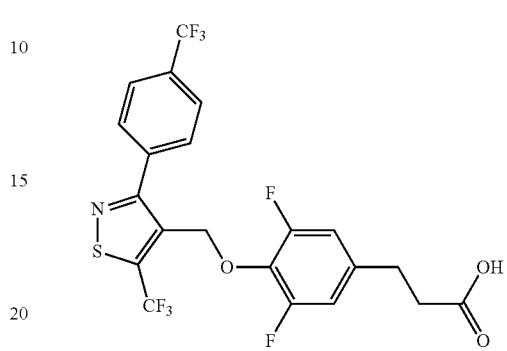

The title compound was prepared according to the procedure described in Example 1 starting following Step 5 and 6 coupling (5-(trifluoromethyl)-3-(4-(trifluoromethyl)phenyl)isothiazol-4-yl)methyl methanesulfonate and ethyl 3-(4-hydroxy-3,5-difluorophenyl)propanoate followed by hydrolysis to afford the desired product as an off-white solid. $^1$H NMR (300 MHz, CD$_3$OD) δ 7.99 (d, J=8.1 Hz, 2H), 7.82 (d, J=8.1 Hz, 2H), 6.86 (d, J=13.5 Hz, 2H), 5.23 (s, 2H), 2.87 (t, J=7.2 Hz, 2H), 2.60 (t, J=7.5 Hz, 2H). Mass spectrum (ESI, m/z): Calcd. for C$_{21}$H$_{13}$F$_8$NO$_3$S, 510.1 (M−H), found 509.9.

Example 49

3-(4-[[3-(6-methoxypyridin-3-yl)-5-(trifluoromethyl)-1,2-thiazol-4-yl]methoxy]-2,3-dimethylphenyl)propanoic Acid, Cpd 167

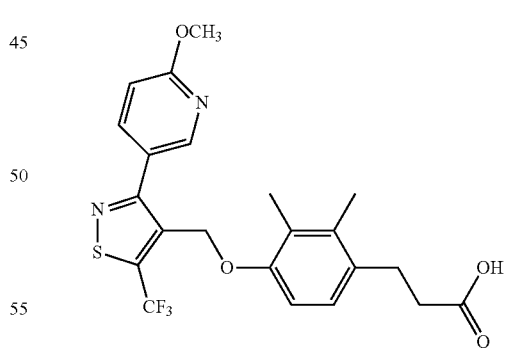

The title compound was prepared according to the procedure described in Example 1 starting following Step 5 and 6 coupling (3-(6-methoxypyridin-3-yl)-5-(trifluoromethyl)isothiazol-4-yl)methyl methanesulfonate and 3-(4-hydroxy-2,3-dimethylphenyl)propanoic acid followed by hydrolysis to afford the desired product as an off-white solid. $^1$H NMR (300 MHz, CD$_3$OD) δ 8.47 (s, 1H), 7.99-8.03 (m, 1H), 6.98 (d, J=8.4 Hz, 1H), 6.87 (d, J=8.7 Hz, 1H), 6.74 (d, J=8.1 Hz, 1H), 5.11 (s, 2H), 3.99 (s, 3H), 2.91 (t, J=7.2 Hz, 2H), 2.51

(t, J=7.5 Hz, 2H), 2.23 (s, 3H), 2.03 (s, 3H). Mass spectrum (ESI, m/z): Calcd. for $C_{20}H_{15}F_5N_2O_4S$, 467.1 (M−H), found 467.0.

Example 50

3-(2, 3-dimethyl-4-[[5-(trifluoromethyl)-3-[4-(trifluoromethyl)phenyl]-1,2-thiazol-4-yl]methoxy]phenyl)propanoic Acid, Cpd 224

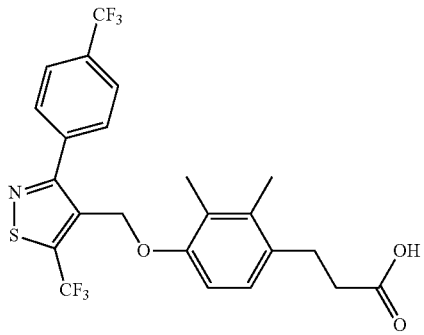 [SMILES: Cc1c(CCC(=O)O)ccc(OCc2c(-c3ccc(C(F)(F)F)cc3)nsc2C(F)(F)F)c1C]

The title compound was prepared according to the procedure described in Example 1 starting following Step 5 and 6 coupling (5-(trifluoromethyl)-3-(4-trifluoromethylphenyl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, CD$_3$OD) δ7.89 (d, J=8.1 Hz, 2H), 7.76 (d, J=8.1 Hz, 2H), 5.14 (s, 2H), 3.89 (s, 3H), 2.88 (t, J=7.2 Hz, 2H), 2.48 (t, J=7.5 Hz, 2H), 2.22 (s, 3H), 1.76 (s, 3H). Mass spectrum (ESI, m/z): Calcd. for $C_{23}H_{19}F_6NO_3S$, 502.1 (M−H), found 502.0.

Example 51

3-(4-[[3-(3-methoxyphenyl)-5-(trifluoromethyl)-1,2-thiazol-4-yl]methoxy]-2,3-dimethylphenyl) propanoic Acid, Cpd 126

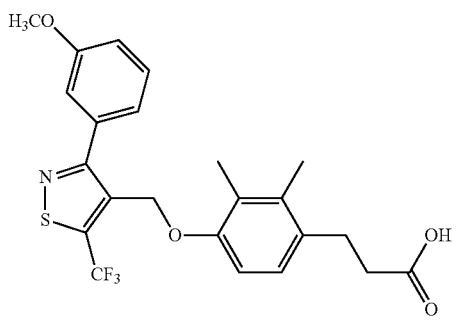 [SMILES: COc1cccc(-c2nsc(C(F)(F)F)c2COc2ccc(CCC(=O)O)c(C)c2C)c1]

The title compound was prepared according to the procedure described in Example 1 starting following Step 5 and 6 coupling (5-(trifluoromethyl)-3-(3-methoxyphenyl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, CD$_3$OD) δ 7.21-7.38 (m, 3H), 6.96-7.04 (m, 2H), 6.72 (d, J=7.8 Hz, 1H), 5.08 (s, 2H), 3.60 (s, 3H), 2.91 (t, J=7.2 Hz, 2H), 2.51 (t, J=7.5 Hz, 2H), 2.23 (s, 3H), 2.067 (s, 3H). Mass spectrum (ESI, m/z): Calcd. for $C_{23}H_{22}F_3NO_4S$, 464.1 (M−H), found 464.0.

Example 52

3-(3, 5-difluoro-4-[[3-(3-methoxyphenyl)-5-(trifluoromethyl)-1,2-thiazol-4-yl]methoxy] phenyl)propanoic Acid, Cpd 94

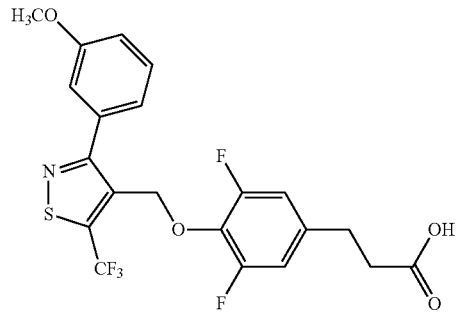 [SMILES: COc1cccc(-c2nsc(C(F)(F)F)c2COc2c(F)cc(CCC(=O)O)cc2F)c1]

The title compound was prepared according to the procedure described in Example 1 starting following Step 5 and 6 coupling (5-(trifluoromethyl)-3-(3-methoxyphenyl)isothiazol-4-yl)methyl methanesulfonate and ethyl 3-(3,5-difluoro-4-hydroxyphenyl)propanoate followed by hydrolysis to afford the desired product as an off-white solid. $^1$H NMR (300 MHz, CD$_3$OD) δ7.40 (t, J=7.8 Hz, 1H), 7.24-7.31 (m, 2H), 7.06-7.11 (m, 1H), 6.82 (d, J=13.5 Hz, 2H), 5.23 (s, 2H), 3.84 (s, 3H), 2.87 (t, J=7.2 Hz, 2H), 2.60 (t, J=7.5 Hz, 2H). Mass spectrum (ESI, m/z): Calcd. for $C_{21}H_{16}F_5NO_4S$, 474.1 (M+H), found 474.0.

Example 53

3-(4-[[3-(2,6-difluoro-4-methoxyphenyl)-5-(trifluoromethyl)-1,2-thiazol-4-yl]methoxy]-2,3-dimethylphenyl)propanoic Acid, Cpd 229

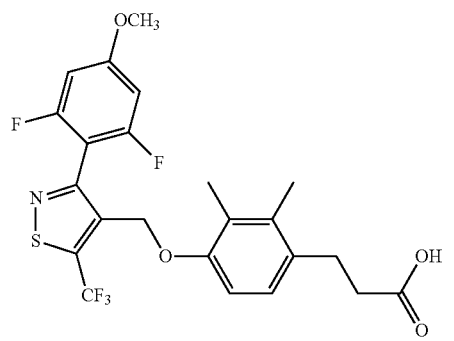 [SMILES: COc1cc(F)c(-c2nsc(C(F)(F)F)c2COc2ccc(CCC(=O)O)c(C)c2C)c(F)c1]

The title compound was prepared according to the procedure described in Example 1 starting following Step 5 and 6 coupling (5-(trifluoromethyl)-3-(2,6-difluoro-4-methoxyphenyl) isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, CDCl$_3$) δ 6.93 (d, J=8.4 Hz, 1H), 6.52-6.59 (m, 3H), 5.02 (s, 2H), 3.85 (s, 3H), 2.94 (t, J=7.2

Hz, 2H), 2.60 (t, J=7.5 Hz, 2H), 2.20 (s, 3H), 1.97 (s, 3H). Mass spectrum (ESI, m/z): Calcd. for $C_{23}H_{20}F_5NO_4S$, 502.1 (M+H), found 502.1.

Example 54

3-(2, 3-dimethyl-4-[[3-phenyl-5-(trifluoromethyl)-1, 2-thiazol-4-yl]methoxy]phenyl)propanoic Acid, Cpd 134

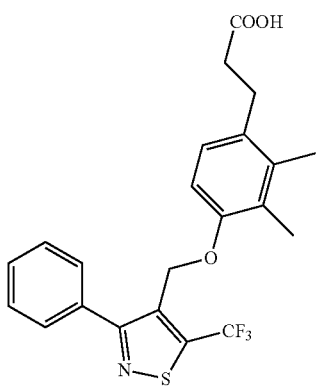 [SMILES: Cc1c(CCC(=O)O)ccc(OCc2c(-c3ccccc3)nsc2C(F)(F)F)c1C]

The title compound was prepared according to the procedure described in Example 1 starting following Step 5 and 6 coupling (5-(trifluoromethyl)-3-phenyl) isothiazol-4-yl) methyl methanesulfonate and ethyl 3-(4-hydroxy-2,3-dimethylphenyl)propanoate followed by hydrolysis to afford the desired product as an off-white solid. $^1$H NMR (300 MHz, $CD_3Cl$) δ: 7.68-7.70 (m, 2H), 7.43-7.51 (m, 3H), 6.97 (d, J=8.4 Hz, 1H), 6.67 (d, J=8.4 Hz, 1H), 5.02 (s, 2H), 2.95 (t, J=8.0 Hz, 2H), 2.61 (t, J=8.0 Hz, 2H), 2.28 (s, 3H), 2.11 (s, 3H). Mass spectrum (ESI, m/z): Calcd. for $C_{22}H_{20}F_3NO_3S$, 434.1 (M−H), found 434.1.

Example 55

3-(3, 5-difluoro-4-[[3-(2-fluoro-4-methylphenyl)-5-(trifluoromethyl)-1,2-thiazol-4-yl]methoxy]phenyl) propanoic Acid, Cpd 65

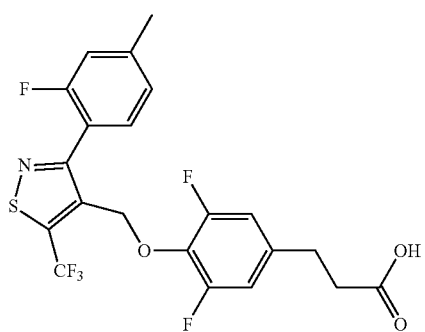 [SMILES: Cc1ccc(-c2nsc(C(F)(F)F)c2COc2c(F)cc(CCC(=O)O)cc2F)c(F)c1]

The title compound was prepared according to the procedure described in Example 1 starting following Step 5 and 6 coupling (3-(2-fluoro-4-methylphenyl)-5-(trifluoromethyl)isothiazol-4-yl)methyl methanesulfonate and ethyl 3-(3,5-difluoro-4-hydroxyphenyl)propanoate followed by hydrolysis to afford the desired product as an off-white solid. $^1$H NMR (400 MHz, $CD_3OD$) δ 7.22-7.26 (m, 1H), 7.05-7.09 (m, 2H), 6.73-6.78 (m, 2H), 5.17 (s, 2H), 2.84 (t, J=7.2 Hz, 2H), 2.59 (t, J=7.8 Hz, 2H), 2.44 (s, 3H). Mass spectrum (ESI, m/z): Calcd. for $C_{21}H_{15}F_6NO_3S$, 476.1 (M+H), found 476.1.

Example 56

3-(4-[[3-(4-chloro-2-fluorophenyl)-5-(trifluoromethyl)-1,2-thiazol-4-yl]methoxy]-3,5-difluorophenyl) propanoic Acid, Cpd 74

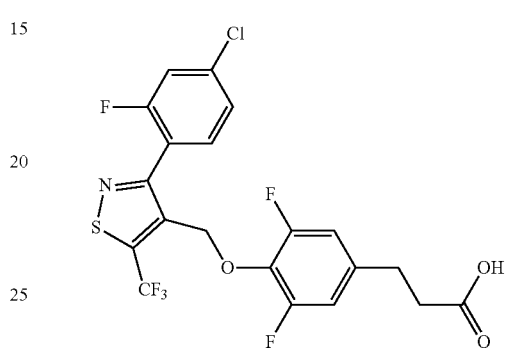

The title compound was prepared according to the procedure described in Example 1 starting following Step 5 and 6 coupling (3-(2-fluoro-4-chlorophenyl)-5-(trifluoromethyl) isothiazol-4-yl)methyl methanesulfonate and ethyl 3-(3,5-difluoro-4-hydroxyphenyl)propanoate followed by hydrolysis to afford the desired product as an off-white solid. $^1$H NMR (300 MHz, $CD_3OD$) δ 7.30-7.44 (m, 3H), 6.73-6.81 (m, 2H), 5.16 (s, 2H), 2.84 (t, J=7.5 Hz, 2H), 2.58 (t, J=7.5 Hz, 2H) Mass spectrum (ESI, m/z): Calcd. for $C_{20}H_{12}ClF_6NO_3S$, 496.0 (M+H), found 496.0.

Example 57

3-(4-[[3-cyclopentyl-5-(trifluoromethyl)-1,2-thiazol-4-yl]methoxy]-3,5-difluorophenyl)propanoic Acid, Cpd 71

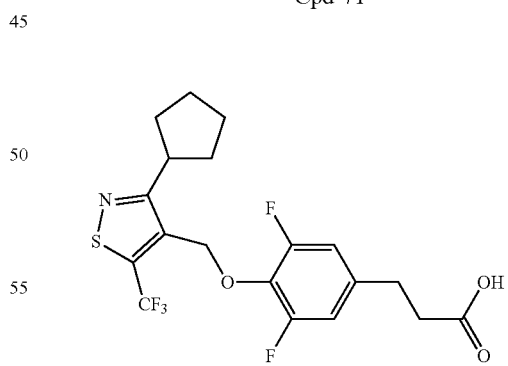

The title compound was prepared according to the procedure described in Example 1 starting following Step 5 and 6 coupling (3-cyclopentyl-5-(trifluoromethyl)isothiazol-4-yl)methyl methanesulfonate and ethyl 3-(3,5-difluoro-4-hydroxyphenyl)propanoate followed by hydrolysis to afford the desired product as an off-white solid. $^1$H NMR (400 MHz, $CD_3OD$) δ 6.89-6.96 (m, 2H), 5.26 (s, 2H), 3.57 (m, 1H), 2.89 (t, J=7.6 Hz, 2H), 2.61 (t, J=7.6 Hz, 2H), 2.06-2.12

(m, 2H), 1.81-1.97 (m, 4H), 1.69-1.79 (m, 2H). Mass spectrum (ESI, m/z): Calcd. for $C_{19}H_{18}F_5NO_3S$, 436.1 (M+H), found 436.1.

Example 58

3-(4-[[3-(4-chlorophenyl)-5-(trifluoromethyl)-1,2-thiazol-4-yl]methoxy]-3,5-difluorophenyl)-2-methylpropanoic Acid, Cpd 108

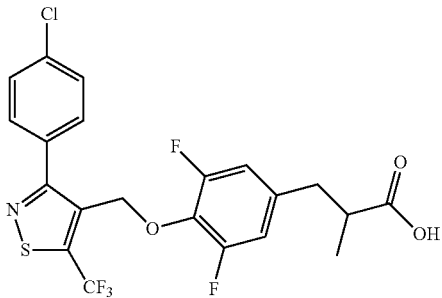 [SMILES: CC(Cc1cc(F)c(OCc2c(-c3ccc(Cl)cc3)nsc2C(F)(F)F)c(F)c1)C(=O)O]

The title compound was prepared according to the procedure described in Example 1 starting following Step 5 and 6 coupling (3-(4-chlorophenyl)-5-(trifluoromethyl)isothiazol-4-yl)methyl methanesulfonate and ethyl 3-(3,5-difluoro-4-hydroxyphenyl)-2-methylpropanoate (prepared according to PCT Application WO2010/048207A2) followed by hydrolysis to afford the desired product as an off-white solid. $^1$H NMR (300 MHz, CD$_3$OD): δ 7.76 (d, J=8.4 Hz, 2H), 7.52 (d, J=8.4 Hz, 2H), 6.81 (d, J=9.6 Hz, 2H), 5.18 (s, 2H), 2.88-2.93 (m, 1H), 2.51-2.59 (m, 2H), 1.11 (d, J=6.3 Hz, 3H). Mass spectrum (ESI, m/z): Calcd. for: $C_{21}H_{15}ClF_5NO_3S$: 492.0 (M+H), found 492.0.

Example 59

3-(4-[[3-(4-ethylphenyl)-5-(trifluoromethyl)-1,2-thiazol-4-yl]methoxy]-3,5-difluorophenyl)-2-methylpropanoic Acid, Cpd 80

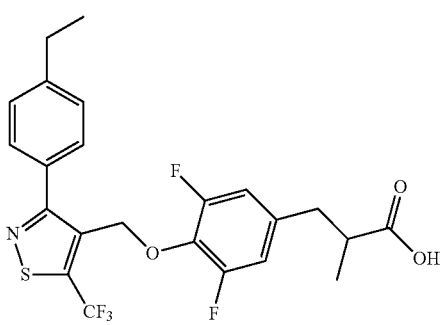 [SMILES: CCc1ccc(-c2nsc(C(F)(F)F)c2COc2c(F)cc(CC(C)C(=O)O)cc2F)cc1]

The title compound was prepared according to the procedure described in Example 1 starting following Step 5 and 6 coupling (3-(4-ethylphenyl)-5-(trifluoromethyl)isothiazol-4-yl)methyl methanesulfonate and ethyl 3-(3,5-difluoro-4-hydroxyphenyl)-2-methylpropanoate followed by hydrolysis to afford the desired product as an off-white solid. $^1$H NMR (400 MHz, CD3OD) δ 7.69 (d, J=8.0 Hz, 2H), 7.35 (d, J=8.0 Hz, 2H), 6.82-6.88 (m, 2H), 5.19 (s, 2H), 2.89-2.97 (m, 1H), 2.75 (q, J=7.6 Hz, 2H), 2.58-2.65 (m, 2H), 1.30 (t, J=7.6 Hz, 3H), 1.14 (d, J=6.4 Hz, 3H). Mass spectrum (ESI, m/z): Calcd. for $C_{23}H_{20}F_5NO_3S$, 486.1 (M+H), found 486.1.

Example 60

3-(4-[[3-(4-methoxyphenyl)-5-(trifluoromethyl)-1,2-thiazol-4-yl]methoxy]-2,3-dimethylphenyl)propanoic Acid, Cpd 86

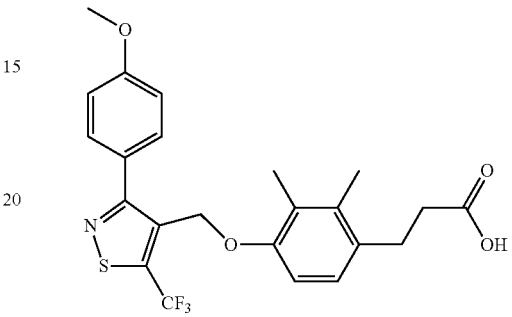

The title compound was prepared according to the procedure described in Example 1 starting following Step 5 and 6 coupling (5-(trifluoromethyl)-3-(4-methoxyphenyl) isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, CD$_3$OD) δ: 7.65 (d, J=6.9 Hz, 2H), 6.96-7.02 (m, 3H), 6.72 (d, J=8.4 Hz, 1H), 5.13 (s, 2H), 3.55 (s, 3H), 2.92 (t, J=8.4 Hz, 2H), 2.51 (t, J=8.1 Hz, 2H), 2.28 (s, 3H), 2.07 (s, 3H). Mass spectrum (ESI, m/z): Calcd. for $C_{23}H_{22}F_3NO_4S$, 466.1 (M+H), found 466.1.

Example 61

3-(4-[[3-(2-fluoro-4-methylphenyl)-5-(trifluoromethyl)-1,2-thiazol-4-yl]methoxy]-2,3-dimethylphenyl)propanoic Acid, Cpd 89

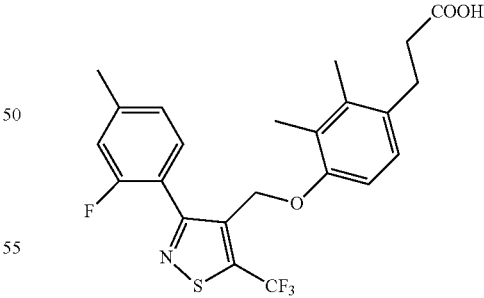

The title compound was prepared according to the procedure described in Example 1 starting following Step 5 and 6 coupling (3-(2-fluoro-4-methylphenyl)-5-(trifluoromethyl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, CD$_3$OD) δ 7.36 (t, J=7.6 Hz, 1H), 7.10 (d, J=8.4 Hz, 1H), 7.07 (d, J=11.4 Hz, 1H), 6.90 (d, J=8.4 Hz, 1H), 6.50 (d, J=8.7 Hz, 2H), 5.05 (s, 2H), 2.85 (t, J=8.4

Hz, 2H), 2.42 (s, 3H), 2.34 (t, J=8.4 Hz, 2H), 2.18 (s, 3H), 1.88 (s, 3H). Mass spectrum (ESI, m/z): Calcd. for $C_{23}H_{21}F_4NO_3S$, 466.1 (M−H), found 466.2.

Example 62

3-(4-[[3-(3-fluoro-4-methylphenyl)-5-(trifluoromethyl)-1,2-thiazol-4-yl]methoxy]-2,3-dimethylphenyl)propanoic Acid, Cpd 109

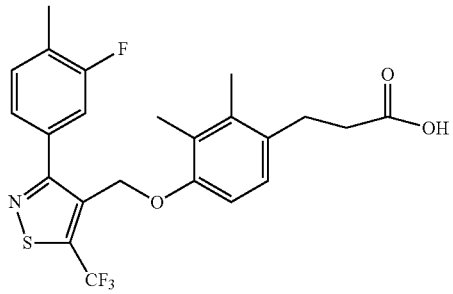 [SMILES: Cc1ccc(-c2nsc(C(F)(F)F)c2COc2ccc(CCC(=O)O)c(C)c2C)cc1F]

The title compound was prepared according to the procedure described in Example 1 starting following Step 5 and 6 coupling (3-(3-fluoro-4-methylphenyl)-5-(trifluoromethyl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (300 MHz, CD$_3$OD) δ 7.29-7.42 (m, 3H), 6.98 (d, J=8.4 Hz, 1H), 6.72 (d, J=8.4 Hz, 1H), 5.09 (s, 2H), 2.92 (t, J=7.5 Hz, 2H), 2.52 (t, J=7.5 Hz, 2H), 2.32 (s, 3H), 2.24 (s, 3H), 2.03 (s, 3H). Mass spectrum (ESI, m/z): Calcd. for $C_{23}H_{21}F_4NO_3S$, 466.1 (M−H), found 466.1.

Example 63

3-(3, 5-difluoro-4-[[3-(3-fluoro-4-methylphenyl)-5-(trifluoromethyl)-1,2-thiazol-4-yl]methoxy] phenyl)propanoic Acid, Cpd 91

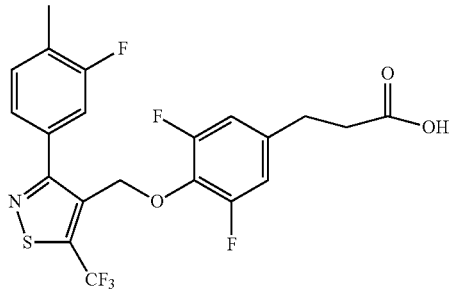 [SMILES: Cc1ccc(-c2nsc(C(F)(F)F)c2COc2c(F)cc(CCC(=O)O)cc2F)cc1F]

The title compound was prepared according to the procedure described in Example 1 starting following Step 5 and 6 coupling (3-(3-fluoro-4-methylphenyl)-5-(trifluoromethyl)isothiazol-4-yl)methyl methanesulfonate and ethyl 3-(3,5-difluoro-4-hydroxyphenyl)propanoate followed by hydrolysis to afford the desired product as an off-white solid. $^1$H NMR (300 MHz, CD$_3$OD) δ 7.34-7.52 (m, 3H), 6.83-6.91 (m, 2H), 5.21 (s, 2H), 2.88 (t, J=7.5 Hz, 2H), 2.61 (t, J=7.2 Hz, 2H), 2.368 (s, 3H). Mass spectrum (ESI, m/z): Calcd. for $C_{21}H_{15}F_6NO_3S$, 474.1 (M−H), found 474.1.

Example 64

3-(4-[[3-(3, 3-difluorocyclopentyl)-5-(trifluoromethyl)-1,2-thiazol-4-yl]methoxy]-2,3-dimethylphenyl)propanoic Acid, Cpd 199

Step 1: Methyl 3-oxocyclopentane-1-carboxylate

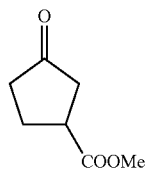

Into a 100-mL 3-necked round-bottom flask purged and maintained with an inert atmosphere of nitrogen, was placed 3-oxocyclopentane-1-carboxylic acid (1.0 g, 7.80 mmol, 1.00 equiv), potassium carbonate (1.62 g, 11.72 mmol, 1.50 equiv), Acetone (20 mL). This was followed by the addition of iodomethane (11.1 g, 78.20 mmol, 10.02 equiv) dropwise with stirring at 0° C. The resulting solution was stirred overnight at 60° C. in an oil bath. The reaction progress was monitored by GCMS. The solids were collected by filtration. The filtrate was concentrate. The resulting mixture was diluted with 10 mL of H$_2$O. The resulting solution was extracted with 3×10 mL of ether and the organic layers combined and dried over anhydrous sodium sulfate and concentrated. This resulted in 1.0 g (crude) of methyl 3-oxocyclopentane-1-carboxylate as yellow oil. The crude could be used for the next step directly.

Step 2: Methyl 3,3-difluorocyclopentane-1-carboxylate

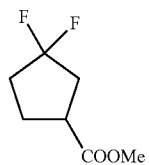 [SMILES: COC(=O)C1CCC(F)(F)C1]

Into a 50-mL round-bottom flask, was placed methyl 3-oxocyclopentane-1-carboxylate (1.1 g, 7.74 mmol, 1.00 equiv). This was followed by the addition of dichloromethane (20 mL). To this was added ethanol (0.05 mL) and BAST (4.28 g, 19.37 mmol, 2.50 equiv) dropwise with stirring at 0° C. The resulting solution was stirred for 2 days at 30° C. The reaction progress was monitored by GCMS. The reaction was poored into 100 mL of ice aq.NaHCO$_3$ solution and stirred for 10 min. The resulting solution was extracted with 3×20 mL of dichloromethane and the organic layers combined. The resulting mixture was washed with 1×50 mL of hydrogen chloride and 1×30 mL of NaCl. The mixture was dried over anhydrous sodium sulfate and concentrated under vacuum. This resulted in 1.86 g (crude) of methyl 3, 3-difluorocyclopentane-1-carboxylate as a solid. The crude could be used for the next step directly.

Step 3: 3, 3, 3-difluorocyclopentane-1-carboxamide

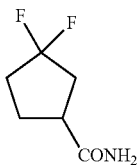

Into a 100-mL round-bottom flask, was placed methyl 3,3-difluorocyclopentane-1-carboxylate (1.8 g, 10.97 mmol, 1.00 equiv), methanol (10 mL), NH₄OH(aq) (10 mL). The resulting solution was stirred for overnight at 25° C. The resulting mixture was concentrated under vacuum. This resulted in 1.5 g (crude) of 3,3-difluorocyclopentane-1-carboxamide as a brown solid.

Step 4: 5-(3, 3-difluorocyclopentyl)-2H-1, 3, 4-oxathiazol-2-one

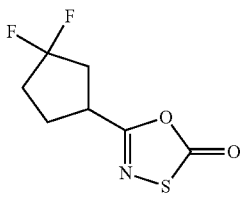

Into a 100-mL round-bottom flask, was placed 3,3-difluorocyclopentane-1-carboxamide (1.5 g, 10.06 mmol, 1.00 equiv), tol (30 mL), chloro(chlorosulfanyl)methanone (2.6 g, 19.85 mmol, 1.97 equiv). The resulting solution was stirred for overnight at 100° C. The resulting mixture was concentrated under vacuum. The residue was applied onto a silica gel column with ethyl acetate/petroleum ether (1/10-1/30). This resulted in 300 mg of 5-(3,3-difluorocyclopentyl)-2H-1,3,4-oxathiazol-2-one as brown oil.

Step 5: Ethyl 3-(3, 3-difluorocyclopentyl)-5-(trifluoromethyl)-1,2-thiazole-4-carboxylate

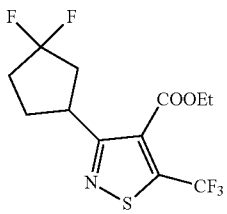 [SMILES: CCOC(=O)c1c(C2CCC(F)(F)C2)nsc1C(F)(F)F]

Into a 10-mL sealed tube, was placed 5-(3,3-difluorocyclopentyl)-2H-1,3,4-oxathiazol-2-one (300 mg, 1.45 mmol, 1.00 equiv), 1,3-dichlorobenzene (2 mL), ethyl 4,4,4-trifluorobut-2-ynoate (481 mg, 2.90 mmol, 2.00 equiv). The resulting solution was stirred overnight at 160° C. The resulting mixture was concentrated under vacuum. The residue was applied onto a silica gel column with ethyl acetate/petroleum ether (1/30). This resulted in 200 mg of ethyl 3-(3,3-difluorocyclopentyl)-5-(trifluoromethyl)-1,2-thiazole-4-carboxylate as brown oil.

Step 6. [3-(3, 3-difluorocyclopentyl)-5-(trifluoromethyl)-1,2-thiazol-4-yl]methanol

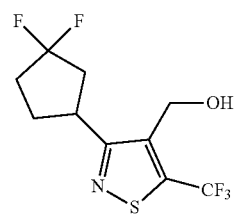 [SMILES: OCc1c(C2CCC(F)(F)C2)nsc1C(F)(F)F]

Into a 100-mL round-bottom flask, was placed ethyl 3-(3,3-difluorocyclopentyl)-5-(trifluoromethyl)-1,2-thiazole-4-carboxylate (200 mg, 0.61 mmol, 1.00 equiv), ether (5 mL), LAH (46 mg, 1.21 mmol, 2.00 equiv). The resulting solution was stirred for 1 h at 0° C. The reaction was then quenched by the addition of 10 ml of EA. The resulting mixture was concentrated under vacuum. The residue was applied onto a silica gel column with ethyl acetate/petroleum ether (1/30-1/10). This resulted in 100 mg (crude) of [3-(3, 3-difluorocyclopentyl)-5-(trifluoromethyl)-1,2-thiazol-4-yl]methanol as yellow oil Step 7: Ethyl 3-(4-[[3-(3,3-difluorocyclopentyl)-5-(trifluoromethyl)-1,2-thiazol-4-yl]methoxy]-2,3-dimethylphenyl)propanoate

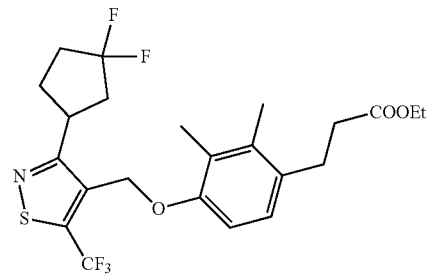 [SMILES: CCOC(=O)CCc1ccc(OCc2c(C3CCC(F)(F)C3)nsc2C(F)(F)F)c(C)c1C]

Into a 50-mL round-bottom flask purged and maintained with an inert atmosphere of nitrogen, was placed [3-(3,3-difluorocyclopentyl)-5-(trifluoromethyl)-1,2-thiazol-4-yl]methanol (50 mg, 0.17 mmol, 1.00 equiv), tol (3 mL), ethyl 3-(4-hydroxy-2,3-dimethylphenyl)propanoate (77 mg, 0.35 mmol, 1.99 equiv), ADDP (87 mg, 0.35 mmol, 2.00 equiv), n-Bu₃P (70 mg, 0.35 mmol, 1.99 equiv). The resulting solution was stirred for overnight at 60° C. The resulting mixture was concentrated under vacuum. The residue was applied onto a TLC plate with ethyl acetate/petroleum ether (1/5). This resulted in 50 mg (crude) of ethyl 3-(4-[[3-(3,3-difluorocyclopentyl)-5-(trifluoromethyl)-1,2-thiazol-4-yl]methoxy]-2,3-dimethylphenyl)propanoate as yellow oil.

Step 8: 3-(4-[[3-(3, 3-difluorocyclopentyl)-5-(trifluoromethyl)-1,2-thiazol-4-yl]methoxy]-2,3-dimethylphenyl)propanoic Acid

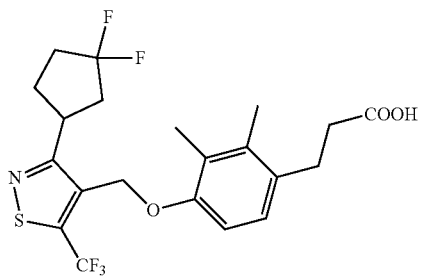 [SMILES: Cc1c(CCC(=O)O)ccc(OCc2c(C3CCC(F)(F)C3)nsc2C(F)(F)F)c1C]

The title compound was prepared according to the procedure described in Example following Step 6 by hydrolysis of ethyl 3-(4-[[3-(3,3-difluorocyclopentyl)-5-(trifluoromethyl)-1,2-thiazol-4-yl]methoxy]-2,3-dimethylphenyl)propanoate to afford the title product as an off-white solid. $^1$H NMR (300 MHz, CD$_3$OD) δ 7.04 (d, J=8.1 Hz, 1H), 6.88 (d, J=8.4 Hz, 1H), 5.12 (s, 2H), 3.70-3.77 (m, 1H), 2.93 (t, J=7.5 Hz, 2H), 2.42-2.68 (m, 4H), 2.06-2.37 (m, 4H), 2.21 (s, 3H), 2.10 (s, 3H), 1.20-1.40 (m, 2H). Mass spectrum (ESI, m/z): Calcd. for C$_{21}$H$_{22}$F$_5$NO$_3$S, 462.1 (M−H), found 462.1.

Example 65

3-(4-[[3-(3, 3-difluorocyclobutyl)-5-(trifluoromethyl)-1,2-thiazol-4-yl]methoxy]-2,3-dimethylphenyl) propanoic Acid, Cpd 137

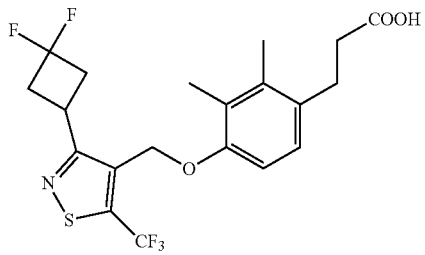 [SMILES: Cc1c(CCC(=O)O)ccc(OCc2c(C3CC(F)(F)C3)nsc2C(F)(F)F)c1C]

The title compound was prepared according to the procedure described in Example 75 following Step 1-8 starting from ethyl 3-oxocyclobutane-1-carboxylate afford the title product as an off-white solid. $^1$H NMR (300 MHz, CD$_3$OD) δ 7.05 (d, J=8.4 Hz, 1H), 6.85 (d, J=8.4 Hz, 1H), 5.09 (s, 2H), 3.70-3.75 (m, 1H), 2.88-3.12 (m, 6H), 2.53 (t, J=4.8 Hz, 2H), 2.28 (s, 3H), 2.09 (s, 3H). Mass spectrum (ESI, m/z): Calcd. for C$_{20}$H$_{20}$F$_5$NO$_3$S, 448.1 (M−H), found 448.1.

Example 66

3-(4-[[3-(3,3-difluorocyclopentyl)-5-(trifluoromethyl)-1,2-thiazol-4-yl]methoxy]-3,5-difluorophenyl)propanoic Acid, Cpd 164

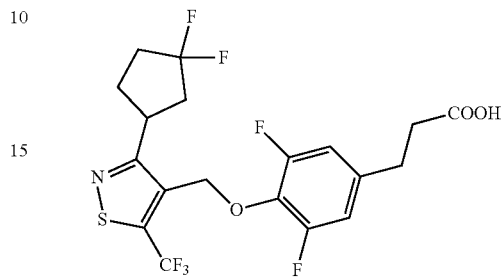

The title compound was prepared according to the procedure described in Example 1 starting following Step 5 and 6 coupling [3-(3, 3-difluorocyclopentyl)-5-(trifluoromethyl)-1,2-thiazol-4-yl]methanol and ethyl 3-(3,5-difluoro-4-hydroxyphenyl)propanoate followed by hydrolysis to afford the desired product as an off-white solid. $^1$H NMR (300 MHz, CD$_3$OD) δ 6.90-6.98 (m, 2H), 5.22 (s, 2H), 3.88-3.94 (m, 1H), 2.89 (t, J=7.5 Hz, 2H), 2.50-2.64 (m, 4H), 2.20-2.41 (m, 4H). $^{19}$F NMR (300 MHz, CD$_3$OD) δ −56.37, −90.10, −90.91, −130.13. Mass spectrum (ESI, m/z): Calcd. for C$_{19}$H$_{16}$F$_7$NO$_3$S, 470.1 (M−H), found 470.1.

Example 67

3-(4-[[3-(3, 3-difluorocyclobutyl)-5-(trifluoromethyl)-1,2-thiazol-4-yl]methoxy]-3,5-difluorophenyl) Propanoic Acid, Cpd 147

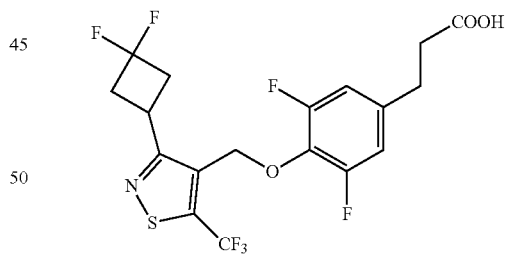

The title compound was prepared according to the procedure described in Example 1 starting following Step 5 and 6 coupling (3-(3,3-difluorocyclobutyl)-5-(trifluoromethyl)isothiazol-4-yl)methanol and ethyl 3-(3,5-difluoro-4-hydroxyphenyl)propanoate followed by hydrolysis to afford the desired product as an off-white solid. $^1$H NMR (300 MHz, CD3OD) δ 6.96 (d, J=7.2 Hz, 2H), 5.19 (s, 2H), 3.80-3.93 (m, 1H), 2.99-3.16 (m, 4H), 2.89 (t, J=7.5 Hz, 2H), 2.61 (t, J=7.2 Hz, 3H). Mass spectrum (ESI, m/z): Calcd. for C$_{18}$H$_{14}$F$_7$NO$_3$S, 456.1 (M−H), found 456.1.

Example 68

3-(3,5-difluoro-4-[[3-(2-fluoro-4-methylphenyl)-5-(trifluoromethyl)-1,2-thiazol-4-yl]methoxy]phenyl)-2-methylpropanoic Acid, Cpd 76

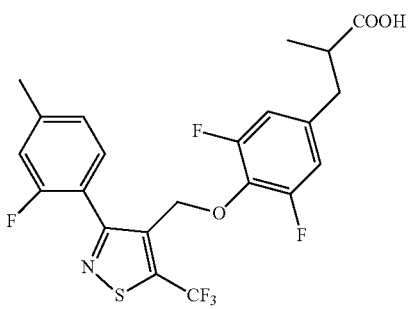 [SMILES: Cc1ccc(-c2nsc(C(F)(F)F)c2COc2c(F)cc(CC(C)C(=O)O)cc2F)c(F)c1]

The title compound was prepared according to the procedure described in Example 1 starting following Step 5 and 6 coupling (3-(2-fluoro-4-methylphenyl)-5-(trifluoromethyl)isothiazol-4-yl)methanol and ethyl 3-(3,5-difluoro-4-hydroxyphenyl)-2-methylpropanoate followed by hydrolysis to afford the desired product as an off-white solid. $^1$H NMR (300 MHz, CD3OD) δ 7.29 (t, J=7.8 Hz, 1H), 7.10 (d, J=7.5 Hz, 1H), 7.07 (d, J=11.4 Hz, 1H), 6.73 (d, J=9.7 Hz, 2H), 5.13 (s, 2H), 2.94-2.85 (m, 1H), 2.54-2.44 (m, 2H), 2.44 (s, 3H), 1.09 (d, J=6.3 Hz, 3H). Mass spectrum (ESI, m/z): Calcd. for $C_{22}H_{17}F_6NO_3S$, 488.1 (M−H), found 488.1.

Example 69

3-(4-[[3-(2-fluoro-4-methylphenyl)-5-(trifluoromethyl)-1,2-thiazol-4-yl]methoxy]-2-(trifluoromethyl)phenyl)propanoic Acid, Cpd 171

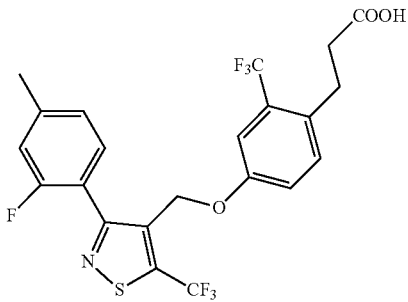 [SMILES: Cc1ccc(-c2nsc(C(F)(F)F)c2COc2ccc(CCC(=O)O)c(C(F)(F)F)c2)c(F)c1]

The title compound was prepared according to the procedure described in Example 1 starting following Step 5 and 6 coupling (3-(2-fluoro-4-methylphenyl)-5-(trifluoromethyl)isothiazol-4-yl)methanol and ethyl 3-(4-hydroxy-2-(trifluoromethyl)phenyl)propanoate followed by hydrolysis to afford the desired product as an off-white solid. $^1$H NMR (400 MHz, CD$_3$OD) δ 7.39-7.34 (m, 2H), 7.16 (d, J=7.6 Hz, 1H), 7.07 (d, J=10.0 Hz, 1H), 6.96 (d, J=8.8 Hz, 1H), 6.89 (d, J=2.4 Hz, 1H), 5.18 (s, 2H), 3.01 (t, J=7.6 Hz, 2H), 2.44 (t, J=8.4 Hz, 2H), 2.43 (s, 3H). Mass spectrum (ESI, m/z): Calcd. for $C_{22}H_{16}F_7NO_3S$, 506.1 (M−H), found 506.1.

Example 70

3-(4-[[3-(4-acetylphenyl)-5-(trifluoromethyl)-1,2-thiazol-4-yl]methoxy]-3,5-difluorophenyl) Propanoic Acid, Cpd 131

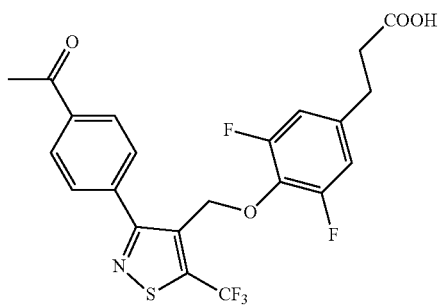 [SMILES: CC(=O)c1ccc(-c2nsc(C(F)(F)F)c2COc2c(F)cc(CCC(=O)O)cc2F)cc1]

The title compound was prepared according to the procedure described in Example 1 starting following Step 5 and 6 coupling 1-(4-(4-(hydroxymethyl)-5-(trifluoromethyl)isothiazol-3-yl)phenyl)ethanone and ethyl 3-(3,5-difluoro-4-hydroxyphenyl)propanoate followed by hydrolysis to afford the desired product as an off-white solid. $^1$H NMR (300 MHz, CD$_3$OD) δ: 8.08 (d, J=7.2 Hz, 2H), 7.87 (d, J=7.2 Hz, 2H), 6.78-6.85 (m, 2H), 5.19 (s, 2H), 2.80-2.85 (m, 2H), 2.64 (s, 3H), 2.53-2.58 (m, 2H). Mass spectrum (ESI, m/z): Calcd. for $C_{22}H_{16}F_5NO_4S$, 484.1 (M−H), found 484.1.

Example 71

3-[4-([3-[4-(1-fluoroethyl)phenyl]-5-(trifluoromethyl)-1,2-thiazol-4-yl]methoxy)-2,3-dimethylphenyl]propanoic Acid, Cpd 146

Step 1: Ethyl 3-[4-(1-fluoroethyl)phenyl]-5-(trifluoromethyl)-1,2-thiazole-4-carboxylate

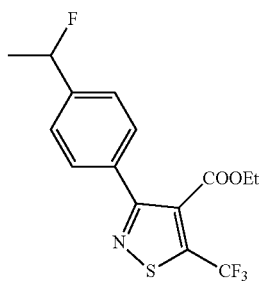 [SMILES: CCOC(=O)c1c(-c2ccc(C(C)F)cc2)nsc1C(F)(F)F]

Into a 50-mL round-bottom flask, was placed ethyl 3-[4-(1-hydroxyethyl)phenyl]-5-(trifluoromethyl)-1,2-thiazole-4-carboxylate (300 mg, 0.87 mmol, 1.00 equiv), dichloromethane (18 mL), BAST (230.6 mg). The resulting solution was stirred for 2 h at 0° C. in a water/ice bath. The reaction was then quenched by the addition of 10 mL of NaHSO$_3$/H$_2$O (10%). The resulting solution was extracted with 3×15 mL of ethyl acetate and the organic layers combined and dried in an oven under reduced pressure. and concentrated under vacuum. The residue was applied onto TLC-Plate with ethyl acetate/petroleum ether (1:2). This resulted in 290 mg (96%) of ethyl 3-[4-(1-fluoroethyl)

phenyl]-5-(trifluoromethyl)-1,2-thiazole-4-carboxylate as yellow oil. Mass spectrum (ESI, m/z): Calcd. for $C_{15}H_{13}F_4NO_2S$, 348.1 (M+H), found 348.1.

Step 2: [3-[4-(1-fluoroethyl)phenyl]-5-(trifluoromethyl)-1,2-thiazol-4-yl]methanol

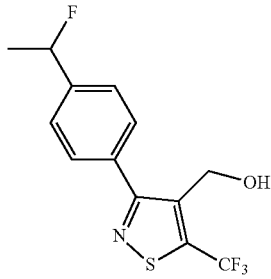 [SMILES: CC(F)c1ccc(-c2nsc(C(F)(F)F)c2CO)cc1]

Into a 8-mL vial, was placed ethyl 3-[4-(1-fluoroethyl) phenyl]-5-(trifluoromethyl)-1,2-thiazole-4-carboxylate (290 mg, 0.83 mmol, 1.00 equiv), tetrahydrofuran (1 mL). This was followed by the addition of LiAlH$_4$ (0.83 mL) dropwise with stirring at 0° C. in 1 min. The resulting solution was stirred for 1 h at 0° C. in a water/ice bath. The reaction was then quenched by the addition of 1 mL of water. The resulting solution was extracted with 3×3 mL of ethyl acetate and the organic layers combined and concentrated under vacuum. The residue was applied onto a silica gel column with ethyl acetate/petroleum ether (1:3). This resulted in 72 mg (28%) of [3-[4-(1-fluoroethyl)phenyl]-5-(trifluoromethyl)-1,2-thiazol-4-yl]methanol as a white solid.

Step 4: 3-[4-([3-[4-(1-fluoroethyl)phenyl]-5-(trifluoromethyl)-1,2-thiazol-4-yl]methoxy)-2,3-dimethylphenyl]propanoic Acid

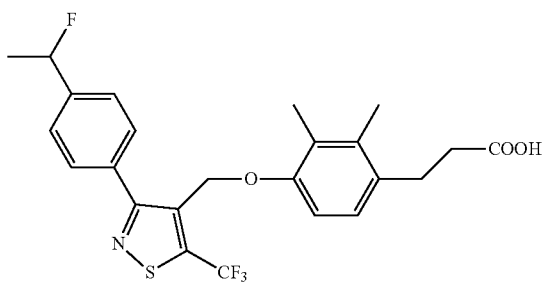 [SMILES: Cc1c(CCC(=O)O)ccc(OCc2c(-c3ccc(C(C)F)cc3)nsc2C(F)(F)F)c1C]

The title compound was prepared according to the procedure described in Example 1 starting following Step 5 and 6 coupling [3-[4-(1-fluoroethyl)phenyl]-5-(trifluoromethyl)-1,2-thiazol-4-yl]methanol and ethyl 3-(4-hydroxy-2,3-dimethylphenyl)propanoate followed by hydrolysis to afford the desired product as an off-white solid. $^1$HNMR (300 MHz, CD$_3$OD) δ 7.67 (d, J=8.1 Hz, 2H), 7.41 (d, J=8.1 Hz, 2H), 6.92 (d, J=8.1 Hz, 1H), 6.67 (d, J=8.4 Hz, 1H), 5.53-5.75 (m, 1H), 5.06 (s, 2H), 2.89 (t, J=7.5 Hz, 2H), 2.47 (t, J=7.5 Hz, 2H), 2.18 (s, 3H), 2.00 (s, 3H), 1.53-1.65 (m, 3H). Mass spectrum (ESI, m/z): Calcd. for $C_{24}H_{23}F_4NO_3S$, 480.1 (M−H), found 480.1.

Example 72

3-[4-([3-[4-(1,1-difluoroethyl)phenyl]-5-(trifluoromethyl)-1,2-thiazol-4-yl]methoxy)-2,3-dimethylphenyl]propanoic Acid, Cpd 178

Step 1: Ethyl 3-[4-(1,1-difluoroethyl)phenyl]-5-(trifluoromethyl)-1,2-thiazole-4-carboxylate

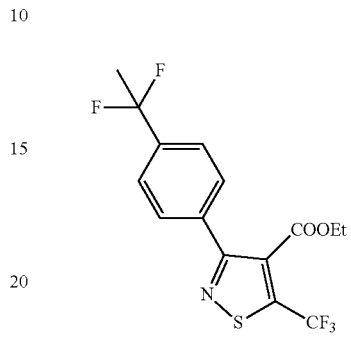

Into a 40-mL sealed tube purged and maintained with an inert atmosphere of nitrogen, was placed ethyl 3-(4-acetylphenyl)-5-(trifluoromethyl)-1, 2-thiazole-4-carboxylate (1.5 g, 4.37 mmol, 1.00 equiv), BAST (10 mL), [C$_8$ min PF$_6$] (10 mL). The resulting solution was stirred overnight at 55° C. in an oil bath. The reaction was then quenched by the addition of 15 mL of water. The resulting solution was extracted with 3×15 mL of ethyl acetate and the organic layers combined and dried over anhydrous sodium sulfate. The residue was applied onto a silica gel column with ethyl acetate/petroleum ether (0:100). This resulted in 600 mg (38%) of ethyl 3-[4-(1, 1-difluoroethyl)phenyl]-5-(trifluoromethyl)-1,2-thiazole-4-carboxylate as colorless oil. Mass spectrum (ESI, m/z): Calcd. for $C_{15}H_{12}F_5NO_2S$, 366.1 (M+H), found 366.1.

Step 2: [3-[4-(1, 1-difluoroethyl)phenyl]-5-(trifluoromethyl)-1,2-thiazol-4-yl]methanol

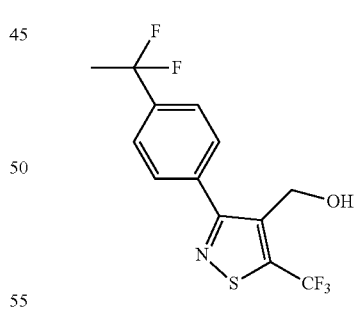

Into a 25-mL round-bottom flask, was placed ethyl 3-[4-(1,1-difluoroethyl)phenyl]-5-(trifluoromethyl)-1,2-thiazole-4-carboxylate (450 mg, 1.23 mmol, 1.00 equiv), tetrahydrofuran (4 mL). This was followed by the addition of LiAlH$_4$ (2.5 mL) dropwise with stirring at 0° C. The resulting solution was stirred for 15 min at room temperature (20 degree). The reaction was then quenched by the addition of 5 mL of water. The resulting solution was extracted with 5×5 mL of ethyl acetate and the organic layers combined. The residue was applied onto a silica gel column with ethyl acetate/petroleum ether (16:84). This resulted in 110 mg (28%) of [3-[4-(1, 1-difluoroethyl)phenyl]-5-(trifluoromethyl)-1,2-thiazol-4-yl]methanol as a yellow solid. Mass spectrum (ESI, m/z): Calcd. for $C_{13}H_{10}F_5NOS$, 324.0 (M+H), found 324.0.

Step 3: 3-[4-([3-[4-(1,1-difluoroethyl)phenyl]-5-(trifluoromethyl)-1,2-thiazol-4-yl]methoxy)-2,3-dimethylphenyl]propanoic Acid

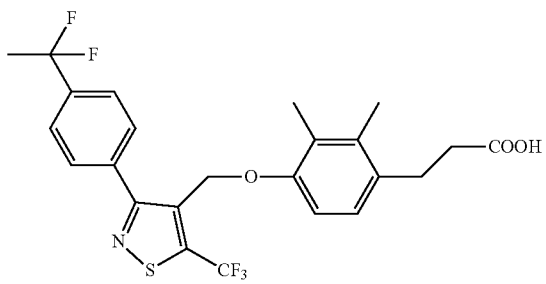 [SMILES: Cc1c(CCC(=O)O)ccc(OCc2c(-c3ccc(C(C)(F)F)cc3)nsc2C(F)(F)F)c1C]

The title compound was prepared according to the procedure described in Example 1 starting following Step 5 and 6 coupling [3-[4-(1, 1-difluoroethyl)phenyl]-5-(trifluoromethyl)-1,2-thiazol-4-yl]methanol and ethyl 3-(4-hydroxy-2,3-dimethylphenyl)propanoate followed by hydrolysis to afford the desired product as an off-white solid. $^1$H NMR (400 MHz, $CD_3OD$) δ 7.79 (d, J=8.4 Hz, 2H), 7.63 (d, J=8.4 Hz, 2H), 6.97 (d, J=8.4 Hz, 1H), 6.710 (d, J=8.4 Hz, 1H), 5.12 (s, 2H), 2.92 (t, J=7.6 Hz, 2H), 2.52 (t, J=8.4 Hz, 2H), 2.23 (s, 3H), 2.05 (s, 3H), 1.90-2.02 (m, 3H). Mass spectrum (ESI, m/z): Calcd. for $C_{24}H_{22}F_5NO_3S$, 498.1 (M−H), found 498.1.

Example 73

3-(3, 5-difluoro-4-((3-(6-methoxypyridin-3-yl)-5-(trifluoromethyl)isothiazol-4-yl)methoxy)phenyl) Propanoic Acid, Cpd 98

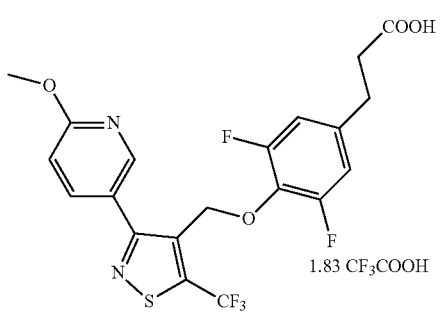 [SMILES: COc1ccc(-c2nsc(C(F)(F)F)c2COc2c(F)cc(CCC(=O)O)cc2F)cn1]

Into a 25-mL round-bottom flask, was placed ethyl 3-(3, 5-difluoro-4-[[3-(6-methoxypyridin-3-yl)-5-(trifluoromethyl)-1,2-thiazol-4-yl]methoxy]phenyl)propanoate (prepared according to the procedure following Example 1 step 1-5 using 6-methoxynicotinamide as starting material) (50 mg, 0.10 mmol, 1.00 equiv), tetrahydrofuran (1 mL), LiOH (50 mg, 2.09 mmol, 20.98 equiv), water (1 mL). The resulting solution was stirred overnight at 20° C. The resulting mixture was concentrated under vacuum. The pH value of the solution was adjusted to 6 with hydrogen chloride (2 mol/L). The solids were collected by filtration. The crude product (20 mg) was purified by Flash-Prep-HPLC with the following conditions (IntelFlash-1): Reversed Column, C18 silica gel; mobile phase, 0.05% TFA/ACN=1/4 increasing to 0.05% TFA/ACN=0/1 within 20 min; Detector, UV 254 nm. This resulted in 8.8 mg (18%) of 3-(3,5-difluoro-4-((3-(6-methoxypyridin-3-yl)-5-(trifluoromethyl)isothiazol-4-yl)methoxy)phenyl)propanoic acid as a white solid. $^1$H NMR (300 MHz, $CD_3OD$) δ 8.51 (s, 1H), 8.06 (d, J=6.3 Hz, 1H), 6.80-6.89 (m, 3H), 5.19 (s, 2H), 3.96 (s, 3H), 2.83 (t, J=7.5 Hz, 2H), 2.56 (t, J=7.5 Hz, 2H). Mass spectrum (ESI, m/z): Calcd. for $C_{20}H_{15}F_5N_2O_4S$, 475.1 (M+H), found 475.1.

Example 74

3-(4-((3-(5-chloro-3-fluoropyridin-2-yl)-5-(trifluoromethyl)isothiazol-4-yl)methoxy)-3,5-difluorophenyl)propanoic Acid, Cpd 153

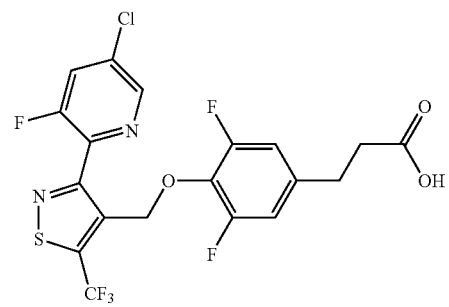

The title compound was prepared according to the procedure described in Example 1 starting from 5-chloro-3-fluoropicolinamide following Step 1-6 using ethyl 3-(3,5-difluoro-4-hydroxyphenyl)propanoate as coupling agent to afford the desired product as an off-white solid. $^1$H NMR (400 MHz, $CDCl_3$) δ 8.42 (br, s, 1H), 7.62 (d, J 5=7.2 Hz, 1H), 6.68 (d, J=7.5 Hz, 2H), 5.48 (s, 2H), 2.88 (t, J=7.2 Hz, 2H), 2.68 (t, J=7.2 Hz, 2H).

Example 75

3-(4-((3-(5-chloro-3-fluoropyridin-2-yl)-5-(trifluoromethyl)isothiazol-4-yl)methoxy)-2,3-dimethylphenyl)propanoic Acid, Cpd 180

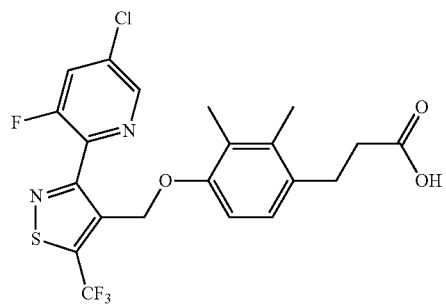 [SMILES: Cc1c(CCC(=O)O)ccc(OCc2c(-c3ncc(Cl)cc3F)nsc2C(F)(F)F)c1C]

The title compound was prepared according to the procedure described in Example 1 starting from 5-chloro-3-fluoropicolinamide following Step 1-6 using ethyl 3-(4- hydroxy-2,3-dimethylphenyl)propanoate as coupling agent to afford the desired product as an off-white solid. ¹H NMR (400 MHz, CDCl₃) δ 8.38 (s, 1H), 7.62 (d, J=7.5 Hz, 1H), 6.92 (d, J=7.6 Hz, 6.62 (d, J=7.6 Hz, 1H), 5.31 (s, 2H), 2.92 (t, J=7.8 Hz, 2H), 2.62 (t, J=7.8 Hz, 2H), 2.18 (s, 3H), 1.78 (s, 3H).

Example 76

3-(4-((3-(5-chloro-3-fluoropyridin-2-yl)-5-(trifluoromethyl)isothiazol-4-yl)methoxy)-5-fluoro-2-methylphenyl)propanoic Acid, Cpd 206

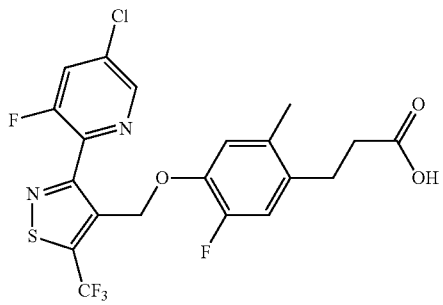 [SMILES: Cc1cc(OCc2c(-c3ncc(Cl)cc3F)nsc2C(F)(F)F)c(F)cc1CCC(=O)O]

The title compound was prepared according to the procedure described in Example 1 starting from 5-chloro-3-fluoropicolinamide following Step 1-6 using ethyl 3-(5-fluoro-4-hydroxy-2-methylphenyl)propanoate as coupling agent to afford the desired product as an off-white solid. ¹H NMR (400 MHz, CDCl₃) δ 8.32 (br, s, 1H), 7.61 (d, J=7.5 Hz, 1H), 6.78 (d, J=8.0 Hz, 1H), 6.62 (d, J=7.0 Hz, 1H), 5.38 (s, 2H), 2.78 (t, J=8.5 Hz, 2H), 2.62 (t, J=8.5 Hz, 2H), 2.21 (s, 3H).

Example 77

3-(4-[[3-(4-ethylphenyl)-5-(trifluoromethyl)-1,2-thiazol-4-yl]methoxy]naphthalen-1-yl)propanoic Acid, Cpd 130

Step 1: Ethyl (2E)-3-(4-hydroxynaphthalen-1-yl)prop-2-enoate

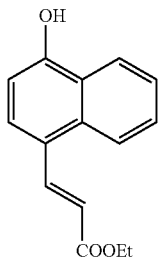 [SMILES: CCOC(=O)/C=C/c1ccc(O)c2ccccc12]

Into a 100-mL round-bottom flask (1 atm) purged and maintained with an inert atmosphere of nitrogen, was placed 4-hydroxynaphthalene-1-carbaldehyde (1.72 g, 9.99 mmol, 1.00 equiv), ethyl 2-(triphenyl-[5]-phosphanylidene)acetate (3.48 g, 9.99 mmol, 1.00 equiv), toluene (50 mL). The resulting solution was stirred overnight at 110° C. in an oil bath. The resulting mixture was concentrated under vacuum. The residue was applied onto a silica gel column with ethyl acetate/petroleum ether (23/77). This resulted in 970 mg (40%) of ethyl (2E)-3-(4-hydroxynaphthalen-1-yl)prop-2-enoate as a yellow solid.

Step 2: Ethyl 3-(4-hydroxynaphthalen-1-yl)propanoate

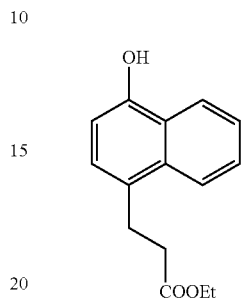

Into a 50-mL round-bottom flask (1 atm) purged and maintained with an inert atmosphere of nitrogen, was placed ethyl (2E)-3-(4-hydroxynaphthalen-1-yl)prop-2-enoate (242 mg, 1.00 mmol, 1.00 equiv), TsNHNH₂ (0.744 g), NaOAc (0.41 g), ethylene glycol dimethyl ether (15 mL), water (3 mL). The resulting solution was stirred overnight at 80° C. in an oil bath. The resulting solution was diluted with 30 mL of ethyl acetate. The resulting mixture was washed with 2×10 mL of water. The resulting mixture was concentrated under vacuum. The residue was applied onto a silica gel column with ethyl acetate/petroleum ether (16/84). This resulted in 194 mg (80%) of ethyl 3-(4-hydroxynaphthalen-1-yl)propanoate as colorless oil Step 3: 3-(4-[[3-(4-ethylphenyl)-5-(trifluoromethyl)-1,2-thiazol-4-yl]methoxy]naphthalen-1-yl)propanoic Acid

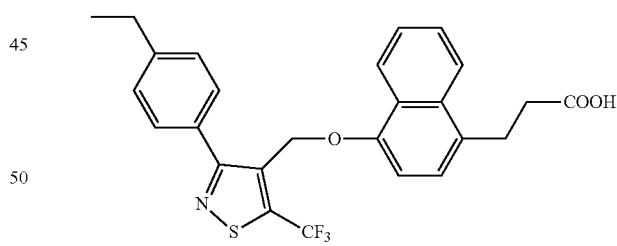

The title compound was prepared according to the procedure described in Example 1 starting from (3-(4-ethylphenyl)-5-(trifluoromethyl)isothiazol-4-yl)methyl methanesulfonate following Step 5 and 6 using ethyl 3-(4-hydroxynaphthalen-1-yl)propanoate as coupling agent to afford the desired product as an off-white solid. ¹H-NMR (300 MHz, CDCl₃) δ 8.22 (d, J=8.1 Hz, 2H), 7.98 (d, J=8.4 Hz, 2H), 7.63 (d, J=8.4 Hz, 2H), 7.58 (t, J=7.5 Hz, 1H), 7.46 (t, J=7.5 Hz, 1H), 7.22 (d, J=8.1 Hz, 3H), 6.77 (d, J=7.8 Hz, 1H), 5.22 (s, 2H), 3.39 (t, J=7.8 Hz, 2H), 2.82 (t, J=8.1 Hz, 2H), 2.65 (q, J=15.5 Hz, J₂=7.5 Hz, 2H), 1.20 (t, J=7.8 Hz, 3H). Mass spectrum (ESI, m/z): Calcd. for C₂₆H₂₂F₃NO₃S, 486.1 (M+H), found 486.1.

Example 78

3-(4-[[3-(4-ethylphenyl)-5-(trifluoromethyl)-1,2-thiazol-4-yl]methoxy]-1-benzothiophen-7-yl)propanoic Acid, Cpd 92

Step 1: 2-hydroxy-2-(4-hydroxy-1-benzothiophen-7-yl)acetic acid

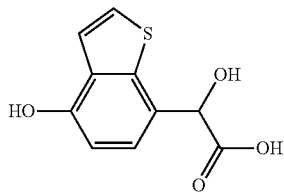 [SMILES: O=C(O)C(O)c1ccc(O)c2ccsc12]

Into a 100-mL 3-necked round-bottom flask purged and maintained with an inert atmosphere of nitrogen, was placed 1-benzothiophen-4-ol (1.0 g, 6.32 mmol, 1.00 equiv, 95%), potassium hydroxide (821 mg, 1.46 mmol, 2.20 equiv, 10%). This was followed by the addition of 2-oxoacetic acid (592 mg, 4.00 mmol, 1.20 equiv) at 0-5° C. with 30 min. If necessary, more 2-oxoacetic acid is added such that the pH of he solution at the end of the addition was 11.5. After stirring for 3 h at 0-5 degree C. 20 mL of tert-butyl methyl ether were added to the reaction mixture followed by HCl (25%) solution in water such that the pH was 7. The biphasic mixture was filtered through Speedex, then HCl (25%) solution in water were added to the aqueous phase such that the pH was 2.0. After addition of tert-butyl methyl ether (3*20 mL), the organic phase was separated at 25° C., and 50 mL acetonitrile was added to organic phase. To the resulting clear solution was added portions wise at 20-30° C., a solution of tributylamine (1.23 g, 1.00 equiv) in 20 mL of tert-butyl methyl ether under seeding with crystals of the product. The resulting suspension was stirred over night at 20-30 degree C., and then filtered off. The filter cake was dried oven at 60° C. The result afford (1.0 g, 63%) of 2-hydroxy-2-(4-hydroxy-1-benzothiophen-7-yl)acetic acid as gray solid.

Step 2: 4-hydroxy-1-benzothiophene-7-carbaldehyde

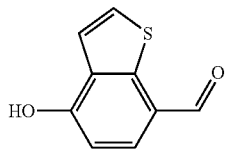

Into a 100-mL 3-necked round-bottom flask purged and maintained with an inert atmosphere of nitrogen, was placed 2-hydroxy-2-(4-hydroxy-1-benzothiophen-7-yl)acetic acid (500 mg, 2.01 mmol, 1.00 equiv, 90%), $Fe_2(SO_4)_3$ (750 mg, 1.88 mmol, 1.15 equiv), ethanol (0.75 mL), sulfuric acid (0.4N) (3.75 mL). The resulting solution was stirred for 5 h at 55-60° C. in an oil bath. After cooling to 25° C., 15 mL of isopropyl acetate and 5 ml of water were added under stirring, then the organic phase was separated and organic phase was diluted by 10 ml of water (pH was 3), then used NaOH (2N) solution were added dropwise at 20 degree C. until a pH of 12-12.5 was reached. The organic phase was removed and to the aqueous phase were added $H_2SO_4$ (2N) solution until a pH was 4-4.5. The product precipitated during the addition. The suspension was stirred overnight at 25° C., then for 1.2 h in an ice bath and then filtered. This resulted in 200 mg (53%) of 4-hydroxy-1-benzothiophene-7-carbaldehyde as a gray solid.

Step 3: Ethyl (2E)-3-(4-hydroxy-1-benzothiophen-7-yl)prop-2-enoate

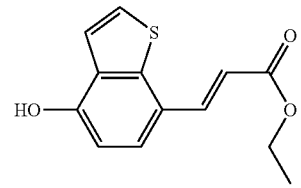 [SMILES: CCOC(=O)/C=C/c1ccc(O)c2ccsc12]

Into a 50-mL 3-necked round-bottom flask purged and maintained with an inert atmosphere of nitrogen, was placed 4-hydroxy-1-benzothiophene-7-carbaldehyde (168 mg, 0.85 mmol, 1.00 equiv, 90%), Ethyl (triphenylphosphoranylidene)acetate (493 mg, 1.42 mmol, 1.50 equiv), Tolune (6 mL). The resulting solution was stirred for 4 h at 120° C. in an oil bath. The resulting mixture was concentrated under vacuum. The resulting solution was diluted with 5 mL of $H_2O$. The resulting solution was extracted with 3×5 mL of ethyl acetate and the organic layers combined. The resulting mixture was washed with 1×10 mL of sodium chloride(aq). The mixture was dried over anhydrous sodium sulfate. The residue was purified by thin layer chromatography developed with ethyl acetate/petroleum ether (1:8). This resulted in 200 mg (81%) of ethyl (2E)-3-(4-hydroxy-1-benzothiophen-7-yl)prop-2-enoate as brown oil.

Step 4: Ethyl 3-(4-hydroxy-1-benzothiophen-7-yl)propanoate

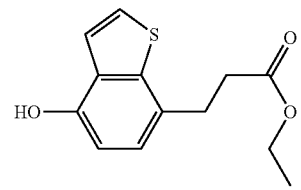

Into a 100-mL round-bottom flask purged and maintained with an inert atmosphere of $H_2$, was placed ethyl (2E)-3-(4-hydroxy-1-benzothiophen-7-yl)prop-2-enoate (200 mg, 0.68 mmol, 1.00 equiv, 85%), Palladium carbon (100 mg), ethanol (4 mL). The resulting solution was stirred overnight at 25° C. The solids were filtered out. The resulting mixture was concentrated under vacuum. The residue was purified by thin layer chromatography developed with ethyl acetate/petroleum ether (1:5). This resulted in 150 mg (79%) of ethyl 3-(4-hydroxy-1-benzothiophen-7-yl)propanoate as colorless oil

Step 5: 3-(4-[[3-(4-ethylphenyl)-5-(trifluoromethyl)-1,2-thiazol-4-yl]methoxy]-1-benzothiophen-7-yl) propanoic Acid

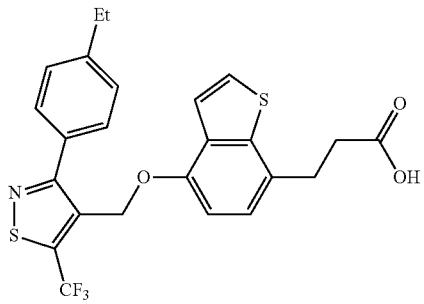 [SMILES: CCc1ccc(-c2nsc(C(F)(F)F)c2COc2ccc(CCC(=O)O)c3sccc23)cc1]

The title compound was prepared according to the procedure described in Example 1 starting from 4-ethyl-benzamide following Step 1-6 using Ethyl 3-(4-hydroxy-1-benzothiophen-7-yl)propanoate as coupling agent to afford the desired product as an off-white solid. $^1$H NMR (300 MHz, DMSO) δ 12.25 (brs, 1H), 7.58-7.65 (m, 3H), 7.27-7.37 (m, 3H), 7.15 (d, J=8.1 Hz, 1H), 6.91-6.97 (m, 1H), 5.28 (s, 2H), 2.98 (t, J=6.9 Hz, 2H), 2.60-2.73 (m, 4H), 1.15-1.23 (m, 3H). Mass spectrum (ESI, m/z): Calcd. for $C_{24}H_{20}F_3NO_3S_2$, 492.1 (M+H), found 492.1.

Example 79

3-(7-[[3-(4-ethylphenyl)-5-(trifluoromethyl)-1,2-thiazol-4-yl]methoxy]-2,3-dihydro-1H-inden-4-yl) propanoic Acid, Cpd 103

Step 1: 7-hydroxy-2,3-dihydro-1H-indene-4-carbaldehyde

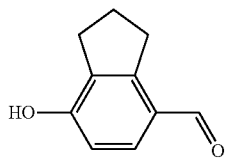 [SMILES: O=Cc1ccc(O)c2c1CCC2]

Into a 100-mL round-bottom flask, was placed a solution of 2,3-dihydro-1H-inden-4-ol (3.0 g, 22.36 mmol, 1.00 equiv) in dichloromethane (20 ml) and TiCl$_4$ (7.66 g, 40.38 mmol, 1.80 equiv). After 5 minutes, dichloro(methoxy) methane (2.81 g, 24.44 mmol, 1.10 equiv) was added at 0° C. in a water/ice bath and the resulting solution stirred for 3 h at 0° C. The reaction was then quenched by the addition of 25 mL of water. The resulting solution was extracted with 2×150 mL of dichloromethane. The organic layers were combined, washed with 1×50 mL of H$_2$O, dried over anhydrous sodium sulfate and concentrated under vacuum. The residue was applied onto a silica gel column and eluted with ethyl acetate/petroleum ether (1:2.3). This resulted in 1.26 g (35%) of 7-hydroxy-2, 3-dihydro-1H-indene-4-carbaldehyde as a light yellow solid. Mass spectrum (ESI, m/z): Calcd. for $C_{10}H_{10}O_2$, 163.1 (M+H), found 163.1.

Step 2: Ethyl (2E)-3-(7-hydroxy-2, 3-dihydro-1H-inden-4-yl)prop-2-enoate

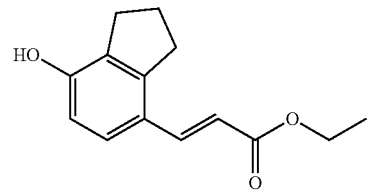 [SMILES: CCOC(=O)/C=C/c1ccc(O)c2c1CCC2]

Into a 25-mL round-bottom flask, under nitrogen, was placed a solution of 7-hydroxy-2,3-dihydro-1H-indene-4-carbaldehyde (115 mg, 0.71 mmol, 1.00 equiv) in toluene (4 mL), ethyl 2-(triphenyl-^5-phosphanylidene)acetate (371 mg, 1.06 mmol, 1.50 equiv). The resulting solution was stirred for 4 h at 120° C. The resulting solution was concentrated. The residue was applied onto a silica gel column and eluted with ethyl acetate/petroleum ether (1:2.3). This resulted in 87.4 mg (53%) of ethyl (2E)-3-(7-hydroxy-2, 3-dihydro-1H-inden-4-yl)prop-2-enoate as a white solid.

Step 3: Ethyl 3-(7-hydroxy-2,3-dihydro-1H-inden-4-yl)propanoate

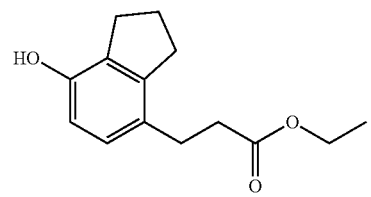 [SMILES: CCOC(=O)CCc1ccc(O)c2c1CCC2]

Into a 25-mL round-bottom flask, was placed a solution of ethyl (2E)-3-(7-hydroxy-2,3-dihydro-1H-inden-4-yl)prop-2-enoate (87.4 mg, 0.38 mmol, 1.00 equiv) in ethanol (4 mL) and palladium on carbon (80 mg). The mixture was then subject to an atmosphere of hydrogen and stirred for 12 h at 25° C. The solids were filtered out. The resulting mixture was concentrated under vacuum. The residue was applied onto a silica gel column with ethyl acetate/petroleum ether (1:10). This resulted in 79.8 mg (91%) of ethyl 3-(7-hydroxy-2,3-dihydro-1H-inden-4-yl)propanoate as yellow oil.

Step 4: 3-(7-[[3-(4-ethylphenyl)-5-(trifluoromethyl)-1,2-thiazol-4-yl]methoxy]-2,3-dihydro-1H-inden-4-yl)propanoic Acid

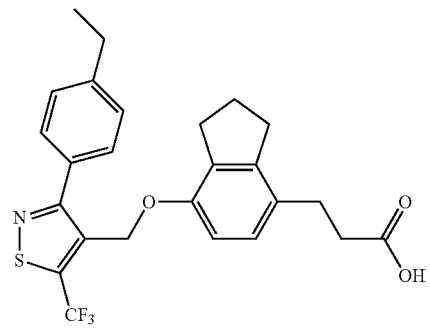 [SMILES: CCc1ccc(-c2nsc(C(F)(F)F)c2COc2ccc(CCC(=O)O)c3c2CCC3)cc1]

The title compound was prepared according to the procedure described in Example 1 starting from 4-ethyl-benzamide following Step 1-6 using ethyl 3-(7-hydroxy-2,3-dihydro-1H-inden-4-yl)propanoate as coupling agent to afford the desired product as an off-white solid. $^1$H NMR (300 MHz, CD$_3$OD) δ 7.06 (d, J=8.1 Hz, 2H), 7.28 (d, J=8.1 Hz, 2H), 6.93 (d, J=8.1 Hz, 1H), 6.65 (d, J=8.1 Hz, 1H), 5.09 (s, 2H), 3.32-337 (m, 4H), 2.81-2.91 (m, 4H), 2.54 (t, J=7.5 Hz, 2H), 2.03 (t, J=7.5 Hz, 2H), 1.25 (t, J=7.5 Hz, 3H). Mass spectrum (ESI, m/z): Calcd. for C$_{25}$H$_{24}$F$_3$NO$_3$S, 476.1 (M+H), found 476.0.

Example 80

3-(4-((3-(4-chloro-3-fluorophenyl)-5-(trifluoromethyl)isothiazol-4-yl)methoxy)phenyl)-2-methylpropanoic Acid, Cpd 165

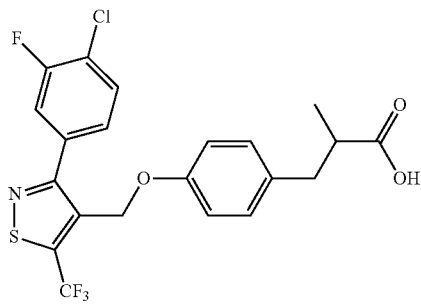 [SMILES: CC(Cc1ccc(OCc2c(-c3ccc(Cl)c(F)c3)nsc2C(F)(F)F)cc1)C(=O)O]

The title compound was prepared according to the procedure described in Example 1 starting from 3-fluoro-4-chloro-benzamide following Step 1-6 using ethyl 3-(4-hydroxyphenyl)-2-methylpropanoate (prepared according to PCT Application WO2010/048207A2) as coupling agent to afford the desired product as an off-white solid. $^1$H NMR (400 MHz, CDCl$_3$) δ 7.58 (d, J=7.0 Hz, 1H), 7.49 (m, 2H), 7.18 (d, J=8.1 Hz, 2H), 6.87 (d, J=8.0 Hz, 2H), 5.05 (s, 2H), 3.03 (m, J=7.2 Hz, 1H), 2.75 (m, J=6.5 Hz, 1H), 2.70 (m, J=7.5 Hz, 1H), 1.21 (d, J=6.5 Hz, 3H).

Example 81

3-(4-((3-(4-chlorophenyl)-5-(trifluoromethyl)isothiazol-4-yl)methoxy)-3,5-difluorophenyl)-2-methylpropanoic Acid, Cpd 108

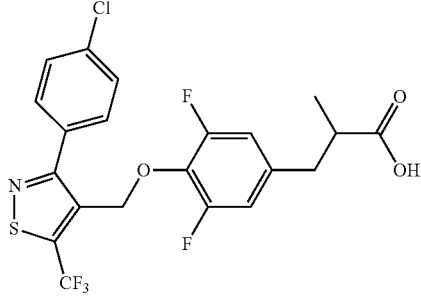 [SMILES: CC(Cc1cc(F)c(OCc2c(-c3ccc(Cl)cc3)nsc2C(F)(F)F)c(F)c1)C(=O)O]

The title compound was prepared according to the procedure described in Example 1 starting from 4-chloro-benzamide following Step 1-6 using ethyl 3-(3,5-difluoro-4-hydroxyphenyl)-2-methylpropanoate (prepared according to PCT Application WO2010/048207A2) as coupling agent to afford the desired product as an off-white solid. $^1$H NMR (400 MHz, CDCl$_3$) δ 7.88 (d, J=7.1 Hz, 2H), 7.48 (d, J=7.1 Hz, 2H), 6.72 (d, J=8.0 Hz, 2H), 5.07 (s, 2H), 3.02 (m, J=6.5 Hz, 1H), 2.76 (m, J=7.5 Hz, 1H), 2.68 (m, J=7.0 Hz, 1H), 1.20 (d, J=7.8 Hz, 3H).

Example 82

3-(4-((3-(4-chlorophenyl)-5-(trifluoromethyl)isothiazol-4-yl)methoxy)phenyl)-2-methylpropanoic Acid, Cpd 195

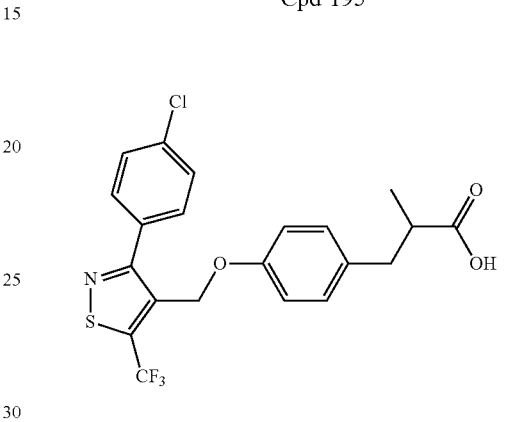

The title compound was prepared according to the procedure described in Example 1 starting from 4-chloro-benzamide following Step 1-6 using ethyl 3-(4-hydroxyphenyl)-2-methylpropanoate as coupling agent to afford the desired product as an off-white solid.

$^1$H NMR (400 MHz, CDCl$_3$) δ 7.65 (d, J=8.1 Hz, 2H), 7.42 (d, J=8.0 Hz, 2H), 7.16 (d, J=7.0 Hz, 2H), 6.88 (d, J=6.8 Hz, 2H), 5.01 (s, 2H), 3.04 (m, J=7.1 Hz, 1H), 2.80 (m, J=6.8 Hz, 1H), 2.75 (m, J=7.0 Hz, 1H), 1.22 (d, J=7.0 Hz, 3H).

Example 83

3-(4-((3-(4-chloro-3-fluorophenyl)-5-(trifluoromethyl)isothiazol-4-yl)methoxy)-3,5-difluorophenyl)-2-methylpropanoic Acid, Cpd 90

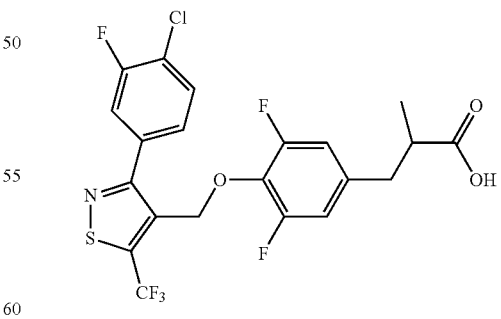

The title compound was prepared according to the procedure described in Example 1 starting from 3-fluoro-4-chloro-benzamide following Step 1-6 using ethyl 3-(3,5-difluoro-4-hydroxyphenyl)-2-methylpropanoate as coupling agent to afford the desired product as an off-white solid. $^1$H NMR (400 MHz, CDCl$_3$) δ 7.75 (d, J=8.0 Hz, 1H), 7.68 (d, J=6.5 Hz, 1H), 7.58 (dd, J=8.0, 6.5 Hz, 1H), 6.78 (d, J=8.5 Hz, 2H), 5.11 (s, 2H), 3.02 (m, 1H), 2.78 (m, 1H), 2.65 (m, 1H), 1.22 (d, J=7.5 Hz, 3H).

Example 84

3-(4-((3-(4-ethyl-2-fluorophenyl)-5-(trifluoromethyl) isothiazol-4-yl)methoxy)-3,5-difluorophenyl)-2-methylpropanoic Acid, Cpd 188

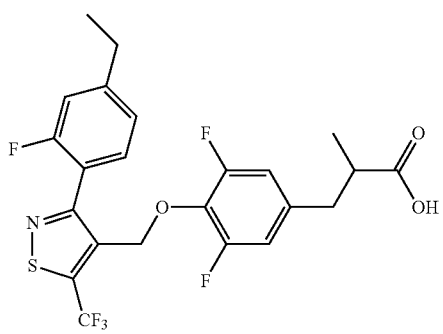 [SMILES: CCc1ccc(-c2nsc(C(F)(F)F)c2COc2c(F)cc(CC(C)C(=O)O)cc2F)c(F)c1]

The title compound was prepared according to the procedure described in Example 1 starting from 2-fluoro-4-ethyl-benzamide following Step 1-6 using ethyl 3-(3,5-difluoro-4-hydroxyphenyl)-2-methylpropanoate as coupling agent to afford the desired product as an off-white solid. $^1$H NMR (400 MHz, CDCl$_3$) δ 7.48 (m, J=7.2 Hz, 1H), 7.08 (d, J=6.0 Hz, 1H), 7.02 (d, J=8.5 Hz, 1H), 6.65 (d, J=7.3 Hz, 2H), 5.15 (s, 2H), 2.98 (m, J=8.0 Hz, 1H), 2.72 (m, 3H), 2.55 (dd, J=8.0, 4.5 Hz, 1H), 1.32 (t, J=8.5 Hz, 3H), 1.25 (d, J=7.5 Hz, 3H).

Example 85

3-(4-((3-(4-ethyl-3-fluorophenyl)-5-(trifluoromethyl) isothiazol-4-yl)methoxy)-3,5-difluorophenyl)-2-methylpropanoic Acid, Cpd 212

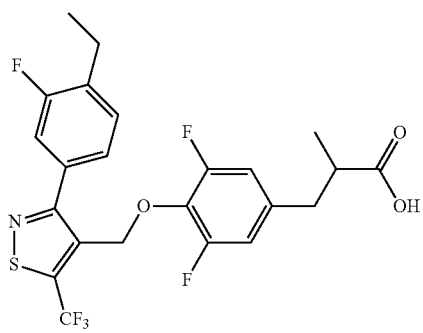 [SMILES: CCc1ccc(-c2nsc(C(F)(F)F)c2COc2c(F)cc(CC(C)C(=O)O)cc2F)cc1F]

The title compound was prepared according to the procedure described in Example 1 starting from 3-fluoro-4-ethyl-benzamide following Step 1-6 using ethyl 3-(3,5-difluoro-4-hydroxyphenyl)-2-methylpropanoate as coupling agent to afford the desired product as an off-white solid. $^1$H NMR (400 MHz, CDCl$_3$) δ 7.65 (d, J=7.5 Hz, 1H), 7.61 (d, J=8.6 Hz, 1H), 7.37 (t, J=7.1 Hz, 1H), 6.78 (d, J=8.5 Hz, 2H), 5.18 (s, 2H), 3.01 (m, 1H), 2.78 (m, 3H), 2.65 (m, 1H), 1.29 (t, J=8.6 Hz, 3H), 1.25 (d, J=6.5 Hz, 3H).

Example 86

3-(4-((3-(2,4-difluorophenyl)-5-(trifluoromethyl) isothiazol-4-yl)methoxy)-3,5-difluorophenyl)-2-methylpropanoic Acid, Cpd 196

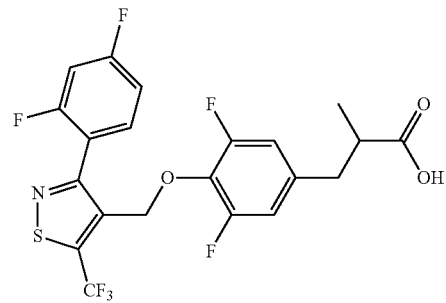 [SMILES: CC(Cc1cc(F)c(OCc2c(-c3ccc(F)cc3F)nsc2C(F)(F)F)c(F)c1)C(=O)O]

The title compound was prepared according to the procedure described in Example 1 starting from 2,4-difluorobenzamide following Step 1-6 using ethyl 3-(3,5-difluoro-4-hydroxyphenyl)-2-methylpropanoate as coupling agent to afford the desired product as an off-white solid. $^1$H NMR (400 MHz, CDCl$_3$) δ 7.62 (t, J=7.5 Hz, 1H), 7.05 (d, J=6.5 Hz, 1H), 6.92 (d, J=7.8 Hz, 1H), 6.68 (d, J=8.5 Hz, 2H), 5.08 (s, 2H), 2.96 (t, J=7.0 Hz, 1H), 2.72 (q, J=6.5 Hz, 1H), 2.60 (t, J=7.0 Hz, 1H), 1.18 (d, J=7.5 Hz, 3H).

Example 87

2-(4-((3-(4-chlorophenyl)-5-(trifluoromethyl)isothiazol-4-yl)methoxy)phenyl) cyclopropanecarboxylic Acid, Cpd 205

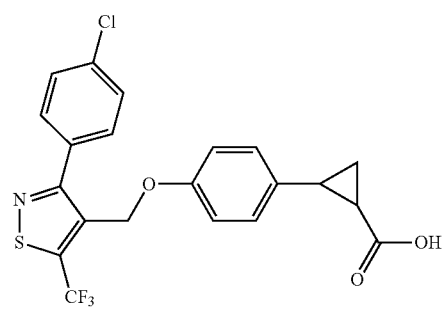 [SMILES: O=C(O)C1CC1c1ccc(OCc2c(-c3ccc(Cl)cc3)nsc2C(F)(F)F)cc1]

The title compound was prepared according to the procedure described in Example 1 starting from 4-chlorobenzamide following Step 1-6 using ethyl 2-(4-hydroxyphenyl) cyclopropanecarboxylate as coupling agent to afford the desired product as an off-white solid. $^1$H NMR (400 MHz, CDCl$_3$) δ 7.67 (d, J=7.0 Hz, 2H), 7.42 (d, J=7.5 Hz, 2H), 7.10 (d, J=7.6 Hz, 2H), 6.88 (d, J=7.6 Hz, 2H), 5.01 (s, 2H), 2.62 (m, 1H), 1.85 (dd, J=7.5, 4.0 Hz, 1H), 1.64 (dd, J=7.6, 4.5 Hz, 1H), 1.38 (m, 1H).

Example 88

3-(3,5-difluoro-4-((3-(tetrahydrofuran-3-yl)-5-(trifluoromethyl)isothiazol-4-yl)methoxy)phenyl)propanoic Acid, Cpd 214

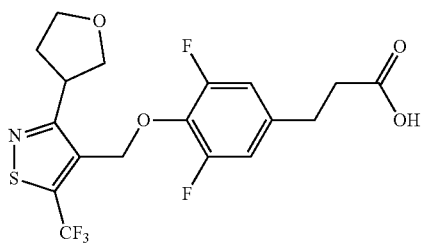 [SMILES: O=C(O)CCc1cc(F)c(OCc2c(C3CCOC3)nsc2C(F)(F)F)c(F)c1]

The title compound was prepared according to the procedure described in Example 1 Step 5-6 using tetrahydrofuran-3-carboxamide and ethyl 3-(4-hydroxy-2,3-dimethylphenyl) propanoate coupling agent followed by hydrolysis to afford the desired product as an off-white solid. $^1$H NMR (300 MHz, CD$_3$OD) δ 6.92-6.95 (m, 2H), 5.24 (s, 2H), 3.85-4.17 (m, 5H), 2.89 (t, J=7.5 Hz, 2H), 2.59 (t, J=7.5 Hz, 2H), 2.27-2.39 (m, 2H). Mass spectrum (ESI, m/z): Calcd. for C$_{18}$H$_{16}$F$_5$NO$_4$S, 438.1[M+H], found 438.1.

Example 89

3-(4-[[5-(1,1-difluoroethyl)-3-(4-ethylphenyl)-1,2-thiazol-4-yl]methoxy]-2,3-dimethylphenyl)propanoic Acid, Cpd 200

Step 1: Ethyl 4, 4-difluoropent-2-ynoate

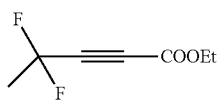

Into a 50-mL 3-necked round-bottom flask (1 atm) purged and maintained with an inert atmosphere of nitrogen, was placed ethyl 4-oxopent-2-ynoate (420 mg, 3.00 mmol, 1.00 equiv), dichloromethane (5 mL), the solution was cooled to 0 degree C. DAST (2.415 g, 14.98 mmol, 5.00 equiv) and ethanol (13.8 mg, 0.30 mmol, 0.10 equiv) were added. The resulting solution was stirred overnight at 25° C. The reaction mixture was added carefully to the water/ice to break the DAST. The organic phase was separated and the aqueous phase was extracted with 3×10 mL of dichloromethane and the organic layers combined. The resulting mixture was washed with 2×20 mL of sodium chloride. The mixture was dried over anhydrous sodium sulfate and concentrated under vacuum. This resulted in 0.37 g (crude) of ethyl 4, 4-difluoropent-2-ynoate as orange oil. The crude could be used for the next step reaction directly.

Step 2: Ethyl 5-(1, 1-difluoroethyl)-3-(4-ethylphenyl)-1,2-thiazole-4-carboxylate

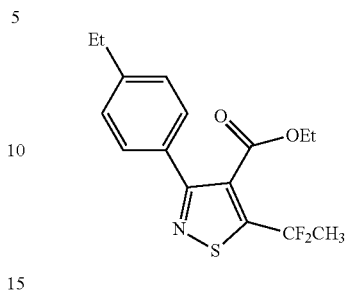

Into a 10-mL sealed tube, was placed 5-(4-ethylphenyl)-2H-1,3,4-oxathiazol-2-one (227 mg, 1.10 mmol, 1.00 equiv), ethyl 4,4-difluoropent-2-ynoate (357 mg, 2.20 mmol, 2.01 equiv), 1,3-dichlorobenzene (3 mL). The resulting solution was stirred for 16 h at 150° C. in an oil bath. The reaction progress was monitored by LCMS. The resulting mixture was concentrated under vacuum. The residue was applied onto a silica gel column with ethyl acetate/petroleum ether (1:10). This resulted in 0.191 g (54%) of ethyl 5-(1, 1-difluoroethyl)-3-(4-ethylphenyl)-1,2-thiazole-4-carboxylate as orange oil.

Step 3: [5-(1, 1-difluoroethyl)-3-(4-ethylphenyl)-1, 2-thiazol-4-yl]methanol

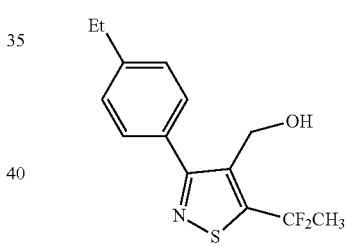

Into a 50-mL round-bottom flask (1 atm) purged and maintained with an inert atmosphere of nitrogen, was placed ethyl 5-(1,1-difluoroethyl)-3-(4-ethylphenyl)-1,2-thiazole-4-carboxylate (191 mg, 0.59 mmol, 1.00 equiv), toluene (3 mL). This was followed by the addition of DIBAL-H (25% in toluene) (1.67 g, 5.00 equiv) dropwise with stirring at −78° C. The resulting solution was stirred for 2 h at 30° C. The reaction progress was monitored by LCMS. The reaction mixture was cooled to 0° C. with a water/ice bath, then quenched by the addition of 10 mL of water and 10 mL NH$_4$Cl. The resulting solution was extracted with 4×10 mL of ethyl acetate and the organic layers combined. The resulting mixture was washed with 2×20 mL of sodium chloride. The mixture was dried over anhydrous sodium sulfate and concentrated under vacuum. The residue was purified by TLC-plate. This resulted in 32 mg (19%) of [5-(1,1-difluoroethyl)-3-(4-ethylphenyl)-1,2-thiazol-4-yl]methanol as a orange solid. Mass spectrum (ESI, m/z): Calcd. For C$_{14}$H$_{15}$F$_2$NOS, 284.1 (M+H), found 284.1.

Step 4: [5-(1, 1-difluoroethyl)-3-(4-ethylphenyl)-1,2-thiazol-4-yl]methyl methanesulfonate

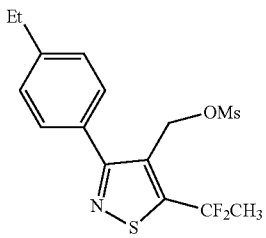

Into a 25-mL round-bottom flask, was placed [5-(1,1-difluoroethyl)-3-(4-ethylphenyl)-1,2-thiazol-4-yl]methanol (32 mg, 0.11 mmol, 1.00 equiv), dichloromethane (2 mL), MsCl (0.0258 g), triethylamine (34.2 mg, 0.34 mmol, 2.99 equiv). The resulting solution was stirred for 0.5 h at 28° C. The reaction progress was monitored by LCMS. The reaction was then quenched by the addition of 10 mL of water, the organic phase was collected. The aqueous phase was extracted with 3×10 mL of dichloromethane and the organic layers combined. The resulting mixture was washed with 2×20 mL of sodium chloride. The mixture was dried over anhydrous sodium sulfate and concentrated under vacuum. This resulted in 0.061 g (crude) of [5-(1,1-difluoroethyl)-3-(4-ethylphenyl)-1,2-thiazol-4-yl]methyl methanesulfonate as yellow oil. Mass spectrum (ESI, m/z): Calcd. for $C_{15}H_{17}F_2NO_3S_2$, 362.4 (M+H), found 362.4.

Step 5: 3-(4-[[5-(1,1-difluoroethyl)-3-(4-ethylphenyl)-1,2-thiazol-4-yl]methoxy]-2,3-dimethylphenyl) propanoic Acid

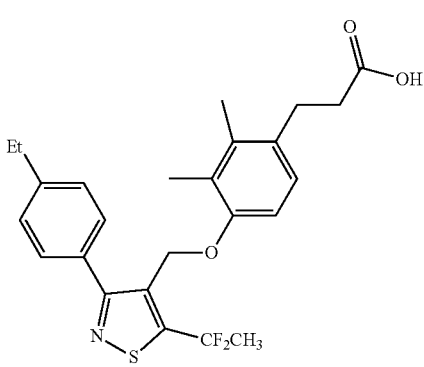

The title compound was prepared according to the procedure described in Example 1 following Step 5 and 6 by coupling [5-(1, 1-difluoroethyl)-3-(4-ethylphenyl)-1,2-thiazol-4-yl]methyl methanesulfonate and ethyl 3-(4-hydroxy-2,3-dimethylphenyl)propanoate to afford the desired product as an off-white solid. $^1$H-NMR (300 MHz, $CD_3OD$) δ 7.58 (d, J=8.1 Hz, 2H), 7.25 (d, J=8.4 Hz, 2H), 6.98 (d, J=8.4 Hz, 1H), 6.73 (d, J=8.4 Hz, 1H), 5.02 (s, 2H), 2.92 (t, J=7.5 Hz, 2H), 2.68 (q, J=15.2 Hz, $J_2$=7.5 Hz, 2H), 2.52 (t, J=8.1 Hz, 2H), 2.24 (s, 3H), 2.13 (t, J=18.6 Hz, 3H), 2.09 (s, 3H), 1.24 (t, J=7.8 Hz, 3H). Mass spectrum (ESI, m/z): Calcd. for $C_{25}H_{27}F_2NO_3S$, 460.2 (M+H), found 460.2.

Example 90

3-(4-[[3-(4-ethylphenyl)-5-(pentafluoroethyl)-1,2-thiazol-4-yl]methoxy]-2,3-dimethylphenyl)propanoic Acid, Cpd 192

Step 1: Ethyl 4, 4, 5, 5, 5-pentafluoro-3-oxo-2-(triphenyl-[5]-phosphanylidene)pentanoate

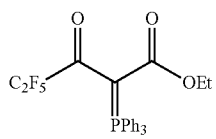

Into a 250-mL 3-necked round-bottom flask (1 atm) purged and maintained with an inert atmosphere of nitrogen, was placed (2-ethoxy-2-oxoethyl)triphenylphosphanium bromide (17.16 g, 39.97 mmol, 1.00 equiv), tetrahydrofuran (100 mL). The solution was cooled to 0° C. in the ice/water bath. Triethylamine (8.888 g, 87.83 mmol, 2.20 equiv) was added dropwise and stirred at this temperature, stirred for 15 min. Then pentafluoropropanoyl 2,2,3,3,3-pentafluoropropanoate (13.64 g, 43.99 mmol, 1.10 equiv) was added dropwise and stirred for another 2 h. The solids were collected by filtration, washed by the cool THF, collected the organic phase and concentrated. 100 mL distilled water was added to the residue, and stirred violently. The white solid appeared. Filtered and dried under the vacuum. This resulted in 14.4 g (73%) of ethyl 4,4,5,5,5-pentafluoro-3-oxo-2-(triphenyl-[5]-phosphanylidene) pentanoate as a white solid. Mass spectrum (ESI, m/z): Calcd. for $C_{25}H_{20}F_5O_3P$, 495.4 (M+H), found 495.4.

Step 2: Ethyl 4,4,5,5,5-pentafluoropent-2-ynoate

Into a 10-mL round-bottom flask, was placed ethyl 4,4,5,5,5-pentafluoro-3-oxo-2-(triphenyl-[5]-phosphanylidene) pentanoate (7.4 g, 14.97 mmol, 1.00 equiv). It was thermolyzed under reduced pressure (0.1-10 torr). Once the distillation pot reached to 140 degree C., the solid phosphorane began to melt and evolution of acetylene. The mixture was heated to 220-240 degree C. and the acetylene was collected in the Ethanol-Liquid nitrogen bath. This resulted in 0.6 g (19%) of ethyl 4,4,5,5,5-pentafluoropent-2-ynoate as orange oil.

Step 3: Ethyl 3-(4-ethylphenyl)-5-(perfluoroethyl) isothiazole-4-carboxylate

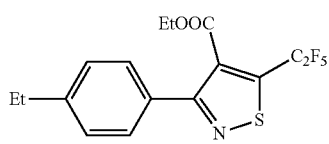

Into a 10-mL sealed tube, was placed 5-(4-ethylphenyl)-2H-1,3,4-oxathiazol-2-one (155 mg, 0.75 mmol, 1.00 equiv), ethyl 4,4,5,5,5-pentafluoropent-2-ynoate (250 mg, 1.16 mmol, 1.55 equiv), 1,3-dichlorobenzene (3 mL). The resulting solution was stirred for 16 h at 150° C. in an oil bath. The reaction progress was monitored by LCMS. The resulting mixture was concentrated under vacuum. The residue was applied onto a silica gel column with ethyl acetate/petroleum ether (1:19). The resulted in a mixture of the product 0.192 g as the yellow oil. Mass spectrum (ESI, m/z): Calcd. for $C_{16}H_{14}F_5NO_2S$, 380.3 (M+H), found 380.3.

Step 4: 3-(4-ethylphenyl)-5-(pentafluoroethyl)-1,2-thiazol-4-yl]methanol

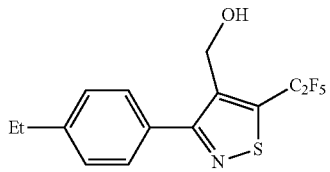

Into a 50-mL 3-necked round-bottom flask (1 atm) purged and maintained with an inert atmosphere of nitrogen, was placed ethyl 3-(4-ethylphenyl)-5-(pentafluoroethyl)-1,2-thiazole-4-carboxylate (180 mg, 0.47 mmol, 1.00 equiv), toluene (10 mL). This was followed by the addition of DIBAL-H (25% in toluene) (1.35 g, 5.00 equiv) dropwise with stirring at −78° C. The resulting solution was warmed to 30° C. naturally and stirred for 2 h. The reaction progress was monitored by LCMS. The reaction was then quenched by the addition of 10 mL of water at 0° C., the organic phase was separated and the aqueous phase was extracted with 3×20 mL of ethyl acetate and the organic layers combined. The resulting mixture was washed with 2×30 mL of sodium chloride. The mixture was dried over anhydrous sodium sulfate and concentrated under vacuum. The residue was purified by TLC. This resulted in 0.108 g (67%) of [3-(4-ethylphenyl)-5-(pentafluoroethyl)-1, 2-thiazol-4-yl]methanol as light yellow oil. Mass spectrum (ESI, m/z): Calcd. for $C_{14}H_{12}F_5NOS$, 338.3 (M+H), found 338.3.

Step 5: [3-(4-ethylphenyl)-5-(pentafluoroethyl)-1,2-thiazol-4-yl]methyl methanesulfonate

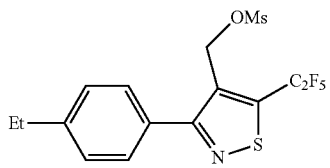

Into a 100-mL round-bottom flask, was placed [3-(4-ethylphenyl)-5-(pentafluoroethyl)-1,2-thiazol-4-yl]methanol (108 mg, 0.32 mmol, 1.00 equiv), dichloromethane (10 mL). The solution was cooled to 0 degree C. MsCl (73 mg, 0.64 mmol, 2.00 equiv) and triethylamine (0.097 g, 0.96 mmol, 3.00 equiv) were added dropwise. The resulting solution was stirred for 2 h at 25° C. The reaction progress was monitored by LCMS. The reaction was then quenched by the addition of 5 mL of water. Organic phase was separated and the aqueous phase was extracted with 3×10 mL of dichloromethane and the organic layers combined. The resulting mixture was washed with 2×20 mL of sodium chloride. The mixture was dried over anhydrous sodium sulfate and concentrated under vacuum. This resulted in 0.150 g (crude) of [3-(4-ethylphenyl)-5-(pentafluoroethyl)-1,2-thiazol-4-yl]methyl methanesulfonate as a white solid. And it could been used for the next step directly. Mass spectrum (ESI, m/z): Calcd. for $C_{15}H_{14}F_5NO_3S_2$, 416.4 (M+H), found 416.4.

Step 6: 3-(4-[[3-(4-ethylphenyl)-5-(pentafluoroethyl)-1, 2-thiazol-4-yl]methoxy]-2,3-dimethylphenyl)propanoic Acid

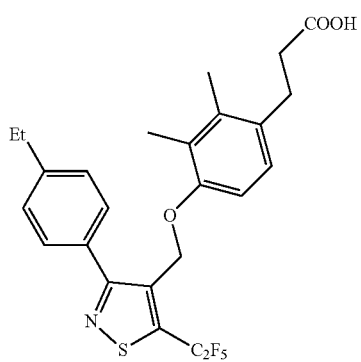

The title compound was prepared according to the procedure described in Example 1 following Step 5 and 6 by coupling [3-(4-ethylphenyl)-5-(pentafluoroethyl)-1,2-thiazol-4-yl]methyl methanesulfonate and ethyl 3-(4-hydroxy-2,3-dimethylphenyl)propanoate to afford the desired product as an off-white solid. $^1$H-NMR (300 MHz, $CD_3OD$) δ 7.60 (d, J=8.1 Hz, 2H), 7.26 (d, J=8.1 Hz, 2H), 6.97 (d, J=8.4 Hz, 1H), 6.69 (d, J=8.4 Hz, 1H), 5.03 (s, 2H), 2.91 (t, J=8.1 Hz, 2H), 2.68 (q, J=15.3 Hz, $J_2$=7.5 Hz, 2H), 2.51 (t, J=8.4 Hz, 2H), 2.23 (s, 3H), 2.03 (s, 3H), 1.02 (t, J=7.8 Hz, 3H). Mass spectrum (ESI, m/z): Calcd. for $C_{25}H_{24}F_5NO_3S$, 514.1 (M+H), found 514.1.

Example 91

3-(4-((3-(4-chlorophenyl)isothiazol-4-yl)methoxy)-3,5-difluorophenyl)propanoic Acid, Cpd 179

Step 1: 4,5-diethyl 3-(4-chlorophenyl)-1,2-thiazole-4,5-dicarboxylate

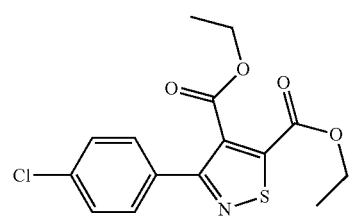 [SMILES: CCOC(=O)c1snc(-c2ccc(Cl)cc2)c1C(=O)OCC]

Into a 150-mL sealed tube, was placed 5-(4-chlorophenyl)-2H-1,3,4-oxathiazol-2-one (2 g, 9.65 mmol, 1.00 equiv), 1,4-diethyl but-2-ynedioate (3.29 g, 19.33 mmol, 2.00 equiv), 1,3-dichlorobenzene (30 mL). The resulting solution was stirred for 16 h at 148° C. The resulting mixture was concentrated under vacuum. This resulted in 1 g (31%) of 4,5-diethyl 3-(4-chlorophenyl)-1,2-thiazole-4,5-dicarboxylate as brown oil.

Step 2: 3-(4-chlorophenyl)-1,2-thiazole-4,5-dicarboxylic acid

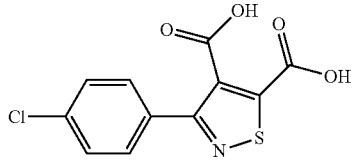 [SMILES: O=C(O)c1snc(-c2ccc(Cl)cc2)c1C(=O)O]

Into a 100-mL round-bottom flask, was placed a solution of 4,5-diethyl 3-(4-chlorophenyl)-1,2-thiazole-4,5-dicarboxylate (3.28 g, 9.84 mmol, 1.00 equiv) in ethanol (20 mL) and a solution of sodium hydroxide (2.36 g, 59.00 mmol, 6.00 equiv) in water (20 mL). The resulting solution was stirred for 2.5 h at 90° C. in an oil bath. The pH value of the solution was adjusted to 3 with hydrogen chloride (1 mol/L). The resulting solution was extracted with 3×150 mL of dichloromethane. The organic layers were combined, washed with 1×10 mL of brine, dried over anhydrous sodium sulfate and concentrated under vacuum. This resulted in 1.86 g (69%) of 3-(4-chlororphenyl)-1,2-thiazole-4,5-dicarboxylic acid as a yellow solid.

Step 3: 3-(4-chlorophenyl)-1,2-thiazole-4-carboxylic acid

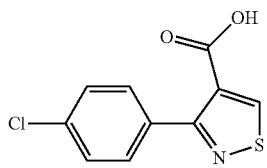 [SMILES: O=C(O)c1csnc1-c1ccc(Cl)cc1]

Into a 50-mL round-bottom flask, was placed 3-(4-chlorophenyl)-1, 2-thiazole-4,5-dicarboxylic acid (1.8697 g, 6.74 mmol, 1.00 equiv), 1,2-dichlorobenzene (20 mL). The resulting solution was stirred for 20 min at 200° C. The resulting mixture was concentrated, and then added 30 mL of petroleum ether slowly when it is hot. The solids were collected by filtration, washed with petroleum ether. This resulted in 1.35 g (86%) of 3-(4-chlorophenyl)-1, 2-thiazole-4-carboxylic acid as a white solid.

Step 4: Ethyl 3-(4-chlorophenyl)-1,2-thiazole-4-carboxylate

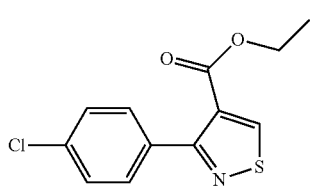 [SMILES: CCOC(=O)c1csnc1-c1ccc(Cl)cc1]

Into a 50-mL round-bottom flask, was placed ethanol (10 mL), thionyl chloride (440 mg, 3.70 mmol, 1.00 equiv), 3-(4-chlorophenyl)-1, 2-thiazole-4-carboxylic acid (860 mg, 3.69 mmol, 1.00 equiv). The resulting solution was stirred for 6 h at 90° C. in an oil bath. The resulting mixture was concentrated under vacuum and taken up in 150 mL of dichloromethane, washed with 1×30 mL of brine. The solution was dried over anhydrous sodium sulfate and concentrated under vacuum. This resulted in 0.72 g (75%) of ethyl 3-(4-chlorophenyl)-1, 2-thiazole-4-carboxylate as brown oil.

Step 5: (3-(4-Chlorophenyl)isothiazol-4-yl)methyl methanesulfonate

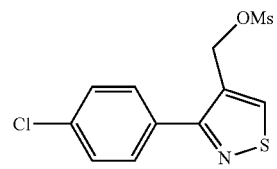 [SMILES: CS(=O)(=O)OCc1csnc1-c1ccc(Cl)cc1]

The title compound was prepared according to the procedure described in Example 1 following Step 4 and 5 by reduction of ethyl 3-(4-chlorophenyl)-1,2-thiazole-4-carboxylate followed by mesylation to afford the desired product as an off-white oil.

Step 6: 3-(4-((3-(4-chlorophenyl)-5-(trifluoromethyl)isothiazol-4-yl)methoxy)-3,5-difluorophenyl)propanoic Acid

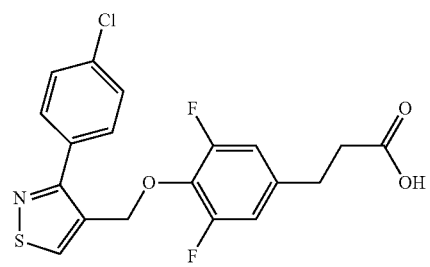 [SMILES: O=C(O)CCc1cc(F)c(OCc2csnc2-c2ccc(Cl)cc2)c(F)c1]

The title compound was prepared according to the procedure described in Example 1 following Step 5-6 by coupling (3-(4-chlorophenyl)isothiazol-4-yl)methyl methanesulfonate and ethyl 3-(3,5-difluoro-4-hydroxyphenyl)propanoate followed by hydrolysis to afford the desired product as an off-white solid. $^{1}$H NMR (400 MHz, CDCl$_3$) δ 8.76 (s, 1H), 7.78 (d, J=8.1 Hz, 2H), 7.48 (d, J=8.0 Hz, 2H), 6.78 (d, J=8.5 Hz, 2H), 5.15 (s, 2H), 2.92 (t, J=7.5 Hz, 2H), 2.65 (t, J=7.5 Hz, 2H).

Example 92

3-(4-((3-(4-chlorophenyl)isothiazol-4-yl)methoxy)-2,3-dimethylphenyl)propanoic Acid, Cpd 166

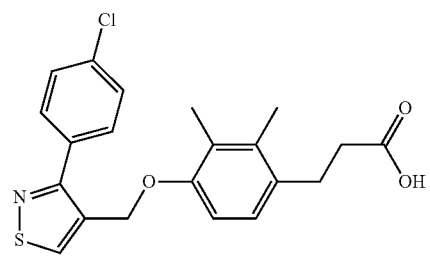 [SMILES: Cc1c(CCC(=O)O)ccc(OCc2csnc2-c2ccc(Cl)cc2)c1C]

The title compound was prepared according to the procedure described in Example 91 following Step 5 and 6 by coupling (3-(4-chlorophenyl)isothiazol-4-yl)methyl methanesulfonate and ethyl 3-(4-hydroxy-2,3-dimethylphenyl) propanoate followed by hydrolysis to afford the desired product as an off-white solid. ¹H NMR (400 MHz, CDCl₃) δ 8.78 (s, 1H), 7.70 (d, J=7.5 Hz, 2H), 7.42 (d, J=7.5 Hz, 2H), 6.98 (d, J=7.6 Hz, 1H), 6.68 (d, J=7.8 Hz, 1H), 5.05 (s, 2H), 2.96 (t, J=7.5 Hz, 2H), 2.62 (t, J=7.6 Hz, 2H), 2.24 (s, 3H), 2.15 (s, 3H).

Example 93

3-(4-((3-(4-chlorophenyl)isothiazol-4-yl)methoxy)-2,3-difluorophenyl)propanoic Acid, Cpd 189

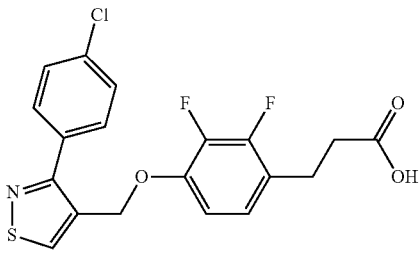 [SMILES: O=C(O)CCc1ccc(OCc2csnc2-c2ccc(Cl)cc2)c(F)c1F]

The title compound was prepared according to the procedure described in Example 91 following Step 5 and 6 by coupling (3-(4-chlorophenyl)isothiazol-4-yl)methyl methanesulfonate and ethyl 3-(2,3-difluoro-4-hydroxyphenyl)propanoate followed by hydrolysis to afford the desired product as an off-white solid. ¹H NMR (400 MHz, CDCl₃) δ 8.88 (s, 2H), 7.66 (d, J=7.0 Hz, 2H), 7.43 (d, J=7.5 Hz, 2H), 6.84 (m, J=8.1 Hz, 1H), 6.64 (m, J=7.2 Hz, 1H), 2.95 (m, 2H), 2.68 (m, 2H).

Example 94

3-(4-((3-(4-chlorophenyl)isothiazol-4-yl)methoxy)-3,5-difluoro-2-methylphenyl)propanoic Acid, Cpd 231

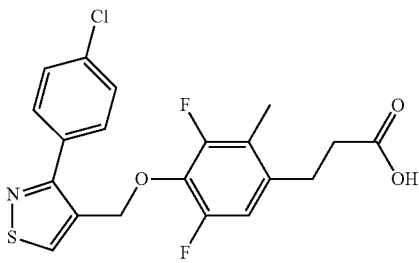 [SMILES: Cc1c(CCC(=O)O)cc(F)c(OCc2csnc2-c2ccc(Cl)cc2)c1F]

The title compound was prepared according to the procedure described in Example 91 following Step 5 and 6 by coupling (3-(4-chlorophenyl)isothiazol-4-yl)methyl methanesulfonate and ethyl 3-(2,6-difluoro-4-hydroxy-3-methylphenyl)propanoate followed by hydrolysis to afford the desired product as an off-white solid. ¹H NMR (400 MHz, CDCl₃) δ 8.76 (s, 1H), 7.78 (d, J=7.8 Hz, 2H), 7.48 (d, J=7.8 Hz, 2H), 6.76 (d, J=7.5 Hz, 2H), 5.14 (s, 2H), 2.91 (t, J=8.5 Hz, 2H), 2.62 (t, J=8.5 Hz, 2H), 2.20 (s, 3H).

Example 95

3-(4-((3-(4-bromophenyl)isothiazol-4-yl)methoxy)-2,3-dimethylphenyl)propanoic Acid, Cpd 170

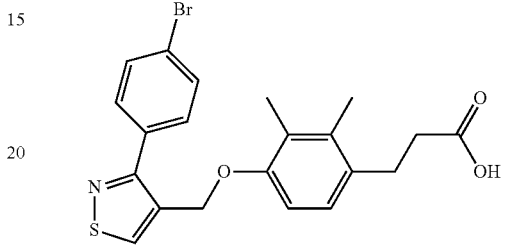

The title compound was prepared according to the procedure described in Example 91 following Step 5 and 6 by coupling (3-(4-bromophenyl)isothiazol-4-yl)methyl methanesulfonate and ethyl 3-(4-hydroxy-2,3-dimethylphenyl)propanoate followed by hydrolysis to afford the desired product as an off-white solid. ¹H NMR (400 MHz, CDCl₃) δ 8.78 (s, 1H), 7.60 (abq, J=10.5, 4.5 Hz, 4H), 6.98 (d, J=7.5 Hz, 1H), 6.68 (d, J=7.5 Hz, 1H), 5.05 (s, 2H), 2.95 (t, J=7.0 Hz, 2H), 2.62 (t, J=7.0 Hz, 2H), 2.25 (s, 3H), 2.18 (s, 3H).

Example 96

3-(4-((3-(4-bromophenyl)isothiazol-4-yl)methoxy)-3,5-difluorophenyl)propanoic Acid, Cpd 169

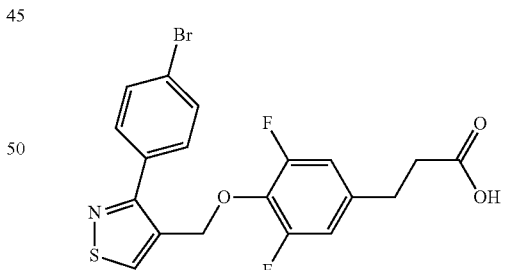

The title compound was prepared according to the procedure described in Example 91 following Step 5 and 6 by coupling (3-(4-bromophenyl)isothiazol-4-yl)methyl methanesulfonate and ethyl 3-(3,5-difluoro-4-hydroxyphenyl)propanoate followed by hydrolysis to afford the desired product as an off-white solid. ¹H NMR (400 MHz, CDCl₃) δ 8.76 (s, 1H), 7.71 (d, J=6.8 Hz, 2H), 6.76 (d, J=7.2 Hz, 2H), 5.15 (s, 2H), 2.92 (t, J=7.5 Hz, 2H), 2.68 (t, J=7.5 Hz, 2H).

Example 97

3-(4-((3-(4-bromophenyl)isothiazol-4-yl)methoxy)-2,3-difluorophenyl)propanoic Acid, Cpd 187

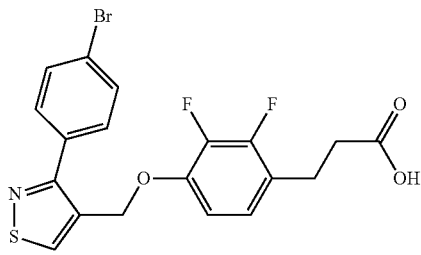 [SMILES: O=C(O)CCc1ccc(OCc2csnc2-c2ccc(Br)cc2)c(F)c1F]

The title compound was prepared according to the procedure described in Example 91 following Step 5 and 6 by coupling (3-(4-bromophenyl)isothiazol-4-yl)methyl methanesulfonate and ethyl 3-(2,3-difluoro-4-hydroxyphenyl)propanoate followed by hydrolysis to afford the desired product as an off-white solid. $^1$H NMR (400 MHz, CDCl$_3$) δ 8.85 (s, 1H), 7.62 (s, 4H), 6.87 (t, J=6.5 Hz, 1H), 6.68 (t, J=6.5 Hz, 1H), 5.12 (s, 2H), 2.95 (t, J=6.1 Hz, 2H), 2.72 (t, J=6.2 Hz, 1H).

Example 98

3-(4-((3-(4-ethynylphenyl)isothiazol-4-yl)methoxy)-2,3-dimethylphenyl)propanoic Acid, Cpd 161

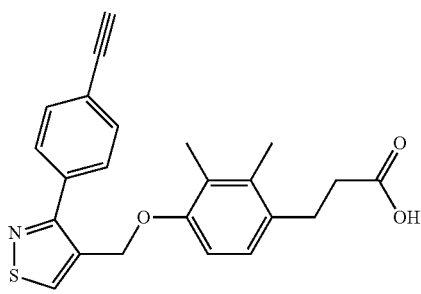 [SMILES: C#Cc1ccc(-c2nscc2COc2ccc(CCC(=O)O)c(C)c2C)cc1]

The title compound was prepared according to the procedure described in Example 91 following Step 5 and 6 by coupling (3-(4-ethynylphenyl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (400 MHz, CDCl$_3$) δ 7.45 (s, 1H), 7.31 (m, 4H), 6.86 (t, J=7.0 Hz, 1H), 6.62 (t, J=7.0 Hz, 1H), 5.21 (s, 2H), 2.95 (t, J=6.1 Hz, 2H), 2.68 (m, 4H), 1.26 (t, J=7.5 Hz, 3H).

Example 99

3-(4-((3-(5-chlorothiophen-2-yl)isothiazol-4-yl)methoxy)-2,3-dimethylphenyl)propanoic Acid, Cpd 204

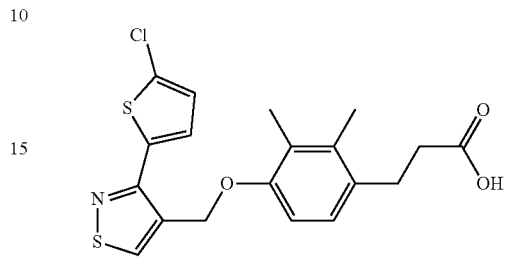

The title compound was prepared according to the procedure described in Example 91 following Step 5 and 6 by coupling (3-(5-chlorothiophen-2-yl)isothiazol-4-yl)methyl methanesulfonate and ethyl 3-(4-hydroxy-2,3-dimethylphenyl)propanoate followed by hydrolysis to afford the desired product as an off-white solid. $^1$H NMR (400 MHz, CDCl$_3$) δ 8.70 (s, 1H), 7.19 (s, 1H), 7.03 (d, J=5.5 Hz, 1H), 6.89 (s, 1H), 6.76 (d, J=5.5 Hz, 1H), 5.15 (s, 2H), 2.96 (t, J=5.0 Hz, 2H), 2.62 (t, J=5.1 Hz, 2H), 2.24 (s, 3H), 2.18 (s, 3H).

Example 100

3-(4-((3-(5-chlorothiophen-2-yl)isothiazol-4-yl)methoxy)-2,3-difluorophenyl)propanoic Acid, Cpd 226

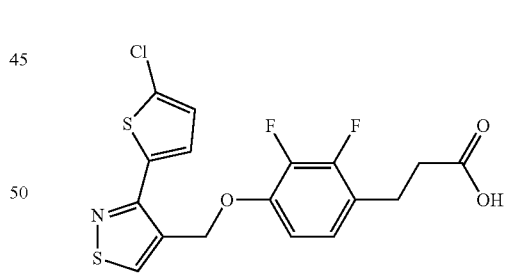

The title compound was prepared according to the procedure described in Example 91 following Step 5 and 6 by coupling (3-(5-chlorothiophen-2-yl)isothiazol-4-yl)methyl methanesulfonate and ethyl 3-(4-hydroxy-2,3-difluorophenyl)propanoate followed by hydrolysis to afford the desired product as an off-white solid. $^1$H NMR (400 MHz, CDCl$_3$) δ 8.75 (s, 1H), 7.27 (m, 1H), 6.95 (m, 1H), 6.90 (m, 1H), 6.73 (m, 1H), 5.24 (s, 2H), 2.98 (t, J=4.5 Hz, 2H), 2.74 (t, J=7.5 Hz, 2H).

Example 101

3-(4-((3-(5-chlorothiophen-2-yl)isothiazol-4-yl)methoxy)-3,5-difluorophenyl)propanoic Acid, Cpd 202

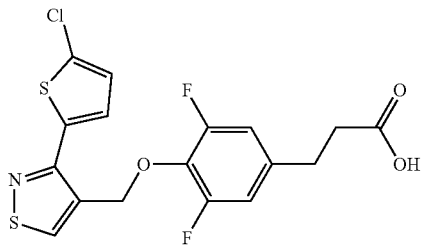 [SMILES: O=C(O)CCc1cc(F)c(OCc2csnc2-c2ccc(Cl)s2)c(F)c1]

The title compound was prepared according to the procedure described in Example 91 following Step 5 and 6 by coupling (3-(5-chlorothiophen-2-yl)isothiazol-4-yl)methyl methanesulfonate and ethyl 3-(3,5-difluoro-4-hydroxyphenyl)propanoate followed by hydrolysis to afford the desired product as an off-white solid. $^1$H NMR (400 MHz, CDCl$_3$) δ 8.71 (s, 1H), 7.45 (d, J=2.5 Hz, 1H), 6.97 (d, J=2.5 Hz, 1H), 6.76 (d, J=7.0 Hz, 2H), 5.25 (s, 2H), 2.90 (d, J=6.3 Hz, 2H), 2.68 (d, J=6.3 Hz, 2H).

Example 102

3-(4-((3-(4-chlorophenyl)-5-methylisothiazol-4-yl)methoxy)-2,3-difluorophenyl)propanoic Acid, Cpd 119

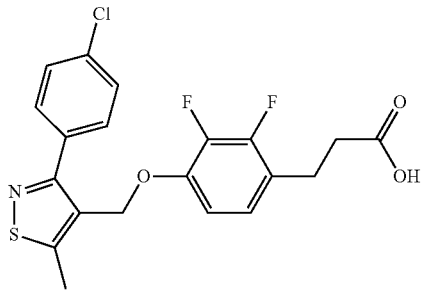 [SMILES: Cc1snc(-c2ccc(Cl)cc2)c1COc1ccc(CCC(=O)O)c(F)c1F]

The title compound was prepared according to the procedure described in Example 91 following Step 5 and 6 by coupling ((3-(4-chlorophenyl)-5-methylisothiazol-4-yl)methanol and ethyl 3-(2,3-difluoro-4-hydroxyphenyl)propanoate followed by hydrolysis to afford the desired product as an off-white solid. $^1$H NMR (400 MHz, CDCl$_3$) δ 7.64 (d, J=7.1 Hz, 2H), 7.42 (d, J=7.0 Hz, 2H), 6.90 (m, J=5.6 Hz, 1H), 6.72 (m, J=5.6 Hz, 1H), 4.98 (s, 2H), 2.96 (m, 2H), 2.68 (m, 2H), 2.62 (s, 3H).

Example 103

3-(4-[[3-(4-ethylphenyl)-5-(propan-2-yl)-1,2-thiazol-4-yl]methoxy]-2,3-dimethylphenyl)propanoic Acid, Cpd 64

Step 1: Ethyl 3-(4-ethylphenyl)-5-iodo-1,2-thiazole-4-carboxylate

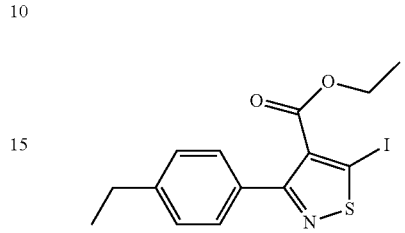

Into a 100-mL round-bottom flask purged and maintained with an inert atmosphere of nitrogen, was placed tetrahydrofuran (15 mL). This was followed by the addition of bis(propan-2-yl)amine (1.34 g, 13.24 mmol, 1.50 equiv). The mixture was cooled to −78° C. To this was added n-BuLi (2.5M) (5.28 mL). The mixture was stirred at −78° C. for 40 minutes. To the mixture was added a solution of ethyl 3-(4-ethylphenyl)-1,2-thiazole-4-carboxylate (2.3 g, 8.80 mmol, 1.00 equiv) in tetrahydrofuran (5 mL). The mixture was stirred at −78° C. for 40 minutes. To the mixture was added a solution of I$_2$ (3.35 g, 13.19 mmol, 1.50 equiv) in tetrahydrofuran (5 mL). The resulting solution was stirred for 40 min at −78° C. The reaction was then quenched by the addition of 80 mL of water. The resulting solution was extracted with 3×80 mL of ethyl acetate and the organic layers combined and concentrated under vacuum. The residue was applied onto a silica gel column and eluted with ethyl acetate/petroleum ether (1:20). The collected fractions were combined and concentrated under vacuum. This resulted in 2.1 g (62%) of ethyl 3-(4-ethylphenyl)-5-iodo-1,2-thiazole-4-carboxylate as red oil.

Step 2: Ethyl 3-(4-ethylphenyl)-5-(prop-1-en-2-yl)-1,2-thiazole-4-carboxylate

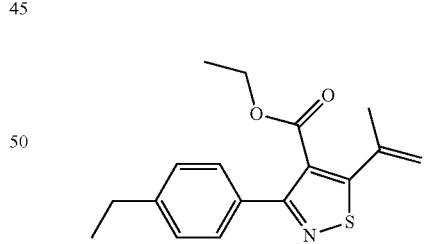

Into a 25-mL round-bottom flask, was placed ethyl 3-(4-ethylphenyl)-5-iodo-1,2-thiazole-4-carboxylate (200 mg, 0.52 mmol, 1.00 equiv), 4,4,5,5-tetramethyl-2-(prop-1-en-2-yl)-1,3,2-dioxaborolane (130.24 mg, 0.78 mmol, 1.50 equiv), sodium carbonate (164.34 mg, 1.55 mmol, 3.00 equiv), Pd(dppf)Cl$_2$ (37.82 mg, 0.05 mmol, 0.10 equiv), DME/H$_2$O (6 mL). The resulting solution was stirred for 16 h at 95° C. in an oil bath under nitrogen. The resulting solution was extracted with 150 mL of dichloromethane. The organic layer was washed with 1×30 mL of brine, dried over anhydrous sodium sulfate and concentrated. The residue was applied onto a silica gel column and eluted with ethyl acetate/petroleum ether (1:20). This resulted in 287.4 mg of ethyl 3-(4-ethylphenyl)-5-(prop-1-en-2-yl)-1,2-thiazole-4-carboxylate as brown oil. Mass spectrum (ESI, m/z): Calcd. for $C_{17}H_{19}NO_2S$, 302.4 (M+H), found 302.4.

Step 3: [3-(4-ethylphenyl)-5-(prop-1-en-2-yl)-1,2-thiazol-4-yl]methanol

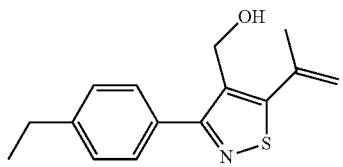 [SMILES: C=C(C)c1snc(-c2ccc(CC)cc2)c1CO]

Into a 50-mL round-bottom flask purged and maintained with an inert atmosphere of nitrogen, was placed a solution of ethyl 3-(4-ethylphenyl)-5-(prop-1-en-2-yl)-1,2-thiazole-4-carboxylate (280 mg, 0.93 mmol, 1.00 equiv) in toluene (6 mL). DIBAL-H (1.32 g, 2.50 equiv) was added at −78° C. The resulting solution was stirred for 4 h at −78° C. The reaction was then quenched by the addition of 5 mL of water. The resulting solution was extracted with 200 mL of ethyl acetate. The organic layer was washed with 1×30 mL of brine, dried over anhydrous sodium sulfate and concentrated under vacuum. The crude product was purified by TLC method with petroleum ether/ethyl acetate (3:1). This resulted in 305.3 mg (crude) of [3-(4-ethylphenyl)-5-(prop-1-en-2-yl)-1,2-thiazol-4-yl]methanol as yellow oil. Mass spectrum (ESI, m/z): Calcd. for $C_{15}H_{17}NOS$, 260.4 (M+H), found 260.4.

Step 4: 4-(chloromethyl)-3-(4-ethylphenyl)-5-(prop-1-en-2-yl)isothiazole

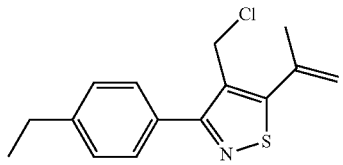 [SMILES: C=C(C)c1snc(-c2ccc(CC)cc2)c1CCl]

Into a 50-mL round-bottom flask, was placed a solution of [3-(4-ethylphenyl)-5-(prop-1-en-2-yl)-1,2-thiazol-4-yl]methanol (305.3 mg, 1.18 mmol, 1.00 equiv) in dichloromethane (15 mL), MsCl (268.8 mg, 2.00 equiv), triethylamine (297.6 mg, 2.94 mmol, 2.50 equiv). The resulting solution was stirred for 40 min at 25° C. 10.0 mL water was added to the mixture. The organic phase was separated and washed by 10.0 mL brine, dried over anhydrous sodium sulfate. The resulting mixture was concentrated under vacuum and residue used in next step directly without further purification. Mass spectrum (ESI, m/z): Calcd. for $C_{15}H_{16}ClNS$, 278.8 (M+H), found 278.8.

Step 5: Ethyl 3-(4-[[3-(4-ethylphenyl)-5-(prop-1-en-2-yl)-1,2-thiazol-4-yl]methoxy]-2,3-dimethylphenyl)propanoate

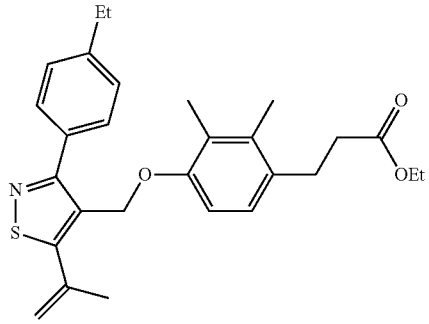 [SMILES: C=C(C)c1snc(-c2ccc(CC)cc2)c1COc1ccc(CCC(=O)OCC)c(C)c1C]

Into a 50-mL round-bottom flask, was placed a solution of 4-(chloromethyl)-3-(4-ethylphenyl)-5-(prop-1-en-2-yl)-1,2-thiazole (326.5 mg, 1.18 mmol, 1.00 equiv) in N,N-dimethylformamide (6 mL), potassium carbonate (488.0 mg, 3.53 mmol, 3.00 equiv), ethyl 3-(4-hydroxy-2,3-dimethylphenyl)propanoate (392.5 mg, 1.77 mmol, 1.50 equiv). The resulting solution was stirred for 12 h at 25° C. and 30 mL ethyl acetate and 20 mL water were added to the mixture. The organic layer was separated and washed with 3×10 mL of brine, dried over anhydrous sodium sulfate and concentrated under vacuum. The crude product was purified by TLC method with petroleum ether/ethyl acetate (6:1). This resulted in 111.3 mg (20%) of ethyl 3-(4-[[3-(4-ethylphenyl)-5-(prop-1-en-2-yl)-1,2-thiazol-4-yl]methoxy]-2,3-dimethyl phenyl) propanoate as yellow oil. Mass spectrum (ESI, m/z): Calcd. for $C_{28}H_{33}NO_3S$, 464.6 (M+H), found 464.6.

Step 6: Ethyl 3-(4-[[3-(4-ethylphenyl)-5-(propan-2-yl)-1,2-thiazol-4-yl]methoxy]-2,3-dimethylphenyl)propanoate

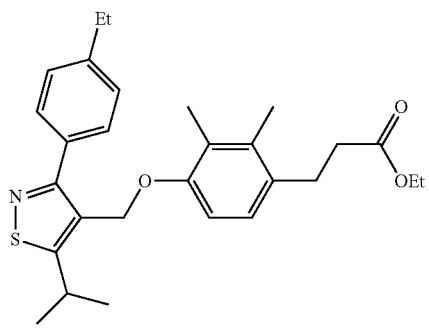 [SMILES: CCOC(=O)CCc1ccc(OCc2c(-c3ccc(CC)cc3)nsc2C(C)C)c(C)c1C]

Into a 25-mL round-bottom flask, was placed a solution of ethyl 3-(4-[[3-(4-ethylphenyl)-5-(prop-1-en-2-yl)-1,2-thiazol-4-yl]methoxy]-2,3-dimethylphenyl)propanoate (76.3 mg, 0.16 mmol, 1.00 equiv) in ethanol (5 mL) and palladium on carbon (10%, 76 mg). The mixture was then subject to an atmosphere of hydrogen and stirred for 12 h at 25° C. The solids were filtered out. The resulting mixture was concentrated under vacuum. This resulted in 73.1 mg (95%) of ethyl 3-(4-[[3-(4-ethylphenyl)-5-(propan-2-yl)-1,2-thiazol-4-yl]methoxy]-2,3-dimethylphenyl)propanoate as white oil.

127

Step 7: 3-(4-[[3-(4-ethylphenyl)-5-(propan-2-yl)-1,2-thiazol-4-yl]methoxy]-2,3-dimethylphenyl)propanoic Acid

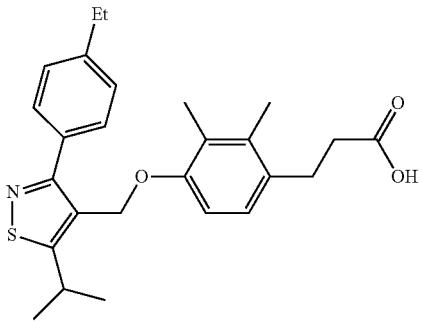 [SMILES: CCc1ccc(-c2nsc(C(C)C)c2COc2ccc(CCC(=O)O)c(C)c2C)cc1]

Into a 25-mL round-bottom flask, was placed ethyl 3-(4-[[3-(4-ethylphenyl)-5-(propan-2-yl)-1,2-thiazol-4-yl]methoxy]-2,3-dimethylphenyl)propanoate (73.1 mg, 0.16 mmol, 1.00 equiv), LiOH (73 mg, 3.05 mmol, 19.42 equiv), tetrahydrofuran/$H_2O$ (5 mL). The resulting solution was stirred for 12 h at 25° C. The resulting solution was concentrated. The pH value of the residue was adjusted to 3 with 1M hydrogen chloride. The resulting solution was extracted with 3×40 mL of dichloromethane and the organic layers combined and concentrated. The crude product was purified by Prep-HPLC with the following conditions (1#-Waters 2767-5): Column, SunFire Prep $C_{18}$, 5 um, 19*100 mm; mobile phase, Water and $CH_3CN$ (30% $CH_3CN$ up to 90% in 10 min, up to 100% in 2 min, down to 30% in 2 min; Detector, UV 220&254 nm. This resulted in 3.4 mg (5%) of 3-(4-[[3-(4-ethylphenyl)-5-(propan-2-yl)-1, 2-thiazol-4-yl]methoxy]-2,3-dimethylphenyl) propanoic acid as a white solid. $^1H$ NMR (300 MHz, $CD_3OD$) δ 7.58 (d, J=8.4 Hz, 2H), 7.26 (d, J=8.1 Hz, 2H), 6.98 (d, J=8.7 Hz, 1H), 6.75 (d, J=8.4 Hz, 1H), 4.94 (s, 2H), 3.44-3.53 (m, 1H), 2.92 (t, J=8.1 Hz, 2H), 2.68 (m, 2H), 2.52 (t, J=7.2 Hz, 2H), 2.24 (s, 3H), 2.10 (s, 3H), 2.14 (s, 6H), 1.25 (t, J=7.5 Hz, 3H). Mass spectrum (ESI, m/z): Calcd. for $C_{26}H_{31}NO_3S$, 438.2 (M+H), found 438.2.

Example 104

3-(4-[[5-ethyl-3-(4-ethylphenyl)-1,2-thiazol-4-yl]methoxy]-2,3-dimethylphenyl)propanoic Acid, Cpd 217

Step 1: 4-(chloromethyl)-3-(4-ethylphenyl)-5-vinylisothiazole

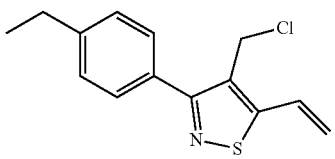 [SMILES: C=Cc1snc(-c2ccc(CC)cc2)c1CCl]

The title compound was prepared according to the procedure described in Example 122 following Step 2 by Stille coupling of ethyl 3-(4-ethylphenyl)-5-iodo-1,2-thiazole-4-carboxylate and tributyl(vinyl)stannane to afford the desired product as a yellow oil. Mass spectrum (ESI, m/z): Calcd. for $C_{14}H_{14}ClNS$, 264.1 (M−H), found 264.1.

128

Step 2: Ethyl 3-(4-[[5-ethenyl-3-(4-ethylphenyl)-1,2-thiazol-4-yl]methoxy]-2,3-dimethylphenyl)propanoate

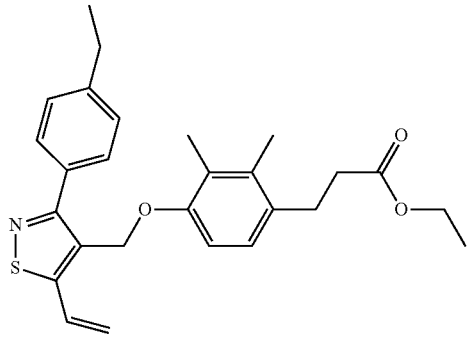 [SMILES: C=Cc1snc(-c2ccc(CC)cc2)c1COc1ccc(CCC(=O)OCC)c(C)c1C]

The title compound was prepared according to the procedure described in Example 122 following Step 5 by coupling of 4-(chloromethyl)-3-(4-ethylphenyl)-5-vinylisothiazole with ethyl 3-(4-hydroxy-2,3-dimethylphenyl)propanoate to afford the desired product as a yellow oil. Mass spectrum (ESI, m/z): Calcd. for $C_{27}H_{31}NO_3S$, 450.2 (M−H), found 450.2.

Step 3: Ethyl 3-(4-[[5-ethyl-3-(4-ethylphenyl)-1,2-thiazol-4-yl]methoxy]-2,3-dimethylphenyl)propanoate

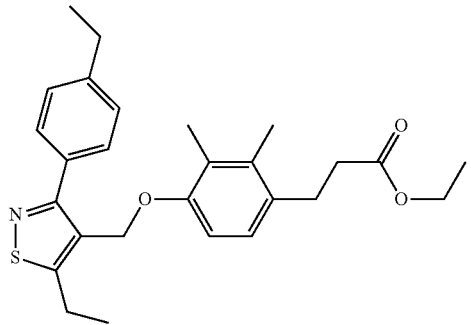 [SMILES: CCOC(=O)CCc1ccc(OCc2c(-c3ccc(CC)cc3)nsc2CC)c(C)c1C]

The title compound was prepared according to the procedure described in Example 122 following Step 6 by hydrogenation of ethyl 3-(4-[[5-ethenyl-3-(4-ethylphenyl)-1,2-thiazol-4-yl]methoxy]-2,3-dimethylphenyl)propanoate to afford the desired product as a yellow oil. Mass spectrum (ESI, m/z): Calcd. for $C_{27}H_{33}NO_3S$, 452.2 (M−H), found 452.2.

Step 4: 3-(4-[[5-ethyl-3-(4-ethylphenyl)-1,2-thiazol-4-yl]methoxy]-2,3-dimethylphenyl)propanoic Acid

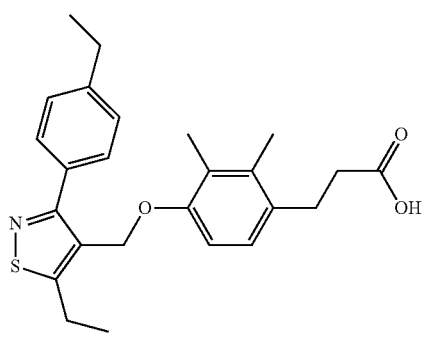 [SMILES: CCc1ccc(-c2nsc(CC)c2COc2ccc(CCC(=O)O)c(C)c2C)cc1]

The title compound was prepared according to the procedure described in Example 122 following Step 7 by hydrolysis of ethyl 3-(4-[[5-ethyl-3-(4-ethylphenyl)-1,2-thiazol-4-yl]methoxy]-2,3-dimethylphenyl)propanoate to afford the desired product as an off-white solid. $^1$H NMR (300 MHz, CD$_3$OD) δ 7.58 (d, J=8.1 Hz, 2H), 7.27 (d, J=8.1 Hz, 2H), 6.97 (d, J=8.7 Hz, 1H), 6.74 (d, J=9.0 Hz, 1H), 5.04 (s, 2H), 3.05 (m, 2H), 2.92 (t, J=8.1 Hz, 2H), 2.69 (m, 2H), 2.52 (t, J=7.8 Hz, 2H), 2.24 (s, 3H), 2.09 (s, 3H), 1.39 (t, J=7.5 Hz, 3H), 1.28 (t, J=7.8 Hz, 3H). Mass spectrum (ESI, m/z): Calcd. for C$_{25}$H$_{29}$NO$_3$S, 424.2 (M−H), found 424.2.

Example 105

3-(4-[[5-cyclopropyl-3-(4-ethylphenyl)-1,2-thiazol-4-yl]methoxy]-2,3-dimethylphenyl)propanoic Acid, Cpd 149

Step 1: Ethyl 5-cyclopropyl-3-(4-ethylphenyl)-1,2-thiazole-4-carboxylate

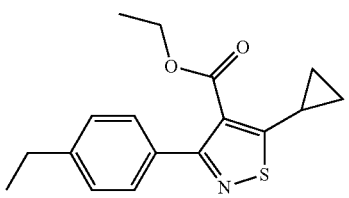 [SMILES: CCOC(=O)c1c(-c2ccc(CC)cc2)nsc1C1CC1]

Into a 50-mL 3-necked round-bottom flask (1 atm) purged and maintained with an inert atmosphere of nitrogen, was placed ethyl 3-(4-ethylphenyl)-5-iodo-1,2-thiazole-4-carboxylate (300 mg, 0.77 mmol, 1.00 equiv), cyclopropylboronic acid (100 mg, 1.16 mmol, 1.50 equiv), sodium carbonate (246 mg, 2.32 mmol, 3.00 equiv), Pd(dppf)Cl$_2$ (56.7 mg, 0.08 mmol, 0.10 equiv), ethylene glycol dimethyl ether (6 mL), water (3 mL). The resulting solution was stirred for 16 h at 95° C. The resulting mixture was concentrated under vacuum. The residue was applied onto a silica gel column with ethyl acetate/petroleum ether (1:20). The collected fractions were combined and concentrated under vacuum. This resulted in 90 mg (39%) of ethyl 5-cyclopropyl-3-(4-ethylphenyl)-1, 2-thiazole-4-carboxylate as yellow oil.

Step 2: 4-(chloromethyl)-5-cyclopropyl-3-(4-ethylphenyl)-1, 2-thiazole

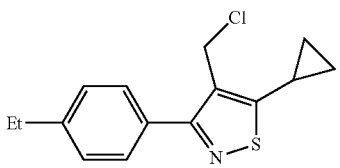 [SMILES: CCc1ccc(-c2nsc(C3CC3)c2CCl)cc1]

The title compound was prepared according to the procedure described in Example 122 following Steps 3 and 4 by reduction of ethyl 5-cyclopropyl-3-(4-ethylphenyl)-1, 2-thiazole-4-carboxylate and then chlorination to afford the desired product as a yellow oil.

Step 3: 3-(4-[[5-cyclopropyl-3-(4-ethylphenyl)-1,2-thiazol-4-yl]methoxy]-2,3-dimethylphenyl)propanoic Acid

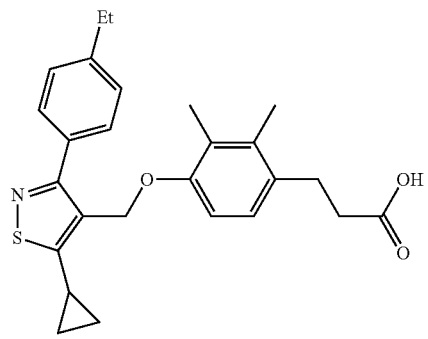 [SMILES: CCc1ccc(-c2nsc(C3CC3)c2COc2ccc(CCC(=O)O)c(C)c2C)cc1]

The title compound was prepared according to the procedure described in Example 122 following Steps 5 and 7 by coupling of 4-(chloromethyl)-5-cyclopropyl-3-(4-ethylphenyl)-1, 2-thiazole with ethyl 3-(4-hydroxy-2,3-dimethylphenyl)propanoate to afford the desired product as a yellow oil. $^1$H NMR (400 MHz, CD$_3$OD) δ 7.59 (d, J=8.4 Hz, 2H), 7.28 (d, J=8.0 Hz, 2H), 6.97 (d, J=8.4 Hz, 1H), 6.77 (d, J=8.4 Hz, 1H), 5.06 (s, 2H), 2.92 (t, J=8.0 Hz, 2H), 2.70 (q, J=7.6, 15.6 Hz, 2H), 2.52 (t, J=7.2 Hz, 2H), 2.25-2.27 (m, 4H), 2.11 (s, 3H), 1.20-1.28 (m, 5H), 0.88-0.87 (m, 2H). Mass spectrum (ESI, m/z): Calcd. for C$_{26}$H$_{29}$NO$_3$S, 436.2 (M+H), found 436.2.

Example 106

3-(4-[[3-(4-ethylphenyl)-5-phenyl-1,2-thiazol-4-yl]methoxy]-2,3-dimethylphenyl)propanoic Acid, Cpd 233

Step 1: Ethyl 3-(4-ethylphenyl)-5-phenyl-1,2-thiazole-4-carboxylate

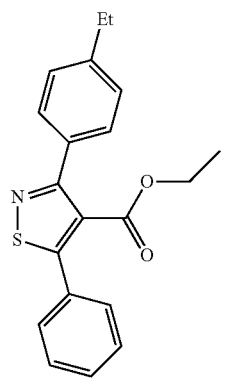 [SMILES: CCOC(=O)c1c(-c2ccc(CC)cc2)nsc1-c1ccccc1]

Into a 8-mL round-bottom flask purged and maintained with an inert atmosphere of nitrogen, was placed ethylene glycol dimethyl ether (2 mL), water (1 mL), ethyl 3-(4-ethylphenyl)-5-iodo-1,2-thiazole-4-carboxylate (50 mg, 0.13 mmol, 1.00 equiv), phenylboronic acid (18.9 mg, 0.16 mmol, 1.20 equiv), Pd(dppf)Cl$_2$ (5.2 mg, 0.01 mmol, 0.06 equiv), sodium carbonate (41 mg, 0.39 mmol, 3.00 equiv). The resulting solution was stirred for 2 h at 90° C. The resulting mixture was concentrated under vacuum. The residue was applied onto a silica gel column and eluted with ethyl acetate/petroleum ether (1:20). The collected fractions were combined and concentrated under vacuum. This resulted in 56 mg of ethyl 3-(4-ethylphenyl)-5-phenyl-1,2-thiazole-4-carboxylate as yellow oil. Mass spectrum (ESI, m/z): Calcd. for $C_{20}H_{19}NO_2S$, 338.1 (M+H), found 338.1.

Step 2: 3-(4-[[3-(4-ethylphenyl)-5-phenyl-1,2-thiazol-4-yl]methoxy]-2,3-dimethylphenyl)propanoic Acid

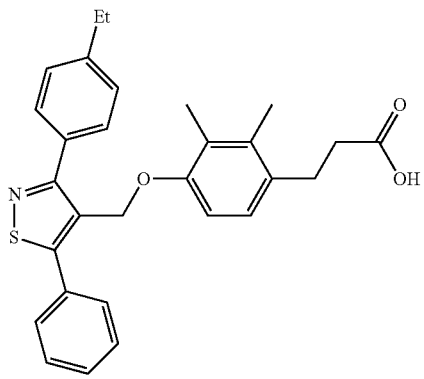 [SMILES: CCc1ccc(-c2nsc(-c3ccccc3)c2COc2ccc(CCC(=O)O)c(C)c2C)cc1]

The title compound was prepared according to the procedure described in Example 1 following Steps 2-6 by coupling of (3-(4-ethylphenyl)-5-phenylisothiazol-4-yl) methyl methanesulfonate and ethyl 3-(4-hydroxy-2,3-dimethylphenyl)propanoate to afford the desired product as an off-white solid. $^1$H NMR (300 MHz, CDCl$_3$) δ 7.73 (d, J=8.1 Hz, 2H), 7.58-7.59 (m, 2H), 7.42 (t, J=3.0 Hz, 3H), 7.22 (s, 2H), 6.94 (d, J=8.4 Hz, 1H), 6.63 (d, J=8.4 Hz, 1H), 4.83 (s, 2H), 2.97 (t, J=8.4 Hz, 2H), 2.60-2.70 (m, 2H), 2.28 (s, 3H), 2.24 (s, 3H). Mass spectrum (ESI, m/z): Calcd. for $C_{29}H_{29}NO_3S$, 472.2 (M+H), found 472.2.

Example 107

3-(4-[[3-(4-ethylphenyl)-5-methoxy-1,2-thiazol-4-yl]methoxy]-2,3-dimethylphenyl)propanoic Acid, Cpd 228

Step 1: Ethyl 3-(4-ethylphenyl)-5-methanesulfonyl-1,2-thiazole-4-carboxylate

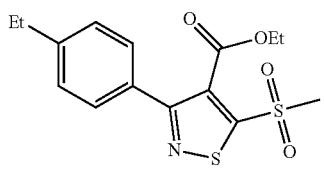 [SMILES: CCOC(=O)c1c(-c2ccc(CC)cc2)nsc1S(C)(=O)=O]

Into a 50-mL round-bottom flask, was placed N,N-dimethylformamide (8 mL), CuI (391 mg, 2.05 mmol, 1.99 equiv), ethyl 3-(4-ethylphenyl)-5-iodo-1,2-thiazole-4-carboxylate (400 mg, 1.03 mmol, 1.00 equiv), sodium methanesulfinate (421.7 mg, 4.13 mmol, 4.00 equiv). The resulting solution was stirred for 16 h at 80° C. The resulting mixture was concentrated under vacuum. The residue was applied onto a silica gel column with ethyl acetate/petroleum ether (1:20). The collected fractions were combined and concentrated under vacuum. This resulted in 170 mg (48%) of ethyl 3-(4-ethylphenyl)-5-methanesulfonyl-1,2-thiazole-4-carboxylate as a yellow solid. Mass spectrum (ESI, m/z): Calcd. for $C_{15}H_{17}NO_4S_2$, 340.1 (M+H), found 340.1.

Step 2: Methyl 3-(4-ethylphenyl)-5-methoxy-1,2-thiazole-4-carboxylate

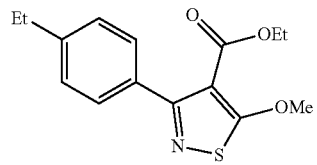 [SMILES: CCOC(=O)c1c(-c2ccc(CC)cc2)nsc1OC]

Into a 100-mL round-bottom flask, was placed a solution of ethyl 3-(4-ethylphenyl)-5-methanesulfonyl-1,2-thiazole-4-carboxylate (150 mg, 0.44 mmol, 1.00 equiv), methanol (15 mL), MeONa (119.47 mg, 5.00 equiv). The resulting solution was stirred for 2 h at 70° C. in an oil bath. The resulting solution was extracted with 2×15 mL of dichloromethane and the organic layers combined. The resulting mixture was washed with 2×30 mL of brine, dried over anhydrous Na$_2$SO$_4$. The solids were filtered out. The resulting mixture was concentrated under vacuum. This resulted in 141.4 mg (crude) of methyl 3-(4-ethylphenyl)-5-methoxy-1, 2-thiazole-4-carboxylate as white oil. Mass spectrum (ESI, m/z): Calcd. for $C_{15}H_{17}NO_3S$, 292.1 (M+H), found 292.1.

Step 3: 3-(4-[[3-(4-ethylphenyl)-5-methoxy-1,2-thiazol-4-yl]methoxy]-2,3-dimethylphenyl)propanoic Acid

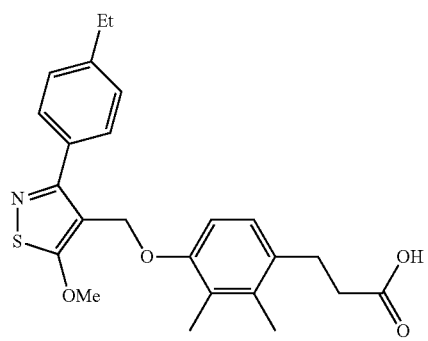 [SMILES: CCc1ccc(-c2nsc(OC)c2COc2ccc(CCC(=O)O)c(C)c2C)cc1]

The title compound was prepared according to the procedure described in Example 1 following Steps 2-6 by coupling of (3-(4-ethylphenyl)-5-methoxyisothiazol-4-yl) methyl methanesulfonate and ethyl 3-(4-hydroxy-2,3-dimethylphenyl)propanoate followed by hydrolysis to afford the desired product as an off-white solid.
$^1$H-NMR (300 MHz, CDCl$_3$) δ 7.63 (d, J=8.1 Hz, 2H), 7.25 (d, J=7.8 Hz, 1H), 6.95 (d, J=8.1 Hz, 1H), 6.75 (d, J=8.1 Hz, 1H), 4.86 (s, 2H), 4.14 (s, 3H), 2.91 (t, J=7.8 Hz, 2H), 2.68 (q, J$_{1=15.2}$ Hz, J$_2$=7.5 Hz, 2H), 2.51 (t, J=7.8 Hz, 2H), 2.23 (s, 3H), 2.06 (s, 3H), 1.25 (t, J=7.8 Hz, 3H). Mass spectrum (ESI, m/z): Calcd. for $C_{24}H_{27}NO_4S$, 426.2 (M+H), found 426.2.

Example 108

3-(4-((3-(4-ethylphenyl)-5-(trifluoromethyl)isothiazol-4-yl)methoxy)-3-fluorophenyl)-2-methylpropanoic Acid, Cpd 105

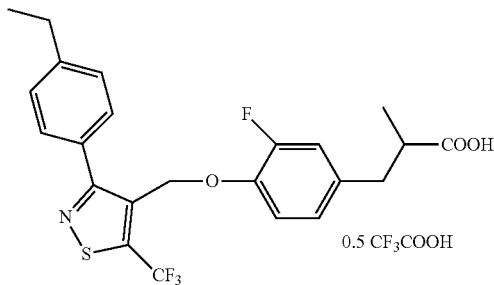 [SMILES: CCc1ccc(-c2nsc(C(F)(F)F)c2COc2ccc(CC(C)C(=O)O)cc2F)cc1]

0.5 CF₃COOH

Into a 50-mL round-bottom flask, was placed ethyl 3-(4-[[3-(4-ethylphenyl)-5-(trifluoromethyl)-1,2-thiazol-4-yl]methoxy]-3-fluorophenyl)-2-methylpropanoate (74 mg, 0.15 mmol, 1.00 equiv) (prepared according to the procedure of Example 1 step 5 by coupling (3-(4-ethylphenyl)-5-(trifluoromethyl)isothiazol-4-yl)methanol and ethyl 3-(3-fluoro-4-hydroxy phenyl)-2-methylpropanoate), tetrahydrofuran (1.5 mL). This was followed by the addition of a solution of LiOH (74 mg, 3.09 mmol, 20.69 equiv) in water (1.5 mL) dropwise with stirring. The resulting solution was stirred overnight at 25° C. The reaction progress was monitored by LCMS. The resulting mixture was concentrated under vacuum. Hydrogen chloride (2N) was employed to adjust the pH to 1. The solids were collected by filtration. The crude product (35 mg) was purified by Prep-HPLC with the following conditions (1# water 2767-16): Column, SunFire Prep C18 5 um, 19*150 nm; mobile phase, water with 0.05% trifluoroacetic acid and CH₃CN. (70% CH₃CN up to 90% in 7.0 min, up to 100% in 2.0 min, down to 70% in 2.0 min); Detector, 254 nm. This resulted in 3.4 mg (5%) of 3-(4-((3-(4-ethylphenyl)-5-(trifluoro methyl)isothiazol-4-yl)methoxy)-3-fluorophenyl)-2-methylpropanoic acid as a white solid. $^1$H NMR (300 Hz, CD₃OD): 7.64 (d, J=8.4 Hz, 2H), 7.32 (d, J=8.1 Hz, 2H), 6.92-7.03 (m, 3H), 5.14 (s, 2H), 2.89-2.97 (m, 1H), 2.62-2.75 (m, 4H), 1.27 (t, J=7.8 Hz, 3H), 1.16 (d, J=3.3 Hz, 3H). $^{19}$F NMR (300 Hz, CD₃OD): δ −56.57, −76.95, −135.59. Mass spectrum (ESI, m/z): Calcd. for $C_{24}H_{21.5}F_{5.5}NO_4S$, 468.1 (M−0.5CF₃COOH+H), found 468.1.

Example 109

3-(4-[[3-(4-chlorophenyl)-5-(trifluoromethyl)-1,2-thiazol-4-yl]methoxy]phenyl)-2-methylpropanoic Acid, Cpd 195

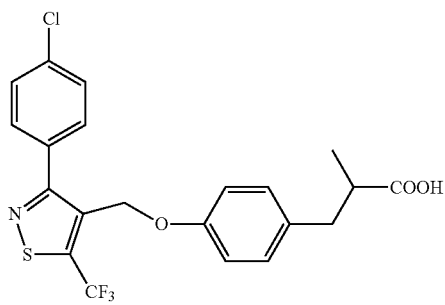 [SMILES: CC(Cc1ccc(OCc2c(-c3ccc(Cl)cc3)nsc2C(F)(F)F)cc1)C(=O)O]

The title compound was prepared according to the procedure described in Example 1 following Steps 5 and 6 by coupling (3-(4-chlorophenyl)-5-(trifluoromethyl)isothiazol-4-yl)methyl methanesulfonate and ethyl 3-(4-hydroxyphenyl)-2-methyl-propanoate followed by hydrolysis to afford the desired product as an off-white solid. $^1$H NMR (300 MHz, CD₃OD) δ: 7.71 (d, J=8.8 Hz, 2H), 7.48 (d, J=8.4 Hz, 2H), 7.16 (d, J=8.4 Hz, 1H), 6.87 (d, J=8.4 Hz, 1H), 5.09 (s, 2H), 2.93-2.98 (m, 1H), 2.63-2.74 (m, 2H), 1.15 (d, J=6.8 Hz, 3H). Mass spectrum (ESI, m/z): Calcd. for $C_{21}H_{17}ClF_3NO_3S$, 454.0 (M−H), found 454.0.

Example 110

2-(4-[[3-(4-ethylphenyl)-5-(trifluoromethyl)-1,2-thiazol-4-yl]methoxy]-3,5-difluorophenyl) cyclopropane-1-carboxylic Acid, Cpd 163

Step 1: Ethyl (2Z)-3-(3,5-difluoro-4-hydroxyphenyl)prop-2-enoate

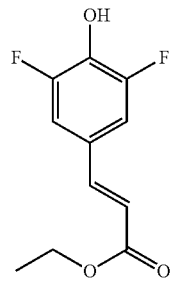

Into a 250-mL round-bottom flask purged and maintained with an inert atmosphere of nitrogen, was placed 4-bromo-2,6-difluorophenol (6.3 g, 30.15 mmol, 1.00 equiv), ethyl prop-2-enoate (17.2 g, 171.80 mmol, 5.70 equiv), P(toly)₃ (18.24 g), DIEA (11.6 g, 89.76 mmol, 2.98 equiv), PdCl₂ (0.531 g), N,N-dimethylformamide (100 mL). The resulting solution was stirred overnight at 80° C. The reaction was then quenched by the addition of 30 mL water. The resulting solution was extracted with 3×50 mL of ethyl acetate and the organic layers combined and concentrated under vacuum. The residue was applied onto a silica gel column with ethyl acetate/petroleum ether (30/70). The collected fractions were combined and concentrated under vacuum. This resulted in 6 g (79%) of ethyl (2Z)-3-(3, 5-difluoro-4-hydroxyphenyl)prop-2-enoate as yellow oil. Mass spectrum (ESI, m/z): Calcd. for $C_{11}H_{10}F_2O_3$, 229.1 (M+H), found 229.1.

Step 2: Ethyl 2-(3,5-difluoro-4-hydroxyphenyl)cyclopropane-1-carboxylate

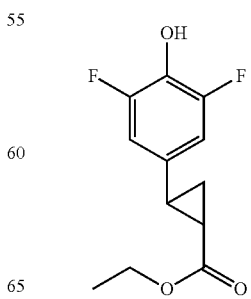

Into a 100-mL round-bottom flask, was placed a solution of 3-methyl-1-nitro-3-nitrosoguanidine (1.25 g, 8.50 mmol, 6.80 equiv) in ether (19 mL). This was followed by the addition of a solution of potassium hydroxide (1.57 g, 27.98 mmol, 22.40 equiv) in water (2.5 mL) dropwise with stirring at 0° C. the mixture were stirred at 0 degree for 2 min, the diazomethane was made. The ether phase was separated and dried over anhyarous anhydrous sodium sulfate. Then it was used for the reaction directly. 100-mL round-bottom flask, was placed ethyl (2E)-3-(3,5-difluoro-4-hydroxyphenyl) prop-2-enoate (285 mg, 1.25 mmol, 1.00 equiv), Pd(OAc)$_2$ (47 mg, 0.21 mmol, 0.17 equiv), ether (12 mL). The mixture was cooled to 0 degree C., the ether solution of diazomethane which got above was added dropwise with stirring at 0° C. The resulting solution was stirred overnight at 0° C. in a water/ice bath. The reaction was then quenched by the addition of acetic acid. The resulting mixture was concentrated under vacuum. The residue was applied onto a silica gel column with ethyl acetate/petroleum ether (30/70). The collected fractions were combined and concentrated under vacuum. This resulted in 130 mg (39%) of ethyl 2-(3,5-difluoro-4-hydroxyphenyl) cyclopropane-1-carboxylate as colorless oil. Mass spectrum (ESI, m/z): Calcd. for $C_{12}H_{12}F_2O_3$, 243.1 (M+H), found 243.1.

Step 3: 2-(4-[[3-(4-ethylphenyl)-5-(trifluoromethyl)-1,2-thiazol-4-yl]methoxy]-3,5-difluorophenyl) cyclopropane-1-carboxylic acid

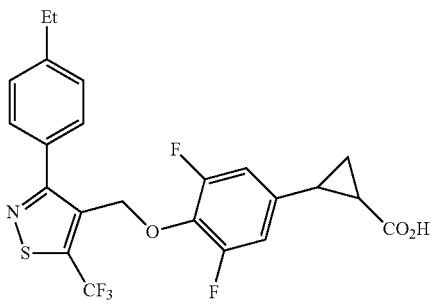 [SMILES: CCc1ccc(-c2nsc(C(F)(F)F)c2COc2c(F)cc(C3CC3C(=O)O)cc2F)cc1]

The title compound was prepared according to the procedure described in Example 1 following Steps 5 and 6 by coupling [3-(4-ethylphenyl)-5-(trifluoromethyl)-1,2-thiazol-4-yl]methyl methanesulfonate and ethyl 2-(3,5-difluoro-4-hydroxyphenyl)cyclopropane-1-carboxylate followed by hydrolysis to afford the desired product as an off-white solid. $^1$HNMR (300 MHz, CDCl$_3$) δ 7.75 (d, J=8.1 Hz, 2H), 7.32 (d, J=8.1 Hz, 2H), 6.63-6.71 (m, 2H), 5.16 (s, 2H), 2.69-2.77 (m, 2H), 2.49-2.55 (m, 2H), 1.64-1.89 (m, 2H), 1.29-1.37 (m, 4H). Mass spectrum (ESI, m/z): Calcd. for $C_{23}H_{18}F_5NO_3S$, 482.1 [M−H], found 482.1.

Example 111

3-(4-[[3-(4-chlorophenyl)-5-(trifluoromethyl)-1,2-thiazol-4-yl]methoxy]-3,5-difluorophenyl)propan-1-ol, Cpd 100

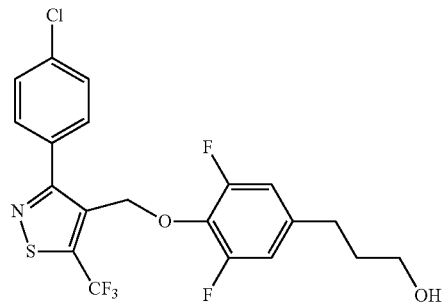 [SMILES: OCCCc1cc(F)c(OCc2c(-c3ccc(Cl)cc3)nsc2C(F)(F)F)c(F)c1]

Into a 25-mL round-bottom flask, was placed ethyl 3-(4-[[3-(4-chlorophenyl)-5-(trifluoromethyl)-1,2-thiazol-4-yl] methoxy]-3,5-difluorophenyl)propanoate (100 mg, 0.20 mmol, 1.00 equiv), tetrahydrofuran (2 mL). This was followed by the addition of a solution of LAH (7.5 mg, 0.20 mmol, 1.00 equiv) in tetrahydrofuran (1 mL) dropwise with stirring at 0° C. The resulting solution was stirred for 60 min at 0° C. in a water/ice bath. The reaction progress was monitored by TLC/LCMS (ethyl acetate/petroleum ether=1: 5). The reaction was then quenched by the addition of 5 mL of water. The resulting solution was extracted with 5×5 mL of ethyl acetate and the organic layers combined. The solvent was removed under vacuum. The crude product (90 mg) was purified by Flash-Prep-HPLC with the following conditions (IntelFlash-1): Column, C18 silica gel; mobile phase, 0.05% TFA/ACN=4/1 increasing to 0.05% TFA/ACN=0/1 within 20 min; Detector, UV 254 nm. This resulted in 28.9 mg (32%) of 3-(4-[[3-(4-chlorophenyl)-5-(trifluoromethyl)-1,2-thiazol-4-yl]methoxy]-3,5-difluorophenyl)propan-1-ol as a off-white solid. $^1$H NMR (300 MHz, CD$_3$OD) δ 7.79 (d, J=6.6 Hz, 2H), 7.51 (d, J=8.7 Hz, 2H), 6.83 (d, J=9.6 Hz, 2H), 5.19 (s, 2H), 3.56 (t, J=6.3 Hz, 2H), 2.65 (t, J=7.5 Hz, 2H), 1.80-1.85 (m, 2H). Mass spectrum (ESI, m/z): Calcd. for $C_{20}H_{15}ClF_5NO_2S$, 464.0 (M+H), found 464.0.

Example 112

3-(4-((3-(4-chlorophenyl)-5-(trifluoromethyl)isothiazol-4-yl)methoxy)-2,3-difluorophenyl)propan-1-ol, Cpd 132

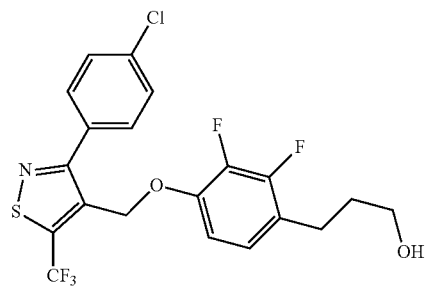 [SMILES: OCCCc1ccc(OCc2c(-c3ccc(Cl)cc3)nsc2C(F)(F)F)c(F)c1F]

The title compound was prepared according to the procedure described in Example 111 by LAH reduction of ethyl 3-(4-((3-(4-chlorophenyl)-5-(trifluoromethyl)isothiazol-4-yl)methoxy)-2,3-difluorophenyl)propanoate to afford the desired product as an off-white solid. ¹H NMR (400 MHz, CDCl₃) δ 7.72 (d, J=8.5 Hz, 2H), 7.46 (d, J=8.4 Hz, 2H), 6.89 (dd, J=10.5, 4.2 Hz, 1H), 6.72 (dd, J=10.5, 4.2 Hz, 1H), 5.06 (s, 2H), 3.71 (t, J=9.2 Hz, 2H), 2.74 (t, J=9.0 Hz, 2H), 1.87 (m, 2H), 1.45 (br, s, 1H).

Example 113

3-(4-((3-(4-ethylphenyl)-5-(trifluoromethyl)isothiazol-4-yl)methoxy)-2,3-difluorophenyl)propan-1-ol, Cpd 139

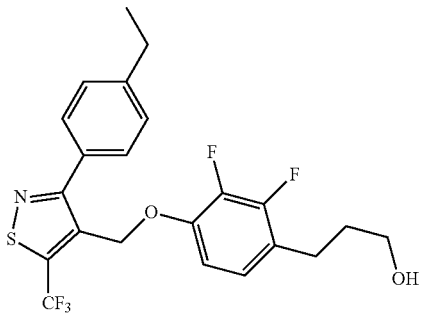 [SMILES: CCc1ccc(-c2nsc(C(F)(F)F)c2COc2ccc(CCCO)c(F)c2F)cc1]

The title compound was prepared according to the procedure described in Example 111 by LAH reduction of ethyl 3-(4-((3-(4-ethylphenyl)-5-(trifluoromethyl)isothiazol-4-yl)methoxy)-2,3-difluorophenyl)propanoate to afford the desired product as an off-white solid. ¹H NMR (400 MHz, CDCl₃) δ 7.65 (d, J=8.3 Hz, 2H), 7.32 (d, J=8.1 Hz, 2H), 6.83 (t, J=7.8 Hz, 1H), 6.72 (t, J=7.5 Hz, 1H), 5.08 (s, 2H), 3.71 (q, J=7.0 Hz, 2H), 2.72 (m, 4H), 1.87 (m, J=9.5 Hz, 2H), 1.25 (t, J=9.1 Hz, 3H).

Example 114

3-(4-((3-(4-ethylphenyl)-5-(trifluoromethyl)isothiazol-4-yl)methoxy)-3,5-difluorophenyl)propan-1-ol, Cpd 135

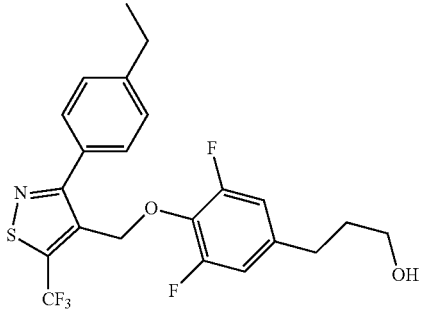 [SMILES: CCc1ccc(-c2nsc(C(F)(F)F)c2COc2c(F)cc(CCCO)cc2F)cc1]

The title compound was prepared according to the procedure described in Example 111 by LAH reduction of ethyl 3-(4-((3-(4-ethylphenyl)-5-(trifluoromethyl)isothiazol-4-yl)methoxy)-3,5-difluorophenyl)propanoate to afford the desired product as an off-white solid. ¹H NMR (400 MHz, CDCl₃) δ 7.78 (d, J=7.9 Hz, 2H), 7.37 (d, J=7.8 Hz, 2H), 6.76 (d, J=8.3 Hz, 2H), 5.14 (s, 2H), 3.67 (t, J=7.5 Hz, 2H), 2.74 (q, J=8.1 Hz, 2H), 2.67 (d, J=7.2 Hz, 2H), 1.84 (m, J=6.7 Hz, 2H), 1.52 (br, s, 1H), 1.27 (t, J=7.3 Hz, 3H).

Example 115

3-(4-((3-(4-chlorophenyl)-5-(trifluoromethyl)isothiazol-4-yl)methoxy)-5-fluoro-2-methylphenyl)propan-1-ol, Cpd 63

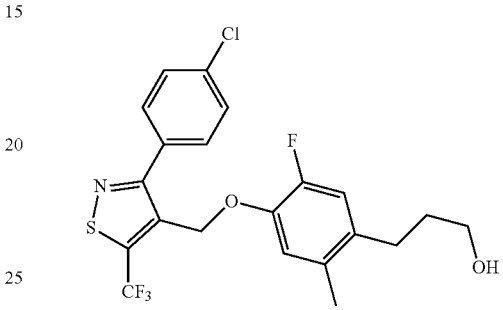

The title compound was prepared according to the procedure described in Example 111 by LAH reduction of ethyl 3-(4-((3-(4-chlorophenyl)-5-(trifluoromethyl)isothiazol-4-yl)methoxy)-5-fluoro-2-methylphenyl)propanoate to afford the desired product as an off-white solid. ¹H NMR (400 MHz, CDCl₃) δ 7.75 (d, J=7.5 Hz, 2H), 7.52 (d, J=7.5 Hz, 2H), 6.98 (d, J=8.2 Hz, 2H), 6.80 (d, J=8.2 Hz, 2H), 5.02 (s, 2H), 3.72 (t, J=7.0 Hz, 2H), 2.68 (t, J=7.0 Hz, 2H), 2.28 (s, 3H), 1.88 (m, J=7.3 Hz, 2H), 1.60 (br, s, 1H).

Example 116

3-(4-((3-(4-chlorophenyl)-5-(trifluoromethyl)isothiazol-4-yl)methoxy)-3,5-difluoro-2-methylphenyl)propan-1-ol, Cpd 223

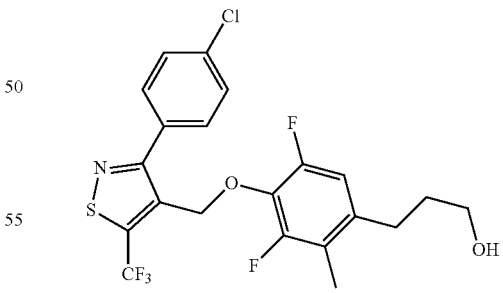

The title compound was prepared according to the procedure described in Example 111 by LAH reduction of ethyl 3-(4-((3-(4-chlorophenyl)-5-(trifluoromethyl)isothiazol-4-yl)methoxy)-3,5-difluoro-2-methylphenyl)propanoate to afford the desired product as an off-white solid. ¹H NMR (400 MHz, CDCl₃) δ 7.78 (d, J=7.0 Hz, 2H), 7.42 (d, J=7.5 Hz, 2H), 6.68 (d, J=8.0 Hz, 1H), 5.02 (s, 2H), 3.62 (m, 2H), 2.62 (m, 2H), 2.12 (s, 3H), 1.75 (m, 2H), 1.55 (br, s, 1H).

Example 117

3-(3, 5-difluoro-4-[[3-(4-methoxyphenyl)-5-(trifluoromethyl)-1,2-thiazol-4-yl]methoxy] phenyl)propan-1-ol, Cpd 234

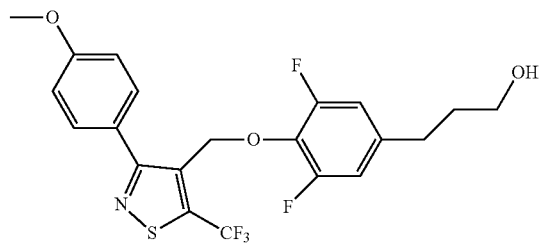 [SMILES: COc1ccc(-c2nsc(C(F)(F)F)c2COc2c(F)cc(CCCO)cc2F)cc1]

The title compound was prepared according to the procedure described in Example 111 by LAH reduction of ethyl 3-(3,5-difluoro-4-((3-(4-methoxyphenyl)-5-(trifluoromethyl)isothiazol-4-yl)methoxy)phenyl)propanoate to afford the desired product as an off-white solid. $^1$H NMR (300 MHz, CD$_3$OD) δ 7.71 (d, J=8.7 Hz, 2H), 6.99 (d, J=6.6 Hz, 2H), 6.79 (d, J=9.3 Hz, 2H), 5.16 (s, 2H), 3.84 (s, 3H), 3.53 (t, J=6.3 Hz, 2H), 2.61 (t, J=8.1 Hz, 2H), 1.77-1.81 (m, 2H). Mass spectrum (ESI, m/z): Calcd. for C$_{21}$H$_{18}$F$_5$NO$_3$S, 460.1 (M+H), found 460.1.

Example 118

3-(3, 5-difluoro-4-[[3-(6-methoxypyridin-3-yl)-5-(trifluoromethyl)-1,2-thiazol-4-yl]methoxy] phenyl)propan-1-ol, Cpd 81

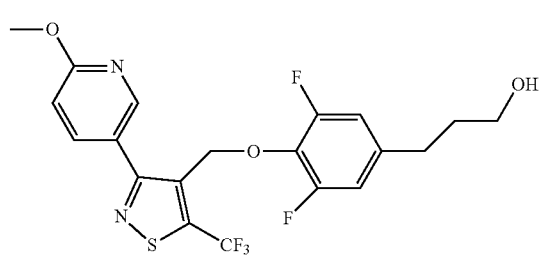 [SMILES: COc1ccc(-c2nsc(C(F)(F)F)c2COc2c(F)cc(CCCO)cc2F)cn1]

The title compound was prepared according to the procedure described in Example 110 by LAH reduction of ethyl 3-(3,5-difluoro-4-((3-(6-methoxypyridin-3-yl)-5-(trifluoromethyl)isothiazol-4-yl)methoxy)phenyl)propanoate to afford the desired product as an off-white solid. $^1$HNMR (300 MHz, CD3OD) δ 8.57 (s, 1H), 8.13 (d, J=8.7 Hz, 1H), 6.84-6.93 (m, 3H), 5.23 (s, 2H), 3.99 (s, 3H), 3.56 (t, J=6.3 Hz, 2H), 2.65 (t, J=8.1 Hz, 2H), 1.80-1.85 (m, 2H). Mass spectrum (ESI, m/z): Calcd. for C$_{20}$H$_{17}$F$_5$N$_2$O$_3$S, 461.1 (M+H), found 461.1.

Example 119

3-(4-[[3-(2H-1,3-benzodioxol-5-yl)-5-(trifluoromethyl)-1,2-thiazol-4-yl]methoxy]-3,5-difluorophenyl) propan-1-ol, Cpd 93

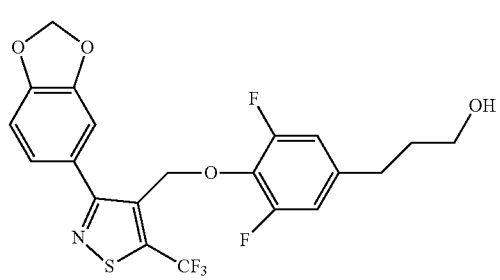 [SMILES: OCCCc1cc(F)c(OCc2c(-c3ccc4c(c3)OCO4)nsc2C(F)(F)F)c(F)c1]

The title compound was prepared according to the procedure described in Example 111 by LAH reduction of ethyl 3-(4-((3-(benzo[d][1,3]dioxol-5-yl)-5-(trifluoromethyl) isothiazol-4-yl)methoxy)-3,5-difluorophenyl)propanoate to afford the desired product as an off-white solid. $^1$H NMR (300 MHz, CD3OD) δ 7.28 (d, J=8.1 Hz, 1H), 7.18 (s, 1H), 6.89 (d, J=8.1 Hz, 1H), 6.80 (d, J=9.3 Hz, 2H), 6.03 (s, 2H), 5.20 (s, 2H), 3.52 (t, J=6.3 Hz, 2H), 2.62 (t, J=7.2 Hz, 2H), 1.82-1.76 (m, 2H). Mass spectrum (ESI, m/z): Calcd. for C$_{21}$H$_{16}$F$_5$NO$_4$S, 474.1 (M+H), found 474.1.

Example 120

3-(4-((3-(4-ethylphenyl)-5-(trifluoromethyl)isothiazol-4-yl)methoxy)-2,3,5-trifluorophenyl)propan-1-ol, Cpd 238

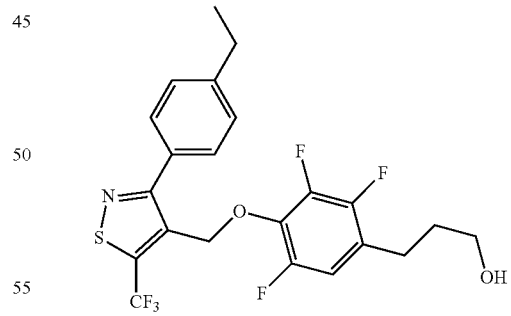

The title compound was prepared according to the procedure described in Example 111 by LAH reduction of ethyl 3-(4-((3-(4-ethylphenyl)-5-(trifluoromethyl)isothiazol-4-yl) methoxy)-2,3,5-trifluorophenyl)propanoate to afford the desired product as an off-white solid. $^1$H NMR (400 MHz, CDCl$_3$) δ 7.75 (d, J=7.5 Hz, 2H), 7.84 (d, J=7.8 Hz, 2H), 6.76 (m, 1H), 3.70 (t, J=8.5 Hz, 2H), 2.74 (m, 4H), 1.85 (m, 2H), 1.52 (br, s, 1H), 1.27 (t, J=9.5 Hz, 3H).

Example 121

3-(4-[[3-cyclopentyl-5-(trifluoromethyl)-1,2-thiazol-4-yl]methoxy]-3,5-difluorophenyl)propan-1-ol, Cpd 141

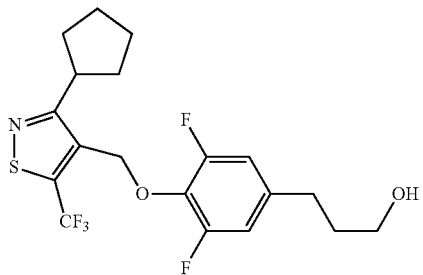 [SMILES: OCCCc1cc(F)c(OCc2c(C3CCCC3)nsc2C(F)(F)F)c(F)c1]

The title compound was prepared according to the procedure described in Example 111 by LAH reduction of ethyl 3-(4-((3-cyclopentyl-5-(trifluoromethyl)isothiazol-4-yl)methoxy)-3,5-difluorophenyl)propanoate to afford the desired product as an off-white solid. $^1$H NMR (300 MHz, CD$_3$OD) δ 7.39 (d, J=9.6 Hz, 2H), 5.20 (s, 2H), 3.64-3.54 (m, 3H), 2.66 (t, J=7.8 Hz, 2H), 2.05-2.09 (m, 2H), 1.70-1.95 (m, 8H). Mass spectrum (ESI, m/z): Calcd. for C$_{19}$H$_{20}$F$_5$NO$_2$S, 422.1 (M+H), found 422.1.

Example 122

3-(4-[[3-(4-chlorophenyl)-5-(trifluoromethyl)-1,2-thiazol-4-yl]methoxy]-3,5-difluorophenyl)-2-methylpropan-1-ol, Cpd 230

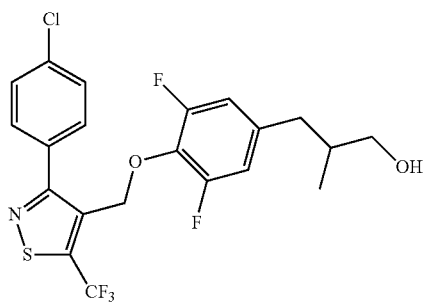 [SMILES: CC(CO)Cc1cc(F)c(OCc2c(-c3ccc(Cl)cc3)nsc2C(F)(F)F)c(F)c1]

The title compound was prepared according to the procedure described in Example 111 by LAH reduction of ethyl 3-(4-((3-(4-chlorophenyl)-5-(trifluoromethyl)isothiazol-4-yl)methoxy)-3,5-difluorophenyl)-2-methylpropanoate to afford the desired product as an off-white solid. $^1$H NMR (CDCl3): 7.82 (d, J=7.2 Hz, 2H), 7.52 (d, J=7.2 Hz, 2H), 6.79-6.85 (m, 2H), 5.20 (s, 2H), 3.33-3.41 (m, 2H), 2.76 (dd, J$_1$=5.2 Hz, J$_2$=5.2 Hz, 1H), 2.74-2.79 (m, 1H), 1.82-1.91 (m, 1H), 0.89 (s, 3H). Mass spectrum (ESI, m/z): Calcd. for C$_{21}$H$_{17}$ClF$_5$NO$_2$S, 478.1 (M+H), found 478.1.

Example 123

3-(4-[[3-(4-ethylphenyl)-5-(trifluoromethyl)-1,2-thiazol-4-yl]methoxy]-3,5-difluorophenyl)-2-methyl-propan-1-ol, Cpd 216

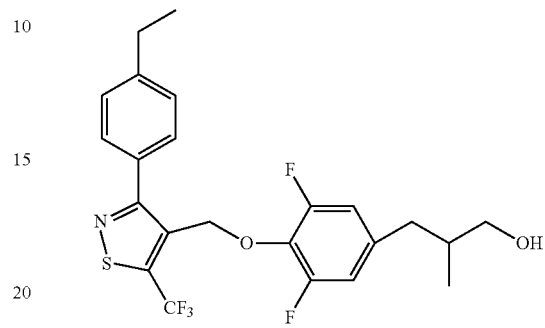

The title compound was prepared according to the procedure described in Example 111 by LAH reduction of ethyl 3-(4-((3-(4-ethylphenyl)-5-(trifluoromethyl)isothiazol-4-yl)methoxy)-3,5-difluorophenyl)-2-methylpropanoate to afford the desired product as an off-white solid. $^1$H NMR (400 MHz, CD$_3$OD) δ 7.71 (d, J=8.0 Hz, 2H), 7.35 (d, J=8.0 Hz, 2H), 6.78-6.84 (m, 2H), 5.21 (s, 2H), 3.41 (d, J=6.8 Hz, 2H), 2.71-2.79 (m, 3H), 2.30-2.36 (m, 1H), 1.82-1.91 (m, 1H), 1.30 (t, J=7.6 Hz, 3H), 0.89 (d, J=6.8 Hz, 3H). Mass spectrum (ESI, m/z): Calcd. for C$_{23}$H$_{22}$F$_5$NO$_2$S, 472.2 (M+H), found 472.2.

Example 124

(E)-3-(4-((3-(4-chlorophenyl)-5-(trifluoromethyl)isothiazol-4-yl)methoxy)-3,5-difluorophenyl)acrylic Acid, Cpd 201

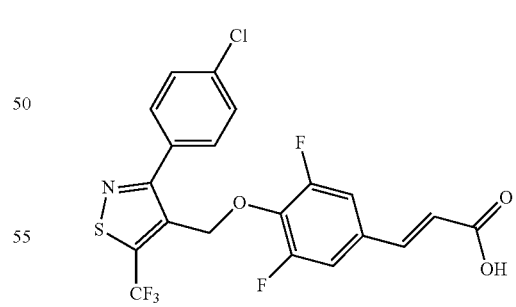

The title compound was prepared according to the procedure described in Example 1 following Steps 5 and 6 by hydrolysis of (E)-ethyl 3-(4-((3-(4-chlorophenyl)-5-(trifluoromethyl)isothiazol-4-yl)methoxy)-3,5-difluorophenyl)acrylate to afford the desired product as an off-white solid. $^1$H NMR (400 MHz, CDCl$_3$) δ 7.80 (d, J=7.8 Hz, 2H), 7.62 (d, J=11.5 Hz, 1H), 7.48 (d, J=7.5 Hz, 2H), 7.12 (d, J=8.1 Hz, 2H), 6.38 (d, J=12.0 Hz, 1H), 5.23 (s, 2H).

Example 125

(E)-3-(4-((3-(4-chlorophenyl)-5-(trifluoromethyl)isothiazol-4-yl)methoxy)-2,3-difluorophenyl)acrylic Acid, Cpd 240

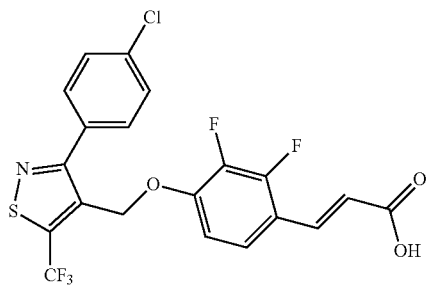 [SMILES: O=C(O)/C=C/c1ccc(OCc2c(-c3ccc(Cl)cc3)nsc2C(F)(F)F)c(F)c1F]

The title compound was prepared according to the procedure described in Example 1 following Steps 5 and 6 by coupling of (3-(4-chlorophenyl)-5-(trifluoromethyl)isothiazol-4-yl)methanol and (E)-ethyl 3-(2,3-difluoro-4-hydroxyphenyl)acrylate then hydrolysis to afford the desired product as an off-white solid. $^1$H NMR (400 MHz, CDCl$_3$) δ 7.80 (d, J=9.5 Hz, 1H), 7.64 (d, J=7.2 Hz, 1H), 7.47 (d, J=7.2 Hz, 1H), 6.52 (d, J=9.0 Hz, 2H), 7.28 (t, J=6.8 Hz, 1H), 6.82 (t, J=6.8 Hz, 1H), 5.14 (s, 2H).

Example 126

(E)-3-(4-((3-(4-chlorophenyl)-5-(trifluoromethyl)isothiazol-4-yl)methoxy)-2,3-dimethylphenyl)acrylic Acid, Cpd 244

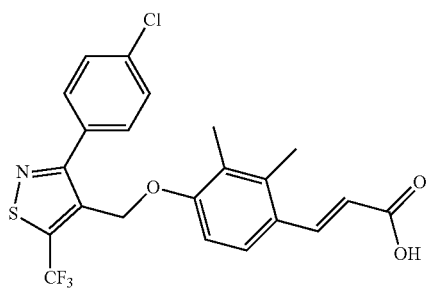 [SMILES: Cc1c(/C=C/C(=O)O)ccc(OCc2c(-c3ccc(Cl)cc3)nsc2C(F)(F)F)c1C]

The title compound was prepared according to the procedure described in Example 1 following Steps 5 and 6 by coupling of (3-(4-chlorophenyl)-5-(trifluoromethyl)isothiazol-4-yl)methanol and (E)-ethyl 3-(2,3-dimethyl-4-hydroxyphenyl)acrylate then hydrolysis to afford the desired product as an off-white solid. $^1$H NMR (400 MHz, CDCl$_3$) δ 7.68 (d, J=7.5 Hz, 2H), 7.55 (d, J=11.5 Hz, 1H), 7.45 (d, J=7.8 Hz, 1H), 6.96 (d, J=5.5 Hz, 1H), 6.62 (d, J=12.0 Hz, 1H), 5.08 (s, 2H), 2.21 (s, 3H), 1.95 (s, 3H).

Example 127

3-[4-[(3-chloro-5-phenyl-1,2-thiazol-4-yl)methoxy]-2,3-dimethylphenyl]propanoic Acid, Cpd 101

Step 1: 2-(phenylmethylidene)propanedinitrile

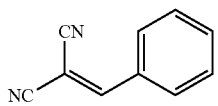

Into a 50-mL round-bottom flask, was placed benzaldehyde (4 g, 37.69 mmol, 1.00 equiv), propanedinitrile (3.3 g, 49.95 mmol, 1.30 equiv), n-butanol (10 mL), piperidine (1 mL). The resulting solution was stirred for 16 h at 20° C. The resulting mixture was concentrated under vacuum. The resulting mixture was washed with 1×33 mL of H$_2$O/EtOH (10/1). The solids were collected by filtration. The solid was dried in an oven. This resulted in 4.2 g (69%) of 2-(phenylmethylidene)propanedinitrile as a yellow solid.

Step 2: 3-chloro-5-phenyl-1,2-thiazole-4-carbonitrile

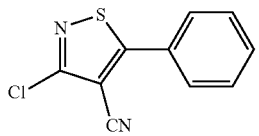 [SMILES: N#Cc1c(Cl)nsc1-c1ccccc1]

Into a 50-mL round-bottom flask, was placed 2-(phenylmethylidene)propanedinitrile (1.5 g, 9.24 mmol, 1.00 equiv, 95%), S$_2$Cl$_2$ (5.3 g, 39.26 mmol, 4.00 equiv), pyridine (76.9 mg, 0.97 mmol, 0.10 equiv). The resulting solution was stirred for 12 h at 145° C. in an oil bath. The reaction was then quenched by the addition of 20 mL of water. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:10). This resulted in 700 mg (33%) of 3-chloro-5-phenyl-1,2-thiazole-4-carbonitrile as a yellow solid.

Step 3: 3-chloro-5-phenyl-1,2-thiazole-4-carboxylic Acid

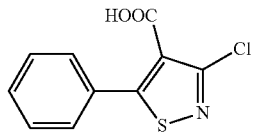 [SMILES: O=C(O)c1c(Cl)nsc1-c1ccccc1]

Into a 50-mL round-bottom flask, was placed 3-chloro-5-phenyl-1,2-thiazole-4-carbonitrile (700 mg, 3.01 mmol, 1.00 equiv, 95%), con.H$_2$SO$_4$ (4 mL). The resulting solution was stirred for 3 hr at 135° C. in an oil bath. This was followed by the addition of a solution of NaNO$_2$ (318 mg, 4.61 mmol, 1.45 equiv) in water (15 mL) dropwise with stirring at 0° C. The resulting solution was allowed to react, with stirring, for an additional 0.5 h while the temperature was maintained at 50° C. in an oil bath. The resulting solution was extracted with 3×20 mL of ethyl acetate and the organic layers combined. The resulting mixture was washed with 2×50 mL of sodium hydroxide/H$_2$O (10%). The resulting solution was extracted with 3×100 mL of ethyl acetate. The aqueous phase was adjusted to 3 with 2N HCl. The resulting solution was extracted with 3×100 mL of ethyl acetate and the organic layers combined and concentrated under vacuum. This resulted in 500 mg (66%) of 3-chloro-5-phenyl-1,2-thiazole-4-carboxylic acid as a white solid.

Step 4: (3-chloro-5-phenyl-1,2-thiazol-4-yl)methanol

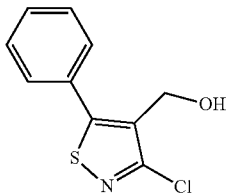 [SMILES: OCc1c(Cl)nsc1-c1ccccc1]

Into a 25-mL round-bottom flask purged and maintained with an inert atmosphere of nitrogen, was placed 3-chloro-5-phenyl-1,2-thiazole-4-carboxylic acid (500 mg, 1.88 mmol, 1.00 equiv, 90%), chlorobenzene (2 mL), BH$_3$ (3.1 mL, 3.00 equiv) at 0° C. The resulting solution was stirred for 12 h at 50° C. in an oil bath. The reaction was then quenched by the addition of 10 mL of sodium bicarbonate/H$_2$O. The resulting solution was extracted with 3×10 mL of ethyl acetate and the organic layers combined. The residue was applied onto a silica gel column with ethyl acetate/petroleum ether (1:4). This resulted in 80 mg (18%) of (3-chloro-5-phenyl-1,2-thiazol-4-yl)methanol as a white solid.

Step 5: 3-chloro-4-(chloromethyl)-5-phenyl-1,2-thiazole

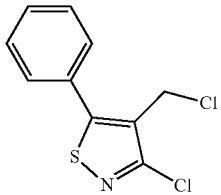 [SMILES: ClCc1c(Cl)nsc1-c1ccccc1]

Into a 25-mL round-bottom flask, was placed (3-chloro-5-phenyl-1,2-thiazol-4-yl)methanol (80 mg, 0.34 mmol, 1.00 equiv, 97%), MsCl (81.6 mg, 0.72 mmol, 2.00 equiv), TEA (107.7 mg, 1.06 mmol, 3.00 equiv), dichloromethane (1.5 mL). The resulting solution was stirred for 1 h at 20° C. The reaction was then quenched by the addition of 5 mL of water. The resulting solution was extracted with 3×5 mL of ethyl acetate and the organic layers combined and dried over anhydrous sodium sulfate. The solids were filtered out. The resulting mixture was concentrated under vacuum. This resulted in 85 mg (96%) of 3-chloro-4-(chloromethyl)-5-phenyl-1,2-thiazole as yellow oil.

Step 6: Ethyl 3-[4-[(3-chloro-5-phenyl-1,2-thiazol-4-yl)methoxy]-2,3-dimethylphenyl]propanoate

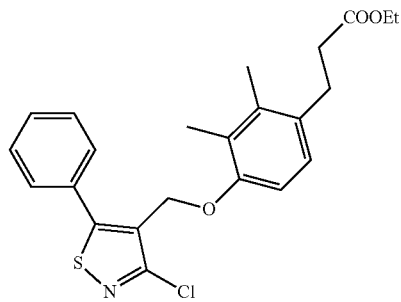 [SMILES: CCOC(=O)CCc1ccc(OCc2c(Cl)nsc2-c2ccccc2)c(C)c1C]

Into a 25-mL round-bottom flask, was placed 3-chloro-4-(chloromethyl)-5-phenyl-1,2-thiazole (70 mg, 0.27 mmol, 1.00 equiv, 95%), ethyl 3-(4-hydroxy-2,3-dimethylphenyl)propanoate (95 mg, 0.41 mmol, 1.50 equiv, 97%), Cs$_2$CO$_3$ (282 mg, 0.84 mmol, 3.00 equiv, 97%), N,N-dimethylformamide (1.5 mL). The resulting solution was stirred overnight at 20° C. The resulting mixture was washed with 1×10 mL of H$_2$O. The resulting solution was extracted with 3×10 mL of ethyl acetate and the organic layers combined and concentrated under vacuum. The residue was applied onto a silica gel column with ethyl acetate/petroleum ether (1:6). This resulted in 90 mg (75%) of ethyl 3-[4-[(3-chloro-5-phenyl-1,2-thiazol-4-yl)methoxy]-2,3-dimethylphenyl]propanoate as a white solid. Mass spectrum (ESI, m/z): Calcd. for C$_{23}$H$_{24}$ClNO$_3$S, 430.1 (M+H), found 430.1.

Step 7: 3-[4-[(3-chloro-5-phenyl-1,2-thiazol-4-yl)methoxy]-2,3-dimethylphenyl]propanoic Acid

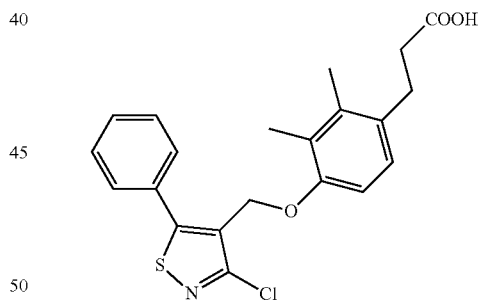

Into a 25-mL round-bottom flask, was placed ethyl 3-[4-[(3-chloro-5-phenyl-1,2-thiazol-4-yl)methoxy]-2,3-dimethylphenyl]propanoate (105 mg, 0.22 mmol, 1.00 equiv, 90%), a solution of LiOH (105 mg, 4.38 mmol, 19.95 equiv) in water (1 mL), tetrahydrofuran (1 mL). The resulting solution was stirred overnight at 20° C. The resulting mixture was concentrated under vacuum. The pH value of the solution was adjusted to 5 with hydrogen chloride (2 mol/L). The solids were collected by filtration. The resulting mixture was concentrated under vacuum, washed with n-hexane. This resulted in 37 mg (41%) of 3-[4-[(3-chloro-5-phenyl-1,2-thiazol-4-yl)methoxy]-2,3-dimethylphenyl]propanoic acid as a white solid. $^1$H-NMR (300 MHz, CD$_3$OD) δ 7.52-7.56 (m, 5H), 6.94 (d, J=8.4 Hz, 1H), 6.74 (d, J=8.4 Hz, 1H), 4.98 (s, 2H), 2.91 (t, J=8.4 Hz, 2H), 2.50 (t, J=7.5 Hz, 2H), 2.22

(s, 3H), 2.07 (s, 3H). Mass spectrum (ESI, m/z): Calcd. for $C_{21}H_{20}ClNO_3S$, 402.0 (M+H), found 402.0.

Example 128

3-(4-[[5-(4-ethylphenyl)-1,2-thiazol-4-yl]methoxy]-2,3-dimethylphenyl)propanoic Acid, Cpd 158

Step 1: [3-chloro-5-(4-ethylphenyl)-1,2-thiazol-4-yl]methyl methanesulfonate

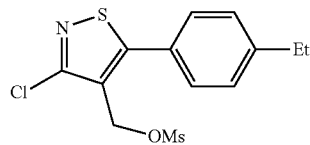 [SMILES: CCc1ccc(-c2snc(Cl)c2COS(C)(=O)=O)cc1]

The title compound was prepared according to the procedure described in Example 126 following Steps 1-5 by using 4-ethyl benzaldehyde as starting material to afford the desired product as a yellow oil.

Step 2: Ethyl 3-(4-[[3-chloro-5-(4-ethylphenyl)-1,2-thiazol-4-yl]methoxy]-2,3-dimethylphenyl)propanoate

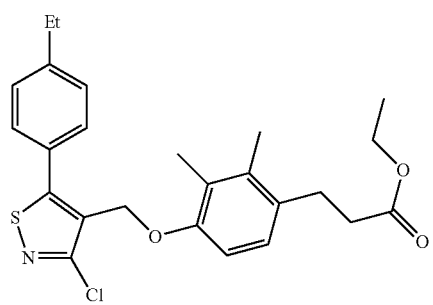 [SMILES: CCOC(=O)CCc1ccc(OCc2c(Cl)nsc2-c2ccc(CC)cc2)c(C)c1C]

The title compound was prepared according to the procedure described in Example 127 following Step 6 by coupling [3-chloro-5-(4-ethylphenyl)-1,2-thiazol-4-yl] methyl methanesulfonate and ethyl 3-(4-hydroxy-2,3-dimethylphenyl)propanoate to afford the desired product as a yellow oil.

Step 3: Ethyl 3-(4-[[5-(4-ethylphenyl)-1,2-thiazol-4-yl]methoxy]-2,3-dimethylphenyl)propanoate

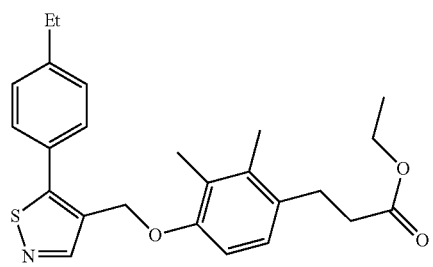 [SMILES: CCOC(=O)CCc1ccc(OCc2cnsc2-c2ccc(CC)cc2)c(C)c1C]

Into a 100-mL round-bottom flask purged and maintained with an inert atmosphere of $H_2$, was placed ethyl 3-(4-[[3-chloro-5-(4-ethylphenyl)-1,2-thiazol-4-yl]methoxy]-2,3-dimethyl phenyl) propanoate (60 mg, 0.12 mmol, 1.00 equiv, 90%), Palladium carbon (60 mg), ethanol (2 mL). The resulting solution was stirred overnight at 25° C. The solids were filtered out. The filter was concentrated. The residue was applied onto a silica gel column with ethyl acetate/ petroleum ether (1:5). This resulted in 20 mg (36%) of ethyl 3-(4-[[5-(4-ethylphenyl)-1,2-thiazol-4-yl]methoxy]-2,3-dimethylphenyl)propanoate as colorless oil.

Step 4: 3-(4-[[5-(4-ethylphenyl)-1,2-thiazol-4-yl]methoxy]-2,3-dimethylphenyl)propanoic Acid

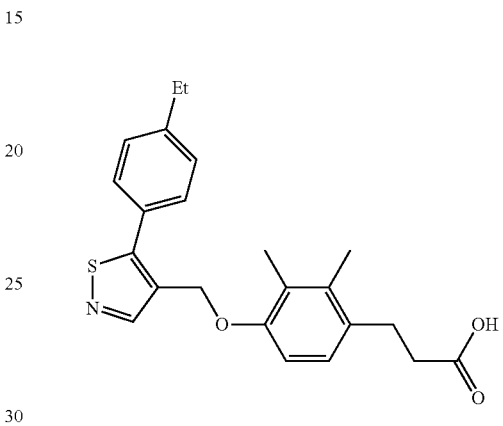

The title compound was prepared according to the procedure described in Example 127 following Step 7 by hydrolysis of ethyl 3-(4-[[5-(4-ethylphenyl)-1,2-thiazol-4-yl]methoxy]-2,3-dimethyl phenyl)propanoate to afford the desired product as an off-white solid. $^1H$ NMR (300 MHz, $CD_3OD$) δ 8.57 (s, 1H), 7.48 (d, J=8.1 Hz, 2H), 7.34 (d, J=8.1 Hz, 2H), 6.95 (d, J=8.1 Hz, 1H), 6.73 (d, J=8.1 Hz, 1H), 5.09 (s, 2H), 2.90 (t, J=6.9 Hz, 2H), 2.71 (dd, J=7.8, 15.3 Hz, 2H), 2.48-2.50 (m, 2H), 2.23 (s, 3H), 2.10 (s, 3H), 1.27 (t, J=7.5 Hz, 3H). Mass spectrum (ESI, m/z): Calcd. for $C_{23}H_{25}NO_3S$, 396.2 (M+H), found 396.2.

Example 129

3-(4-[[3-chloro-5-(4-ethylphenyl)-1,2-thiazol-4-yl]methoxy]-2,3-dimethylphenyl)propanoic Acid, Cpd 85

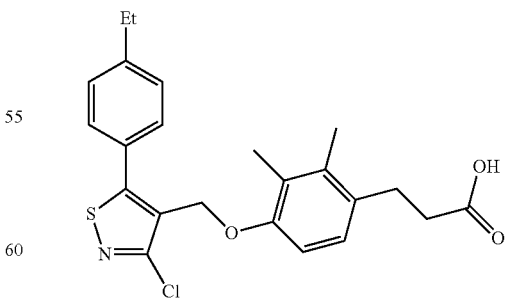

The title compound was prepared according to the procedure described in Example 127 by hydrolysis of ethyl 3-(4-[[3-chloro-5-(4-ethylphenyl)-1,2-thiazol-4-yl]methoxy]-2,3-dimethylphenyl)propanoate to afford the desired product as an off-white solid. $^1$H NMR (400 MHz, CD$_3$OD) δ 7.47 (d, J=8.4 Hz, 2H), 7.35 (d, J=8.0 Hz, 2H), 6.96 (d, J=8.4 Hz, 1H), 6.74 (d, J=8.4 Hz, 1H), 4.98 (s, 2H), 2.92 (t, J=7.2 Hz, 2H), 2.72 (q, J=7.6, 15.2 Hz, 2H), 2.51 (t, J=8.4 Hz, 2H), 2.23 (s, 3H), 2.09 (s, 3H), 1.27 (t, J=8.0 Hz, 3H). Mass spectrum (ESI, m/z): Calcd. for C$_{23}$H$_{24}$ClNO$_3$S, 430.1 (M+H), found 430. 1.

Example 130

3-(4-[[3-chloro-5-(4-ethylphenyl)-1,2-thiazol-4-yl]methoxy]-2,3-difluorophenyl)propanoic Acid, Cpd 66

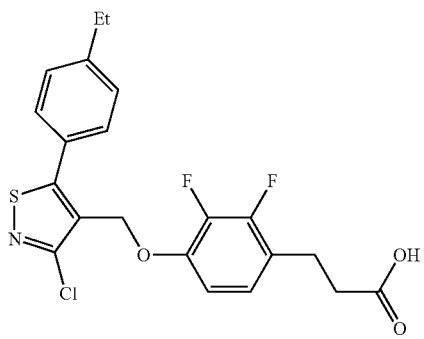 [SMILES: CCc1ccc(-c2snc(Cl)c2COc2ccc(CCC(=O)O)c(F)c2F)cc1]

The title compound was prepared according to the procedure described in Example 127 following Steps 6 and 7 by coupling 3-chloro-4-(chloromethyl)-5-(4-ethylphenyl)isothiazole and ethyl 3-(4-hydroxy-2,3-difluorophenyl)propanoate to afford the desired product as an off-white solid. $^1$H NMR (300 MHz, CD$_3$OD) δ 7.36 (d, J=8.1 Hz, 2H), 7.26 (d, J=8.1 Hz, 2H), 6.87 (t, J=8.4 Hz, 1H), 6.76 (t, J=8.7 Hz, 1H), 4.96 (s, 2H), 2.82 (t, J=7.5 Hz, 2H), 2.61 (q, J=7.5, 15.2 Hz, 2H), 2.49 (t, J=7.5 Hz, 2H), 1.15 (t, J=7.5 Hz, 3H). Mass spectrum (ESI, m/z): Calcd. for C$_{21}$H$_{18}$ClF$_2$NO$_3$S, 438.1 (M+H), found 438.1.

Example 131

3-(4-[[3-chloro-5-(4-ethylphenyl)-1,2-thiazol-4-yl]methoxy]-3,5-difluorophenyl)propanoic Acid, Cpd 124

Step 1: Ethyl 3-(4-[[3-chloro-5-(4-ethylphenyl)-1,2-thiazol-4-yl]methoxy]-3,5-difluorophenyl)propanoate

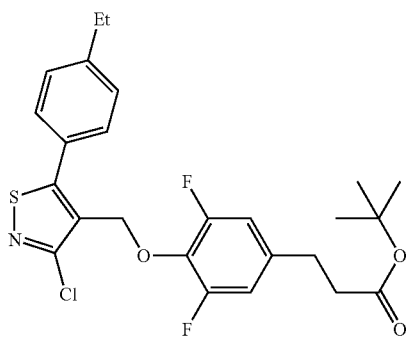 [SMILES: CCc1ccc(-c2snc(Cl)c2COc2c(F)cc(CCC(=O)OC(C)(C)C)cc2F)cc1]

Into a 50-mL round-bottom flask, was placed [3-chloro-5-(4-ethylphenyl)-1,2-thiazol-4-yl]methyl methanesulfonate (20 mg, 0.05 mmol, 1.00 equiv), ethyl 3-(3,5-difluoro-4-hydroxyphenyl)propanoate (16 mg, 0.07 mmol, 1.20 equiv), potassium carbonate (25 mg, 0.18 mmol, 3.00 equiv), N,N-dimethylformamide (2 mL). The resulting solution was stirred overnight at 25° C. The reaction was then quenched by the addition of 5 mL of water. The resulting solution was extracted with 3×5 mL of ethyl acetate and the organic layers combined. The resulting mixture was washed with 1×10 mL of brine. The mixture was dried over anhydrous sodium sulfate. The residue was applied onto the TLC with ethyl acetate/petroleum ether (1:15). This resulted in 20 mg (71%) of ethyl 3-(4-[[3-chloro-5-(4-ethylphenyl)-1,2-thiazol-4-yl]methoxy]-3,5-difluorophenyl)propanoate as colorless oil.

Step 2: 3-(4-[[3-chloro-5-(4-ethylphenyl)-1,2-thiazol-4-yl]methoxy]-3,5-difluorophenyl)propanoic Acid

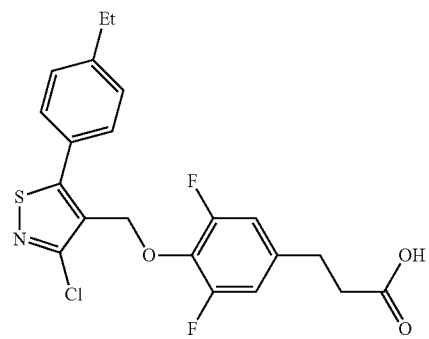 [SMILES: CCc1ccc(-c2snc(Cl)c2COc2c(F)cc(CCC(=O)O)cc2F)cc1]

Into a 50-mL round-bottom flask, was placed ethyl 3-(4-[[3-chloro-5-(4-ethylphenyl)-1,2-thiazol-4-yl]methoxy]-3,5-difluorophenyl)propanoate (20 mg, 0.04 mmol, 1.00 equiv, 90%), TFA (0.5 mL), CH$_2$Cl$_2$ (2 mL). The resulting solution was stirred overnight at 25° C. The resulting mixture was concentrated under vacuum. The crude product (2 mL) was purified by Prep-HPLC with the following conditions: Column, SunFire Prep C18, 5 um, 19*100 mm; mobile phase, Water of 0.05% TFA and CH$_3$CN (40% CH$_3$CN up to 100% in 6 min, hold 100% in 2 min, down to 40% in 0.1 min, hold 40% in 1.9 min); Detector, UV 220&254 nm. This resulted in 10 mg (59%) of 3-(4-[[3-chloro-5-(4-ethylphenyl)-1,2-thiazol-4-yl]methoxy]-3,5-difluorophenyl)propanoic acid as a brown solid. $^1$H NMR (400 MHz, CD$_3$OD) δ 7.49 (d, J=8.0 Hz, 2H), 7.38 (d, J=8.0 Hz, 2H), 6.83 (d, J=9.2 Hz, 2H), 5.10 (s, 2H), 2.87 (t, J=7.2 Hz, 2H), 2.75 (q, J=7.2, 15.2 Hz, 2H), 2.61 (t, J=7.6 Hz, 2H), 1.30 (t, J=7.6 Hz, 3H). Mass spectrum (ESI, m/z): Calcd. for C$_{21}$H$_{18}$ClF$_2$NO$_3$S, 438.1 (M+H), found 438.2.

Example 132

3-(4-((3-chloro-5-(4-ethylphenyl)isothiazol-4-yl)methoxy)-2,3-dimethylphenyl)propanoic Acid, Cpd 85

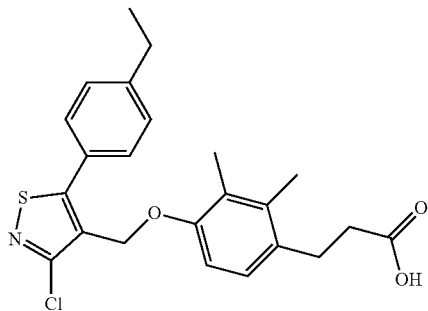 [SMILES: CCc1ccc(-c2snc(Cl)c2COc2ccc(CCC(=O)O)c(C)c2C)cc1]

The title compound was prepared according to the procedure described in Example 127 following Steps 1-7 by using 4-ethylbenzaldehyde as starting material and coupled with ethyl 3-(4-hydroxy-2,3-dimethylphenyl)propanoate to afford the desired product as an off-white solid. $^1$H NMR (400 MHz, CDCl$_3$) δ 7.45 (d, J=7.0 Hz, 1H), 7.32 (d, J=7.1 Hz, 2H), 6.95 (d, J=7.5 Hz, 1H), 6.76 (d, J=7.5 Hz, 1H), 4.91 (s, 2H), 2.96 (t, J=7.6 Hz, 2H), 2.75 (q, J=7.5 Hz, 2H), 2.62 (t, J=7.0 Hz, 2H), 2.25 (s, 3H), 2.14 (s, 3H), 1.25 (t, J=7.8 Hz, 3H). LCMS (ESI, M/Z) for C$_{23}$H$_{24}$ClNO$_3$S: 429.1, 431.1.

Example 133

3-(4-[[3-chloro-5-(4-fluorophenyl)-1,2-thiazol-4-yl]methoxy]-2,3-dimethylphenyl)propanoic Acid, Cpd 154

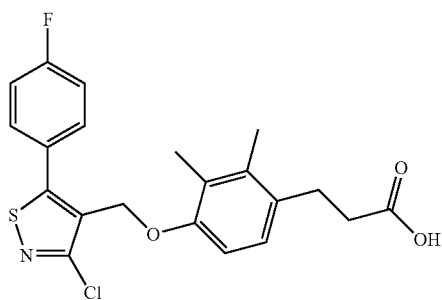 [SMILES: Cc1c(CCC(=O)O)ccc(OCc2c(Cl)nsc2-c2ccc(F)cc2)c1C]

The title compound was prepared according to the procedure described in Example 127 following Steps 1-7 by using 4-fluorobenzaldehyde as starting material and coupled with ethyl 3-(4-hydroxy-2,3-dimethylphenyl)propanoate to afford the desired product as an off-white solid. $^1$H NMR (300 MHz, CD$_3$OD): δ 7.56-7.61 (m, 2H), 7.23-7.29 (m, 2H), 6.96 (d, J=8.1 Hz, 1H), 6.74 (d, J=8.4 Hz, 1H), 4.99 (s, 2H), 2.91 (t, J=8.0 Hz, 2H), 2.51 (t, J=8.0 Hz, 2H), 2.22 (s, 1H), 2.07 (s, 1H); Mass spectrum (ESI, m/z): Calcd. for: C$_{21}$H$_{19}$ClFNO$_3$S: 420.1 (M+H), found 420.1.

Example 134

3-(4-[[3-chloro-5-(4-propylphenyl)-1,2-thiazol-4-yl]methoxy]-2,3-dimethylphenyl)propanoic Acid, Cpd 218

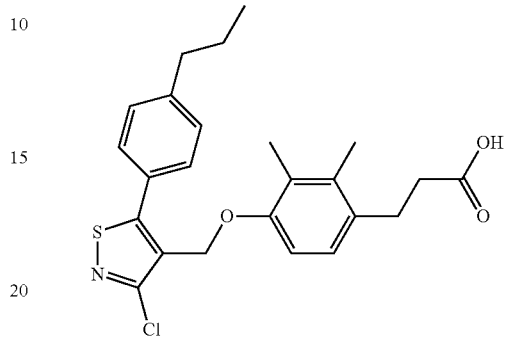

The title compound was prepared according to the procedure described in Example 127 following Step 1-7 by using 4-n-propylbenzaldehyde as starting material and coupled with ethyl 3-(4-hydroxy-2,3-dimethylphenyl)propanoate to afford the desired product as an off-white solid. $^1$H-NMR (300 MHz, CD$_3$OD) δ 7.34 (d, J=8.1 Hz, 2H), 7.21 (d, J=8.1 Hz, 2H), 6.84 (d, J=8.4 Hz, 1H), 6.62 (d, J=8.1 Hz, 1H), 4.86 (s, 2H), 2.79 (t, J=7.2 Hz, 2H), 2.55 (t, J=7.2 Hz, 2H), 2.38 (t, J=7.5 Hz, 2H), 2.12 (s, 3H), 1.96 (s, 3H), 1.51-1.63 (m, 2H), 0.88 (t, J=7.5 Hz, 3H). Mass spectrum (ESI, m/z): Calcd. for C$_{24}$H$_{26}$ClNO$_3$S, 444.1 (M+H), found 444.1.

Example 135

3-(4-[[3-chloro-5-(4-methoxyphenyl)-1,2-thiazol-4-yl]methoxy]-2,3-dimethylphenyl)propanoic Acid, Cpd 186

Step 1: 2-(2, 4-dithia-1,5-disodapentan-3-ylidene)propanedinitrile

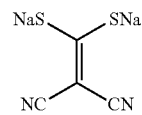

Into a 2500-mL plastic beaker, was placed sodium hydroxide (80 g, 2.00 mol, 2.00 equiv), ethanol (900 mL). This was followed by the addition of propanedinitrile (66 g, 999.07 mmol, 1.00 equiv) dropwise with stirring at 10-15° C. To this was added methanedithione (76 g, 998.15 mmol, 1.00 equiv) at 0° C. The resulting solution was stirred for 1 h at room temperature. The solids were collected by filtration and washed with EtOH (50 mL*3) The solid was dried in an oven. This resulted in 120 g (65%) of 2-(2,4-dithia-1,5-disodapentan-3-ylidene)propanedinitrile as a yellow solid.

Step 2: Dichloro-1, 2-thiazole-4-carbonitrile

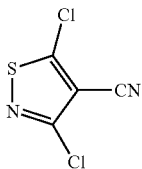

Into a 500-mL 3-necked round-bottom flask purged and maintained with an inert atmosphere of nitrogen, was placed a solution of 2-(2,4-dithia-1,5-disodapentan-3-ylidene)propanedinitrile (40 g, 214.86 mmol, 1.00 equiv) in CCl₄ (300 mL). To the above Cl₂(g) was introduced in. The resulting solution was stirred for 4 h at 25° C. The solids were filtered out, washed with 3×50 mL of DCM. The DCM phase were combined and concentrated. This resulted in 3.5 g (crude) of dichloro-1,2-thiazole-4-carbonitrile as brown oil.

Step 3: 3, 5-dichloroisothiazole-4-carboxamide

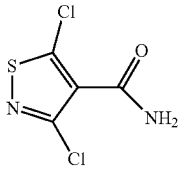

Into a 50-mL round-bottom flask, was placed dichloro-1,2-thiazole-4-carbonitrile (3.7 g, 20.67 mmol, 1.00 equiv), sulfuric acid (15 mL). The resulting solution was stirred for 2 h at 110° C. The solution was used for the next step directly.

Step 4: Dichloro-1, 2-thiazole-4-carboxylic Acid

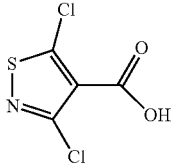

NaNO₂ (1 g, 14.49 mmol, 1.13 equiv), water (30 ml), dichloro-1,2-thiazole-4-carboxamide (2 g, 10.15 mmol, 1.00 equiv) was added to the sulfuric acid solution of the 3, 5-dichloroisothiazole-4-carboxamide. The resulting solution was stirred for 30 min at 50° C. The resulting solution was extracted with 3×30 mL of dichloromethane and the organic layers combined and dried over anhydrous sodium sulfate and concentrated. This resulted in 400 mg (crude) of dichloro-1,2-thiazole-4-carboxylic acid as a brown solid.

Step 5: Methyl 3, 5-dichloro-1,2-thiazole-4-carboxylate

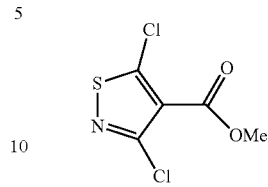

Into a 50-mL round-bottom flask, was placed dichloro-1, 2-thiazole-4-carboxylic acid (400 mg, 2.02 mmol, 1.00 equiv), methanol (10 mL), sulfuric acid (2 mL). The resulting solution was heated to reflux overnight. The resulting mixture was concentrated under vacuum. The resulting solution was extracted with 3×20 mL of ethyl acetate and the organic layers combined and dried over anhydrous sodium sulfate. The solids were filtered out. The resulting mixture was concentrated under vacuum. The residue was applied onto a silica gel column with ethyl acetate/petroleum ether (5:100). This resulted in 350 mg (82%) of methyl 3,5-dichloro-1,2-thiazole-4-carboxylate as yellow oil.

Step 6: Methyl 3-chloro-5-(4-methoxyphenyl)-1, 2-thiazole-4-carboxylate

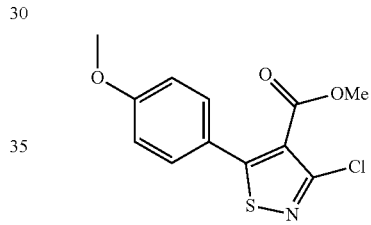

Into a 25-mL round-bottom flask purged and maintained with an inert atmosphere of nitrogen, was placed a solution of methyl 3,5-dichloro-1,2-thiazole-4-carboxylate (300 mg, 1.41 mmol, 1.00 equiv) in Tol (5 mL), (4-methoxyphenyl)boronic acid (270 mg, 1.78 mmol, 1.26 equiv), Pd(OAc)₂ (17 mg, 0.08 mmol, 0.05 equiv), KF (260 mg), 18-Crown-6 (180 mg, 0.68 mmol, 0.48 equiv). The resulting solution was stirred for 2 h at 110° C. in an oil bath. The resulting mixture was concentrated under vacuum. The residue was applied onto a silica gel column with ethyl acetate/petroleum ether (1:19). This resulted in 330 mg (74%) of methyl 3-chloro-5-(4-methoxyphenyl)-1,2-thiazole-4-carboxylate as a white crystal.

Step 7: [3-chloro-5-(4-methoxyphenyl)-1,2-thiazol-4-yl]methanol

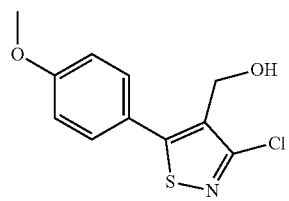 [SMILES: COc1ccc(-c2snc(Cl)c2CO)cc1]

Into a 25-mL round-bottom flask (1 atm) purged and maintained with an inert atmosphere of nitrogen, was placed methyl 3-chloro-5-(4-methoxyphenyl)-1,2-thiazole-4-carboxylate (450 mg, 1.59 mmol, 1.00 equiv), tetrahydrofuran (25 mL). This was followed by the addition of LAH (90 mg, 2.37 mmol, 1.50 equiv), in portions at 0° C. The resulting solution was stirred for 30 min at 0° C. in a water/ice bath. The reaction was then quenched by the addition of 2 mL of MeOH. The resulting mixture was concentrated under vacuum. The residue was applied onto a silica gel column with ethyl acetate/petroleum ether (20/80). This resulted in 223 mg (55%) of [3-chloro-5-(4-methoxyphenyl)-1,2-thiazol-4-yl]methanol as a light yellow solid.

Step 8: 3-chloro-4-(chloromethyl)-5-(4-methoxyphenyl)-1,2-thiazole

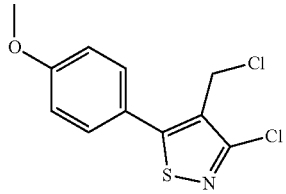

Into a 100-mL round-bottom flask, was placed [3-chloro-5-(4-methoxyphenyl)-1,2-thiazol-4-yl]methanol (223 mg, 0.87 mmol, 1.00 equiv), dichloromethane (20 mL), TEA (261 mg, 2.58 mmol, 2.96 equiv). This was followed by the addition of MsCl (200 mg) dropwise with stirring at 0° C. The resulting solution was stirred for 2 h at room temperature. The resulting solution was diluted with 40 mL of DCM. The resulting mixture was washed with 3×10 mL of water. The mixture was dried over anhydrous sodium sulfate and concentrated under vacuum. This resulted in 430 mg (crude) of 3-chloro-4-(chloromethyl)-5-(4-methoxyphenyl)-1,2-thiazole as yellow oil.

Step 9: 3-(4-[[3-chloro-5-(4-methoxyphenyl)-1,2-thiazol-4-yl]methoxy]-2,3-dimethylphenyl)propanoic Acid

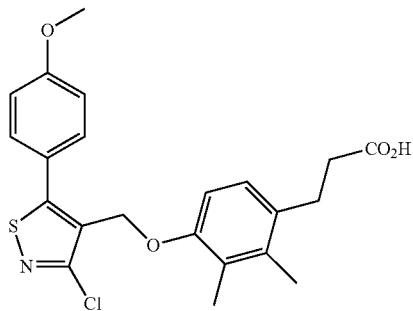 [SMILES: COc1ccc(-c2snc(Cl)c2COc2ccc(CCC(=O)O)c(C)c2C)cc1]

The title compound was prepared according to the procedure described in Example 127 following Step 6 and 7 by coupling of 3-chloro-4-(chloromethyl)-5-(4-methoxyphenyl)-1,2-thiazole and ethyl 3-(4-hydroxy-2,3-dimethylphenyl)propanoate followed by hydrolysis to afford the desired product as an off-white solid. $^1$H NMR: (300 MHz, CDCl$_3$) δ: 7.502 (d, J=6.6 Hz, 2H), 7.00 (t, J=6.0 Hz, 3H), 6.784 (d, J=6.0 Hz, 1H), 4.925 (s, 2H), 3.87 (s, 3H), 2.99 (t, J=6.0 Hz, 2H), 2.64 (t, J=6.0 Hz, 2H), 2.27 (s, 3H), 2.18 (s, 3H). Mass spectrum (ESI, m/z): Calcd. for C$_{22}$H$_{22}$ClNO$_4$S, 430.1 (M−H), found 430.1.

Example 136

3-[4-([3-chloro-5-[4-(trifluoromethyl)phenyl]-1,2-thiazol-4-yl]methoxy)-2,3-dimethylphenyl]propanoic Acid, Cpd 112

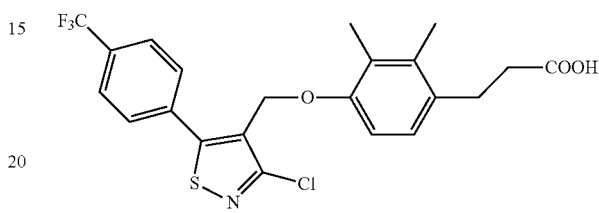

The title compound was prepared according to the procedure described in Example 127 following Step 1-7 by using 4-trifluoromethylbenzaldehyde as starting material and coupled with ethyl 3-(4-hydroxy-2,3-dimethylphenyl)propanoate to afford the desired product as an off-white solid. $^1$H-NMR (300 MHz, CD$_3$OD) δ 7.77 (d, J=8.4 Hz, 2H), 7.67 (d, J=8.1 Hz, 2H), 6.89 (d, J=8.4 Hz, 1H), 6.66 (d, J=8.4 Hz, 1H), 4.99 (s, 2H), 2.86 (t, J=8.1 Hz, 2H), 2.45 (t, J=6.9 Hz, 2H), 2.16 (s, 3H), 1.97 (s, 3H). Mass spectrum (ESI, m/z): Calcd. for C$_{22}$H$_{19}$ClF$_3$NO$_3$S, 470.1 (M+H), found 470.1.

Example 137

3-(4-[[5-(4-chloro-2-fluorophenyl)-1,2-thiazol-4-yl]methoxy]-2,3-dimethylphenyl)propanoic Acid, Cpd 122

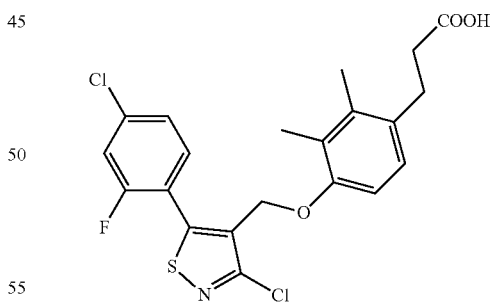

The title compound was prepared according to the procedure described in Example 127 following Step 1-7 by using 2-fluoro-4-chlorobenzaldehyde as starting material and coupled with ethyl 3-(4-hydroxy-2,3-dimethylphenyl)propanoate to afford the desired product as an off-white solid. $^1$H-NMR (300 MHz, CD$_3$OD) δ 7.30-7.44 (m, 3H), 6.90 (d, J=8.4 Hz, 1H), 6.62 (d, J=8.7 Hz, 1H), 5.02 (s, 2H), 2.88 (t, J=8.4 Hz, 2H), 2.46 (t, J=7.8 Hz, 2H), 2.17 (s, 3H), 1.89 (s, 3H). Mass spectrum (ESI, m/z): Calcd. for C$_{21}$H$_{18}$C$_{12}$FNO$_3$S, 455.0 (M+H), found 455.0.

Example 138

3-(4-[[3-chloro-5-(3-chlorophenyl)-1,2-thiazol-4-yl]methoxy]-2,3-dimethylphenyl)propanoic Acid, Cpd 156

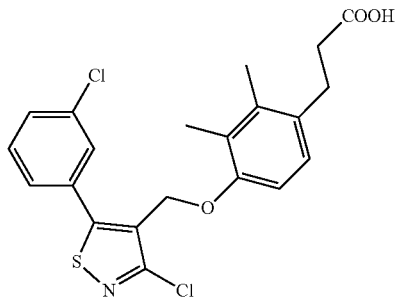 [SMILES: Cc1c(CCC(=O)O)ccc(OCc2c(Cl)nsc2-c2cccc(Cl)c2)c1C]

The title compound was prepared according to the procedure described in Example 127 following Step 1-7 by using 3-chlorobenzaldehyde as starting material and coupled with ethyl 3-(4-hydroxy-2,3-dimethylphenyl)propanoate to afford the desired product as an off-white solid. $^1$H-NMR (300 MHz, CD$_3$OD) δ 7.44-7.55 (m, 4H), 6.95 (d, J=8.4 Hz, 1H), 6.73 (d, J=8.4 Hz, 1H), 5.02 (s, 2H), 2.91 (t, J=8.4 Hz, 2H), 2.50 (t, J=7.5 Hz, 2H), 2.23 (s, 3H), 2.07 (s, 3H). Mass spectrum (ESI, m/z): Calcd. for C$_{21}$H$_{19}$Cl$_2$NO$_3$S, 436.1 (M+H), found 436.1.

Example 139

3-(4-[[3-chloro-5-(2-chlorophenyl)-1,2-thiazol-4-yl]methoxy]-2,3-dimethylphenyl)propanoic Acid, Cpd 104

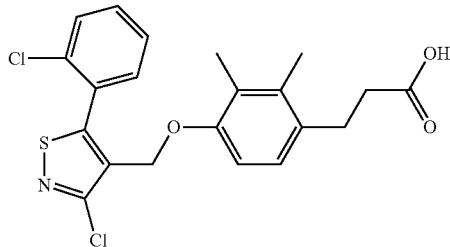 [SMILES: Cc1c(CCC(=O)O)ccc(OCc2c(Cl)nsc2-c2ccccc2Cl)c1C]

The title compound was prepared according to the procedure described in Example 127 following Steps 1-7 by using 2-chlorobenzaldehyde as starting material and coupled with ethyl 3-(4-hydroxy-2,3-dimethylphenyl)propanoate to afford the desired product as an off-white solid. $^1$H-NMR (400 MHz, CD$_3$OD) 7.57-7.59 (m, 1H), 7.47-7.52 (m, 1H), 7.36-7.40 (m, 1H), 7.28-7.31 (m, 1H), 6.87 (d, J=8.4 Hz, 1H), 6.54 (d, J=8.4 Hz, 1H), 4.94 (s, 2H), 2.87 (t, J=8.0 Hz, 2H), 2.48 (t, J=7.8 Hz, 2H), 2.18 (s, 3H), 1.90 (s, 3H). Mass spectrum (ESI, m/z): Calcd. for C$_{21}$H$_{19}$C1$_2$NO$_3$S, 436.0 (M+H), found 435.9.

Example 140

3-(4-[[3-chloro-5-(4-chlorophenyl)-1,2-thiazol-4-yl]methoxy]-2,3-dimethylphenyl)propanoic Acid, Cpd 88

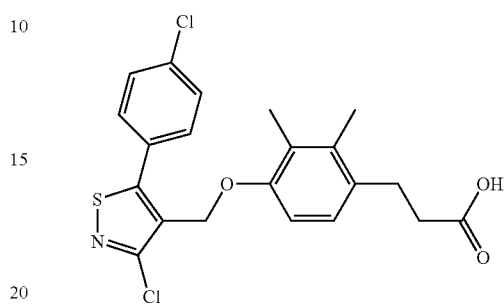

The title compound was prepared according to the procedure described in Example 127 following Step 1-7 by using 4-chlorobenzaldehyde as starting material and coupled with ethyl 3-(4-hydroxy-2,3-dimethylphenyl)propanoate to afford the desired product as an off-white solid. $^1$H NMR (400 MHz, CD$_3$OD) δ 7.53 (s, 4H), 6.96 (d, J=8.0 Hz, 1H), 6.73 (d, J=8.4 Hz, 1H), 5.00 (s, 2H), 2.91 (t, J=8.0 Hz, 2H), 2.52 (t, J=7.6 Hz, 2H), 2.23 (s, 3H), 2.06 (s, 3H). Mass spectrum (ESI, m/z): Calcd. for C$_{21}$H$_{19}$Cl$_2$NO$_3$S, 436.1 (M+H), found 436.1.

Example 141

3-(4-[[3-chloro-5-(4-chlorophenyl)-1,2-thiazol-4-yl]methoxy]-2,3-difluorophenyl)propanoic Acid, Cpd 72

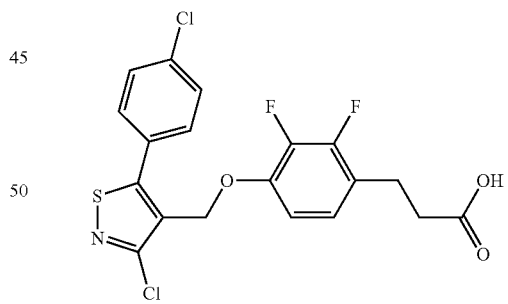

The title compound was prepared according to the procedure described in Example 127 following Step 1-7 by using 2-fluror-4-chlorobenzaldehyde as starting material and coupled with ethyl 3-(4-hydroxy-2,3-difluorophenyl)propanoate to afford the desired product as an off-white solid. $^1$H NMR (400 MHz, CD$_3$OD) δ 7.56 (s, 4H), 6.98 (t, J=2.0 Hz, 1H), 6.90 (d, J=2.0 Hz, 1H), 5.09 (s, 2H), 2.94 (t, J=7.6 Hz, 2H), 2.61 (t, J=7.2 Hz, 2H). Mass spectrum (ESI, m/z): Calcd. for C$_{21}$H$_{21}$FO$_5$, 444.0 (M+H), found 444.0.

Example 142

3-(4-[[3-chloro-5-(4-chlorophenyl)-1,2-thiazol-4-yl]methoxy]-3,5-difluorophenyl)propanoic Acid, Cpd 75

Step 1: Tert-butyl 3-(4-[[3-chloro-5-(4-chlorophenyl)-1,2-thiazol-4-yl]methoxy]-2,6-difluorophenyl)propanoate

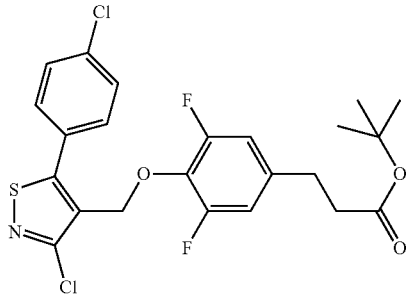 [SMILES: CC(C)(C)OC(=O)CCc1cc(F)c(OCc2c(Cl)nsc2-c2ccc(Cl)cc2)c(F)c1]

Into a 50-mL round-bottom flask, was placed [3-chloro-5-(4-chlorophenyl)-1,2-thiazol-4-yl]methyl methanesulfonate (50 mg, 0.13 mmol, 1.00 equiv, 90%), tert-butyl 3-(3,5-difluoro-4-hydroxyphenyl)propanoate (46 mg, 0.18 mmol, 1.20 equiv), potassium carbonate (61 mg, 0.44 mmol, 3.00 equiv), N,N-dimethylformamide (2 mL). The resulting solution was stirred overnight at 25° C. The reaction was then quenched by the addition of 5 mL of water. The resulting solution was extracted with 3×10 mL of ethyl acetate and the organic layers combined. The resulting mixture was washed with 1×10 mL of brine. The residue was applied onto the TLC with ethyl acetate/petroleum ether (1:10). This resulted in 60 mg (81%) of tert-butyl 3-(4-[[3-chloro-5-(4-chlorophenyl)-1,2-thiazol-4-yl]methoxy]-2,6-difluorophenyl) propanoate as colorless oil.

Step 2: 3-(4-[[3-chloro-5-(4-chlorophenyl)-1,2-thiazol-4-yl]methoxy]-3,5-difluorophenyl)propanoic Acid

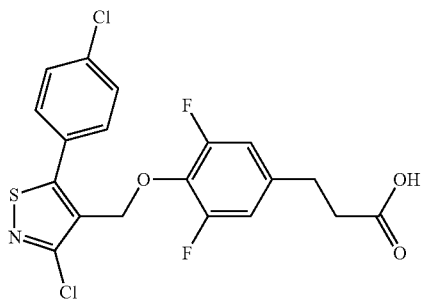 [SMILES: O=C(O)CCc1cc(F)c(OCc2c(Cl)nsc2-c2ccc(Cl)cc2)c(F)c1]

Into a 50-mL round-bottom flask, was placed tert-butyl 3-(4-[[3-chloro-5-(4-chlorophenyl)-1,2-thiazol-4-yl]methoxy]-3,5-difluorophenyl)propanoate (50 mg, 0.09 mmol, 1.00 equiv, 90%), CF3COOH (0.4 mL), dichloromethane (2 mL). The resulting solution was stirred overnight at 25° C. The resulting mixture was concentrated under vacuum. The resulting mixture was washed with 2×5 mL of methanol. The solids were collected by filtration. This resulted in 3.8 mg (9%) of 3-(4-[[3-chloro-5-(4-chlorophenyl)-1,2-thiazol-4-yl]methoxy]-3,5-difluorophenyl)propanoic acid as a white solid. $^1$H NMR (300 MHz, CD$_3$OD) δ 7.56 (s, 4H), 6.84 (d, J=9.3 Hz, 2H), 5.09 (s, 2H), 2.88 (t, J=7.2 Hz, 2H), 2.61 (t, J=7.5 Hz, 2H). Mass spectrum (ESI, m/z): Calcd. for C$_{19}$H$_{13}$Cl$_2$F$_2$NO$_3$S, 444.0 (M+H), found 444.0.

Example 143

3-(4-((3-chloro-5-(4-ethylphenyl)isothiazol-4-yl)methoxy)-2,3,5-trifluorophenyl)propanoic Acid, Cpd 111

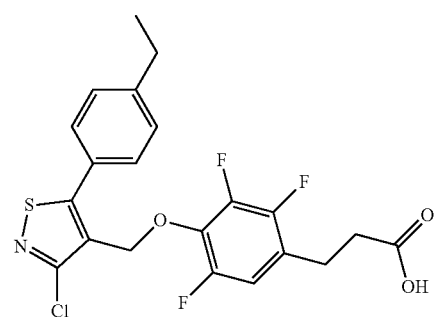 [SMILES: CCc1ccc(-c2snc(Cl)c2COc2c(F)cc(CCC(=O)O)c(F)c2F)cc1]

The title compound was prepared according to the procedure described in Example 127 following Step 1-7 by using 4-ethylbenzaldehyde as starting material and coupled with ethyl 3-(2,3,5-trifluoro-4-hydroxyphenyl)propanoate to afford the desired product as an off-white solid. $^1$H NMR (400 MHz, CDCl$_3$) δ 7.62 (d, J=7.5 Hz, 1H), 7.35 (d, J=7.1 Hz, 2H), 6.76 (m, J=4.5 Hz, 1H), 5.08 (s, 2H), 2.96 (t, J=7.5 Hz, 2H), 2.75 (m, J=7.0 Hz, 2H), 2.68 (m, J=7.2 Hz, 2H), 1.30 (t, J=7.8 Hz, 3H). LCMS (ESI, M/Z) for C$_{21}$H$_{17}$ClF$_3$NO$_3$S: 455.1, 457.1.

Example 144

3-(4-[[3-chloro-5-(2-fluoro-4-methylphenyl)-1,2-thiazol-4-yl]methoxy]-3,5-difluorophenyl)propanoic Acid, Cpd 77

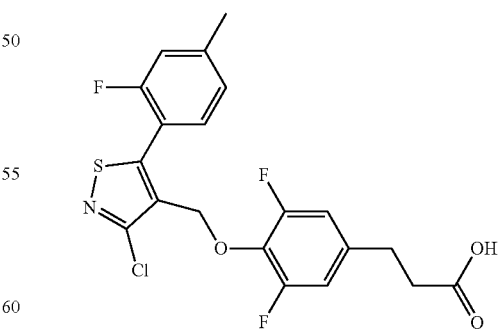

The title compound was prepared according to the procedure described in Example 127 following Step 1-7 by using 2-fluoro-4-methylbenzaldehyde as starting material and coupled with ethyl 3-(3,5-difluoro-4-hydroxyphenyl)propanoate followed by hydrolysis to afford the desired product as an off-white solid. ¹H NMR (300 MHz, CD₃OD) δ 7.29 (t, J=7.8 Hz, 1H), 7.08 (t, J=5.4 Hz, 2H), 6.73 (d, J=9.3 Hz, 2H), 5.04 (s, 2H), 2.80 (t, J=7.2 Hz, 2H), 2.55 (t, J=7.5 Hz, 2H), 2.40 (s, 3H). Mass spectrum (ESI, m/z): Calcd. for $C_{20}H_{15}ClF_3NO_3S$, 442.0 [M+H], found 442.0.

Example 145

3-(4-((3-chloro-5-(4-chloro-2-fluorophenyl)isothiazol-4-yl)methoxy)-3,5-difluorophenyl)propanoic Acid, Cpd 114

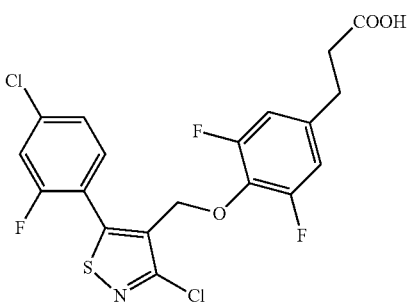 [SMILES: O=C(O)CCc1cc(F)c(OCc2c(Cl)nsc2-c2ccc(Cl)cc2F)c(F)c1]

The title compound was prepared according to the procedure described in Example 127 following Step 1-7 by using 2-fluoro-4-chlorobenzaldehyde as starting material and coupled with ethyl 3-(3,5-difluoro-4-hydroxyphenyl)propanoate followed by hydrolysis to afford the desired product as an off-white solid. ¹H NMR (300 MHz, CD3OD) δ 7.31-7.45 (m, 3H), 6.74 (d, J=9.3 Hz, 2H), 5.04 (s, 2H), 2.81 (t, J=7.5 Hz, 2H), 2.55 (t, J=7.2 Hz, 2H). Mass spectrum (ESI, m/z): Calcd. for $C_{19}H_{12}Cl_2F_3NO_3S$, 462.0 [M+H], found 462.0.

Example 146

3-(4-[[3-chloro-5-(4-methoxyphenyl)-1,2-thiazol-4-yl]methoxy]-2,3-difluorophenyl)propanoic Acid, Cpd 245

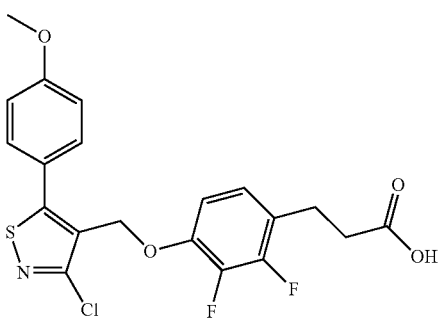 [SMILES: COc1ccc(-c2snc(Cl)c2COc2ccc(CCC(=O)O)c(F)c2F)cc1]

The title compound was prepared according to the procedure described in Example 127 following Step 1-7 by using 4-methoxybenzaldehyde as starting material and coupled with ethyl 3-(2,3-difluoro-4-hydroxyphenyl)propanoate followed by hydrolysis to afford the desired product as an off-white solid. ¹H NMR (300 MHz, CD₃OD): δ ppm 7.52 (d, J=9.0 Hz, 2H), 7.08 (d, J=9.0 Hz, 2H), 5.07 (s, 2H), 3.87 (s, 3H), 2.94 (t, J=7.5 Hz, 2H), 2.61 (t, J=7.5 Hz, 2H). Mass spectrum (ESI, m/z): Calcd. for: $C_{20}H_{16}ClF_2NO_4S$: 440.0 (M+H), found 440.0.

Example 147

3-(4-[[3-chloro-5-(4-methoxyphenyl)-1,2-thiazol-4-yl]methoxy]-3,5-difluorophenyl)propanoic Acid, Cpd 97

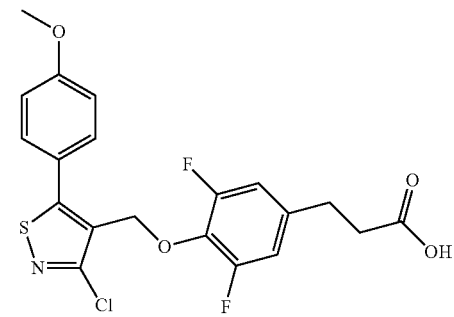 [SMILES: COc1ccc(-c2snc(Cl)c2COc2c(F)cc(CCC(=O)O)cc2F)cc1]

The title compound was prepared according to the procedure described in Example 127 following Step 1-7 by using 4-methoxybenzaldehyde as starting material and coupled with ethyl 3-(3,5-difluoro-4-hydroxyphenyl)propanoate followed by hydrolysis to afford the desired product as an off-white solid. ¹H NMR (300 MHz, CD₃OD): δ 7.54 (d, J=8.7 Hz, 2H), 7.08 (d, J=8.7 Hz, 2H), 6.85 (d, J=9.3 Hz, 2H), 5.09 (s, 2H), 3.92 (s, 3H), 2.88 (t, J=7.5 Hz, 2H), 2.61 (t, J=7.5 Hz, 2H). Mass spectrum (ESI, m/z): Calcd. for: $C_{20}H_{16}ClF_2NO_4S$: 440.0 (M+H), found 440.0.

Example 148

3-(4-[[3-chloro-5-(2-fluoro-4-methylphenyl)-1,2-thiazol-4-yl]methoxy]-2-(trifluoromethyl)phenyl)propanoic Acid, Cpd 175

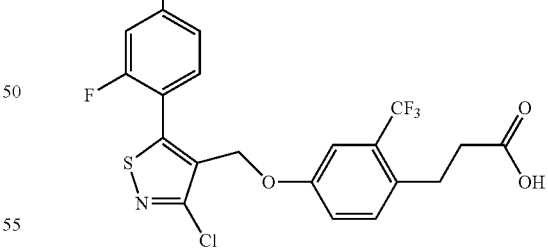

The title compound was prepared according to the procedure described in Example 127 following Step 1-7 by using 2-fluoro-4-methylbenzaldehyde as starting material and coupled with ethyl 3-(2-trifluoromethyl-4-hydroxyphenyl)propanoate followed by hydrolysis to afford the desired product as an off-white solid. ¹H NMR (400 MHz, CD₃OD) δ 7.36 (t, J=8.4 Hz, 2H), 7.14 (t, J=8.0 Hz, 2H), 7.07 (d, J=8.0 Hz, 2H), 5.09 (s, 2H), 3.03 (t, J=8.0 Hz, 2H), 2.57 (t, J=8.0 Hz, 2H), 2.43 (s, 3H). Mass spectrum (ESI, m/z): Calcd. for $C_{21}H_{16}ClF_4NO_3S$, 472.1 (M–H), found 472.1.

Example 149

3-(4-[[3-chloro-5-(2-methylphenyl)-1,2-thiazol-4-yl]methoxy]-3,5-difluorophenyl)propanoic Acid, Cpd 193

Step 1: 3-chloro-5-(2-methylphenyl)-1,2-thiazole-4-carbonitrile

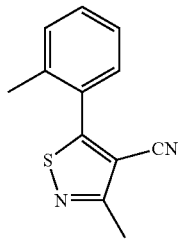

Into a 250-mL round-bottom flask, was placed 2-[(2-methylphenyl)methylidene] propanedinitrile (9.8 g, 58.27 mmol, 1.00 equiv), S₂Cl₂ (39 g), pyridine (458 mg, 5.79 mmol, 0.10 equiv). The resulting solution was stirred overnight at 140° C. in an oil bath. The reaction was then quenched by the addition of water. The solids were filtered out. The resulting solution was extracted with 3×50 mL of ethyl acetate and the organic layers combined and concentrated under vacuum. The residue was applied onto a silica gel column with ethyl acetate/petroleum ether (6/94). The collected fractions were combined and concentrated under vacuum. This resulted in 2 g (12%) of 3-chloro-5-(2-methylphenyl)-1,2-thiazole-4-carbonitrile as yellow oil.

Step 2: 3-chloro-5-(2-methylphenyl)-1,2-thiazole-4-carboxylic acid

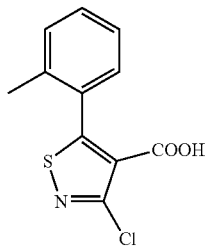 [SMILES: Cc1ccccc1-c1snc(Cl)c1C(=O)O]

Into a 100-mL round-bottom flask, was placed 3-chloro-5-(2-methylphenyl)-1,2-thiazole-4-carbonitrile (6 g, 25.56 mmol, 1.00 equiv). This was followed by the addition of sulfuric acid (8 mL). The mixture was stirred at 120° C. for 1 h. To this was added a solution of NaNO₂ (3.54 g, 51.30 mmol, 2.01 equiv) in water (5 mL) dropwise with stirring at 0° C. The resulting solution was stirred for 1 h at 50° C. in an oil bath. The resulting solution was extracted with 3×50 mL of ethyl acetate and the organic layers combined, washed with 20 mL 2N HCl, dried over anhydrous sodium sulfate and concentrated under vacuum. This resulted in 5 g (crude) of 3-chloro-5-(2-methylphenyl)-1,2-thiazole-4-carboxylic acid as yellow oil.

Step 3: [3-chloro-5-(2-methylphenyl)-1,2-thiazol-4-yl]methanol

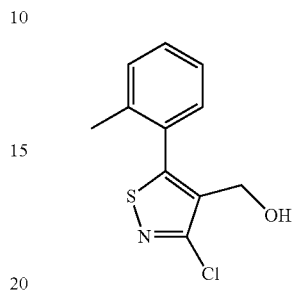

Into a 100-mL round-bottom flask, was placed 3-chloro-5-(2-methylphenyl)-1,2-thiazole-4-carboxylic acid (3 g, 11.82 mmol, 1.00 equiv), tetrahydrofuran (30 mL). This was followed by the addition of BH₃ (1M) (30 mL) dropwise with stirring at 0° C. The resulting solution was stirred overnight at 30° C. The reaction was then quenched by the addition of 30 mL of methanol. The resulting mixture was concentrated under vacuum. The residue was applied onto a silica gel column with ethyl acetate/petroleum ether (26/84). The collected fractions were combined and concentrated under vacuum. This resulted in 260 mg (9%) of [3-chloro-5-(2-methylphenyl)-1,2-thiazol-4-yl]methanol as yellow oil.

Step 4: Ethyl 3-(4-[[3-chloro-5-(2-methylphenyl)-1,2-thiazol-4-yl]methoxy]-3,5-difluorophenyl)propanoate

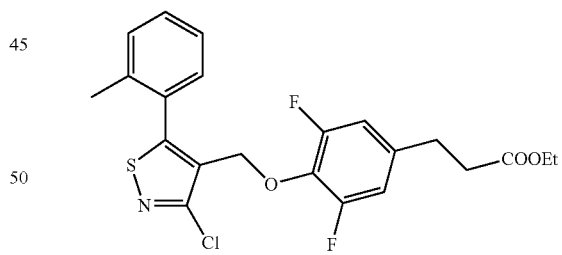

Into a 40-mL vial purged and maintained with an inert atmosphere of nitrogen, was placed [3-chloro-5-(2-methylphenyl)-1,2-thiazol-4-yl]methanol (90 mg, 0.38 mmol, 1.00 equiv), ethyl 3-(3,5-difluoro-4-hydroxyphenyl)propanoate (130 mg, 0.56 mmol, 1.50 equiv), ADDP (197 mg, 0.79 mmol, 2.10 equiv), n-Bu₃P (190 mg), toluene (5 mL). The resulting solution was stirred overnight at 60° C. in an oil bath. The residue was applied onto TLC with ethyl acetate/petroleum ether (1/4). This resulted in 100 mg (53%) of ethyl 3-(4-[[3-chloro-5-(2-methylphenyl)-1,2-thiazol-4-yl]methoxy]-3,5-difluorophenyl)propanoate as colorless oil.

165

Step 5: 3-(4-[[3-chloro-5-(2-methylphenyl)-1,2-thiazol-4-yl]methoxy]-3,5-difluorophenyl)propanoic Acid

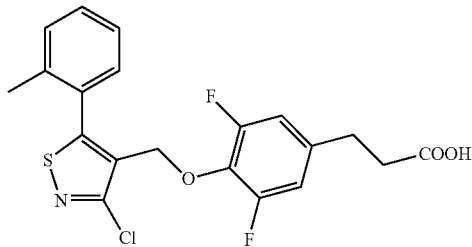 [SMILES: Cc1ccccc1-c1snc(Cl)c1COc1c(F)cc(CCC(=O)O)cc1F]

The title compound was prepared according to the procedure described in Example 127 following Step 7 by hydrolysis of ethyl 3-(4-[[3-chloro-5-(2-methylphenyl)-1,2-thiazol-4-yl]methoxy]-3,5-difluorophenyl)propanoate to afford the desired product as an off-white solid. $^1$H NMR (300 MHz, CD$_3$OD) δ: 7.32-7.42 (m, 2H), 7.23 (t, J=7.5 Hz, 1H), 6.95 (d, J=6.9 Hz, 1H), 2.74-6.82 (m, 2H), 2.85 (t, J=7.5 Hz, 2H), 2.60 (t, J=7.2 Hz, 2H), 2.14 (s, 3H). Mass spectrum (ESI, m/z): Calcd. for C$_{20}$H$_{16}$ClF$_2$NO$_3$S, 424.1 (M+H), found 424.0.

Example 150

3-(4-[[3-chloro-5-(2,4-dimethylphenyl)-1,2-thiazol-4-yl]methoxy]-3,5-difluorophenyl)propanoic Acid, Cpd 236

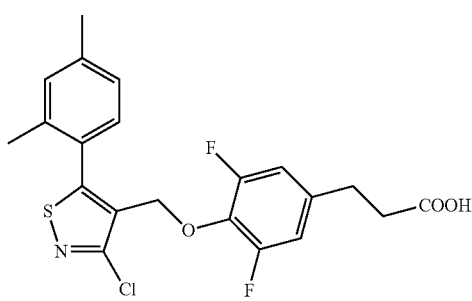 [SMILES: Cc1ccc(-c2snc(Cl)c2COc2c(F)cc(CCC(=O)O)cc2F)c(C)c1]

The title compound was prepared according to the procedure described in Example 149 following Steps 4 and 5 with hydrolysis of ethyl 3-(4-((3-chloro-5-(2,4-dimethylphenyl)isothiazol-4-yl)methoxy)-3,5-difluorophenyl)propanoate to afford the desired product as an off-white solid. $^1$H NMR (300 MHz, CD$_3$OD) δ: 7.16 (s, 1H), 7.05 (d, J=7.8 Hz, 1H), 6.74-6.86 (m, 3H), 2.86 (t, J=7.2 Hz, 2H), 2.61 (t, J=7.2 Hz, 2H), 2.38 (s, 3H), 2.10 (s, 3H). Mass spectrum (ESI, m/z): Calcd. for C$_{21}$H$_{18}$ClF$_2$NO$_3$S, 438.1 (M+H), found 438.1.

166

Example 151

3-(4-[[3-chloro-5-(2-methylphenyl)-1,2-thiazol-4-yl]methoxy]-2-ethylphenyl)propanoic Acid, Cpd 227

Step 1: Dichloro-1,2-thiazole-4-carboxylic Acid

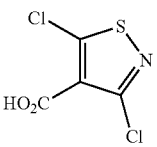

Into a 500-mL round-bottom flask, was placed dichloro-1,2-thiazole-4-carbonitrile (36 g, 201.09 mmol, 1.00 equiv), Conc. sulfuric acid (100 mL). The resulting solution was stirred for 2 h at 100° C. in an oil bath. This was followed by the addition of a solution of NaNO$_2$ (15 g, 217.39 mmol, 1.08 equiv) in water (100 mL) dropwise with stirring at 0° C. The resulting solution was allowed to react, with stirring, for overnight while the temperature was maintained at 50° C. in an oil bath. The resulting solution was diluted with 500 mL of water. The resulting solution was extracted with 5×500 mL of ethyl acetate and the organic layers combined. The resulting mixture was washed with 1×500 mL of brine. The mixture was dried over anhydrous sodium sulfate and concentrated under vacuum. This resulted in 30 g (75%) of dichloro-1,2-thiazole-4-carboxylic acid as red oil. Mass spectrum (ESI, m/z): Calcd. for C$_4$HCl$_2$NO$_2$S, 197.1 (M+H), found 197.1.

Step 2: Ethyl 3,5-dichloro-1,2-thiazole-4-carboxylate

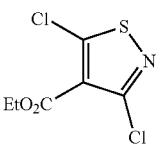

Into a 500-mL round-bottom flask, was placed dichloro-1,2-thiazole-4-carboxylic acid (10 g, 50.50 mmol, 1.00 equiv), acetone (100 mL). This was followed by the addition of EtOSO$_3$Et (19.54 g) dropwise with stirring at 0° C. in 3 min. To this was added potassium carbonate (28.02 g, 202.73 mmol, 4.01 equiv). The resulting solution was stirred for 30 min at 58° C. in an oil bath. The resulting mixture was concentrated under vacuum. The resulting solution was diluted with 100 mL of H$_2$O. The resulting solution was extracted with 3×100 mL of ethyl acetate and the organic layers combined and dried over anhydrous sodium sulfate. The residue was applied onto a silica gel column with ethyl acetate/petroleum ether (12:88). This resulted in 1.353 g (12%) of ethyl 3,5-dichloro-1,2-thiazole-4-carboxylate as yellow oil.

Step 3: Ethyl 3-chloro-5-(2-methylphenyl)-1,2-thiazole-4-carboxylate

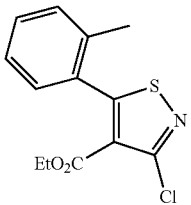 [SMILES: CCOC(=O)c1c(Cl)nsc1-c1ccccc1C]

Into a 100-mL round-bottom flask purged and maintained with an inert atmosphere of nitrogen, was placed ethyl 3,5-dichloro-1,2-thiazole-4-carboxylate (1 g, 4.42 mmol, 1.00 equiv), (2-methylphenyl)boronic acid (665 mg, 4.89 mmol, 1.11 equiv), Pd(OAc)$_2$ (49.7 mg, 0.22 mmol, 0.05 equiv), KF (773 mg), 18-Crown-6 (117 mg, 0.44 mmol, 0.10 equiv), Tol (40 mL). The resulting solution was stirred overnight at 110° C. in an oil bath. The resulting solution was diluted with 50 mL of EA. The resulting mixture was washed with 5×30 mL of sodium chloride(aq). The mixture was dried over anhydrous sodium sulfate and concentrated under vacuum. The residue was applied onto a silica gel column with ethyl acetate/petroleum ether (0:100). This resulted in 730 mg (59%) of ethyl 3-chloro-5-(2-methylphenyl)-1,2-thiazole-4-carboxylate as yellow oil.

Step 4: [3-chloro-5-(2-methylphenyl)-1,2-thiazol-4-yl]methanol

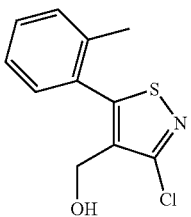

Into a 50-mL round-bottom flask, was placed ethyl 3-chloro-5-(2-methylphenyl)-1,2-thiazole-4-carboxylate (730 mg, 2.59 mmol, 1.00 equiv), tetrahydrofuran (10 mg, 0.14 mmol, 0.05 equiv). This was followed by the addition of LiAlH$_4$ (296 mg, 7.80 mmol, 3.01 equiv), in portions at 0° C. The resulting solution was stirred for 2 h at 30° C. The reaction was then quenched by the addition of 1.5 g of ice/salt. The solids were filtered out. The resulting solution was extracted with 3×10 mL of ethyl acetate and the organic layers combined and concentrated under vacuum. The residue was applied onto a silica gel column with ethyl acetate/petroleum ether (25:75). This resulted in 260 mg (42%) of [3-chloro-5-(2-methylphenyl)-1,2-thiazol-4-yl]methanol as yellow oil. Mass spectrum (ESI, m/z): Calcd. for C$_{11}$H$_{10}$ClNOS, 240.0 (M+H), found 240.0.

Step 5: Ethyl 3-(4-[[3-chloro-5-(2-methylphenyl)-1,2-thiazol-4-yl]methoxy]-2-ethylphenyl)propanoate

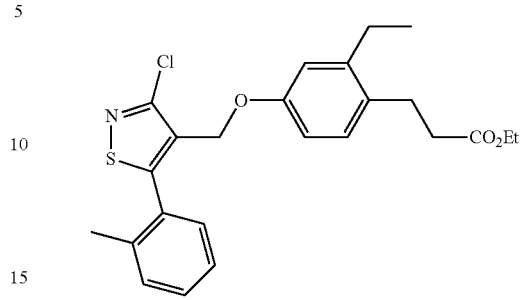

Into a 8-mL vial purged and maintained with an inert atmosphere of nitrogen, was placed [3-chloro-5-(2-methylphenyl)-1,2-thiazol-4-yl]methanol (80 mg, 0.33 mmol, 1.00 equiv), ethyl 3-(2-ethyl-4-hydroxyphenyl)propanoate (89.17 mg, 0.40 mmol, 1.20 equiv), ADDP (210.87 mg, 0.84 mmol, 2.52 equiv), n-Bu$_3$P (101.42 mg), Tol (1.5 mL). The resulting solution was stirred overnight at 60° C. in an oil bath. The resulting mixture was concentrated under vacuum. The residue was applied onto a silica gel column with ethyl acetate/petroleum ether (1:6). This resulted in 123 mg (83%) of ethyl 3-(4-[[3-chloro-5-(2-methylphenyl)-1, 2-thiazol-4-yl]methoxy]-2-ethylphenyl)propanoate as colorless oil. Mass spectrum (ESI, m/z): Calcd. for C$_{21}$H$_{21}$FO$_5$, 444.1 (M+H), found 444.1.

Step 6: 3-(4-[[3-chloro-5-(2-methylphenyl)-1,2-thiazol-4-yl]methoxy]-2-ethylphenyl)propanoic Acid

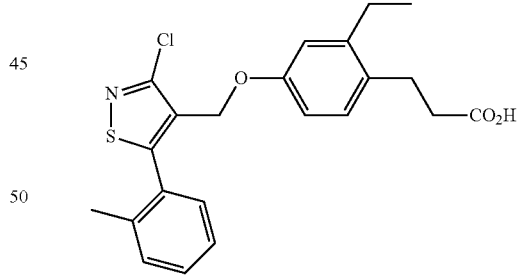

The title compound was prepared according to the procedure described in Example 127 following Step 7 by hydrolysis of ethyl 3-(4-((3-chloro-5-(o-tolyl)isothiazol-4-yl)methoxy)-2-ethylphenyl) propanoate to afford the desired product as an off-white solid. $^1$H NMR (300 MHz, CD$_3$OD) δ 7.20-7.42 (m, 4H), 7.01 (d, J=8.4 Hz, 1H), 6.54-6.60 (m, 2H), 4.81 (s, 2H), 3.33 (t, J=7.8 Hz, 2H), 2.86 (t, J=7.8 Hz, 2H), 2.48-2.63 (m, 2H), 2.20 (s, 3H), 1.18 (t, J=7.6 Hz, 3H). Mass spectrum (ESI, m/z): Calcd. for C$_{22}$H$_{22}$ClNO$_3$S, 414.1 (M−H), found 414.2.

Example 152

3-(4-((3-chloro-5-(o-tolyl)isothiazol-4-yl)methoxy)-2-methoxyphenyl)propanoic Acid, Cpd 222

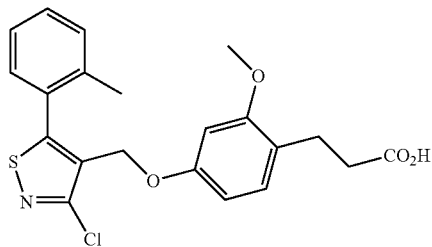 [SMILES: COc1cc(OCc2c(Cl)nsc2-c2ccccc2C)ccc1CCC(=O)O]

The title compound was prepared according to the procedure described in Example 151 following Step 5 and 6 and by hydrolysis of ethyl 3-(4-((3-chloro-5-(o-tolyl)isothiazol-4-yl)methoxy)-2-methoxy-phenyl) propanoate to afford the desired product as an off-white solid. $^1$H NMR (300 MHz, CD$_3$OD) δ7.20-7.43 (m, 4H), 6.97 (d, J=8.4 Hz, 1H), 6.28-6.38 (m, 2H), 4.83 (s, 2H), 3.73 (s, 3H), 2.80 (t, J=7.8 Hz, 2H), 2.49 (t, J=7.8 Hz, 2H), 2.21 (s, 3H). Mass spectrum (ESI, m/z): Calcd. for C$_{21}$H$_{20}$ClNO$_4$S, 416.1 (M−H), found 416.2.

Example 153

3-(4-((3-chloro-5-(o-tolyl)isothiazol-4-yl)methoxy)-5-fluoro-2-(trifluoromethyl)phenyl)propanoic Acid, Cpd 246

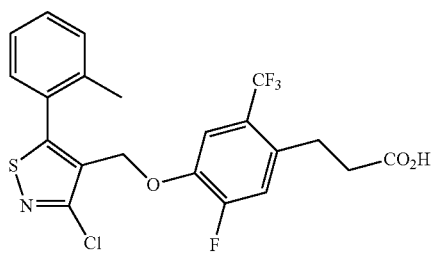 [SMILES: Cc1ccccc1-c1snc(Cl)c1COc1cc(C(F)(F)F)c(CCC(=O)O)cc1F]

The title compound was prepared according to the procedure described in Example 151 following Step 5 and 6 and by hydrolysis of ethyl 3-(4-((3-chloro-5-(o-tolyl)isothiazol-4-yl)methoxy)-5-fluoro-2-(trifluoromethyl)phenyl)propanoate to afford the desired product as an off-white solid. $^1$H NMR (300 MHz, CD3OD) δ 7.33-7.45 (m, 3H), 7.23-7.28 (m, 1H), 7.04-7.20 (m, 2H), 4.91 (s, 2H), 2.88 (t, J=7.8 Hz, 2H), 2.58 (t, J=7.8 Hz, 2H), 2.20 (s, 3H). Mass spectrum (ESI, m/z): Calcd. for C$_{21}$H$_{16}$ClF$_4$NO$_3$S, 472.1 (M−H), found 472.2.

Example 154

3-(4-((3-chloro-5-(o-tolyl)isothiazol-4-yl)methoxy)-5-methyl-2-(trifluoromethyl)phenyl)propanoic Acid, Cpd 210

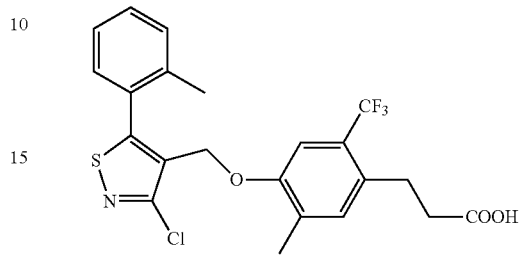

The title compound was prepared according to the procedure described in Example 151 following Step 5 and 6 by hydrolysis of ethyl 3-(4-((3-chloro-5-(o-tolyl)isothiazol-4-yl)methoxy)-5-methyl-2-(trifluoromethyl)phenyl)propanoate to afford the desired product as an off-white solid. $^1$H NMR (400 MHz, CD$_3$OD) δ 7.38-7.42 (m, 2H), 7.33-7.35 (m, 1H), 7.21-7.29 (m, 2H), 6.99 (s, 1H), 4.90 (s, 2H), 2.97 (t, J=7.8 Hz, 2H), 2.54 (t, J=7.8 Hz, 2H), 2.19 (s, 3H), 2.03 (s, 3H). Mass spectrum (ESI, m/z): Calcd. For C$_{22}$H$_{19}$ClF$_3$NO$_3$S, 468.1 (M−H), found 468.1.

Example 155

3-(4-((3-chloro-5-(o-tolyl)isothiazol-4-yl)methoxy)-5-ethyl-2-(trifluoromethyl)phenyl)propanoic Acid, Cpd 215

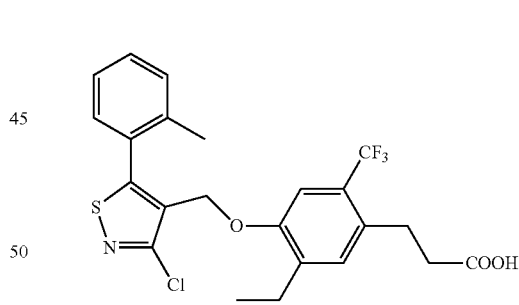

The title compound was prepared according to the procedure described in Example 150 following Step 5 and 6 by hydrolysis of ethyl 3-(4-((3-chloro-5-(o-tolyl)isothiazol-4-yl)methoxy)-5-ethyl-2-(trifluoromethyl)phenyl)propanoate to afford the desired product as an off-white solid. $^1$H NMR (400 MHz, CD$_3$OD) δ 7.39-7.43 (m, 2H), 7.27-7.36 (m, 1H), 7.21 (d, J=8.6 Hz, 1H), 7.02 (s, 1H), 4.93 (s, 2H), 3.00 (t, J=7.8 Hz, 2H), 2.55 (t, J=7.8 Hz, 2H), 2.48 (t, J=7.6 Hz, 2H), 2.20 (s, 3H), 1.09 (t, J=7.6 Hz, 3H). Mass spectrum (ESI, m/z): Calcd. For C$_{23}$H$_{21}$ClF$_3$NO$_3$S, 482.1 (M−H), found 482.2.

Example 156

3-(4-[[3-chloro-5-(4-chlorophenyl)-1,2-thiazol-4-yl]methoxy]-3,5-difluorophenyl)propan-1-ol, Cpd 75

Step 1: Ethyl 3-(4-[[3-chloro-5-(4-chlorophenyl)-1,2-thiazol-4-yl]methoxy]-3,5-difluorophenyl)propanoate

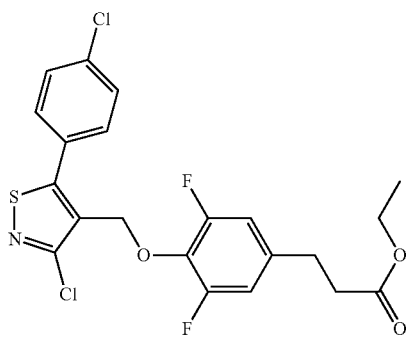 [SMILES: CCOC(=O)CCc1cc(F)c(OCc2c(Cl)nsc2-c2ccc(Cl)cc2)c(F)c1]

Into a 50-mL round-bottom flask, was placed [3-chloro-5-(4-chlorophenyl)-1,2-thiazol-4-yl]methyl methanesulfonate (320 mg, 0.95 mmol, 1.00 equiv), ethyl 3-(3,5-difluoro-4-hydroxyphenyl)propanoate (230 mg, 1.00 mmol, 1.06 equiv), potassium carbonate (420 mg, 3.04 mmol, 3.21 equiv), N,N-dimethylformamide (10 mL). The resulting solution was stirred overnight at 30° C. The resulting solution was diluted with of H$_2$O. The resulting solution was extracted with 3×10 mL of ethyl acetate and the organic layers combined and dried over anhydrous sodium sulfate and concentrated under vacuum. The residue was applied onto a silica gel column with ethyl acetate/petroleum ether (17/83). The collected fractions were combined and concentrated under vacuum. This resulted in 340 mg (68%) of ethyl 3-(4-[[3-chloro-5-(4-chlorophenyl)-1,2-thiazol-4-yl]methoxy]-3,5-difluorophenyl)propanoate as colorless oil. Mass spectrum (ESI, m/z): Calcd. for C$_{21}$H$_{17}$Cl$_2$F$_2$NO$_3$S, 472.0 (M+H), found 472.0.

Step 2: 3-(4-[[3-chloro-5-(4-chlorophenyl)-1,2-thiazol-4-yl]methoxy]-3,5-difluorophenyl)propan-1-ol

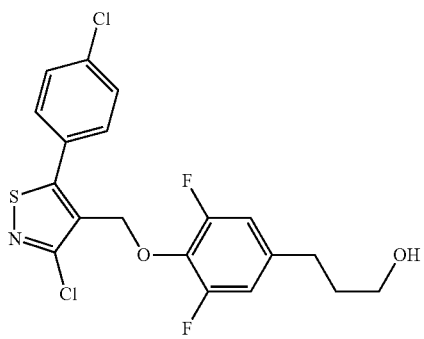 [SMILES: OCCCc1cc(F)c(OCc2c(Cl)nsc2-c2ccc(Cl)cc2)c(F)c1]

Into a 50-mL 3-necked round-bottom flask purged and maintained with an inert atmosphere of nitrogen, was placed ethyl 3-(4-[[3-chloro-5-(4-chlorophenyl)-1,2-thiazol-4-yl]methoxy]-3,5-difluorophenyl)propanoate (250 mg, 0.53 mmol, 1.00 equiv), tetrahydrofuran (10 mL). This was followed by the addition of a solution of LAH (60 mg, 1.58 mmol, 2.99 equiv) in tetrahydrofuran (2 mL) dropwise with stirring at 0° C. The resulting solution was stirred for 20 min at 25° C. The reaction was then quenched by the addition of sodium sulfate.H$_2$O. The solids were filtered out. The resulting mixture was concentrated under vacuum. The residue was applied onto a silica gel column with ethyl acetate/petroleum ether (30/70). The collected fractions were combined and concentrated under vacuum. This resulted in 103 mg (45%) of 3-(4-[[3-chloro-5-(4-chlorophenyl)-1,2-thiazol-4-yl]methoxy]-3,5-difluorophenyl)propan-1-ol as a off-white solid. $^1$H-NMR (300 MHz, CDCl$_3$) δ: 7.62 (d, J=8.4 Hz, 2H), 7.49 (d, J=8.4 Hz, 2H), 6.71-6.91 (m, 1H), 5.01 (s, 2H), 3.64 (t, J=7.5 Hz, 2H), 2.61-2.69 (m, 2H), 1.70-1.90 (m, 2H). Mass spectrum (ESI, m/z): Calcd. for C$_{19}$H$_{15}$Cl$_2$F$_2$NO$_2$S, 430.0 (M+H), found 430.0.

Example 157

3-(4-((3-chloro-5-(4-ethylphenyl)isothiazol-4-yl)methoxy)-2,3-dimethylphenyl)propan-1-ol, Cpd 209

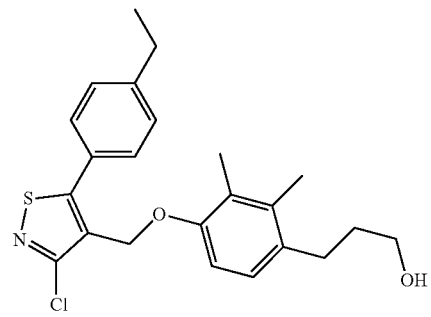 [SMILES: CCc1ccc(-c2snc(Cl)c2COc2ccc(CCCO)c(C)c2C)cc1]

The title compound was prepared according to the procedure described in Example 156 following Step 2 by LAH reduction of ethyl 3-(4-((3-chloro-5-(4-ethylphenyl)isothiazol-4-yl)methoxy)-2,3-dimethylphenyl)propanoate to afford the desired product as an off-white solid. $^1$H NMR (400 MHz, CDCl$_3$) δ 7.46 (d, J=7.5 Hz, 2H), 7.32 (d, J=7.5 Hz, 2H), 6.98 (d, J=6.5 Hz, 1H), 6.75 (d, J=6.5 Hz, 1H), 4.90 (s, 2H), 2.92 (t, J=7.0 Hz, 2H), 2.65 (q, J=6.8 Hz, 2H), 2.60 (t, J=7.5 Hz, 2H), 2.25 (s, 3H), 2.15 (s, 3H), 1.78 (t, J=7.6 Hz, 2H). LCMS (ESI, M/Z) for C$_{23}$H$_{26}$ClNO$_2$S: 415.1, 417.1.

Example 158

3-(4-((3-chloro-5-(4-ethylphenyl)isothiazol-4-yl)methoxy)-2,3-difluorophenyl)propan-1-ol, Cpd 83

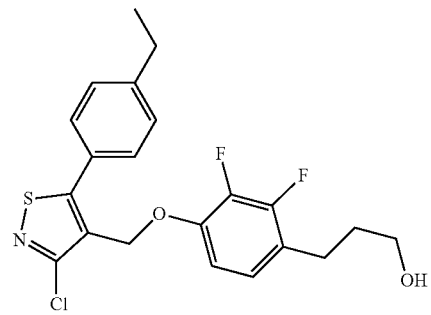 [SMILES: CCc1ccc(-c2snc(Cl)c2COc2ccc(CCCO)c(F)c2F)cc1]

The title compound was prepared according to the procedure described in Example 156 following Step 2 by LAH reduction of ethyl 3-(4-((3-chloro-5-(4-ethylphenyl)isothiazol-4-yl)methoxy)-2,3-difluorophenyl)propanoate to afford the desired product as an off-white solid. ¹H NMR (400 MHz, CDCl₃) δ 7.48 (d, J=8.8 Hz, 2H), 7.35 (d, J=8.5 Hz, 2H), 6.86 (t, J=9.0 Hz, 2H), 6.77 (t, J=9.2 Hz, 2H), 5.01 (s, 2H), 3.69 (t, J=8.5 Hz, 2H), 2.75 (m, 4H), 1.88 (m, 2H), 1.52 (br, s, 1H), 1.26 (t, J=9.0 Hz, 3H).

Example 159

3-(4-((3-chloro-5-(4-chlorophenyl)isothiazol-4-yl)methoxy)-2,3-difluorophenyl)propan-1-ol, Cpd 102

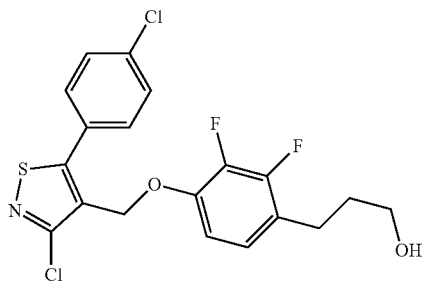 [SMILES: OCCCc1ccc(OCc2c(Cl)nsc2-c2ccc(Cl)cc2)c(F)c1F]

The title compound was prepared according to the procedure described in Example 156 following Step 2 by LAH reduction of ethyl 3-(4-((3-chloro-5-(4-chlorophenyl)isothiazol-4-yl)methoxy)-2,3-difluorophenyl)propanoate to afford the desired product as an off-white solid. ¹H NMR (400 MHz, CDCl₃) δ 7.48 (dd, J=8.5, 4.2 Hz, 4H), 6.88 (t, J=7.5 Hz, 1H), 6.77 (t, J=7.5 Hz, 1H), 4.98 (s, 2H), 3.71 (t, J=8.5 Hz, 2H), 2.73 (t, J=8.5 Hz, 2H), 1.88 (m, 2H), 1.75 (br, s, 1H).

Example 160

3-(4-((3-chloro-5-(4-ethylphenyl)isothiazol-4-yl)methoxy)-2,3,5-trifluorophenyl)propan-1-ol, Cpd 140

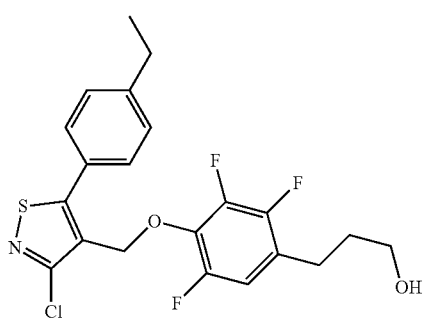 [SMILES: CCc1ccc(-c2snc(Cl)c2COc2c(F)cc(CCCO)c(F)c2F)cc1]

The title compound was prepared according to the procedure described in Example 156 following Step 2 by LAH reduction of ethyl 3-(4-((3-chloro-5-(4-ethylphenyl)isothiazol-4-yl)methoxy)-2,3,5-trifluorophenyl)propanoate to afford the desired product as an off-white solid. ¹H NMR (400 MHz, CDCl₃) 7.65 (d, J=7.5 Hz, 2H), 7.32 (d, J=7.5 Hz, 2H), 6.74 (m, J=5.5 Hz, 1H), 5.10 (s, 2H), 3.72 (t, J=7.0 Hz, 2H), 2.78 (m, J=5.8 Hz, 2H), 1.88 (m, 2H), 1.55 (br, s, 2H), 1.28 (t, J=7.6 Hz, 2H). LCMS (ESI, M/Z) for C₂₁H₁₉ClF₃NO₂S: 441.1, 443.1.

Example 161

3-(4-[[3-chloro-5-(4-ethylphenyl)-1,2-thiazol-4-yl]methoxy]-3,5-difluorophenyl)propan-1-ol, Cpd 183

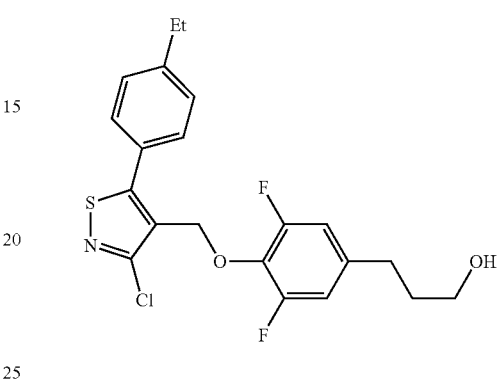

The title compound was prepared according to the procedure described in Example 156 following Step 2 by LAH reduction of ethyl 3-(4-((3-chloro-5-(4-ethylphenyl)isothiazol-4-yl)methoxy)-3,5-difluorophenyl)propanoate to afford the desired product as an off-white solid. ¹H NMR (400 MHz, CD₃OD) δ 7.51 (d, J=8.0 Hz, 2H), 7.37 (d, J=8.0 Hz, 2H), 6.80 (d, J=9.2 Hz, 2H), 5.08 (s, 2H), 3.58 (t, J=6.4 Hz, 2H), 2.63-2.75 (m, 4H), 1.80-1.84 (m, 2H), 1.30 (t, J=7.6 Hz, 3H). Mass spectrum (ESI, m/z): Calcd. for C₂₁H₂₀ClF₂NO₂S, 424.1 (M+H), found 424.1.

Example 162

3-(4-[[3-chloro-5-(4-methoxyphenyl)-1,2-thiazol-4-yl]methoxy]-2,3-dimethylphenyl)propan-1-ol, Cpd 247

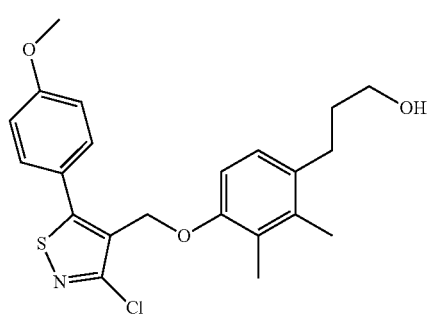 [SMILES: COc1ccc(-c2snc(Cl)c2COc2ccc(CCCO)c(C)c2C)cc1]

The title compound was prepared according to the procedure described in Example 156 following Step 2 by LAH reduction of ethyl 3-(4-((3-chloro-5-(4-methoxyphenyl)isothiazol-4-yl)methoxy)-2,3-dimethylphenyl)propanoate to afford the desired product as an off-white solid. ¹H NMR (300 MHz, CDCl₃) δ:7.50 (d, J=9.0 Hz, 2H), 6.97 (m, 3H), 6.78 (d, J=8.4 Hz, 1H), 5.45 (s, 2H), 3.86 (s, 3H), 3.73 (t, J=6.0 Hz, 2H), 2.71 (t, J=7.8 Hz, 2H), 2.25 (s, 3H), 2.19 (s, 3H), 1.81-1.88 (m, 2H). Mass spectrum (ESI, m/z): Calcd. for C₂₂H₂₄ClNO₃S, 418.1[M+H], found 418.1.

Example 163

3-(4-[[3-chloro-5-(4-methoxyphenyl)-1,2-thiazol-4-yl]methoxy]-2,3-difluorophenyl)propan-1-ol, Cpd 168

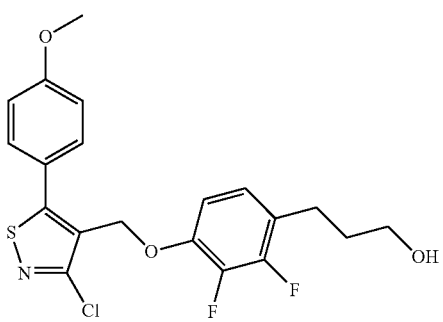 [SMILES: COc1ccc(-c2snc(Cl)c2COc2ccc(CCCO)c(F)c2F)cc1]

The title compound was prepared according to the procedure described in Example 156 following Step 2 by LAH reduction of ethyl 3-(4-((3-chloro-5-(4-methoxyphenyl)isothiazol-4-yl)methoxy)-2,3-difluorophenyl)propanoate to afford the desired product as an off-white solid. $^1$H NMR (300 MHz, CD$_3$OD): δ 7.53 (d, J=8.7 Hz, 2H), 7.08 (d, J=9.0 Hz, 2H), 6.87-7.00 (m, 2H), 5.07 (s, 2H), 3.60 (d, J=6.6 Hz, 2H), 2.18 (d, J=7.2 Hz, 2H), 1.78-1.87 (m, 2H). Mass spectrum (ESI, m/z): Calcd. for C$_{20}$H$_{18}$ClF$_2$NO$_3$S, 426.1 (M+H), found 426.1.

Example 164

3-(4-[[3-chloro-5-(4-methoxyphenyl)-1,2-thiazol-4-yl]methoxy]-2,3-difluorophenyl)propan-1-ol, Cpd 248

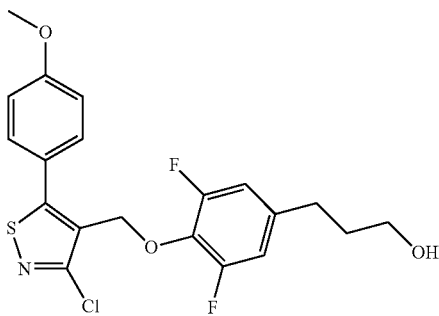 [SMILES: COc1ccc(-c2snc(Cl)c2COc2c(F)cc(CCCO)cc2F)cc1]

The title compound was prepared according to the procedure described in Example 156 following Step 2 by LAH reduction of ethyl 3-(4-((3-chloro-5-(4-methoxyphenyl)isothiazol-4-yl)methoxy)-3,5-difluorophenyl)propanoate to afford the desired product as an off-white solid. $^1$H NMR (300 MHz, CD$_3$OD): δ 7.57 (d, J=9.0 Hz, 2H), 7.07 (d, J=9.0 Hz, 2H), 6.82 (d, J=9.3 Hz, 2H), 5.09 (s, 2H), 3.57 (t, J=6.3 Hz, 2H), 2.66 (t, J=7.5 Hz, 2H), 1.77-1.86 (m, 2H). Mass spectrum (ESI, m/z): Calcd. for: C$_{20}$H$_{18}$ClF$_2$NO$_3$S: 426.1 (M+H), found 426.1.

Example 165

(E)-3-(4-((3-chloro-5-(4-chlorophenyl)isothiazol-4-yl)methoxy)-2,3-difluorophenyl)acrylic Acid, Cpd 185

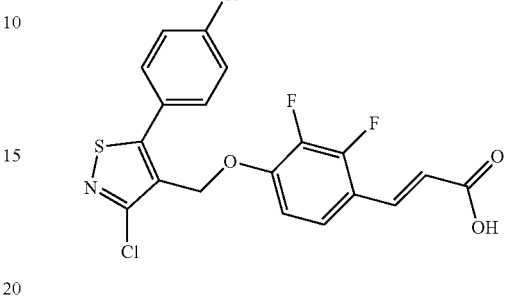

The title compound was prepared according to the procedure described in Example 135 following Step 8 and 9 by coupling of (3-chloro-5-(4-chlorophenyl)isothiazol-4-yl)methanol and (E)-ethyl 3-(2,3-difluoro-4-hydroxyphenyl)acrylate then hydrolysis to afford the desired product as an off-white solid. $^1$H NMR (400 MHz, CDCl$_3$) δ 7.81 (d, J=12.5 Hz, 1H), 7.48 (s, 2H), 7.28 (s, 2H), 6.52 (d, J=11.5 Hz, 1H), 5.04 (s, 2H).

Example 166

3-(3,5-difluoro-4-[[3-methoxy-5-(4-methoxyphenyl)-1,2-thiazol-4-yl]methoxy]phenyl)propanoic Acid, Cpd 182

Step 1: 3-chloro-5-(4-methoxyphenyl)-1,2-thiazole-4-carbonitrile

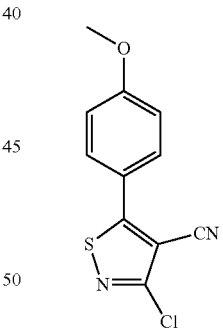

Into a 100-mL round-bottom flask, was placed 2-[(4-methoxyphenyl)methylidene]propanedinitrile (5.1 g, 27.69 mmol, 1.00 equiv), S$_2$Cl$_2$ (18 g), pyridine (200 mg, 2.53 mmol, 0.09 equiv). The resulting solution was stirred overnight at 140° C. in an oil bath. The reaction was then quenched by the addition of 30 mL of water. The solids were filtered out. The resulting solution was extracted with 3×50 mL of ethyl acetate and the organic layers combined and dried over anhydrous sodium sulfate. The solids were filtered out. The resulting mixture was concentrated under vacuum. This resulted in 3.4 g (crude) of 3-chloro-5-(4-methoxyphenyl)-1, 2-thiazole-4-carbonitrile as a yellow solid. Mass spectrum (ESI, m/z): Calcd. for C$_{11}$H$_7$ClN$_2$OS, 251.1 (M+H), found 251.1.

Step 2: 3-chloro-5-(4-methoxyphenyl)-1,2-thiazole-4-carboxamide

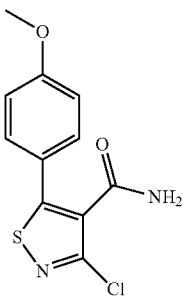 [SMILES: COc1ccc(-c2snc(Cl)c2C(N)=O)cc1]

Into a 100-mL round-bottom flask, was placed a solution of 3-chloro-5-(4-methoxyphenyl)-1,2-thiazole-4-carbonitrile (3.4 g, 13.56 mmol, 1.00 equiv) in ethanol/H$_2$O (20/10 mL), sodium hydroxide (1 g, 25.00 mmol, 1.84 equiv), H$_2$O$_2$ (10 g). The resulting solution was stirred overnight at 25° C. The resulting mixture was concentrated under vacuum. The reaction was then quenched by the addition of 50 mL of water. The resulting solution was extracted with 3×80 mL of ethyl acetate and the organic layers combined and dried over anhydrous sodium sulfate. The solids were filtered out. The resulting mixture was concentrated under vacuum. The residue was applied onto a silica gel column with ethyl acetate/petroleum ether (1:2). This resulted in 680 mg (crude) of 3-chloro-5-(4-methoxyphenyl)-1, 2-thiazole-4-carboxamide as a yellow solid. Mass spectrum (ESI, m/z): Calcd. for C$_{11}$H$_9$ClN$_2$O$_2$S, 269.0 (M+H), found 269.0.

Step 3: 3-methoxy-5-(4-methoxyphenyl)-1,2-thiazole-4-carboxylic Acid

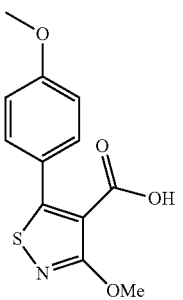 [SMILES: COc1ccc(-c2snc(OC)c2C(=O)O)cc1]

Into a 50-mL round-bottom flask, was placed 3-chloro-5-(4-methoxyphenyl)-1,2-thiazole-4-carboxamide (120 mg, 0.45 mmol, 1.00 equiv), 10N sodium hydroxide (3.0 mL), methanol (3.0 mL). The resulting solution was stirred overnight at 70° C. in an oil bath. The reaction progress was monitored by LCMS. The resulting solution was allowed to react, with stirring, for an additional 5.0 h while the temperature was maintained at 100° C. in an oil bath. The reaction progress was monitored by LCMS. The resulting mixture was concentrated under vacuum. The reaction mixture was cooled to 0° C. with a water/ice bath. The pH value of the solution was adjusted to 3 with hydrogen chloride (6N). The solide was filtered out and dried in an flask under reduced pressure. This resulted in 0.16 g (crude) of 3-methoxy-5-(4-methoxyphenyl)-1, 2-thiazole-4-carboxylic acid as a light brown solid. The crude could be used for the next step directly.

Step 4: [3-methoxy-5-(4-methoxyphenyl)-1,2-thiazol-4-yl]methanol

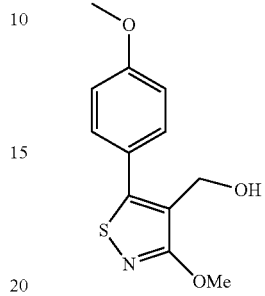

Into a 25-mL round-bottom flask (1 atm) purged and maintained with an inert atmosphere of nitrogen, was placed 3-methoxy-5-(4-methoxyphenyl)-1,2-thiazole-4-carboxylic acid (160 mg, 0.60 mmol, 1.00 equiv), tetrahydrofuran (4.0 mL). This was followed by the addition of BH$_3$.THF(1 M) (1.83 mL) dropwise with stirring at 0° C. The resulting solution was stirred overnight at 45° C. in an oil bath. The reaction progress was monitored by TLC (ethyl acetate/petroleum ether=1:2). The reaction was then quenched by the addition of 5.0 mL of water. The resulting solution was extracted with 3×10.0 mL of ethyl acetate and the organic layers combined. The resulting mixture was washed with 1×20 mL of sodium chloride. The mixture was dried over anhydrous sodium sulfate and concentrated under vacuum. The residue was applied onto a TLC-Plate with ethyl acetate/petroleum ether (1:2). This resulted in 63 mg (42%) of [3-methoxy-5-(4-methoxyphenyl)-1,2-thiazol-4-yl]methanol as a white solid. Mass spectrum (ESI, m/z): Calcd. for C$_{12}$H$_{13}$NO$_3$S, 252.1 (M+H), found 252.1.

Step 5: 3-(3,5-difluoro-4-[[3-methoxy-5-(4-methoxyphenyl)-1,2-thiazol-4-yl]methoxy]phenyl)propanoate

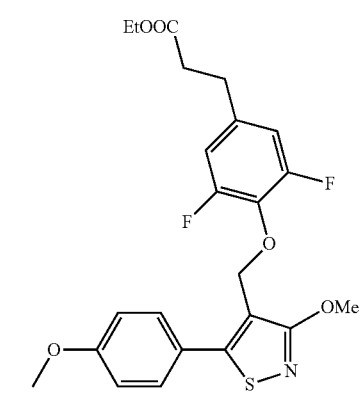 [SMILES: CCOC(=O)CCc1cc(F)c(OCc2c(OC)nsc2-c2ccc(OC)cc2)c(F)c1]

Into a 50-mL round-bottom flask purged and maintained with an inert atmosphere of nitrogen, was placed

[3-methoxy-5-(4-methoxyphenyl)-1,2-thiazol-4-yl]methanol (38.5 mg, 0.15 mmol, 1.00 equiv). This was followed by the addition of ethyl 3-(3,5-difluoro-4-hydroxyphenyl)propanoate (53 mg, 0.23 mmol, 1.50 equiv), in portions. To this was added ADDP (80.9 mg, 0.32 mmol, 2.10 equiv), in portions. To the mixture was added n-Bu₃P (46.5 mg, 1.50 equiv), in portions. To the mixture was added toluene (5 mL), in portions. The resulting solution was stirred overnight at 60° C. in an oil bath. The resulting mixture was concentrated under vacuum. The solids were filtered out. The residue was applied onto TLC with ethyl acetate/petroleum ether (1:3). This resulted in 35 mg (49%) of ethyl 3-(3, 5-difluoro-4-[[3-methoxy-5-(4-methoxyphenyl)-1,2-thiazol-4-yl]methoxy]phenyl)propanoate as yellow oil. Mass spectrum (ESI, m/z): Calcd. for $C_{23}H_{23}F_2NO_5S$, 464.1 (M+H), found 464.1.

Step 6: 3-(3,5-difluoro-4-[[3-methoxy-5-(4-methoxyphenyl)-1,2-thiazol-4-yl]methoxy]phenyl) propanoic Acid

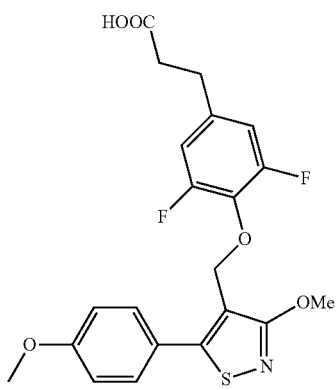 [SMILES: COc1ccc(-c2snc(OC)c2COc2c(F)cc(CCC(=O)O)cc2F)cc1]

Into a 25-mL round-bottom flask, was placed ethyl 3-(3, 5-difluoro-4-[[3-methoxy-5-(4-methoxyphenyl)-1,2-thiazol-4-yl]methoxy]phenyl)propanoate (50 mg, 0.11 mmol, 1.00 equiv), tetrahydrofuran (3 mL), water (1 mL), LiOH (50 mg, 2.09 mmol, 19.30 equiv). The resulting solution was stirred overnight at 25° C. in an oil bath. The resulting mixture was concentrated under vacuum. The pH value of the solution was adjusted to 5 with hydrogen chloride (2 mol/L). The solids were collected by filtration, washed with n-hexane, dried. This resulted in 8.2 mg (17%) of 3-(3,5-difluoro-4-[[3-methoxy-5-(4-methoxyphenyl)-1,2-thiazol-4-yl]methoxy]phenyl) propanoic acid as a white solid. $^1$H NMR (300 MHz, CD₃OD) δ7.53 (d, J=11.6 Hz, 2H), 7.05 (d, J=11.6 Hz, 2H), 6.81 (d, J=11.6 Hz, 2H), 5.16 (s, 2H), 4.06 (s, 3H), 3.92 (s, 3H), 2.88 (m, 2H), 2.71 (m, 2H). Mass spectrum (ESI, m/z): Calcd. for $C_{21}H_{19}F_2NO_5S$, 436.1 (M+H), found 436.0.

Example 167

3-(3, 5-difluoro-4-[[5-(2-fluoro-4-methylphenyl)-3-methyl-1,2-thiazol-4-yl]methoxy]phenyl) propanoic Acid, Cpd 84

Step 1: 5-(2-fluoro-4-methylphenyl)-3-methyl-1, 2-thiazole-4-carbonitrile

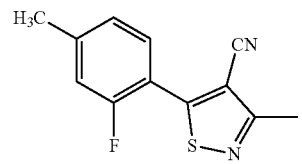

Into a 100-mL round-bottom flask purged and maintained with an inert atmosphere of nitrogen, was placed 3-chloro-5-(2-fluoro-4-methylphenyl)-1,2-thiazole-4-carbonitrile (500 mg, 1.98 mmol, 1.00 equiv), 1,4-dioxane (20 mL), Al(CH₃)₃ (6 mL), Pd(PPh₃)₄ (343 mg, 0.30 mmol, 0.15 equiv). The resulting solution was stirred for 3 h at 110° C. The reaction was then quenched by the addition of 2 mL of water. The resulting mixture was concentrated under vacuum. The residue was applied onto a silica gel column with ethyl acetate/petroleum ether (1:5). This resulted in 200 mg (44%) of 5-(2-fluoro-4-methylphenyl)-3-methyl-1,2-thiazole-4-carbonitrile as a yellow solid.

Step 2: 5-(2-fluoro-4-methylphenyl)-3-methyl-1, 2-thiazole-4-carboxylic Acid

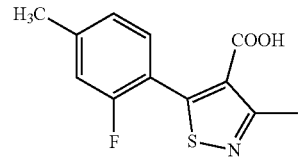

Into a 25-mL round-bottom flask, was placed 5-(2-fluoro-4-methylphenyl)-3-methyl-1, 2-thiazole-4-carbonitrile (200 mg, 0.86 mmol, 1.00 equiv). This was followed by the addition of sulfuric acid (conc.) (10 mL). The mixture was stirred for 1 h at 120° C. To this was added NaNO₂ (aq) (201 mg) at 0-5° C. The resulting solution was stirred for 30 min at 50° C. The resulting solution was diluted with 50 mL of EA. The organic phase was washed with 1×20 mL of 2N HCl and 1×20 mL brine. The mixture was dried over anhydrous sodium sulfate and concentrated. This resulted in 180 mg (crude) of 5-(2-fluoro-4-methylphenyl)-3-methyl-1, 2-thiazole-4-carboxylic acid as a yellow oil.

Step 3: [5-(2-fluoro-4-methylphenyl)-3-methyl-1, 2-thiazol-4-yl]methanol

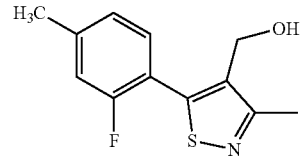

Into a 25-mL round-bottom flask, was placed 5-(2-fluoro-4-methylphenyl)-3-methyl-1,2-thiazole-4-carboxylic acid (180 mg, 0.72 mmol, 1.00 equiv), tetrahydrofuran (10 mL). This was followed by the addition of BH₃ (2.1 mL) at 0-5° C. The resulting solution was stirred overnight at room temperature. The resulting mixture was concentrated under vacuum. The residue was applied onto a silica gel column with ethyl acetate/petroleum ether (1:3). This resulted in 100 mg (59%) of [5-(2-fluoro-4-methylphenyl)-3-methyl-1,2-thiazol-4-yl]methanol as a white solid.

Step 4: Ethyl 3-(3,5-difluoro-4-[[5-(2-fluoro-4-methylphenyl)-3-methyl-1,2-thiazol-4-yl]methoxy] phenyl)propanoate

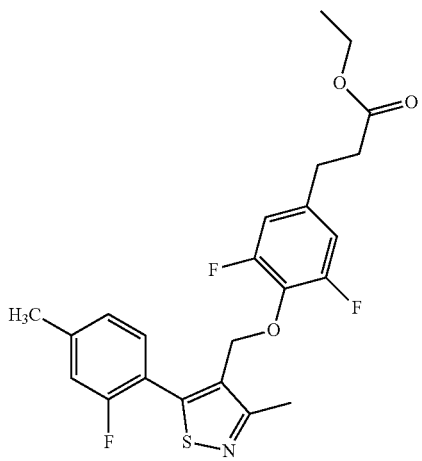 [SMILES: CCOC(=O)CCc1cc(F)c(OCc2c(C)nsc2-c2ccc(C)cc2F)c(F)c1]

Into a 25-mL round-bottom flask purged and maintained with an inert atmosphere of nitrogen, was placed [5-(2-fluoro-4-methylphenyl)-3-methyl-1,2-thiazol-4-yl]methanol (100 mg, 0.42 mmol, 1.00 equiv), ethyl 3-(3,5-difluoro-4-hydroxyphenyl)propanoate (146 mg, 0.63 mmol, 1.50 equiv), ADDP (221.6 mg, 0.89 mmol, 2.10 equiv), Bu$_3$P (128 mg, 0.63 mmol, 1.5 equiv), toluene (10 mL). The resulting solution was stirred overnight at 60° C. The resulting mixture was concentrated under vacuum. The residue was applied onto a silica gel column with ethyl acetate/petroleum ether (1:5). This resulted in 150 mg (79%) of ethyl 3-(3,5-difluoro-4-[[5-(2-fluoro-4-methylphenyl)-3-methyl-1,2-thiazol-4-yl]methoxy] phenyl) propanoate as colorless oil.

Step 5: 3-(3, 5-difluoro-4-[[5-(2-fluoro-4-methylphenyl)-3-methyl-1,2-thiazol-4-yl]methoxy]phenyl) propanoic Acid

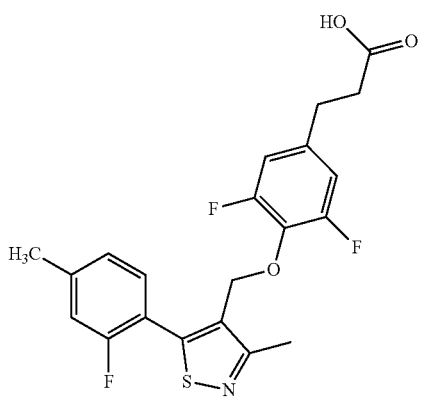 [SMILES: Cc1ccc(-c2snc(C)c2COc2c(F)cc(CCC(=O)O)cc2F)c(F)c1]

The title compound was prepared according to the procedure described in Example 165 following Step 6 by hydrolysis of ethyl 3-(3,5-difluoro-4-[[5-(2-fluoro-4-methylphenyl)-3-methyl-1,2-thiazol-4-yl]methoxy] phenyl)propanoate to afford the desired product as an off-white solid. $^1$H NMR (300 MHz, CD$_3$OD) δ: 7.06-7.17 (m, 3H), 7.79 (d, J=8.1 Hz, 2H), 5.19 (s, 2H), 2.84 (t, J=7.5 Hz, 2H), 2.50-2.67 (m, 5H), 2.42 (s, 3H). Mass spectrum (ESI, m/z): Calcd. for C$_{21}$H$_{18}$F$_3$NO$_3$S, 420.1 (M−H), found 420.1.

Example 168

3-(4-[[3-ethyl-5-(2-fluoro-4-methylphenyl)-1,2-thiazol-4-yl]methoxy]-3,5-difluorophenyl)propanoic Acid, Cpd 150

Step 1: 3-ethyl-5-(2-fluoro-4-methylphenyl)-1,2-thiazole-4-carbonitrile

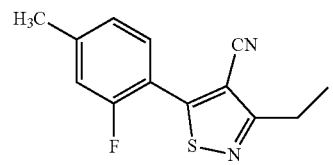 [SMILES: CCc1nsc(-c2ccc(C)cc2F)c1C#N]

Into a 100-mL 3-necked round-bottom flask purged and maintained with an inert atmosphere of nitrogen, was placed 3-chloro-5-(2-fluoro-4-methylphenyl)-1,2-thiazole-4-carbonitrile (500 mg, 1.98 mmol, 1.00 equiv), 1,4-dioxane (20 mL), Pd(PPh$_3$)$_4$ (343 mg, 0.30 mmol, 0.15 equiv), Al(Et)$_3$ (6.0 mL). The resulting solution was stirred for 3 h at 110° C. The reaction was then quenched by the addition of 3 mL of water. The resulting solution was extracted with 3×10 mL of ethyl acetate and the organic layers combined and concentrated under vacuum. The residue was applied onto a silica gel column with ethyl acetate/petroleum ether (1:3). This resulted in 150 mg (31%) of 3-ethyl-5-(2-fluoro-4-methylphenyl)-1,2-thiazole-4-carbonitrile as a yellow solid.

Step 2: 3-ethyl-5-(2-fluoro-4-methylphenyl)-1,2-thiazole-4-carboxylic Acid

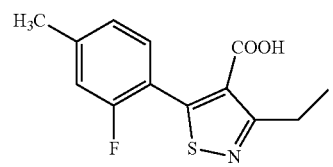 [SMILES: CCc1nsc(-c2ccc(C)cc2F)c1C(=O)O]

Into a 25-mL round-bottom flask, was placed 3-ethyl-5-(2-fluoro-4-methylphenyl)-1,2-thiazole-4-carbonitrile (200 mg, 0.81 mmol, 1.00 equiv). This was followed by the addition of sulfuric acid (conc.) (10 mL). The mixtures were stirred for 1 h at 120° C. To this was added a solution of NaNO$_2$(aq) (168 mg, 2.43 mmol, 3 equiv) in water (0.5 mL) at 0-5° C. The resulting solution was stirred for 30 min at 50° C. The resulting solution was diluted with 50 mL of EA. The organic phase was washed with 1×20 mL of 2N HCl and 1×20 mL brine. The mixture was dried over anhydrous sodium sulfate. The solids were filtered out. The resulting mixture was concentrated under vacuum. This resulted in 150 mg (crude) of 3-ethyl-5-(2-fluoro-4-methylphenyl)-1,2-thiazole-4-carboxylic acid as a yellow solid.

Step 3: [3-ethyl-5-(2-fluoro-4-methylphenyl)-1,2-thiazol-4-yl]methanol

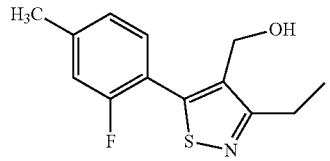 [SMILES: CCc1nsc(-c2ccc(C)cc2F)c1CO]

Into a 25-mL round-bottom flask purged and maintained with an inert atmosphere of nitrogen, was placed 3-ethyl-5-(2-fluoro-4-methylphenyl)-1,2-thiazole-4-carboxylic acid (150 mg, 0.57 mmol, 1.00 equiv), tetrahydrofuran (10 mL). This was followed by the addition of $BH_3$ (1.7 mL) at 0-5° C. The resulting solution was stirred overnight at 20° C. The resulting mixture was concentrated under vacuum. The residue was applied onto a silica gel column with ethyl acetate/petroleum ether (1:2). This resulted in 50 mg (35%) of [3-ethyl-5-(2-fluoro-4-methylphenyl)-1,2-thiazol-4-yl]methanol as colorless oil.

Step 4: Ethyl 3-(4-[[3-ethyl-5-(2-fluoro-4-methylphenyl)-1,2-thiazol-4-yl]methoxy]-3,5-difluorophenyl) propanoate

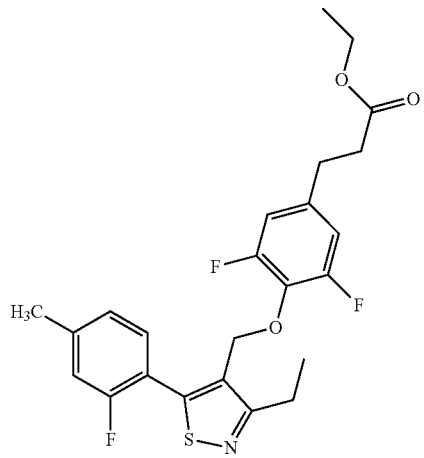 [SMILES: CCOC(=O)CCc1cc(F)c(OCc2c(CC)nsc2-c2ccc(C)cc2F)c(F)c1]

Into a 25-mL round-bottom flask purged and maintained with an inert atmosphere of nitrogen, was placed [3-ethyl-5-(2-fluoro-4-methylphenyl)-1,2-thiazol-4-yl]methanol (50 mg, 0.20 mmol, 1.00 equiv), ethyl 3-(3,5-difluoro-4-hydroxyphenyl)propanoate (69 mg, 0.30 mmol, 1.51 equiv), ADDP (104 mg, 0.42 mmol, 2.09 equiv), $Bu_3P$ (60 mg), toluene (10 mL). The resulting solution was stirred overnight at 60° C. The resulting mixture was concentrated under vacuum. The residue was applied onto a silica gel column with ethyl acetate/petroleum ether (1:5). This resulted in 40 mg (43%) of ethyl 3-(4-[[3-ethyl-5-(2-fluoro-4-methylphenyl)-1,2-thiazol-4-yl]methoxy]-3,5-difluorophenyl)propanoate as colorless oil.

Step 5: 3-(4-[[3-ethyl-5-(2-fluoro-4-methylphenyl)-1,2-thiazol-4-yl]methoxy]-3,5-difluorophenyl)propanoic Acid

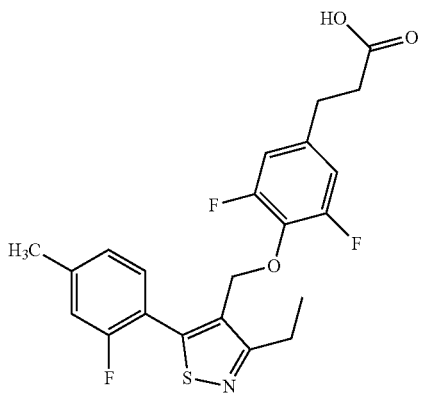 [SMILES: CCc1nsc(-c2ccc(C)cc2F)c1COc1c(F)cc(CCC(=O)O)cc1F]

The title compound was prepared according to the procedure described in Example 165 following Step 6 by hydrolysis of ethyl 3-(3,5-difluoro-4-[[5-(2-fluoro-4-methylphenyl)-3-ethyl-1,2-thiazol-4-yl]methoxy] phenyl)propanoate to afford the desired product as an off-white solid.
$^1$H NMR (300 MHz, $CD_3OD$) δ: 7.18 (t, J=7.6 Hz, 1H), 7.08 (d, J=9.9 Hz, 2H), 6.77 (d, J=9.6 Hz, 2H), 5.30 (s, 2H), 3.04 (q, J=7.5 Hz, $J_2$=4.5 Hz, 2H), 2.86 (m, 2H), 2.51-2.60 (m, 2H), 2.43 (s, 3H), 1.41 (t, J=7.5 Hz, 3H). Mass spectrum (ESI, m/z): Calcd. for $C_{22}H_{20}F_3NO_3S$, 434.1 (M–H), found 434.1.

Example 169

3-(3,5-difluoro-4-[[3-(2-fluoro-4-methylphenyl)-5-(propan-2-yl)-1,2-thiazol-4-yl]methoxy]phenyl) propanoic Acid, Cpd 191

Step 1: 5-(2-fluoro-4-methylphenyl)-3-(prop-1-en-2-yl)-1, 2-thiazole-4-carbonitrile

Into a 25-mL round-bottom flask purged and maintained with an inert atmosphere of nitrogen, was placed 4-cyano-5-(2-fluoro-4-methylphenyl)-1,2-thiazol-3-yl trifluoro methanesulfonate (500 mg, 1.36 mmol, 1.00 equiv), N,N-dimethylformamide (10 mL), CuI (26 mg, 0.14 mmol, 0.10 equiv), CsF (415 mg), Pd(PPh$_3$)$_4$ (79 mg, 0.07 mmol, 0.5 equiv), tributyl(prop-1-en-2-yl)stannane (678 mg, 2.05 mmol, 1.50 equiv). The resulting solution was stirred overnight at 45° C. The resulting solution was diluted with 40 mL of EA. The organic phase was washed with 3×10 mL of brine. The mixture was dried over anhydrous sodium sulfate. The resulting mixture was concentrated under vacuum. This resulted in 200 mg (crude) of 5-(2-fluoro-4-methylphenyl)-3-(prop-1-en-2-yl)-1,2-thiazole-4-carbonitrile as a white solid.

Step 2: 5-(2-fluoro-4-methylphenyl)-3-(propan-2-yl)-1,2-thiazole-4-carbonitrile

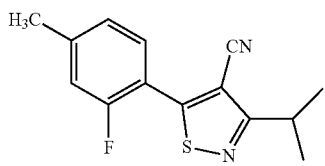 [SMILES: Cc1ccc(-c2snc(C(C)C)c2C#N)c(F)c1]

Into a 25-mL 3-necked round-bottom flask, was placed 5-(2-fluoro-4-methylphenyl)-3-(prop-1-en-2-yl)-1, 2-thiazole-4-carbonitrile (140 mg, 0.54 mmol, 1.00 equiv), ethyl acetate (10 mL), Pd(no water)/C (140 mg). To the above hydrogen gas was introduced. The resulting solution was stirred for 2 h at 20° C. The solids were filtered out. The resulting mixture was concentrated under vacuum. This resulted in 130 mg (crude) of 5-(2-fluoro-4-methylphenyl)-3-(propan-2-yl)-1,2-thiazole-4-carbonitrile as a solid.

Step 3: 3-(3,5-difluoro-4-[[3-(2-fluoro-4-methylphenyl)-5-(propan-2-yl)-1,2-thiazol-4-yl]methoxy]phenyl) propanoic Acid

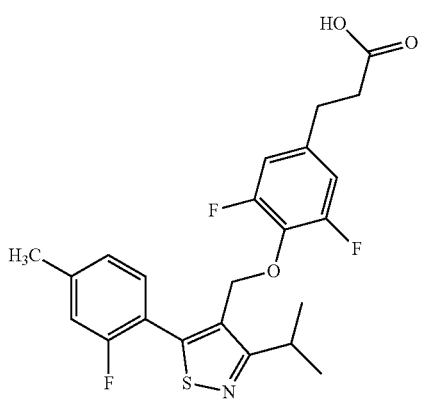 [SMILES: Cc1ccc(-c2snc(C(C)C)c2COc2c(F)cc(CCC(=O)O)cc2F)c(F)c1]

The title compound was prepared according to the procedure described in Example 166 following Step 1-6 then hydrolysis of ethyl 3-(3,5-difluoro-4-[[5-(2-fluoro-4-methylphenyl)-3-iso-propyl-1,2-thiazol-4-yl]methoxy] phenyl) propanoate to afford the desired product as an off-white solid. 1H NMR (300 MHz, CD$_3$OD) δ: 7.21 (t, J=7.5 Hz, 1H), 7.08 (d, J=9.9 Hz, 2H), 6.77 (d, J=9.3 Hz, 2H), 5.30 (s, 2H), 3.48-3.55 (m, 1H), 2.85 (t, J=7.2 Hz, 2H), 2.59 (t, J=7.2 Hz, 2H), 2.43 (s, 3H), 1.39 (d, J=6.9 Hz, 6H). Mass spectrum (ESI, m/z): Calcd. for C$_{23}$H$_{22}$F$_3$NO$_3$S, 448.1 (M−H), found 448.1.

Example 170

3-(3,5-difluoro-4-[[5-(2-fluoro-4-methylphenyl)-3-phenyl-1,2-thiazol-4-yl]methoxy]phenyl)propanoic Acid, Cpd 211

Step 1: 5-(2-fluoro-4-methylphenyl)-3-hydroxy-1,2-thiazole-4-carbonitrile

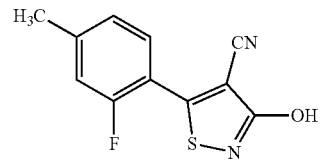 [SMILES: Cc1ccc(-c2snc(O)c2C#N)c(F)c1]

Into a 100-mL round-bottom flask, was placed 5-(2-fluoro-4-methylphenyl)-3-methoxy-1,2-thiazole-4-carbonitrile (800 mg, 3.22 mmol, 1.00 equiv), HBr(CH$_3$COOH) (20 mL). The resulting solution was stirred for 1 h at 80° C. The resulting mixture was concentrated under vacuum. The residue was applied onto a silica gel column with ethyl acetate/petroleum ether (1:5). This resulted in 700 mg (93%) of 5-(2-fluoro-4-methylphenyl)-3-hydroxy-1,2-thiazole-4-carbonitrile as a yellow solid.

Step 2: 4-cyano-5-(2-fluoro-4-methylphenyl)-1,2-thiazol-3-yl trifluoromethanesulfonate

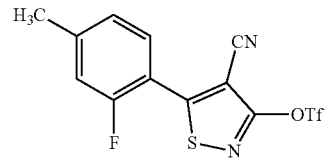 [SMILES: Cc1ccc(-c2snc(OS(=O)(=O)C(F)(F)F)c2C#N)c(F)c1]

Into a 100-mL round-bottom flask, was placed 5-(2-fluoro-4-methylphenyl)-3-hydroxy-1,2-thiazole-4-carbonitrile (700 mg, 2.99 mmol, 1.00 equiv), dichloromethane (20 mL), triethylamine (302 mg, 2.98 mmol, 1.00 equiv). This was followed by the addition of Tf$_2$O (1.69 g, 5.99 mmol, 2.00 equiv) at 0-5° C. The resulting solution was stirred overnight at 20° C. The resulting mixture was concentrated under vacuum. The residue was applied onto a silica gel column with ethyl acetate/petroleum ether (1:5). This resulted in 800 mg (73%) of 4-cyano-5-(2-fluoro-4-methylphenyl)-1,2-thiazol-3-yl trifluoromethanesulfonate as colorless oil.

Step 3: 5-(2-fluoro-4-methylphenyl)-3-phenyl-1,2-thiazole-4-carbonitrile

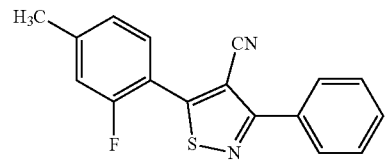 [SMILES: Cc1ccc(-c2snc(-c3ccccc3)c2C#N)c(F)c1]

Into a 25-mL round-bottom flask purged and maintained with an inert atmosphere of nitrogen, was placed 4-cyano-5-(2-fluoro-4-methylphenyl)-1,2-thiazol-3-yl trifluoro methanesulfonate (200 mg, 0.55 mmol, 1.00 equiv), phenylboronic acid (132 mg, 1.08 mmol, 1.98 equiv), sodium carbonate (116 mg, 1.09 mmol, 2.00 equiv), Pd(PPh₃)₄ (96 mg, 0.08 mmol, 0.15 equiv), N,N-dimethylformamide (1 mL), toluene (10 mL). The resulting solution was stirred overnight at 60° C. The resulting solution was diluted with 30 mL of EA. The resulting mixture was washed with 3×10 mL of brine. The mixture was dried over anhydrous sodium sulfate. The solids were filtered out. The resulting mixture was concentrated under vacuum. The residue was applied onto a silica gel column with ethyl acetate/petroleum ether (1:5). This resulted in 150 mg (93%) of 5-(2-fluoro-4-methylphenyl)-3-phenyl-1,2-thiazole-4-carbonitrile as a white solid.

Step 4: 3-(3, 5-difluoro-4-[[5-(2-fluoro-4-methylphenyl)-3-phenyl-1,2-thiazol-4-yl]methoxy]phenyl) propanoic Acid

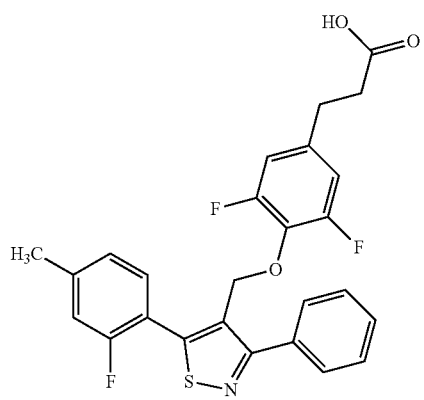 [SMILES: Cc1ccc(-c2snc(-c3ccccc3)c2COc2c(F)cc(CCC(=O)O)cc2F)c(F)c1]

The title compound was prepared according to the procedure described in Example 166 following Step 1-6 then hydrolysis of ethyl 3-(3,5-difluoro-4-[[5-(2-fluoro-4-methylphenyl)-3-phenyl-1,2-thiazol-4-yl]methoxy] phenyl)propanoate to afford the desired product as an off-white solid. ¹H NMR (300 MHz, DMSO) δ: 7.82-7.84 (m, 2H), 7.51-7.53 (m, 3H), 7.33 (t, J=7.8 Hz, 1H), 7.22 (d, J=11.4 Hz, 1H), 7.13 (d, J=8.4 Hz, 1H), 6.86 (d, J=9.3 Hz, 2H), 4.94 (s, 2H), 3.98 (s, 3H), 2.83 (t, J=7.5 Hz, 2H), 2.58 (t, J=7.5 Hz, 2H), 2.42 (s, 3H). Mass spectrum (ESI, m/z): Calcd. for C₂₆H₂₀F₃NO₃S, 482.1 (M–H), found 482.1.

Example 171

3-(3, 5-difluoro-4-[[5-(2-fluoro-4-methylphenyl)-3-methoxy-1,2-thiazol-4-yl]methoxy]phenyl) propanoic Acid, Cpd 123

Step 1: 5-(2-fluoro-4-methylphenyl)-3-methoxy-1,2-thiazole-4-carbonitrile

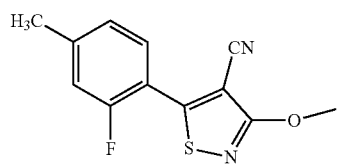

Into a 250-mL round-bottom flask, was placed 3-chloro-5-(2-fluoro-4-methylphenyl)-1,2-thiazole-4-carbonitrile (2.0 g, 7.91 mmol, 1.00 equiv), methanol (100 mL), NaOCH₃ (2.1 g, 38.87 mmol, 4.91 equiv). The resulting solution was stirred for 3 h at 75° C. The resulting mixture was concentrated under vacuum. The residue was applied onto a silica gel column with ethyl acetate/petroleum ether (1:5). This resulted in 1.5 g (76%) of 5-(2-fluoro-4-methylphenyl)-3-methoxy-1,2-thiazole-4-carbonitrile as a white solid.

Step 2: 3-(3, 5-difluoro-4-[[5-(2-fluoro-4-methylphenyl)-3-methoxy-1,2-thiazol-4-yl]methoxy]phenyl) propanoic Acid

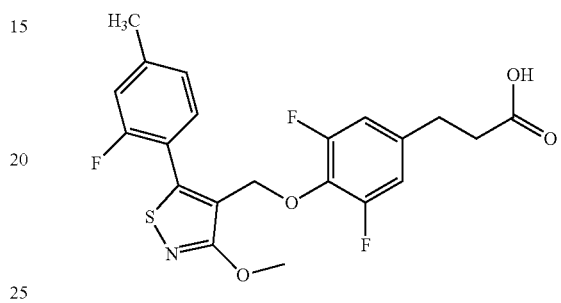

The title compound was prepared according to the procedure described in Example 166 following Step 1-6 then hydrolysis of ethyl 3-(3,5-difluoro-4-[[5-(2-fluoro-4-methylphenyl)-3-methoxy-1,2-thiazol-4-yl]methoxy] phenyl) propanoate to afford the desired product as an off-white solid. ¹H NMR (300 MHz, CD₃OD) δ: 7.31 (t, J=7.8 Hz, 1H), 7.06-7.10 (m, 2H), 6.74 (d, J=9.0 Hz, 2H), 4.94 (s, 2H), 3.98 (s, 3H), 2.83 (t, J=7.5 Hz, 2H), 2.58 (t, J=7.5 Hz, 2H), 2.42 (s, 3H). Mass spectrum (ESI, m/z): Calcd. for C₂₁H₁₈F₃NO₄S, 436.1 (M–H), found 436.1.

Example 172

3-(4-[[5-(2,4-dimethylphenyl)-3-(trifluoromethyl)-1,2-thiazol-4-yl]methoxy]-2,3-dimethylphenyl) propanoic Acid, Cpd 184

Step 1: 5-bromo-3-(trifluoromethyl)-1,2-thiazole-4-carbonitrile

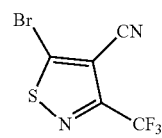

Into a 100-mL round-bottom flask, was placed 3-methyl-1-nitrobutane (14.4 g, 122.92 mmol, 6.00 equiv), isopentyl nitrite (30 mL), Br₂ (32.4 g, 202.74 mmol, 10.00 equiv). This was followed by the addition of 5-amino-3-(trifluoromethyl)-1,2-thiazole-4-carbonitrile (4.0 g, 20.71 mmol, 1.00 equiv), in portions at 0° C. The resulting solution was stirred for 30 min at 0° C. in a water/ice bath. The reaction progress was monitored by TLC (ethyl acetate/petroleum ether=1:4). The resulting solution was diluted with 30 mL of DCM. The resulting mixture was washed with 2×50 mL of Na₂SO₃/H₂O. The resulting mixture was concentrated under vacuum. The residue was applied onto a silica gel column with ethyl acetate/petroleum ether (1:10). This resulted in 4.5 g (85%) of 5-bromo-3-(trifluoromethyl)-1,2-thiazole-4-carbonitrile as yellow crude oil.

Step 2: 5-bromo-3-(trifluoromethyl)-1,2-thiazole-4-carboxylic Acid

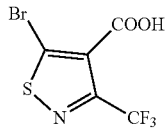

Into a 100-mL round-bottom flask, was placed 5-bromo-3-(trifluoromethyl)-1,2-thiazole-4-carbonitrile (4.2 g, 16.34 mmol, 1.00 equiv), con.$H_2SO_4$ (10 mL). This was followed by the addition of a solution of $NaNO_2$ (1.69 g, 24.49 mmol, 1.50 equiv) in water (5 mL) dropwise with stirring at 0° C. To this was added water (25 mL) dropwise with stirring at 0° C. The resulting solution was stirred for 2 days at 20° C. The resulting solution was allowed to react, with stirring, for an additional 5 h while the temperature was maintained at 50° C. in an oil bath. The reaction progress was monitored by LCMS. The resulting solution was extracted with 3×50 mL of ethyl acetate and the organic layers combined and dried over anhydrous sodium sulfate. The solids were filtered out. The resulting mixture was concentrated under vacuum. This resulted in 4.5 g of 5-bromo-3-(trifluoromethyl)-1,2-thiazole-4-carboxylic acid as yellow crude oil. Mass spectrum (ESI, m/z): Calcd. for $C_5HBrF_3NO_2S$, 273.9 (M−H), found 273.9.

Step 3: [5-bromo-3-(trifluoromethyl)-1, 2-thiazol-4-yl]methanol

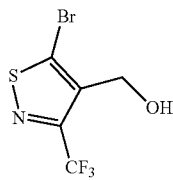

Into a 50-mL round-bottom flask purged and maintained with an inert atmosphere of nitrogen, was placed 5-bromo-3-(trifluoromethyl)-1,2-thiazole-4-carboxylic acid (800 mg, 2.90 mmol, 1.00 equiv), tetrahydrofuran (3 mL). This was followed by the addition of $BH_3$ (14.5 mL, 5.00 equiv) dropwise with stirring at 0° C. The resulting solution was stirred overnight at 25° C. The reaction progress was monitored by TLC (ethyl acetate/petroleum ether=1:5). The reaction was then quenched by the addition of 20 mL of methanol. The reaction mixture was heated to reflux for 1 h. The residue was applied onto a silica gel column with ethyl acetate/petroleum ether (1:5). This resulted in 200 mg (25%) of [5-bromo-3-(trifluoromethyl)-1,2-thiazol-4-yl]methanol as yellow oil.

Step 4: [5-(2,4-dimethylphenyl)-3-(trifluoromethyl)-1,2-thiazol-4-yl]methanol

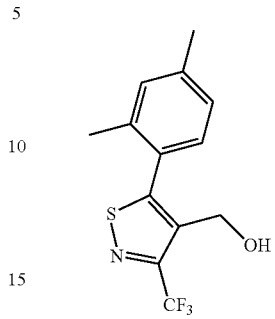

Into a 50-mL round-bottom flask purged and maintained with an inert atmosphere of nitrogen, was placed [5-bromo-3-(trifluoromethyl)-1,2-thiazol-4-yl]methanol (100 mg, 0.38 mmol, 1.00 equiv), dioxane (3 mL), (2,4-dimethylphenyl)boronic acid (113 mg, 0.75 mmol, 1.97 equiv), $Pd(PPh_3)_4$ (44 mg, 0.04 mmol, 0.10 equiv), $K_3PO_4$ (402 mg, 1.89 mmol, 4.96 equiv). The resulting solution was stirred for 3 h at 90° C. in an oil bath. The solvent was removed and the residue was applied onto a TLC plate with ethyl acetate/petroleum ether (1:3). This resulted in 100 mg (crude) of [5-(2,4-dimethylphenyl)-3-(trifluoromethyl)-1,2-thiazol-4-yl]methanol as yellow oil.

Step 5: Ethyl 3-(4-[[5-(2,4-dimethylphenyl)-3-(trifluoromethyl)-1,2-thiazol-4-yl]methoxy]-2,3-dimethylphenyl)propanoate

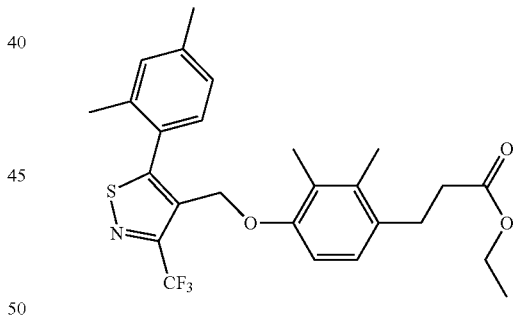

Into a 50-mL round-bottom flask purged and maintained with an inert atmosphere of nitrogen, was placed [5-(2,4-dimethylphenyl)-3-(trifluoromethyl)-1,2-thiazol-4-yl]methanol (100 mg, 0.35 mmol, 1.00 equiv), tol (3 mL), ethyl 3-(4-hydroxy-2,3-dimethylphenyl)propanoate (154 mg, 0.69 mmol, 1.99 equiv), ADDP (174 mg, 0.70 mmol, 2.00 equiv), n-$Bu_3P$ (140 mg, 0.69 mmol, 1.99 equiv). The resulting solution was stirred overnight at 60° C. The resulting mixture was concentrated under vacuum. The residue was applied onto a TLC plate with ethyl acetate/petroleum ether (1/5). This resulted in 90 mg (crude) of ethyl 3-(4-[[5-(2,4-dimethylphenyl)-3-(trifluoromethyl)-1,2-thiazol-4-yl]methoxy]-2,3-dimethylphenyl) propanoate as colorless oil.

Step 6: 3-(4-[[5-(2,4-dimethylphenyl)-3-(trifluoromethyl)-1,2-thiazol-4-yl]methoxy]-2,3-dimethylphenyl) propanoic Acid

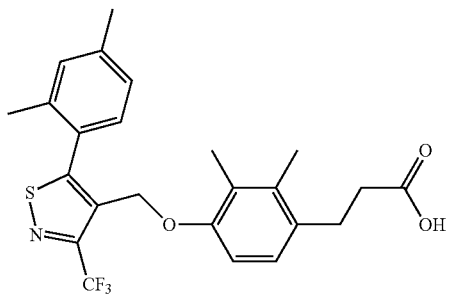 [SMILES: Cc1ccc(-c2snc(C(F)(F)F)c2COc2ccc(CCC(=O)O)c(C)c2C)c(C)c1]

The title compound was prepared according to the procedure described in Example 1 following Step 6 by hydrolysis of ethyl 3-(4-[[5-(2,4-dimethylphenyl)-3-(trifluoromethyl)-1,2-thiazol-4-yl]methoxy]-2,3-dimethylphenyl)propanoate to afford the desired product as an off-white solid. $^1$H NMR (300 MHz, CD$_3$OD) δ: 7.19 (s, 1H), 7.09 (s, 2H), 6.86 (d, J=8.4 Hz, 1H), 6.49 (d, J=8.4 Hz, 1H), 4.85 (s, 2H), 2.87 (t, J=7.2 Hz, 2H), 2.47 (t, J=7.2 Hz, 2H), 2.37 (s, 3H), 2.18 (s, 3H), 2.15 (s, 3H), 1.98 (s, 3H). Mass spectrum (ESI, m/z): Calcd. for C$_{24}$H$_{24}$F$_3$NO$_3$S, 462.1 (M–H), found 462.1.

Example 173

3-(4-[[5-(4-chloro-3-fluorophenyl)-3-(trifluoromethyl)-1,2-thiazol-4-yl]methoxy]-2,3-dimethylphenyl)propanoic Acid, Cpd 136

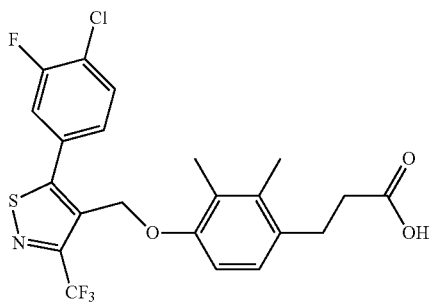 [SMILES: Cc1c(CCC(=O)O)ccc(OCc2c(C(F)(F)F)nsc2-c2ccc(Cl)c(F)c2)c1C]

The title compound was prepared according to the procedure described in Example 172 following Step 1-6 using (4-chloro-3-fluorophenyl)boronic acid for coupling and then hydrolysis of ethyl 3-(4-((5-(4-chloro-3-fluorophenyl)-3-(trifluoromethyl)isothiazol-4-yl)methoxy)-2,3-dimethylphenyl) propanoate to afford the desired product as an off-white solid. $^1$H NMR (300 MHz, CD$_3$OD) δ 7.63 (t, J=7.8 Hz, 1H), 7.43 (d, J=7.5 Hz, 1H), 7.33 (d, J=7.5 Hz, 1H), 6.95 (d, J=8.4 Hz, 1H), 6.68 (d, J=8.4 Hz, 1H), 5.06 (s, 2H), 2.91 (t, J=7.2 Hz, 2H), 2.51 (t, J=7.5 Hz, 2H), 2.22 (s, 3H), 2.06 (s, 3H). Mass spectrum (ESI, m/z): Calcd. for C$_{22}$H$_{18}$ClF$_4$NO$_3$S, 486.1 (M–H), found 486.1.

Example 174

3-(4-[[5-(4-chloro-3-fluorophenyl)-3-(trifluoromethyl)-1,2-thiazol-4-yl]methoxy]-3,5-difluorophenyl) propanoic Acid, Cpd 110

Step 1: Methyl 3-(4-[[5-bromo-3-(trifluoromethyl)-1,2-thiazol-4-yl]methoxy]-3,5-difluorophenyl)propanoate

Into a 25-mL round-bottom flask purged and maintained with an inert atmosphere of nitrogen, was placed [5-bromo-3-(trifluoromethyl)-1,2-thiazol-4-yl]methanol (200 mg, 0.76 mmol, 1.00 equiv), methyl 3-(3,5-difluoro-4-hydroxyphenyl)propanoate (199 mg, 0.92 mmol, 1.20 equiv), PPh$_3$ (401 mg, 1.53 mmol, 2.00 equiv), tetrahydrofuran (3 mL), DIAD (3.9 mg, 0.02 mmol, 2.00 equiv). The resulting solution was stirred overnight at 25° C. The reaction progress was monitored by TLC (ethyl acetate/petroleum ether=1:4). The resulting mixture was concentrated under vacuum. The residue was applied onto a silica gel column with ethyl acetate/petroleum ether (1:4). This resulted in 190 mg (51%) of methyl 3-(4-[[5-bromo-3-(trifluoromethyl)-1,2-thiazol-4-yl]methoxy]-3,5-difluorophenyl)propanoate as yellow oil.

Step 2: Methyl 3-(4-[[5-(4-chloro-3-fluorophenyl)-3-(trifluoromethyl)-1,2-thiazol-4-yl]methoxy]-3,5-difluorophenyl)propanoate

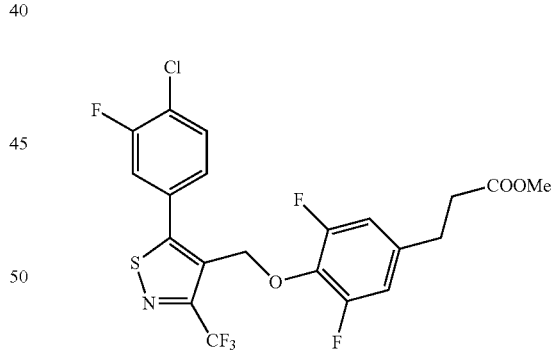

Into a 25-mL round-bottom flask purged and maintained with an inert atmosphere of nitrogen, was placed methyl 3-(4-[[5-bromo-3-(trifluoromethyl)-1,2-thiazol-4-yl]methoxy]-3,5-difluorophenyl)propanoate (70 mg, 0.15 mmol, 1.00 equiv), (4-chloro-3-fluorophenyl)boronic acid (32 mg, 0.18 mmol, 1.20 equiv), K$_3$PO$_4$ (161 mg, 0.76 mmol, 5.00 equiv), Pd(PPh$_3$)$_4$ (17.3 mg, 0.01 mmol, 0.10 equiv), dioxane (1.5 mL). The resulting solution was stirred for 2 h at 90° C. in an oil bath. The reaction progress was monitored by TLC (ethyl acetate/petroleum ether=1:5). The pH value of the solution was adjusted to 6 with hydrogen chloride (2 mol/L). The resulting mixture was washed with 1×2 mL of H$_2$O. The resulting solution was extracted with 3×2 mL of ethyl acetate and the organic layers combined and dried over anhydrous sodium sulfate. The solids were filtered out. The resulting mixture was concentrated under vacuum. The residue was applied onto a TLC-Plate with ethyl acetate/petroleum ether (1:6). This resulted in 80 mg (98%) of methyl 3-(4-[[5-(4-chloro-3-fluorophenyl)-3-(trifluoromethyl)-1,2-thiazol-4-yl]methoxy]-3,5-difluorophenyl)propanoate as yellow oil.

Step 3: 3-(4-[[5-(4-chloro-3-fluorophenyl)-3-(trifluoromethyl)-1,2-thiazol-4-yl]methoxy]-3,5-difluorophenyl) propanoic Acid

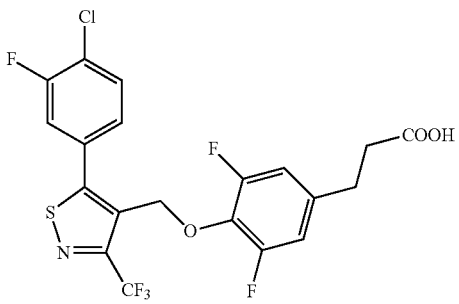 [SMILES: O=C(O)CCc1cc(F)c(OCc2c(C(F)(F)F)nsc2-c2ccc(Cl)c(F)c2)c(F)c1]

The title compound was prepared according to the procedure described in Example 172 following Step 6 by hydrolysis of methyl 3-(4-[[5-(4-chloro-3-fluorophenyl)-3-(trifluoromethyl)-1,2-thiazol-4-yl]methoxy]-3,5-difluorophenyl)propanoate to afford the desired product as an off-white solid. $^1$H NMR (400 MHz, CD$_3$OD) δ 7.66 (t, J=8.0 Hz, 1H), 7.47 (d, J=7.6 Hz, 1H), 7.33 (d, J=7.2 Hz, 1H), 6.84 (d, J=9.6 Hz, 2H), 5.17 (s, 2H), 2.88 (t, J=7.6 Hz, 2H), 2.62 (t, J=7.6 Hz, 2H). Mass spectrum (ESI, m/z): Calcd. for C$_{20}$H$_{12}$ClF$_6$NO$_3$S, 494.0 (M−H), found 494.0.

Example 175

3-(4-[[5-(2-fluoro-4-methylphenyl)-3-(trifluoromethyl)-1,2-thiazol-4-yl]methoxy]-2,3-dimethylphenyl)propanoic Acid, Cpd 155

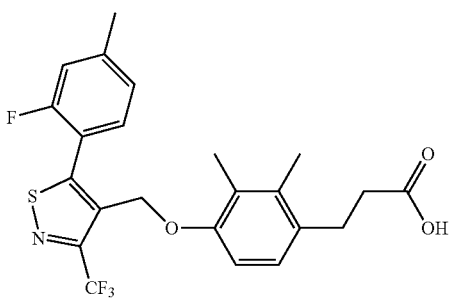 [SMILES: Cc1ccc(-c2snc(C(F)(F)F)c2COc2ccc(CCC(=O)O)c(C)c2C)c(F)c1]

The title compound was prepared according to the procedure described in Example 172 following Step 1-6 using (2-fluoro-4-methylphenyl)boronic acid for coupling and then hydrolysis of ethyl 3-(4-((5-(2-fluoro-4-methylphenyl)-3-(trifluoromethyl)isothiazol-4-yl)methoxy)-2,3-dimethylphenyl) propanoate to afford the desired product as an off-white solid. $^1$H NMR (300 MHz, CD$_3$OD) δ 7.35 (t, J=7.5 Hz, 1H), 7.14 (t, J=8.7 Hz, 2H), 6.93 (d, J=8.7 Hz, 1H), 6.61 (d, J=8.4 Hz, 1H), 5.09 (s, 2H), 2.43 (s, 3H), 2.21 (s, 3H), 1.97 (s, 3H). Mass spectrum (ESI, m/z): Calcd. for C$_{23}$H$_{21}$F$_4$NO$_3$S, 466.1 (M−H), found 466.1.

Example 176

3-(3,5-difluoro-4-[[5-(2-fluoro-4-methylphenyl)-3-(trifluoromethyl)-1,2-thiazol-4-yl]methoxy]phenyl) propanoic Acid, Cpd 95

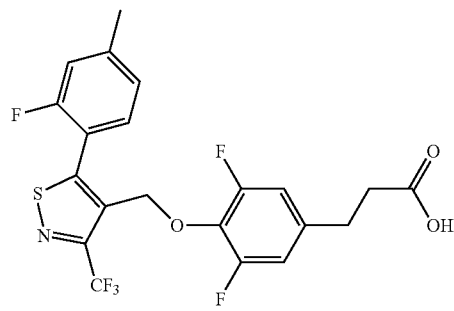 [SMILES: Cc1ccc(-c2snc(C(F)(F)F)c2COc2c(F)cc(CCC(=O)O)cc2F)c(F)c1]

The title compound was prepared according to the procedure described in Example 172 following Step 1-6 using (2-fluoro-4-methylphenyl)boronic acid for coupling and then hydrolysis of ethyl 3-(3,5-difluoro-4-((5-(2-fluoro-4-methylphenyl)-3-(trifluoromethyl)isothiazol-4-yl) methoxy) phenyl) propanoate to afford the desired product as an off-white solid. $^1$H NMR (300 MHz, CD$_3$OD) δ 7.25 (t, J=7.5 Hz, 1H), 7.13 (d, J=9.1 Hz, 2H), 6.76 (d, J=9.0 Hz, 2H), 5.14 (s, 2H), 2.84 (t, J=7.5 Hz, 2H), 2.58 (t, J=7.2 Hz, 2H), 2.45 (s, 3H). Mass spectrum (ESI, m/z): Calcd. for C$_{21}$H$_{21}$FO$_5$, 474.1 (M−H), found 474.1.

Example 177

3-(4-[[5-(2-fluoro-4-methylphenyl)-3-(trifluoromethyl)-1,2-thiazol-4-yl]methoxy]-2-(trifluoromethyl) phenyl)propanoic Acid, Cpd 221

Step 1: Ethyl (2E)-3-[4-hydroxy-2-(trifluoromethyl)phenyl]prop-2-enoate

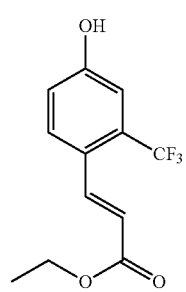 [SMILES: CCOC(=O)/C=C/c1ccc(O)cc1C(F)(F)F]

Into a 500-mL round-bottom flask purged and maintained with an inert atmosphere of nitrogen, was placed 4-bromo-3-(trifluoromethyl)phenol (5 g, 20.75 mmol, 1.00 equiv), N,N-dimethylformamide (60 mL), ethyl prop-2-enoate (10.5 g, 104.88 mmol, 5.06 equiv), PdCl$_2$ (370 mg, 2.09 mmol, 0.10 equiv), P(tolyl)$_3$ (1.28 g, 4.21 mmol, 0.20 equiv), DIEA (16.25 g). The resulting solution was stirred for overnight at 90° C. The resulting mixture was concentrated under vacuum. The residue was applied onto a silica gel column with ethyl acetate/petroleum ether (1/8). This resulted in 2.6 g (42%) of ethyl (2E)-3-[4-hydroxy-2-(trifluoromethyl)phenyl]prop-2-enoate as a light yellow solid.

Step 2: Ethyl 3-[4-hydroxy-2-(trifluoromethyl)phenyl]propanoate

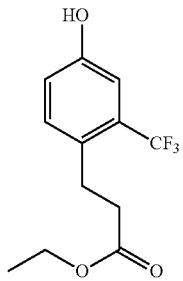 [SMILES: CCOC(=O)CCc1ccc(O)cc1C(F)(F)F]

Into a 500-mL round-bottom flask, was placed ethyl (2E)-3-[4-hydroxy-2-(trifluoromethyl)phenyl]prop-2-enoate (2.6 g, 9.99 mmol, 1.00 equiv), ethanol (40 mL), Palladium carbon (5 g). To the above hydrogen was introduced in. The resulting solution was stirred for overnight at 25° C. The solids were filtered out. The resulting mixture was concentrated under vacuum. This resulted in 1.4 g (crude) of ethyl 3-[4-hydroxy-2-(trifluoromethyl)phenyl]propanoate as light yellow oil.

Step 3: 3-(4-[[5-(2-fluoro-4-methylphenyl)-3-(trifluoromethyl)-1,2-thiazol-4-yl]methoxy]-2-(trifluoromethyl)phenyl)propanoic Acid

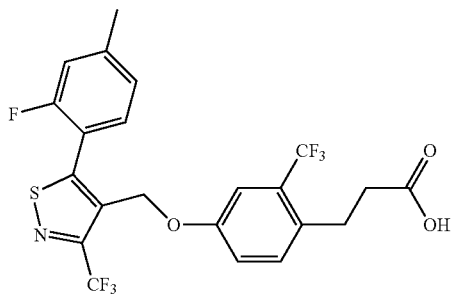 [SMILES: Cc1ccc(-c2snc(C(F)(F)F)c2COc2ccc(CCC(=O)O)c(C(F)(F)F)c2)c(F)c1]

The title compound was prepared according to the procedure described in Example 172 following Step 1-6 using (2-fluoro-4-methylphenyl)boronic acid for coupling and then hydrolysis of ethyl 3-(4-((5-(2-fluoro-4-methylphenyl)-3-(trifluoromethyl)isothiazol-4-yl)methoxy)-2-(trifluoromethyl) phenyl)propanoate to afford the desired product as an off-white solid. $^1$H NMR (400 MHz, CD$_3$OD) δ 7.36 (t, J=7.8 Hz, 2H), 7.17 (t, J=7.6 Hz, 2H), 7.00-7.04 (m, 2H), 5.14 (s, 2H), 3.02 (t, J=8.0 Hz, 2H), 2.52 (t, J=7.6 Hz, 2H), 2.44 (s, 3H). Mass spectrum (ESI, m/z): Calcd. for C$_{22}$H$_{16}$F$_7$NO$_3$S, 506.1 (M−H), found 506.1.

Example 178

3-(4-[[5-(2-methylphenyl)-3-(trifluoromethyl)-1,2-thiazol-4-yl]methoxy]-2-(trifluoromethyl)phenyl) Propanoic Acid, Cpd 203

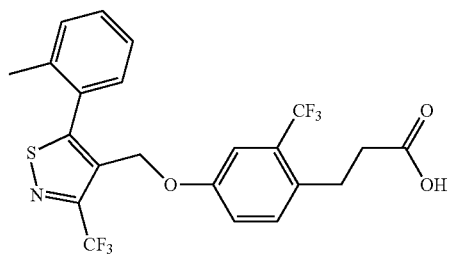 [SMILES: Cc1ccccc1-c1snc(C(F)(F)F)c1COc1ccc(CCC(=O)O)c(C(F)(F)F)c1]

The title compound was prepared according to the procedure described in Example 172 following Step 1-6 using (2-methylphenyl)boronic acid for coupling and then hydrolysis of ethyl 3-(4-((5-(o-tolyl)-3-(trifluoromethyl)isothiazol-4-yl)methoxy)-2-(trifluoromethyl)phenyl) propanoate to afford the desired product as an off-white solid. $^1$H NMR (300 MHz, CD$_3$OD) δ 7.24-7.46 (m, 5H), 6.70-6.96 (m, 2H), 4.98 (s, 2H), 3.01 (t, J=7.5 Hz, 2H), 2.55 (t, J=7.2 Hz, 2H), 2.21 (s, 3H). Mass spectrum (ESI, m/z): Calcd. for C$_{22}$H$_{17}$F$_6$NO$_3$S, 490.1 (M+H), found 490.2.

Example 179

3-(2-chloro-4-[[5-(4-chlorophenyl)-3-(trifluoromethyl)-1,2-thiazol-4-yl]methoxy]phenyl)propanoic Acid, Cpd 208

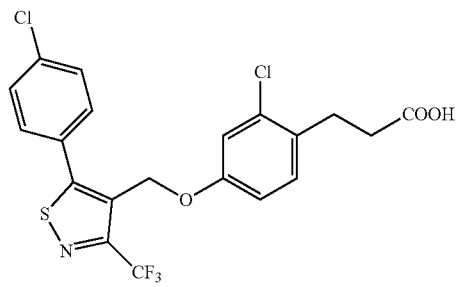 [SMILES: O=C(O)CCc1ccc(OCc2c(C(F)(F)F)nsc2-c2ccc(Cl)cc2)cc1Cl]

The title compound was prepared according to the procedure described in Example 172 following Step 1-6 using (4-chloro-phenyl)boronic acid for coupling and then hydrolysis of ethyl 3-(4-((5-(o-tolyl)-3-(trifluoromethyl)isothiazol-4-yl)methoxy)-2-chloro-phenyl)propanoate to afford the desired product as an off-white solid. $^1$H NMR (300 MHz, CD$_3$OD) δ7.53-7.59 (m, 4H), 7.25 (d, J=8.4 Hz, 1H), 6.97 (s, 1H), 6.81-6.85 (m, 1H), 5.06 (s, 2H), 2.99 (t, J=8.1 Hz, 2H), 2.60 (t, J=8.1 Hz, 2H). Mass spectrum (ESI, m/z): Calcd. for C$_{20}$H$_{14}$Cl$_2$F$_3$NO$_3$S, 474.0 (M−H), found 474.0.

Example 180

3-(2, 3-dichloro-4-[[5-(4-chlorophenyl)-3-(trifluoromethyl)-1,2-thiazol-4-yl]methoxy]phenyl) Propanoic Acid, Cpd 55

Step 1: Ethyl (2Z)-3-(2, 3-dichloro-4-hydroxyphenyl)prop-2-enoate

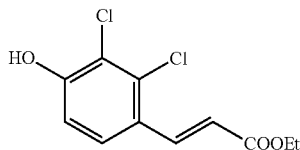 [SMILES: CCOC(=O)/C=C/c1ccc(O)c(Cl)c1Cl]

Into a 50-mL round-bottom flask purged and maintained with an inert atmosphere of nitrogen, was placed 2,3-dichloro-4-hydroxybenzaldehyde (500 mg, 2.62 mmol, 1.00 equiv), (2-ethoxy-2-oxoethylidene)triphenyl-[4]-phosphanium (1.368 g, 3.93 mmol, 1.50 equiv), toluene (20 mL). The resulting solution was stirred overnight at 110° C. The resulting mixture was concentrated under vacuum. The residue was applied onto a silica gel column with ethyl acetate/petroleum ether (1/5). This resulted in 270 mg (38%) of ethyl (2Z)-3-(2,3-dichloro-4-hydroxyphenyl)prop-2-enoate as white oil.

Step 2: Ethyl 3-(2,3-dichloro-4-hydroxyphenyl)propanoate

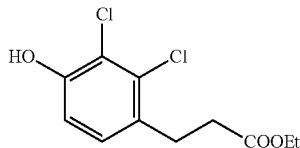 [SMILES: CCOC(=O)CCc1ccc(O)c(Cl)c1Cl]

Into a 50-mL round-bottom flask, was placed ethyl (2Z)-3-(2,3-dichloro-4-hydroxyphenyl)prop-2-enoate (270 mg, 1.03 mmol, 1.00 equiv), TsNHNH$_2$ (193 mg, 1.04 mmol, 1.00 equiv), NaOAc (424 mg, 5.17 mmol, 5.00 equiv), ethylene glycol dimethyl ether (10 mL), water (1 mL). The resulting solution was stirred overnight at 80° C. The resulting mixture was concentrated under vacuum. The residue was applied onto a silica gel column with ethyl acetate/petroleum ether (1:3). This resulted in 150 mg (52%) of ethyl 3-(2,3-dichloro-4-hydroxyphenyl)propanoate as a red solid.

Step 3: 3-(2, 3-dichloro-4-[[5-(4-chlorophenyl)-3-(trifluoromethyl)-1,2-thiazol-4-yl]methoxy]phenyl) propanoic Acid

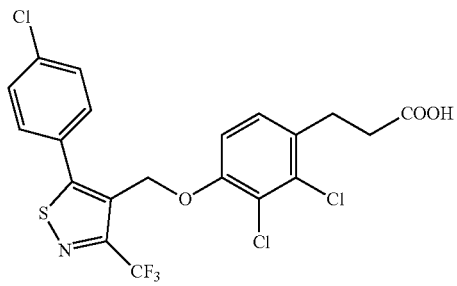 [SMILES: O=C(O)CCc1ccc(OCc2c(C(F)(F)F)nsc2-c2ccc(Cl)cc2)c(Cl)c1Cl]

The title compound was prepared according to the procedure described in Example 172 following Steps 1-7 using (4-chloro-phenyl)boronic acid for coupling and then hydrolysis of ethyl 3-(2,3-dichloro-4-((5-(4-chlorophenyl)-3-(trifluoromethyl)isothiazol-4-yl)methoxy)phenyl) propanoate to afford the desired product as an off-white solid. $^1$H NMR (300 MHz, CD$_3$OD) δ 7.46 (s, 4H), 7.12 (d, J=8.7 Hz, 1H), 6.87 (d, J=8.7 Hz, 1H), 5.04 (s, 2H), 2.93 (t, J=7.5 Hz, 2H), 2.49 (t, J=7.5 Hz, 2H). Mass spectrum (ESI, m/z): Calcd. for C$_{20}$H$_{13}$Cl$_3$F$_3$NO$_3$S, 508.0 (M−H), found 508.1.

Example 181

3-(4-[[5-(4-chlorophenyl)-3-(trifluoromethyl)-1,2-thiazol-4-yl]methoxy]-2-(trifluoromethoxy)phenyl) propanoic Acid, Cpd 159

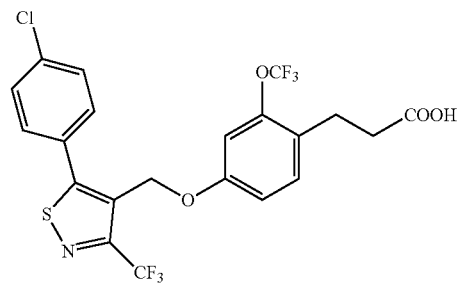 [SMILES: O=C(O)CCc1ccc(OCc2c(C(F)(F)F)nsc2-c2ccc(Cl)cc2)cc1OC(F)(F)F]

The title compound was prepared according to the procedure described in Example 172 following Step 1-7 using (4-chloro-phenyl)boronic acid for coupling and then hydrolysis of ethyl 3-(4-((5-(o-tolyl)-3-(trifluoromethyl)isothiazol-4-yl)methoxy)-2-trifluoromethoxy-phenyl) propanoate to afford the desired product as an off-white solid. $^1$H NMR (300 MHz, CD$_3$OD) δ 7.52-7.59 (m, 4H), 7.31 (d, J=8.4 Hz, 1H), 6.87-6.91 (m, 1H), 6.81 (s, 1H), 5.10 (s, 2H), 2.93 (t, J=8.1 Hz, 2H), 2.58 (t, J=8.1 Hz, 2H). Mass spectrum (ESI, m/z): Calcd. for C$_{21}$H$_{14}$ClF$_6$NO$_4$S, 524.0 (M−H), found 524.1.

Example 182

3-(4-[[5-(2,4-dimethylphenyl)-3-(trifluoromethyl)-1,2-thiazol-4-yl]methoxy]-2-(trifluoromethyl) phenyl) propanoic Acid, Cpd 232

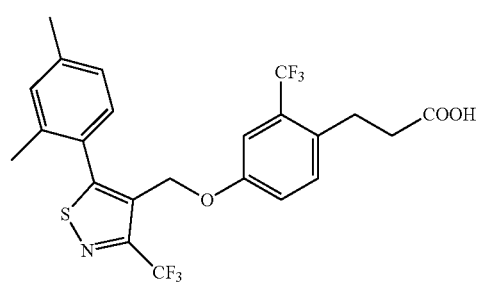 [SMILES: Cc1ccc(-c2snc(C(F)(F)F)c2COc2ccc(CCC(=O)O)c(C(F)(F)F)c2)c(C)c1]

The title compound was prepared according to the procedure described in Example 172 following Step 1-6 using (2,4-dimethyl-phenyl)boronic acid for coupling and then hydrolysis of ethyl 3-(4-((5-(o-tolyl)-3-(trifluoromethyl)isothiazol-4-yl)methoxy)-2-trifluoromethyl-phenyl) propanoate to afford the desired product as an off-white solid. $^1$H NMR (300 MHz, CD$_3$OD) δ 7.33 (d, J=9.0 Hz, 1H), 7.21 (s, 1H), 7.12 (s, 2H), 6.98 (s, 2H), 4.97 (s, 2H), 3.01 (t, J=7.8 Hz, 2H), 2.52 (t, J=7.8 Hz, 2H), 2.37 (s, 3H), 2.02 (s, 3H). Mass spectrum (ESI, m/z): Calcd. for C$_{23}$H$_{19}$F$_6$NO$_3$S, 502.1 (M−H), found 502.2.

Example 183

3-(4-((4-(4-chlorophenyl)-2-(trifluoromethyl)thiophen-3-yl)methoxy)-3,5-difluorophenyl)propanoic Acid, Cpd 35

Step 1: Ethyl 4-hydroxy-2-(trifluoromethyl)thiophene-3-carboxylate

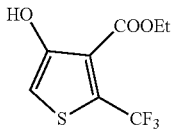

Into a 500-mL round-bottom flask (1 atm) purged and maintained with an inert atmosphere of nitrogen, was placed ethyl 4,4,4-trifluorobut-2-ynoate (5.0 g, 30.10 mmol, 1.00 equiv), methyl 2-sulfanylacetate (3.51 g, 33.07 mmol, 1.10 equiv), ether (250 mL). This was followed by the addition of Triton-B (40% in H$_2$O) (181 mg, 1.08 mmol, 0.04 equiv) dropwise with stirring at 0° C. The resulting solution was stirred for 5.0 h at 25° C. The reaction progress was monitored by GCMS. The resulting mixture was concentrated under vacuum. The resulting solution was diluted with 10 mL of sodium chloride. The resulting solution was extracted with 15 mL of ethyl acetate and the organic layers combined and dried over anhydrous sodium sulfate and concentrated under vacuum. The residue was applied onto a silica gel column with ethyl acetate/petroleum ether (1:10). This resulted in 1.07 g (15%) of ethyl 4-hydroxy-2-(trifluoromethyl)thiophene-3-carboxylate as a white solid. Mass spectrum (ESI, m/z): Calcd. for C$_8$H$_7$F$_3$O$_3$S, 241.0 (M), found 241.0.

Step 2: Ethyl 4-[(trifluoromethane)sulfonyloxy]-2-(trifluoromethyl)thiophene-3-carboxylate

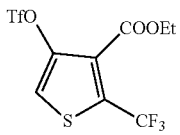 [SMILES: CCOC(=O)c1c(OS(=O)(=O)C(F)(F)F)csc1C(F)(F)F]

Into a 100-mL round-bottom flask, was placed ethyl 4-hydroxy-2-(trifluoromethyl) thiophene-3-carboxylate (1.3 g, 5.41 mmol, 1.00 equiv), dichloromethane (15.0 mL), pyridine (1.33 g, 16.81 mmol, 3.11 equiv). This was followed by the addition of Tf$_2$O (2.29 g, 8.12 mmol, 1.50 equiv) dropwise with stirring at 0° C. The resulting solution was stirred for 2.0 h at 0° C. in a water/ice bath. The reaction progress was monitored by GCMS. The reaction was then quenched by the addition of 10 mL of water. The resulting solution was extracted with 3×15 mL of dichloromethane and the organic layers combined. The resulting mixture was washed with 2×20 mL of sodium chloride. The mixture was dried over anhydrous sodium sulfate and concentrated under vacuum. The residue was applied onto a silica gel column with ethyl acetate/petroleum ether (1:9). This resulted in 1.7 g (84%) of ethyl 4-[(trifluoromethane) sulfonyloxy]-2-(trifluoromethyl)thiophene-3-carboxylate as yellow oil.

Step 3: Ethyl 4-(4-chlorophenyl)-2-(trifluoromethyl) thiophene-3-carboxylate

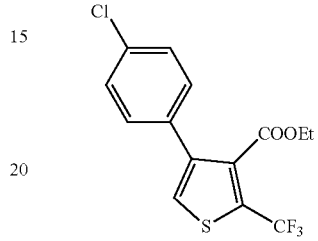

Into a 50-mL sealed tube (1 atm) purged and maintained with an inert atmosphere of nitrogen, was placed ethyl 4-[(trifluoromethane)sulfonyloxy]-2-(trifluoromethyl)thiophene-3-carboxylate (1.7 g, 4.57 mmol, 1.00 equiv), (4-chlorophenyl)boronic acid (858 mg, 5.49 mmol, 1.20 equiv), K$_3$PO$_4$ (3.10 g, 14.60 mmol, 3.20 equiv), Pd(PPh$_3$)$_4$ (129 mg, 0.11 mmol, 0.02 equiv), 1,4-dioxane (17.0 mL). The resulting solution was stirred overnight at 80° C. in an oil bath. The reaction progress was monitored by TLC/LCMS (ethyl acetate/petroleum ether=1:6). The solids were filtered out and washed by 20 mL ethyl acetate. Collected the organic phases and concentrated under vacuum. The residue was applied onto a silica gel column with ethyl acetate/petroleum ether (1:10). This resulted in 1.22 g (80%) of ethyl 4-(4-chlorophenyl)-2-(trifluoromethyl)thiophene-3-carboxylate as light yellow oil.

Step 4: [4-(4-chlorophenyl)-2-(trifluoromethyl)thiophen-3-yl]methanol

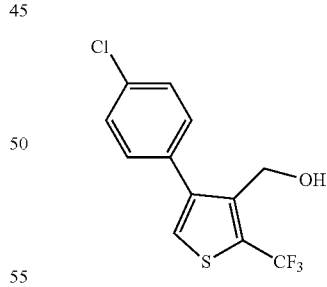

Into a 100-mL 3-necked round-bottom flask (1 atm) purged and maintained with an inert atmosphere of nitrogen, was placed ethyl 4-(4-chlorophenyl)-2-(trifluoromethyl) thiophene-3-carboxylate (1.222 g, 3.65 mmol, 1.00 equiv), tetrahydrofuran (5.0 g, 69.34 mmol, 18.99 equiv). This was followed by the addition of a solution of LiAlH$_4$ (278 mg, 7.33 mmol, 2.01 equiv) in tetrahydrofuran (7.0 mL) dropwise with stirring at 0° C. The resulting solution was stirred for 2.0 h at 25° C. The reaction progress was monitored by LCMS/TLC (ethyl acetate/petroleum ether=1:6). The reaction was then quenched by the addition of 10 mL of water and 5 mL of 2N HCl. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:4). This resulted in 0.9 g (84%) of [4-(4-chlorophenyl)-2-(trifluoromethyl)thiophen-3-yl]methanol as a white solid.

Step 5: [4-(4-chlorophenyl)-2-(trifluoromethyl)thiophen-3-yl]methyl methanesulfonate

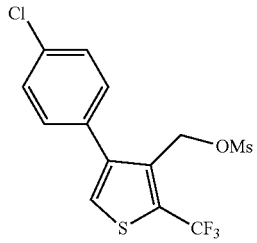 [SMILES: CS(=O)(=O)OCc1c(-c2ccc(Cl)cc2)csc1C(F)(F)F]

Into a 100-mL round-bottom flask, was placed [4-(4-chlorophenyl)-2-(trifluoromethyl) thiophen-3-yl]methanol (500 mg, 1.71 mmol, 1.00 equiv), triethylamine (521 mg, 5.15 mmol, 3.01 equiv), dichloromethane (10.0 mL). This was followed by the addition of MsCl (390 mg, 3.42 mmol, 2.00 equiv) dropwise with stirring at 0° C. The resulting solution was stirred for 0.5 h at 25° C. The reaction progress was monitored by TLC (ethyl acetate/petroleum ether=1:6). The reaction was then quenched by the addition of 10 mL of water. The resulting solution was extracted with 3×15 mL of dichloromethane and the organic layers combined. The resulting mixture was washed with 2×20 mL of sodium chloride. The mixture was dried over anhydrous sodium sulfate and concentrated under vacuum. This resulted in 675 mg of [4-(4-chlorophenyl)-2-(trifluoromethyl)thiophen-3-yl]methyl methanesulfonate as a light yellow solid. The crude could be used for the next step directly. Mass spectrum (ESI, m/z): Calcd. for $C_{13}H_{10}C_1F_3O_3S_2$, 371.0 (M+H), found 371.0.

Step 6: Ethyl 3-(4-[[4-(4-chlorophenyl)-2-(trifluoromethyl)thiophen-3-yl]methoxy]-3,5-difluorophenyl)propanoate

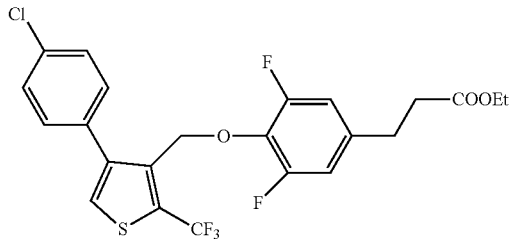 [SMILES: CCOC(=O)CCc1cc(F)c(OCc2c(-c3ccc(Cl)cc3)csc2C(F)(F)F)c(F)c1]

Into a 100-mL round-bottom flask, was placed [4-(4-chlorophenyl)-2-(trifluoromethyl) thiophen-3-yl]methyl methanesulfonate (636 mg, 1.72 mmol, 1.00 equiv), ethyl 3-(3,5-difluoro-4-hydroxyphenyl)propanoate (514 mg, 2.23 mmol, 1.30 equiv), potassium carbonate (712 mg, 5.15 mmol, 3.00 equiv), N,N-dimethylformamide (10.0 mL). The resulting solution was stirred overnight at 25° C. The reaction progress was monitored by TLC (ethyl acetate/ petroleum ether=1:6). The resulting solution was diluted with 20 mL of $H_2O$. The resulting solution was extracted with 4×20 mL of ethyl acetate and the organic layers combined and dried over anhydrous sodium sulfate and concentrated under vacuum. The residue was applied onto a silica gel column with ethyl acetate/petroleum ether (1:4). This resulted in 0.865 g (100%) of ethyl 3-(4-[[4-(4-chlorophenyl)-2-(trifluoromethyl)thiophen-3-yl]methoxy]-3,5-difluorophenyl)propanoate as colorless oil. Mass spectrum (ESI, m/z): Calcd. for $C_{23}H_{18}ClF_5O_3S$, 505.1 (M+H), found 505.1.

Step 7: 3-(4-((4-(4-chlorophenyl)-2-(trifluoromethyl)thiophen-3-yl)methoxy)-3,5-difluorophenyl) propanoic Acid

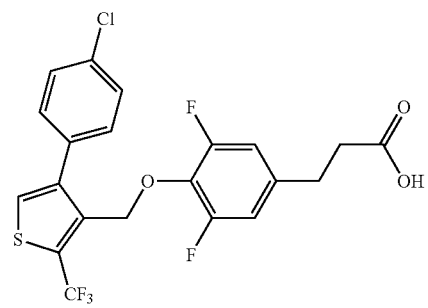 [SMILES: O=C(O)CCc1cc(F)c(OCc2c(-c3ccc(Cl)cc3)csc2C(F)(F)F)c(F)c1]

The title compound was prepared according to the procedure described in Example 1 by hydrolysis of ethyl 3-(4-[[4-(4-chlorophenyl)-2-(trifluoromethyl)thiophen-3-yl] methoxy]-3,5-difluorophenyl)propanoate to afford the desired product as an off-white solid. $^1$H NMR (400 MHz, CDCl$_3$) δ 7.55 (d, J=7.1 Hz, 2H), 7.45 (m, 3H), 6.75 (d, J=7.5 Hz, 2H), 5.02 (s, 2H), 2.95 (t, J=7.8 Hz, 2H), 2.65 (t, J=8.1 Hz, 2H). LCMS (ESI, M/Z) for $C_{21}H_{14}ClF_5O_3S$: 476, 478.

Example 184

3-(4-((4-(4-chlorophenyl)-2-(trifluoromethyl)thiophen-3-yl)methoxy)-2,3-difluorophenyl)propanoic Acid, Cpd 47

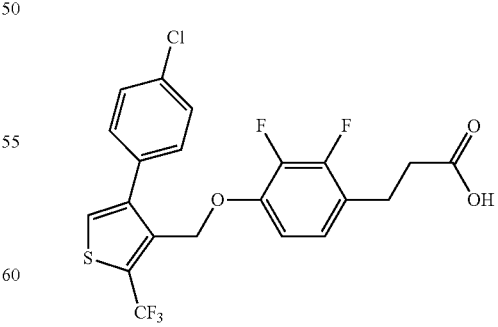

The title compound was prepared according to the procedure described in Example 183 by coupling of [4-(4-chlorophenyl)-2-(trifluoromethyl)thiophen-3-yl]methyl methanesulfonate and ethyl 3-(2,3-difluoro-4-hydroxyphenyl)propanoate followed by hydrolysis of ethyl 3-(4-((4-(4-chlorophenyl)-2-(trifluoromethyl)thiophen-3-yl)methoxy)-2,3-difluorophenyl)propanoate to afford the desired product as an off-white solid. ¹H NMR (400 MHz, CDCl₃) δ 7.50 (s, 1H), 7.45 (m, 4H), 6.85 (t, J=6.5 Hz, 1H), 6.65 (t, J=6.5 Hz, 1H), 4.95 (s, 2H), 2.96 (t, J=8.0 Hz, 2H), 2.68 (t, J=8.0 Hz, 2H). LCMS (ESI, M/Z) for C₂₁H₁₄ClF₅O₃S: 476, 478.

Example 185

3-(4-((4-(4-chlorophenyl)-2-(trifluoromethyl)thiophen-3-yl)methoxy)-2,3-dimethylphenyl)propanoic Acid, Cpd 57

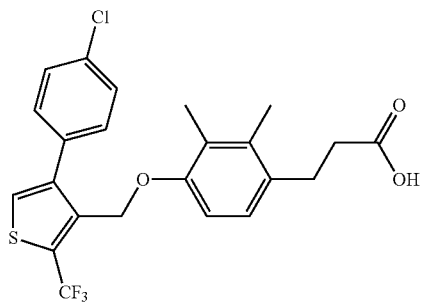 [SMILES: Cc1c(CCC(=O)O)ccc(OCc2c(-c3ccc(Cl)cc3)csc2C(F)(F)F)c1C]

The title compound was prepared according to the procedure described in Example 183 by coupling of [4-(4-chlorophenyl)-2-(trifluoromethyl)thiophen-3-yl]methyl methanesulfonate and ethyl 3-(2,3-dimethyl-4-hydroxyphenyl)propanoate followed by hydrolysis of ethyl 3-(4-((4-(4-chlorophenyl)-2-(trifluoromethyl)thiophen-3-yl)methoxy)-2,3-dimethylphenyl)propanoate to afford the desired product as an off-white solid. ¹H NMR (400 MHz, CDCl₃) δ 7.42 (s, 1H), 7.38 (m, 4H), 6.97 (d, J=6.5 Hz, 1H), 6.63 (d, J=6.5 Hz, 1H), 4.90 (s, 2H), 2.95 (t, J=7.0 Hz, 2H), 2.65 (t, J=7.0 Hz, 2H), 2.24 (s, 3H), 2.12 (s, 3H).

Example 186

3-(4-((4-(4-chlorophenyl)-2-(trifluoromethyl)thiophen-3-yl)methoxy)-2,3,5-trifluorophenyl)propanoic Acid, Cpd 50

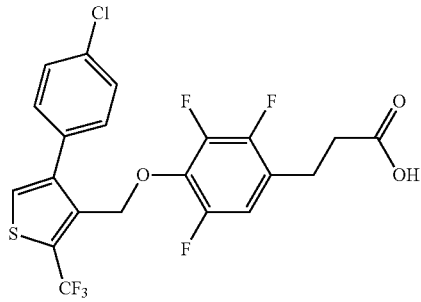 [SMILES: O=C(O)CCc1cc(F)c(OCc2c(-c3ccc(Cl)cc3)csc2C(F)(F)F)c(F)c1F]

The title compound was prepared according to the procedure described in Example 183 by coupling of [4-(4-chlorophenyl)-2-(trifluoromethyl)thiophen-3-yl]methyl methanesulfonate and ethyl 3-(2,3,5-trifluoro-4-hydroxyphenyl)propanoate followed by hydrolysis of ethyl 3-(4-((4-(4-chlorophenyl)-2-(trifluoromethyl)thiophen-3-yl)methoxy)-2,3,5-trifluorophenyl)propanoate to afford the desired product as an off-white solid. ¹H NMR (400 MHz, CDCl₃) δ 7.48 (d, J=7.3 Hz, 2H), 7.41 (s, 1H), 7.40 (d, J=7.0 Hz, 2H), 6.75 (m, 1H), 5.07 (s, 2H), 2.95 (t, J=8.1 Hz, 2H), 2.73 (t, J=8.0 Hz, 2H).

Example 187

3-(4-((4-(4-chloro-2-fluorophenyl)-2-(trifluoromethyl)thiophen-3-yl)methoxy)-2,3-dimethylphenyl) propanoic Acid, Cpd 59

Step 1: [4-(2-fluoro-4-chlorophenyl)-2-(trifluoromethyl)thiophen-3-yl]methyl methanesulfonate

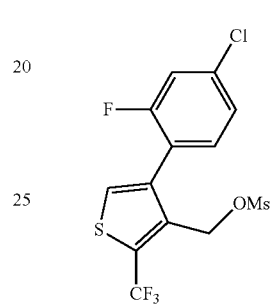

The title compound was prepared according to the procedure described in Example 182 by Suzuki coupling of ethyl 4-[(trifluoromethane) sulfonyloxy]-2-(trifluoromethyl)thiophene-3-carboxylate and 2-fluoro-4-chloroboronic acid followed by synthetic steps to give the desire product as a yellow oil.

Step 2: 3-(4-((4-(4-chloro-2-fluorophenyl)-2-(trifluoromethyl)thiophen-3-yl)methoxy)-2,3-dimethylphenyl)propanoic Acid

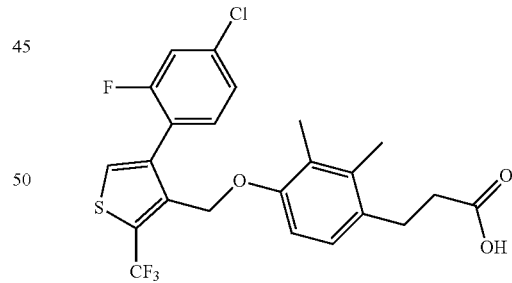

The title compound was prepared according to the procedure described in Example 183 by coupling of [4-(2-fluoro-4-chlorophenyl)-2-(trifluoromethyl)thiophen-3-yl] methyl methanesulfonate and ethyl 3-(2,3-dimethyl-4-hydroxyphenyl)propanoate followed by hydrolysis of ethyl 3-(4-((4-(2-fluoro-4-chlorophenyl)-2-(trifluoromethyl)thiophen-3-yl)methoxy)-2,3-dimethylphenyl) propanoate to afford the desired product as an off-white solid. ¹H NMR (400 MHz, CDCl₃) δ 7.45 (s, 1H), 7.30 (dd, J=11.5, 5.5 Hz, 2H), 7.14 (dd, J=10.7, 4.5 Hz, 2H), 6.92 (d, J=6.5 Hz, 1H), 6.57 (d, J=6.5 Hz, 1H), 4.92 (s, 2H), 2.90 (t, J=7.0 Hz, 2H), 2.58 (t, J=7.0 Hz, 2H), 2.15 (s, 3H), 1.91 (s, 3H).

Example 188

3-(4-((4-(4-methoxyphenyl)-2-(trifluoromethyl)thiophen-3-yl)methoxy)-2,3-dimethylphenyl)propanoic Acid, Cpd 60

Step 1: [4-(4-methoxyphenyl)-2-(trifluoromethyl)thiophen-3-yl]methyl methanesulfonate

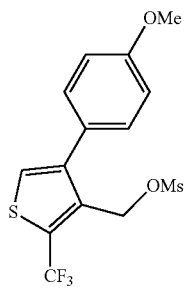 [SMILES: COc1ccc(-c2csc(C(F)(F)F)c2COS(C)(=O)=O)cc1]

The title compound was prepared according to the procedure described in Example 183 by Suzuki coupling of ethyl 4-[(trifluoromethane) sulfonyloxy]-2-(trifluoromethyl)thiophene-3-carboxylate and 4-methoxyboronic acid followed by synthetic steps to give the desire product as a yellow oil.

Step 2: 3-(4-((4-(4-methoxyphenyl)-2-(trifluoromethyl)thiophen-3-yl)methoxy)-2,3-dimethylphenyl)propanoic Acid

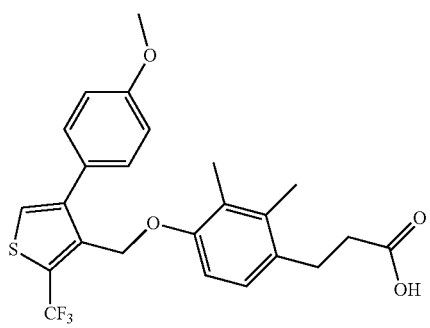 [SMILES: COc1ccc(-c2csc(C(F)(F)F)c2COc2ccc(CCC(=O)O)c(C)c2C)cc1]

The title compound was prepared according to the procedure described in Example 183 by coupling of [4-(4-methoxyphenyl)-2-(trifluoromethyl)thiophen-3-yl]methyl methanesulfonate and ethyl 3-(2,3-dimethyl-4-hydroxyphenyl)propanoate followed by hydrolysis of ethyl 3-(4-((4-(4-methoxphenyl)-2-(trifluoromethyl)thiophen-3-yl)methoxy)-2,3-dimethylphenyl) propanoate to afford the desired product as an off-white solid. $^1$H NMR (400 MHz, CDCl$_3$) δ 7.38 (s, 1H), 7.35 (d, J=7.5 Hz, 2H), 6.95 (d, J=8.0 Hz, 1H), 6.90 (d, J=7.8 Hz, 2H), 6.63 (d, J=8.0 Hz, 1H), 4.88 (s, 2H), 3.82 (s, 3H), 2.95 (t, J=7.0 Hz, 2H), 2.60 (t, J=7.0 Hz, 2H), 2.48 (s, 3H), 2.12 (s, 3H).

Example 189

3-(3,5-difluoro-4-((4-(4-methoxyphenyl)-2-(trifluoromethyl)thiophen-3-yl)methoxy)phenyl)propanoic Acid, Cpd 34

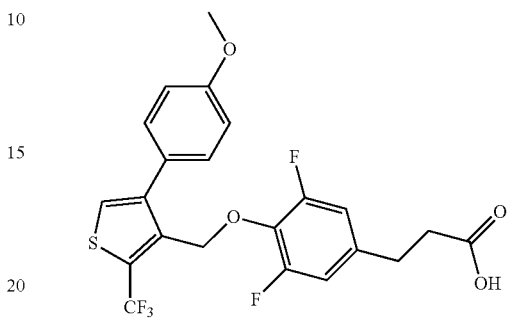

The title compound was prepared according to the procedure described in Example 182 by coupling of [4-(4-methoxyphenyl)-2-(trifluoromethyl)thiophen-3-yl]methyl methanesulfonate and ethyl 3-(2,6-difluoro-4-hydroxyphenyl)propanoate followed by hydrolysis of ethyl 3-(3,5-difluoro-4-((4-(4-methoxyphenyl)-2-(trifluoromethyl)thiophen-3-yl)methoxy)phenyl)propanoate to afford the desired product as an off-white solid. $^1$H NMR (400 MHz, CDCl$_3$) δ 7.58 (d, J=7.0 Hz, 2H), 7.38 (s, 1H), 6.95 (d, J=6.5 Hz, 2H), 6.72 (d, J=7.0 Hz, 1H), 5.08 (s, 2H), 3.85 (s, 3H), 2.90 (t, J=5.5 Hz, 2H), 2.66 (t, J=6.8 Hz, 2H). LCMS (ESI, M/Z) for $C_{22}H_{17}F_5O_4S$: 473.1 (MH$^+$).

Example 190

3-(4-((4-(4-ethylphenyl)-2-(trifluoromethyl)thiophen-3-yl)methoxy)-2,3-dimethylphenyl)propanoic Acid, Cpd 54

Step 1: [4-(4-ethylphenyl)-2-(trifluoromethyl)thiophen-3-yl]methyl methanesulfonate

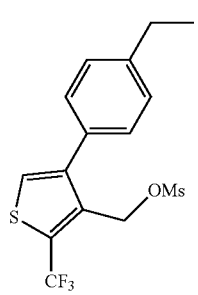 [SMILES: CCc1ccc(-c2csc(C(F)(F)F)c2COS(C)(=O)=O)cc1]

The title compound was prepared according to the procedure described in Example 183 by Suzuki coupling of ethyl 4-[(trifluoromethane) sulfonyloxy]-2-(trifluoromethyl)thiophene-3-carboxylate and 4-ethylboronic acid followed by synthetic steps to give the desire product as a yellow oil.

Step 2: 3-(4-((4-(4-ethylphenyl)-2-(trifluoromethyl)thiophen-3-yl)methoxy)-2,3-dimethylphenyl)propanoic Acid

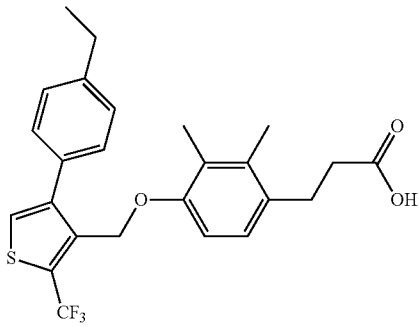 [SMILES: CCc1ccc(-c2csc(C(F)(F)F)c2COc2ccc(CCC(=O)O)c(C)c2C)cc1]

The title compound was prepared according to the procedure described in Example 183 by coupling of [4-(4-ethylphenyl)-2-(trifluoromethyl)thiophen-3-yl]methyl methanesulfonate and ethyl 3-(2,3-dimethyl-4-hydroxyphenyl)propanoate followed by hydrolysis of ethyl 3-(4-((4-(4-ethyl-phenyl)-2-(trifluoromethyl)thiophen-3-yl)methoxy)-2,3-dimethylphenyl) propanoate to afford the desired product as an off-white solid. $^1$H NMR (400 MHz, CDCl$_3$) δ 7.38 (s, 1H), 7.35 (d, J=7.1 Hz, 2H), 7.19 (d, J=7.1 Hz, 2H), 6.94 (d, J=6.7 Hz, 1H), 6.62 (d, J=6.7 Hz, 1H), 4.92 (s, 2H), 2.93 (t, J=7.3 Hz, 2H), 2.65 (q, J=7.5 Hz, 2H), 2.60 (t, J=7.2 Hz, 2H), 2.23 (s, 3H), 2.10 (s, 3H), 1.25 (t, J=8.5 Hz, 3H).

Example 191

3-(4-((4-(4-fluorophenyl)-2-(trifluoromethyl)thiophen-3-yl)methoxy)-2,3-dimethylphenyl)propanoic Acid, Cpd 58

Step 1: [4-(4-fluorophenyl)-2-(trifluoromethyl)thiophen-3-yl]methyl methanesulfonate

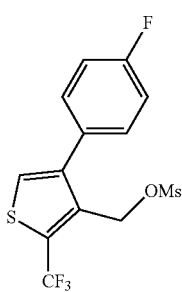 [SMILES: CS(=O)(=O)OCc1c(-c2ccc(F)cc2)csc1C(F)(F)F]

The title compound was prepared according to the procedure described in Example 183 by Suzuki coupling of ethyl 4-[(trifluoromethane) sulfonyloxy]-2-(trifluoromethyl)thiophene-3-carboxylate and 4-fluoroboronic acid followed by synthetic steps to give the desire product as a yellow oil.

Step 2: 3-(4-((4-(4-fluorophenyl)-2-(trifluoromethyl)thiophen-3-yl)methoxy)-2,3-dimethylphenyl)propanoic Acid

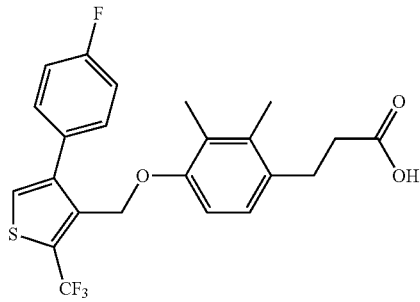 [SMILES: Cc1c(CCC(=O)O)ccc(OCc2c(-c3ccc(F)cc3)csc2C(F)(F)F)c1C]

The title compound was prepared according to the procedure described in Example 183 by coupling of [4-(4-fluorophenyl)-2-(trifluoromethyl)thiophen-3-yl]methyl methanesulfonate and ethyl 3-(2,3-dimethyl-4-hydroxyphenyl)propanoate followed by hydrolysis of ethyl 3-(4-((4-(4-fluoro-phenyl)-2-(trifluoromethyl)thiophen-3-yl)methoxy)-2,3-dimethylphenyl) propanoate to afford the desired product as an off-white solid. $^1$H NMR (400 MHz, CDCl$_3$) δ 7.44 (m, 2H), 7.37 (s, 1H), 7.08 (t, J=8.0 Hz, 2H), 6.95 (d, J=7.0 Hz, 1H), 6.62 (d, J=7.0 Hz, 1H), 4.88 (s, 2H), 2.95 (t, J=6.8 Hz, 2H), 2.62 (t, J=6.8 Hz, 2H), 2.22 (s, 3H), 2.08 (s, 3H).

Example 192

3-(4-((4-(2,3-dihydrobenzofuran-5-yl)-2-(trifluoromethyl)thiophen-3-yl)methoxy)-3,5-difluorophenyl)propanoic Acid, Cpd 51

Step 1: (4-(2,3-dihydrobenzofuran-5-yl)-2-(trifluoromethyl)thiophen-3-yl)methyl methanesulfonate

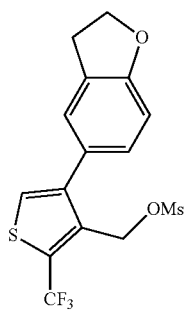 [SMILES: CS(=O)(=O)OCc1c(-c2ccc3c(c2)CCO3)csc1C(F)(F)F]

The title compound was prepared according to the procedure described in Example 183 by Suzuki coupling of ethyl 4-[(trifluoromethane) sulfonyloxy]-2-(trifluoromethyl)thiophene-3-carboxylate and (2,3-dihydrobenzofuran-5-yl) boronic acid followed by synthetic steps to give the desire product as a yellow oil.

Step 2: 3-(4-((4-(2,3-dihydrobenzofuran-5-yl)-2-(trifluoromethyl)thiophen-3-yl)methoxy)-3,5-difluorophenyl)propanoic Acid

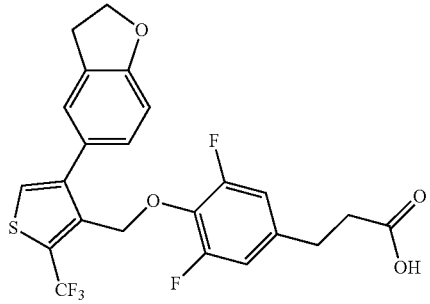 [SMILES: O=C(O)CCc1cc(F)c(OCc2c(-c3ccc4c(c3)CCO4)csc2C(F)(F)F)c(F)c1]

The title compound was prepared according to the procedure described in Example 183 by coupling of (4-(2,3-dihydrobenzofuran-5-yl)-2-(trifluoromethyl)thiophen-3-yl) methyl methanesulfonate and ethyl 3-(2,6-difluoro-4-hydroxyphenyl)propanoate followed by hydrolysis of ethyl 3-(4-((4-(2,3-dihydrobenzofuran-5-yl)-2-(trifluoromethyl)thiophen-3-yl)methoxy)-3,5-difluorophenyl) propanoate to afford the desired product as an off-white solid. $^1$H NMR (400 MHz, CDCl$_3$) δ 7.45 (s, 1H), 7.32 (s, 1H), 7.22 (s, 1H), 6.81 (d, J=7.0 Hz, 1H), 6.75 (d, J=7.5 Hz, 2H), 5.05 (s, 2H), 4.62 (t, J=8.0 Hz, 2H), 3.25 (t, J=7.8 Hz, 2H), 2.90 (t, J=7.8 Hz, 2H), 2.66 (t, J=8.0 Hz, 2H). LCMS (ESI, M/Z) for C$_{23}$H$_{17}$F$_5$O$_4$S: 485.1 (MH$^+$).

Example 193

3-(4-((4-(benzo[d][1,3]dioxol-5-yl)-2-(trifluoromethyl)thiophen-3-yl)methoxy)-3,5-difluorophenyl)propanoic Acid, Cpd 44

Step 1: (4-(benzo[d][1,3]dioxol-5-yl)-2-(trifluoromethyl)thiophen-3-yl)methyl methanesulfonate

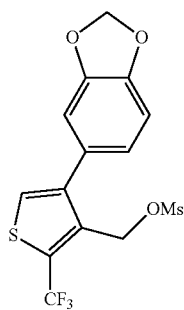 [SMILES: CS(=O)(=O)OCc1c(-c2ccc3c(c2)OCO3)csc1C(F)(F)F]

The title compound was prepared according to the procedure described in Example 183 by Suzuki coupling of ethyl 4-[(trifluoromethane) sulfonyloxy]-2-(trifluoromethyl)thiophene-3-carboxylate and (benzo[d][1,3]dioxol-5-yl)boronic acid followed by synthetic steps to give the desire product as a yellow oil.

Step 2: 3-(4-((4-(benzo[d][1,3]dioxol-5-yl)-2-(trifluoromethyl)thiophen-3-yl)methoxy)-3,5-difluorophenyl)propanoic Acid

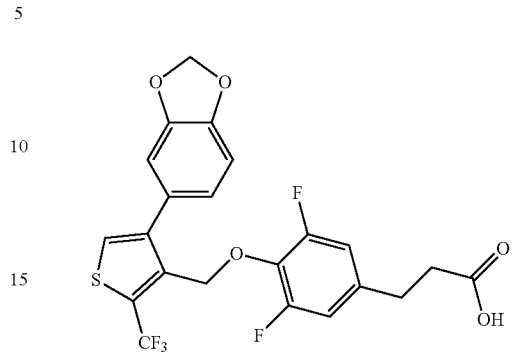

The title compound was prepared according to the procedure described in Example 183 by coupling of (4-(benzo[d][1,3]dioxol-5-yl)-2-(trifluoromethyl)thiophen-3-yl) methyl methanesulfonate and ethyl 3-(2,6-difluoro-4-hydroxyphenyl)propanoate followed by hydrolysis of ethyl 3-(4-((4-(benzo[d][1,3]dioxol-5-yl)-2-(trifluoromethyl)thiophen-3-yl)methoxy)-3,5-difluorophenyl) propanoate to afford the desired product as an off-white solid. $^1$H NMR (400 MHz, CDCl$_3$) 7.35 (s, 1H), 7.10 (s, 1H), 7.05 (d, J=7.5 Hz, 1H), 6.85 (d, J=7.5 Hz, 1H), 6.75 (d, J=7.8 Hz, 2H), 6.02 (s, 2H), 5.05 (s, 2H), 2.86 (t, J=7.5 Hz, 2H), 2.65 (t, J=8.0 Hz, 2H). LCMS (ESI, M/Z) for C$_{22}$H$_{15}$F$_5$O$_5$S: 487.1 (MH$^+$).

Example 194

3-(3,5-difluoro-4-((4-(6-methylpyridin-3-yl)-2-(trifluoromethyl)thiophen-3-yl)methoxy)phenyl)propanoic Acid, Cpd 62

Step 1: (4-(6-methylpyridin-3-yl)-2-(trifluoromethyl)thiophen-3-yl)methyl methanesulfonate

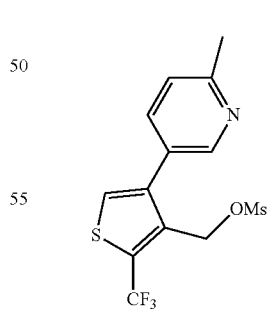

The title compound was prepared according to the procedure described in Example 183 by Suzuki coupling of ethyl 4-[(trifluoromethane) sulfonyloxy]-2-(trifluoromethyl)thiophene-3-carboxylate and (6-methylpyridin-3-yl)boronic acid followed by synthetic steps to give the desire product as a yellow oil.

211

Step 2: 3-(3,5-difluoro-4-((4-(6-methylpyridin-3-yl)-2-(trifluoromethyl)thiophen-3-yl)methoxy)phenyl)propanoic Acid

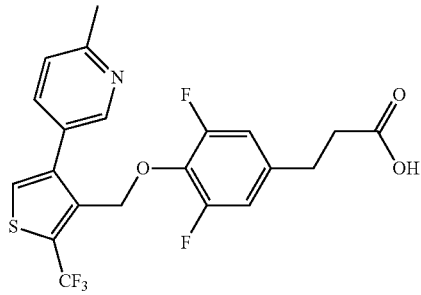 [SMILES: Cc1ccc(-c2csc(C(F)(F)F)c2COc2c(F)cc(CCC(=O)O)cc2F)cn1]

The title compound was prepared according to the procedure described in Example 182 by coupling of (4-(6-methylpyridin-3-yl)-2-(trifluoromethyl)thiophen-3-yl)methyl methanesulfonate and ethyl 3-(2,6-difluoro-4-hydroxyphenyl)propanoate followed by hydrolysis of ethyl 3-(3,5-difluoro-4-((4-(6-methylpyridin-3-yl)-2-(trifluoromethyl)thiophen-3-yl)methoxy)phenyl) propanoate to afford the desired product as an off-white solid. $^1$H NMR (400 MHz, CDCl$_3$) δ 8.85 (s, 1H), 8.52 (d, J=7.5 Hz, 1H), 8.02 (s, 1H), 7.86 (d, J=7.0 Hz, 1H), 6.88 (d, J=7.0 Hz, 2H), 5.15 (s, 2H), 3.35 (s, 3H), 2.88 (t, J=6.8, 2H), 2.58 (t, J=6.9 Hz, 2H).

Example 195

3-(3,5-difluoro-4-((4-(6-methoxypyridin-3-yl)-2-(trifluoromethyl)thiophen-3-yl)methoxy)phenyl)propanoic Acid, Cpd 42

Step 1: (4-(6-methoxypyridin-3-yl)-2-(trifluoromethyl)thiophen-3-yl)methyl methanesulfonate

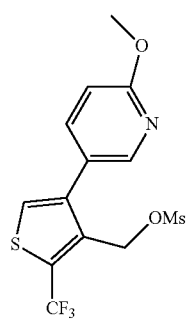 [SMILES: COc1ccc(-c2csc(C(F)(F)F)c2COS(C)(=O)=O)cn1]

The title compound was prepared according to the procedure described in Example 183 by Suzuki coupling of ethyl 4-[(trifluoromethane) sulfonyloxy]-2-(trifluoromethyl)thiophene-3-carboxylate and (6-methoxypyridin-3-yl)boronic acid followed by synthetic steps to give the desire product as a yellow oil.

212

Step 2: 3-(3,5-difluoro-4-((4-(6-methoxypyridin-3-yl)-2-(trifluoromethyl)thiophen-3-yl)methoxy)phenyl)propanoic Acid

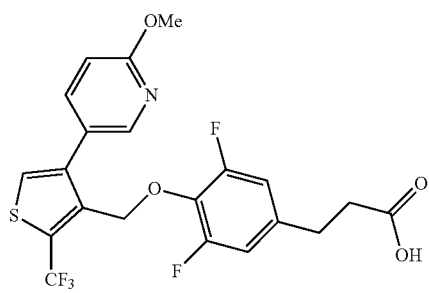 [SMILES: COc1ccc(-c2csc(C(F)(F)F)c2COc2c(F)cc(CCC(=O)O)cc2F)cn1]

The title compound was prepared according to the procedure described in Example 183 by coupling of (4-(6-methoxypyridin-3-yl)-2-(trifluoromethyl)thiophen-3-yl)methyl methanesulfonate and ethyl 3-(2,6-difluoro-4-hydroxyphenyl)propanoate followed by hydrolysis of ethyl 3-(3,5-difluoro-4-((4-(6-methoxypyridin-3-yl)-2-(trifluoromethyl)thiophen-3-yl)methoxy)phenyl) propanoate to afford the desired product as an off-white solid. $^1$H NMR (400 MHz, DMSO-d$_6$) δ 8.21 (s, 1H), 7.98 (s, 1H), 7.82 (d, J=7.5 Hz, 1H), 6.97 (d, J=7.5 Hz, 2H), 6.88 (d, J=7.0 Hz, 1H), 5.10 (s, 2H), 3.90 (s, 3H), 2.72 (t, J=7.5 Hz, 2H), 2.58 (t, J=6.8 Hz, 2H). LCMS (ESI, M/Z) for C$_{21}$H$_{16}$F$_5$NO$_4$S: 474.1 (MH$^+$).

Example 196

3-(4-((4-(cyclopent-1-en-1-yl)-2-(trifluoromethyl)thiophen-3-yl)methoxy)-3,5-difluorophenyl)propanoic Acid, Cpd 31

Step 1: (4-(cyclopent-1-en-1-yl)-2-(trifluoromethyl)thiophen-3-yl)methyl methanesulfonate

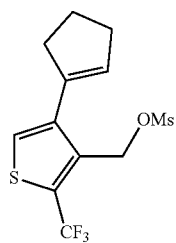 [SMILES: CS(=O)(=O)OCc1c(C2=CCCC2)csc1C(F)(F)F]

The title compound was prepared according to the procedure described in Example 183 by Suzuki coupling of ethyl 4-[(trifluoromethane) sulfonyloxy]-2-(trifluoromethyl)thiophene-3-carboxylate and 2-(cyclopent-1-en-1-yl)-4,4,5,5-tetramethyl-1,3,2-dioxaborolane followed by synthetic steps to give the desire product as a yellow oil.

Step 2: 3-(4-((4-(cyclopent-1-en-1-yl)-2-(trifluoromethyl)thiophen-3-yl)methoxy)-3,5-difluorophenyl) propanoic Acid

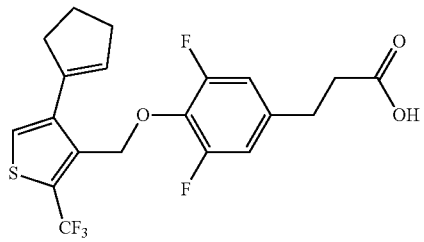 [SMILES: O=C(O)CCc1cc(F)c(OCc2c(C3=CCCC3)csc2C(F)(F)F)c(F)c1]

The title compound was prepared according to the procedure described in Example 183 by coupling of (4-(cyclopent-1-en-1-yl)-2-(trifluoromethyl)thiophen-3-yl)methyl methanesulfonate and ethyl 3-(2,6-difluoro-4-hydroxyphenyl)propanoate followed by hydrolysis of ethyl 3-(4-((4-(cyclopent-1-en-1-yl)-2-(trifluoromethyl)thiophen-3-yl)methoxy)-3,5-difluorophenyl)propanoate to afford the desired product as an off-white solid. $^1$H NMR (400 MHz, CDCl$_3$) δ 6.76 (d, J=7.8 Hz, 2H), 6.27 (m, 1H), 5.18 (s, 2H), 2.81 (t, J=7.5 Hz, 2H), 2.70 (m, 4H), 2.61 (m, J=7.0 Hz, 2H), 1.98 (m, 2H).

Example 197

3-(4-[[5-chloro-3-(4-chlorophenyl)thiophen-2-yl]methoxy]-3,5-difluorophenyl)propanoic Acid, Cpd 10

Step 1: 3-(4-chlorophenyl)thiophene-2-carbaldehyde

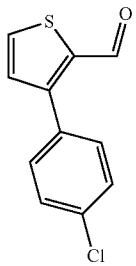 [SMILES: O=Cc1sccc1-c1ccc(Cl)cc1]

Into a 500-mL 3-necked round-bottom flask purged and maintained with an inert atmosphere of nitrogen, was placed 3-bromothiophene-2-carbaldehyde (10 g, 52.34 mmol, 1.00 equiv), ethylene glycol dimethyl ether (120 mL), (4-chlorophenyl)boronic acid (9 g, 57.55 mmol, 1.10 equiv), Pd(PPh$_3$)$_4$ (3 g, 2.60 mmol, 0.05 equiv), sodium carbonate (16.4 g, 154.73 mmol, 2.96 equiv), water (40 mL). The resulting solution was heated to reflux for 4 h. The resulting solution was extracted with 3×100 mL of ethyl acetate and the organic layers combined. The resulting mixture was washed with 3×200 mL of brine. The resulting mixture was concentrated under vacuum. The residue was applied onto a silica gel column with PE/EA (30/1). This resulted in 12 g (93%) of 3-(4-chlorophenyl)thiophene-2-carbaldehyde as a light yellow solid.

Step 2: [3-(4-chlorophenyl)thiophen-2-yl]methanol

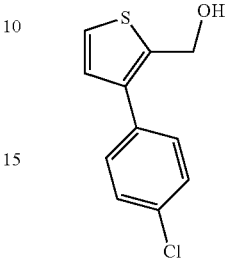

Into a 250-mL round-bottom flask, was placed a solution of 3-(4-chlorophenyl) thiophene-2-carbaldehyde (5.5 g, 24.70 mmol, 1.00 equiv) in tetrahydrofuran (50 ml). This was followed by the addition of LAH (470 mg, 12.38 mmol, 1.00 equiv) in several batches at −10° C. The resulting solution was stirred for 30 min at −10° C. The reaction was then quenched by the addition of 5 g of sodium sulfate.10H$_2$O. The solids were filtered out. The resulting mixture was concentrated under vacuum. The residue was applied onto a silica gel column with PE/EA (30/1-1/1). This resulted in 5 g (81%) of [3-(4-chlorophenyl)thiophen-2-yl]methanol as a white solid.

Step 3: [5-chloro-3-(4-chlorophenyl)thiophen-2-yl]methanol

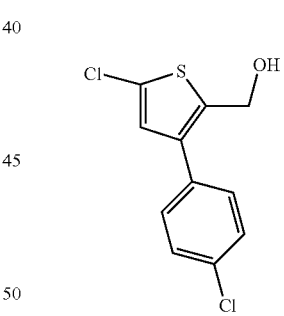

Into a 50-mL round-bottom flask, was placed [3-(4-chlorophenyl)thiophen-2-yl]methanol (500 mg, 2.23 mmol, 1.00 equiv), N,N-dimethylformamide (10 mL), NCS (300 mg, 2.25 mmol, 1.01 equiv). The resulting solution was stirred for 2 h at 25° C. The reaction was then quenched by the addition of 20 ml of water. The resulting solution was extracted with 2×20 mL of ethyl acetate and the organic layers combined. The resulting mixture was washed with 3×50 mL of brine. The resulting mixture was concentrated under vacuum. The residue was applied onto a silica gel column with PE/EA (30/1-10/1). This resulted in 350 mg (55%) of [5-chloro-3-(4-chlorophenyl)thiophen-2-yl]methanol as a white solid.

Step 4: Ethyl 3-(4-[[5-chloro-3-(4-chlorophenyl)thiophen-2-yl]methoxy]-3,5-difluorophenyl)propanoate

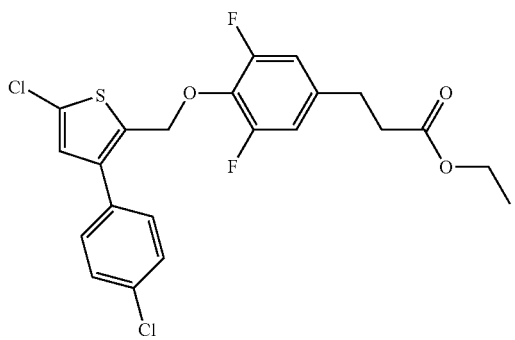 [SMILES: CCOC(=O)CCc1cc(F)c(OCc2sc(Cl)cc2-c2ccc(Cl)cc2)c(F)c1]

Into a 50-mL round-bottom flask, was placed [5-chloro-3-(4-chlorophenyl)thiophen-2-yl]methanol (300 mg, 1.16 mmol, 1.00 equiv), ethyl 3-(3,5-difluoro-4-hydroxyphenyl)propanoate (532 mg, 2.31 mmol, 2.00 equiv), tol (10 mL), ADDP (579 mg, 2.31 mmol, 2.00 equiv), n-Bu$_3$P (467 mg). The resulting solution was stirred for 4 h at 60° C. The resulting mixture was concentrated under vacuum. The residue was applied onto a silica gel column with PE/EA (30/1-10/1). This resulted in 500 mg (crude) of ethyl 3-(4-[[5-chloro-3-(4-chlorophenyl)thiophen-2-yl]methoxy]-3,5-difluorophenyl)propanoate as yellow oil.

Step 5: 3-(4-[[5-chloro-3-(4-chlorophenyl)thiophen-2-yl]methoxy]-3,5-difluorophenyl)propanoic Acid

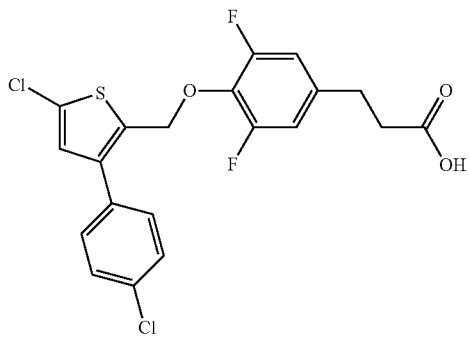 [SMILES: O=C(O)CCc1cc(F)c(OCc2sc(Cl)cc2-c2ccc(Cl)cc2)c(F)c1]

The title compound was prepared according to the procedure described in Example 183 Step 7 by hydrolysis of ethyl 3-(4-[[5-chloro-3-(4-chlorophenyl)thiophen-2-yl]methoxy]-3,5-difluoro phenyl) propanoate to afford the desired product as an off-white solid. $^1$H NMR: (300 MHz, CD$_3$OD, ppm) δ7.36 (s, 4H), 7.02 (s, 1H), 6.82 (d, J=12.0 Hz, 2H), 5.07 (s, 2H), 2.830 (t, J=8.5 Hz, 2H), 2.56 (t, J=8.5 Hz, 2H). Mass spectrum (ESI, m/z): Calcd. for C$_{20}$H$_{14}$Cl$_2$F$_2$O$_3$S, 441.0 (M−H), found 441.0.

Example 198

3-(4-[[5-chloro-3-(4-chlorophenyl)thiophen-2-yl]methoxy]-2,3-dimethylphenyl) Propanoic Acid, Cpd 6

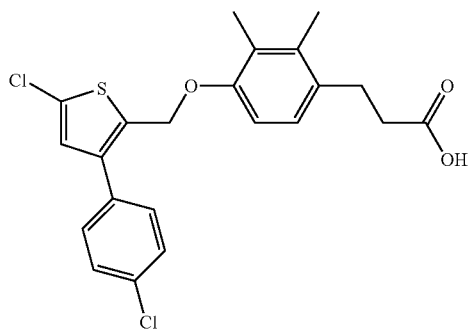 [SMILES: Cc1c(CCC(=O)O)ccc(OCc2sc(Cl)cc2-c2ccc(Cl)cc2)c1C]

The title compound was prepared according to the procedure described in Example 197 by coupling of [5-chloro-3-(4-chlorophenyl)thiophen-2-yl]methanol and ethyl 3-(4-hydroxy-2,3-dimethylphenyl)propanoate followed by hydrolysis of ethyl 3-(4-((5-chloro-3-(4-chlorophenyl)thiophen-2-yl)methoxy)-2,3-dimethylphenyl)propanoate to afford the desired product as an off-white solid. $^1$H NMR (300 MHz, CD3OD) δ 7.40 (s, 4H), 7.03 (s, 1H), 6.89 (d, J=8.4 Hz, 1H), 6.59 (d, J=8.4 Hz, 1H), 5.04 (s, 2H), 2.85 (t, J=5.1 Hz, 2H), 2.46 (t, J=5.1 Hz, 2H), 2.11 (s, 3H), 2.00 (s, 3H). Mass spectrum (ESI, m/z): Calcd. for C$_{22}$H$_{20}$Cl$_2$O$_3$S, 433.1 (M−H), found 433.1.

Example 199

3-(4-[[5-chloro-3-(4-chlorophenyl)thiophen-2-yl]methoxy]-2,3-difluorophenyl)propanoic Acid, Cpd 28

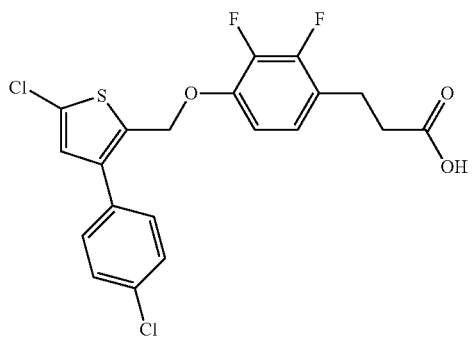 [SMILES: O=C(O)CCc1ccc(OCc2sc(Cl)cc2-c2ccc(Cl)cc2)c(F)c1F]

The title compound was prepared according to the procedure described in Example 197 by coupling of [5-chloro-3-(4-chlorophenyl)thiophen-2-yl]methanol and ethyl 3-(4-hydroxy-2,3-difluorophenyl)propanoate followed by hydrolysis of ethyl 3-(4-((5-chloro-3-(4-chlorophenyl)thiophen-2-yl)methoxy)-2,3-difluorophenyl)propanoate to afford the desired product as an off-white solid. $^1$H NMR (300 MHz, CD3OD) δ: 7.36-7.48 (m, 4H), 7.13 (s, 1H), 6.87-6.93 (m, 1H), 6.66-6.67 (m, 1H), 5.07 (s, 2H), 2.87 (t, J=7.5 Hz, 2H), 2.53 (t, J=7.8 Hz, 2H). Mass spectrum (ESI, m/z): Calcd. for $C_{20}H_{14}Cl_2F_2O_3S$, 441.0 (M−H), found 441.0.

Example 200

3-(4-[[5-chloro-3-(4-ethylphenyl)thiophen-2-yl]methoxy]-2,3-difluorophenyl)propanoic Acid, Cpd 11

Step 1: (5-chloro-3-(4-ethylphenyl)thiophen-2-yl)methanol

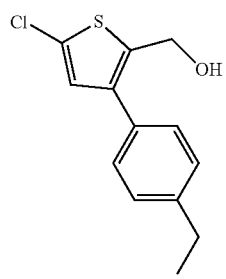 [SMILES: CCc1ccc(-c2cc(Cl)sc2CO)cc1]

The title compound was prepared according to the procedure described in Example 197 by Suzuki coupling of 3-bromothiophene-2-carbaldehyde (10 g, 52.34 mmol, 1.00 equiv), and (4-ethylphenyl)boronic acid followed by synthetic steps to afford the desired product as an off-white oil.

Step 2: 3-(4-[[5-chloro-3-(4-ethylphenyl)thiophen-2-yl]methoxy]-2,3-difluorophenyl)propanoic Acid

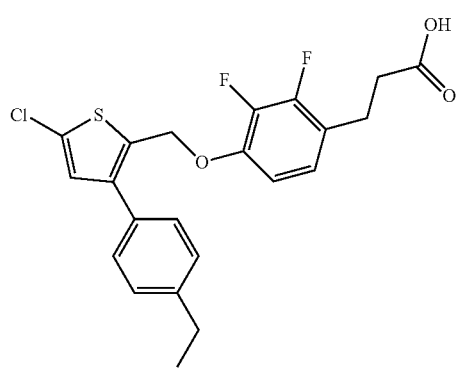 [SMILES: CCc1ccc(-c2cc(Cl)sc2COc2ccc(CCC(=O)O)c(F)c2F)cc1]

The title compound was prepared according to the procedure described in Example 196 by coupling of [5-chloro-3-(4-ethylphenyl)thiophen-2-yl]methanol and ethyl 3-(4-hydroxy-2,3-difluorophenyl)propanoate followed by hydrolysis of ethyl 3-(4-((5-chloro-3-(4-chlorophenyl)thiophen-2-yl)methoxy)-2,3-difluorophenyl)propanoate to afford the desired product as an off-white solid. $^1$H NMR (400 MHz, CDCl$_3$) 7.26-7.33 (m, 4H), 6.95 (s, 2H), 6.85 (t, J=8.8 Hz, 2H), 6.59-6.64 (t, J=8.4 Hz, 1H), 6.62 (t, J=8.4 Hz, 1H), 5.13 (s, 2H), 2.96 (t, J=7.8 Hz, 2H), 2.67-2.74 (m, 4H), 1.29 (t, J=7.6 Hz, 3H). Mass spectrum (ESI, m/z): Calcd. for $C_{22}H_{19}ClF_2O_3S$, 435.1 (M−H), found 435.1.

Example 201

3-(4-((5-chloro-3-(4-ethylphenyl)thiophen-2-yl)methoxy)-3,5-difluorophenyl)propanoic Acid, Cpd 8

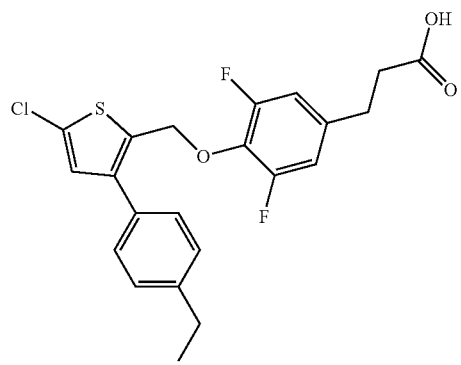 [SMILES: CCc1ccc(-c2cc(Cl)sc2COc2c(F)cc(CCC(=O)O)cc2F)cc1]

The title compound was prepared according to the procedure described in Example 197 by coupling of [5-chloro-3-(4-ethylphenyl)thiophen-2-yl]methanol and ethyl 3-(4-hydroxy-2,3-difluorophenyl)propanoate followed by hydrolysis of ethyl 3-(4-((5-chloro-3-(4-chlorophenyl)thiophen-2-yl)methoxy)-2,6-difluorophenyl)propanoate to afford the desired product as an off-white solid. $^1$H-NMR (300 MHz, CD$_3$OD) δ 7.34 (d, J=8.1 Hz, 2H), 7.24 (d, J=8.1 Hz, 2H), 7.01 (s, 1H), 6.85 (d, J=9.3 Hz, 2H), 5.11 (s, 2H), 2.87 (t, J=7.2 Hz, 2H), 2.59-2.73 (m, 4H), 1.27 (t, J=7.8 Hz, 3H). Mass spectrum (ESI, m/z): Calcd. for $C_{22}H_{19}ClF_2O_3S$, 435.1 (M−H), found 435.1.

Example 202

3-(4-[[5-chloro-3-(4-ethylphenyl)thiophen-2-yl]methoxy]-2,3-dimethylphenyl)propanoic Acid, Cpd 5

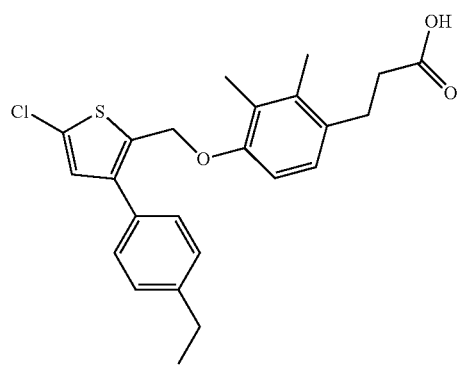 [SMILES: CCc1ccc(-c2cc(Cl)sc2COc2ccc(CCC(=O)O)c(C)c2C)cc1]

The title compound was prepared according to the procedure described in Example 197 by coupling of [5-chloro-3-(4-ethylphenyl)thiophen-2-yl]methanol and ethyl 3-(4-hydroxy-2,3-dimethylphenyl)propanoate followed by hydrolysis of ethyl 3-(4-((5-chloro-3-(4-chlorophenyl)thiophen-2-yl)methoxy)-2,3-dimethylphenyl)propanoate to afford the desired product as an off-white solid. $^1$H NMR (300 MHz, CD$_3$OD) δ7.32 (d, J=8.4 Hz, 2H), 7.26 (d, J=8.4 Hz, 2H), 7.02 (s, 2H), 6.91 (d, J=8.1 Hz, 2H), 6.61 (d, J=8.4

Hz, 2H), 5.07 (s, 2H), 2.89 (t, J=7.5 Hz, 2H), 2.64-2.71 (m, 2H), 2.49 (t, J=8.4 Hz, 2H), 2.28 (s, 3H), 2.16 (s, 3H), 1.28 (t, J=7.8 Hz, 3H). Mass spectrum (ESI, m/z): Calcd. for $C_{24}H_{25}ClO_3S$, 427.1 [M-H], found 427.1.

Example 203

3-(4-[[3-(4-chlorophenyl)-5-fluorothiophen-2-yl]methoxy]-3,5-difluorophenyl) Propanoic Acid, Cpd 7

Step 1: [5-bromo-3-(4-chlorophenyl)thiophen-2-yl]methanol

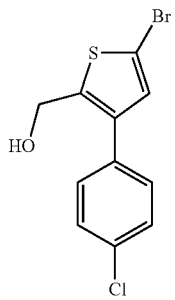

Into a 100-mL round-bottom flask, was placed [3-(4-chlorophenyl)thiophen-2-yl]methanol (3.6 g, 16.02 mmol, 1.00 equiv), N,N-dimethylformamide (20 mL). This was followed by the addition of NBS (2.85 g, 16.01 mmol, 1.00 equiv) portions at −5° C. The resulting solution was stirred for 2 h at room temperature (20 degree C.). The resulting solution was diluted with 100 mL of EA. The resulting mixture was washed with 3×30 mL of brine. The mixture was dried over anhydrous sodium sulfate. The solids were filtered out. The resulting mixture was concentrated under vacuum. The residue was applied onto a silica gel column with ethyl acetate/petroleum ether (1:5). This resulted in 4.8 g (99%) of [5-bromo-3-(4-chlorophenyl)thiophen-2-yl]methanol as a yellow solid.

Step 2: 2-[[5-bromo-3-(4-chlorophenyl)thiophen-2-yl]methoxy]oxane

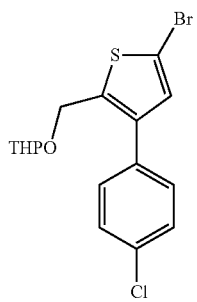

Into a 250-mL round-bottom flask, was placed [5-bromo-3-(4-chlorophenyl)thiophen-2-yl]methanol (4.8 g, 15.81 mmol, 1.00 equiv), dichloromethane (100 mL), PPTS (100 mg, 0.40 mmol, 0.03 equiv), 3,4-dihydro-2H-pyran (2.67 g, 31.74 mmol, 2.01 equiv). The resulting solution was stirred for 3 h at room temperature. The resulting mixture was concentrated under vacuum. The residue was applied onto a silica gel column with ethyl acetate/petroleum ether (1:5). This resulted in 5.0 g (82%) of 2-[[5-bromo-3-(4-chlorophenyl)thiophen-2-yl]methoxy]oxane as yellow oil.

Step 3: 2-1 [[13-(4-chlorophenyl)-5-fluorothiophen-2-yl]methoxy]oxane

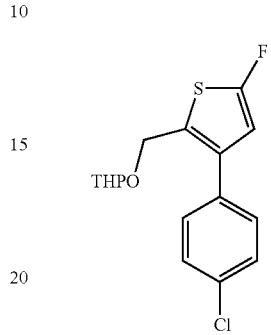

Into a 250-mL round-bottom flask purged and maintained with an inert atmosphere of nitrogen, was placed 2-[[5-bromo-3-(4-chlorophenyl)thiophen-2-yl]methoxy]oxane (2.0 g, 5.16 mmol, 1.00 equiv), tetrahydrofuran (100 mL). This was followed by the addition of BuLi (20.6 mL) at −78° C. The mixture was stirred for 1 h at −78° C. To this was added NFSI (8.1 g). The resulting solution was stirred overnight at room temperature (20° C.). The reaction was then quenched by the addition of 5 mL of water. The resulting mixture was concentrated under vacuum. The residue was applied onto a silica gel column with ethyl acetate/petroleum ether (1:3). This resulted in 1.4 g (83%) of 2-[[3-(4-chlorophenyl)-5-fluorothiophen-2-yl]methoxy]oxane as a yellow solid.

Step 4: [3-(4-chlorophenyl)-5-fluorothiophen-2-yl]methanol

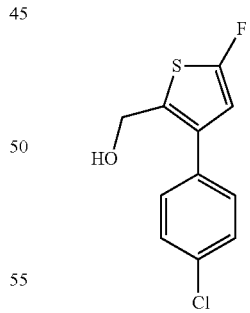

Into a 250-mL round-bottom flask, was placed 2-[[3-(4-chlorophenyl)-5-fluorothiophen-2-yl]methoxy]oxane (1.6 g, 4.90 mmol, 1.00 equiv), ethanol (100 mL), PPTS (120 mg, 0.48 mmol, 0.10 equiv). The resulting solution was stirred overnight at room temperature. The resulting mixture was concentrated under vacuum. The residue was applied onto a silica gel column with ethyl acetate/petroleum ether (1:2). This resulted in 0.7 g (59%) of [3-(4-chlorophenyl)-5-fluorothiophen-2-yl]methanol as yellow oil.

221

Step 5: Ethyl 3-(4-[[3-(4-chlorophenyl)-5-fluorothiophen-2-yl]methoxy]-3,5-difluorophenyl)propanoate

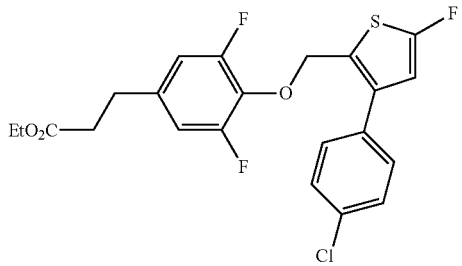 [SMILES: CCOC(=O)CCc1cc(F)c(OCc2sc(F)cc2-c2ccc(Cl)cc2)c(F)c1]

Into a 25-mL round-bottom flask purged and maintained with an inert atmosphere of nitrogen, was placed [3-(4-chlorophenyl)-5-fluorothiophen-2-yl]methanol (200 mg, 0.82 mmol, 1.00 equiv), toluene (10 mL), ADDP (437 mg, 1.75 mmol, 2.12 equiv), Bu₃P (250 mg), ethyl 3-(3,5-difluoro-4-hydroxyphenyl) propanoate (285 mg, 1.24 mmol, 1.50 equiv). The resulting solution was stirred overnight at 60° C. The resulting mixture was concentrated under vacuum. The residue was applied onto a silica gel column with ethyl acetate/petroleum ether (1:5). This resulted in 200 mg (53%) of ethyl 3-(4-[[3-(4-chlorophenyl)-5-fluorothiophen-2-yl]methoxy]-3,5-difluorophenyl)propanoate as a yellow solid.

Step 6: 3-(4-[[3-(4-chlorophenyl)-5-fluorothiophen-2-yl]methoxy]-3,5-difluorophenyl) propanoic Acid

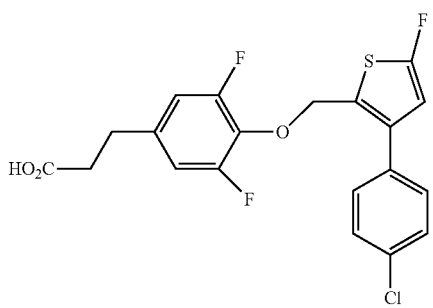 [SMILES: O=C(O)CCc1cc(F)c(OCc2sc(F)cc2-c2ccc(Cl)cc2)c(F)c1]

The title compound was prepared according to the procedure described in Example 197 Step 7 by hydrolysis of ethyl 3-(4-[[5-fluoro-3-(4-chlorophenyl)thiophen-2-yl]methoxy]-3,5-difluoro phenyl) propanoate to afford the desired product as an off-white solid. ¹H NMR (300 MHz, CD₃OD) δ 7.40-7.47 (m, 4H), 6.86 (d, J=9.3 Hz, 2H), 6.66 (s, 1H), 5.09 (s, 2H), 2.88 (t, J=7.5 Hz, 2H), 2.61 (t, J=7.5 Hz, 2H). Mass spectrum (ESI, m/z): Calcd. for $C_{20}H_{14}ClF_3O_3S$, 425.0 (M−H), found 425.0.

222

Example 204

3-(4-((3-(4-chlorophenyl)-5-fluorothiophen-2-yl)methoxy)-2,3-dimethylphenyl)propanoic Acid, Cpd 3

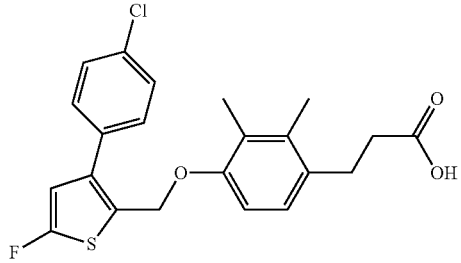 [SMILES: Cc1c(CCC(=O)O)ccc(OCc2sc(F)cc2-c2ccc(Cl)cc2)c1C]

The title compound was prepared according to the procedure described in Example 202 by coupling of [3-(4-chlorophenyl)-5-fluorothiophen-2-yl]methanol and ethyl 3-(4-hydroxy-2,3-dimethylphenyl)propanoate followed by hydrolysis of ethyl 3-(4-((5-fluoro-3-(4-chlorophenyl)thiophen-2-yl)methoxy)-2,3-dimethylphenyl)propanoate to afford the desired product as an off-white solid. ¹H NMR (400 MHz, CDCl₃) δ 7.38 (d, J=8.0 Hz, 2H), 7.30 (d, J=8.0 Hz, 2H), 6.95 (d, J=7.1 Hz, 1H), 6.62 (d, J=7.1 Hz, 1H), 6.51 (s, 1H), 4.98 (s, 2H), 2.97 (t, J=7.5 Hz, 2H), 2.68 (t, J=7.5 Hz, 2H), 2.28 (s, 3H), 2.21 (s, 3H). Mass spectrum (ESI, m/z): Calcd. for $C_{22}H_{20}ClFO_3S$, 417.1 (M−H), found 417.1.

Example 205

3-(4-[[3-(4-ethylphenyl)-5-fluorothiophen-2-yl]methoxy]-2,3-dimethylphenyl)propanoic Acid, Cpd 1

Step 1: [3-(4-ethylphenyl)-5-fluorothiophen-2-yl]methanol

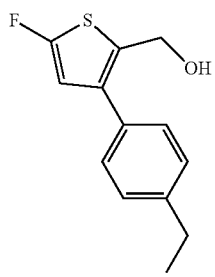 [SMILES: CCc1ccc(-c2cc(F)sc2CO)cc1]

The title compound was prepared according to the procedure described in Example 197 by Suzuki coupling of 3-bromothiophene-2-carbaldehyde and (4-ethylphenyl)boronic acid and followed by synthetic steps to afford the desired product as an off-yellow oil.

Step 2: 3-(4-[[3-(4-ethylphenyl)-5-fluorothiophen-2-yl]methoxy]-2,3-dimethylphenyl)propanoic Acid

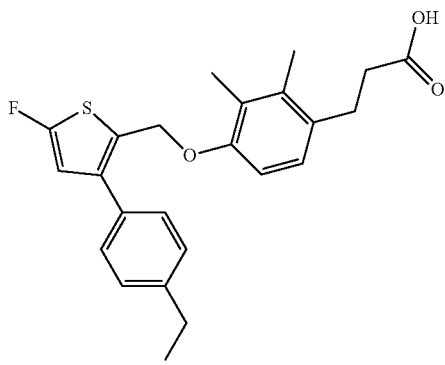 [SMILES: CCc1ccc(-c2cc(F)sc2COc2ccc(CCC(=O)O)c(C)c2C)cc1]

The title compound was prepared according to the procedure described in Example 196 by coupling of [3-(4-ethylphenyl)-5-fluorothiophen-2-yl]methanol and ethyl 3-(4-hydroxy-2,3-dimethylphenyl)propanoate followed by hydrolysis of ethyl 3-(4-((5-fluoro-3-(4-ehtylphenyl)thiophen-2-yl)methoxy)-2,3-dimethylphenyl)propanoate to afford the desired product as an off-white solid. $^1$H-NMR (300 MHz, CD$_3$OD) δ 7.34 (d, J=8.1 Hz, 2H), 7.26 (d, J=8.1 Hz, 2H), 6.92 (d, J=8.4 Hz, 2H), 6.62-6.64 (m, 2H), 5.05 (s, 2H), 2.89 (t, J=8.1 Hz, 2H), 2.65-2.72 (m, 2H), 2.49 (d, J=8.1 Hz, 2H), 2.24 (s, 3H), 2.21 (s, 3H), 1.29 (t, J=7.5 Hz, 3H). Mass spectrum (ESI, m/z): Calcd. for C$_{24}$H$_{25}$FO$_3$S, 411.2 (M−H), found 411.2.

Example 206

3-(4-[[3-(4-ethylphenyl)-5-fluorothiophen-2-yl]methoxy]-2,3-difluorophenyl)propanoic Acid, Cpd 12

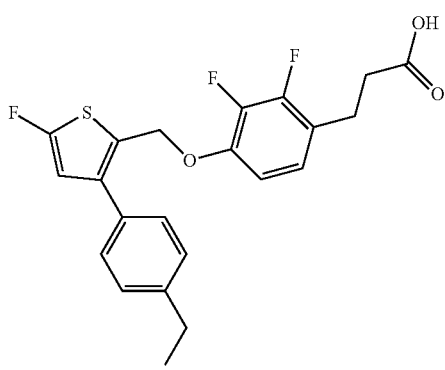 [SMILES: CCc1ccc(-c2cc(F)sc2COc2ccc(CCC(=O)O)c(F)c2F)cc1]

The title compound was prepared according to the procedure described in Example 205 by coupling of [3-(4-ethylphenyl)-5-fluorothiophen-2-yl]methanol and ethyl 3-(4-hydroxy-2,3-difluorophenyl)propanoate followed by hydrolysis of ethyl 3-(4-((5-fluoro-3-(4-ethylphenyl)thiophen-2-yl)methoxy)-2,3-difluorophenyl)propanoate to afford the desired product as an off-white solid. $^1$H NMR (300 MHz, CD$_3$OD) δ 7.25-7.35 (m, 2H), 6.93 (t, J=8.1 Hz, 1H), 6.73 (t, J=8.1 Hz, 1H), 6.65 (s, 1H), 5.13 (s, 2H), 2.92 (t, J=7.5 Hz, 2H), 2.57-2.72 (m, 4H), 1.26 (t, J=7.8 Hz, 3H). Mass spectrum (ESI, m/z): Calcd. for C$_{22}$H$_{19}$F$_3$O$_3$S, 419.1 (M−H), found 419.1.

Example 207

3-(4-((3-(4-ethylphenyl)-5-fluorothiophen-2-yl)methoxy)-3,5-difluorophenyl)propanoic Acid, Cpd 7

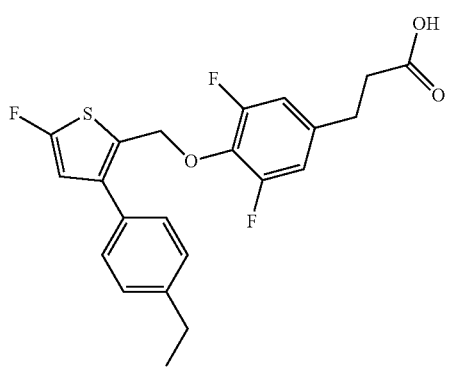 [SMILES: CCc1ccc(-c2cc(F)sc2COc2c(F)cc(CCC(=O)O)cc2F)cc1]

The title compound was prepared according to the procedure described in Example 205 by coupling of [3-(4-ethylphenyl)-5-fluorothiophen-2-yl]methanol and ethyl 3-(2,6-difluoro-4-hydroxyphenyl)propanoate followed by hydrolysis of ethyl 3-(4-((5-fluoro-3-(4-ethylphenyl)thiophen-2-yl)methoxy)-2,6-difluorophenyl)propanoate to afford the desired product as an off-white solid. $^1$H NMR (300 MHz, CD$_3$OD) δ 7.35 (d, J=7.5 Hz, 2H), 7.27 (t, J=8.1 Hz, 1H), 6.84-6.89 (m, 2H), 6.623 (s, 2H), 5.09 (s, 2H), 2.88 (t, J=7.5 Hz, 2H), 2.61-2.77 (m, 4H), 1.30 (t, J=7.8 Hz, 3H). Mass spectrum (ESI, m/z): Calcd. for C$_{22}$H$_{19}$F$_3$O$_3$S, 419.1 (M−H), found 4 19.1.

Example 208

3-(4-((3-(4-ethylphenyl)-5-methylthiophen-2-yl)methoxy)-3,5-difluorophenyl)propanoic Acid, Cpd 25

Step 1: methyl 5-methyl-3-((((trifluoromethyl)sulfonyl)oxy)thiophene-2-carboxylate

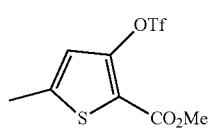

Into a 100-mL round-bottom flask, was placed methyl 3-hydroxy-5-methylthiophene-2-carboxylate (1.04 g, 5.74 mmol), dichloromethane (7 mL), pyridine (1.44 mL, 17.81 mmol). This was followed by the addition of Tf$_2$O (1.45 mL, 8.61 mmol) dropwise with stirring at 0° C. The resulting solution was stirred for 2.0 h at 0° C. in a water/ice bath. The reaction progress was monitored by GCMS. The reaction was then quenched by the addition of 10 mL of water. The resulting solution was extracted with 3×15 mL of dichloromethane and the organic layers combined. The resulting mixture was washed with 2×20 mL of sodium chloride. The mixture was dried over anhydrous sodium sulfate and concentrated under vacuum. The residue was applied onto a silica gel column with ethyl acetate/petroleum ether (1:9). This resulted in 1.74 g (99%) of methyl 5-methyl-3-(((trifluoro methyl)sulfonyl)oxy)thiophene-2-carboxylate as yellow oil.

Step 2: Methyl 3-(4-ethylphenyl)-5-methylthiophene-2-carboxylate

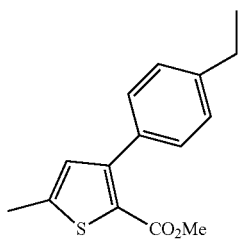

Into a 50-mL sealed tube (1 atm) purged and maintained with an inert atmosphere of nitrogen, was placed methyl 5-methyl-3-(((trifluoro methyl)sulfonyl)oxy)thiophene-2-carboxylate (1.7 g, 5.59 mmol), (4-ethylphenyl)boronic acid (1.0 g, 6.69 mmol), $K_3PO_4$ (3.84 g, 18.1 mmol), $Pd(PPh_3)_4$ (157 mg, 0.136 mmol), 1,4-dioxane (40 mL). The resulting solution was stirred overnight at 80° C. in an oil bath. The reaction progress was monitored by TLC/LCMS (ethyl acetate/petroleum ether=1:6). The solids were filtered out and washed by 20 mL ethyl acetate. Collected the organic phases and concentrated under vacuum. The residue was applied onto a silica gel column with ethyl acetate/petroleum ether (1:10). This resulted in 1.46 g (100%) of methyl 3-(4-ethylphenyl)-5-methylthiophene-2-carboxylate as light yellow oil.

Step 3: (3-(4-ethylphenyl)-5-methylthiophen-2-yl)methanol

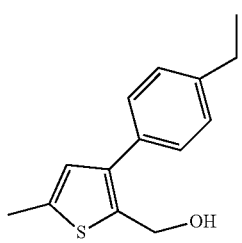 [SMILES: CCc1ccc(-c2cc(C)sc2CO)cc1]

Into a 100-mL 3-necked round-bottom flask (1 atm) purged and maintained with an inert atmosphere of nitrogen, was placed methyl 3-(4-ethylphenyl)-5-methylthiophene-2-carboxylate (1.5 g, 5.76 mmol), anhydrous ether (50 mL). This was followed by the addition of a solution of $LiAlH_4$ (1 M in THF, 7.9 mL, 7.86 mmol) in tetrahydrofuran dropwise with stirring at 0° C. The resulting solution was stirred for 2.0 h at 25° C. The reaction progress was monitored by LCMS/TLC (ethyl acetate/petroleum ether=1: 6). The reaction was then quenched by the addition of 10 mL of water and 5 mL of 2N HCl. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:4). This resulted in 1.26 g (94%) of (3-(4-ethylphenyl)-5-methylthiophen-2-yl)methanol as a white solid.

Step 4: 3-(4-((3-(4-ethylphenyl)-5-methylthiophen-2-yl)methoxy)-3,5-difluorophenyl)propanoic Acid

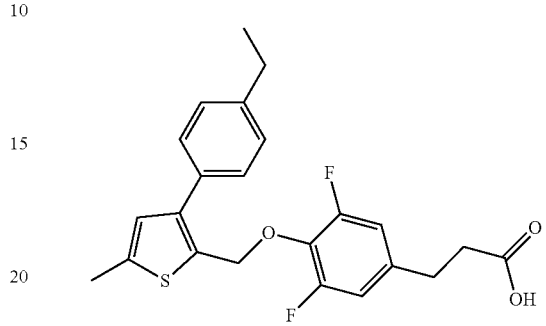

The title compound was prepared according to the procedure described in Example 196 step 7 by coupling of (3-(4-ethylphenyl)-5-methylthiophen-2-yl)methanol and ethyl 3-(4-hydroxy-3,5-difluoro phenyl)propanoate followed by hydrolysis of ethyl 3-(4-((3-(4-ethylphenyl)-5-methylthiophen-2-yl)methoxy)-3,5-difluorophenyl)propanoate to afford the desired product as an off-white solid. $^1$H NMR (400 MHz, $CDCl_3$) δ 7.38 (d, J=7.0 Hz, 2H), 7.21 (d, J=7.1 Hz, 2H), 6.88 (s, 1H), 6.75 (d, J=7.8 Hz, 2H), 5.10 (s, 2H), 2.85 (t, J=7.5 Hz, 2H), 2.65 (t, J=7.0 Hz, 2H), 2.45 (s, 3H), 2.01 (m, J=7.8 Hz, 2H), 1.25 (t, J=7.2 Hz, 3H).

Example 209

3-(4-((3-(4-ethylphenyl)-5-methylthiophen-2-yl) methoxy)-2,3-dimethylphenyl)propanoic Acid, Cpd 13

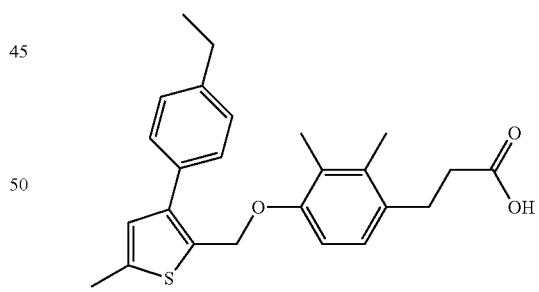

The title compound was prepared according to the procedure described in Example 207 by coupling of (3-(4-ethylphenyl)-5-methylthiophen-2-yl)methanol and ethyl 3-(4-hydroxy-2,3-dimethyl phenyl)propanoate followed by hydrolysis of ethyl 3-(4-((3-(4-ethylphenyl)-5-methylthiophen-2-yl)methoxy)-3,5-difluorophenyl)propanoate to afford the desired product as an off-white solid. $^1$H NMR (400 MHz, $CDCl_3$) δ 7.35 (d, J=7.5 Hz, 2H), 7.26 (s, 1H), 7.18 (d, J=7.5 Hz, 2H), 6.95 (d, J=7.0 Hz, 1H), 6.64 (d, J=7.1 Hz, 1H), 5.05 (s, 2H), 2.95 (t, J=6.5 Hz, 2H), 2.68 (m, J=7.5 Hz, 2H), 2.58 (t, J=6.2 Hz, 2H), 2.51 (s, 3H), 2.21 (s, 3H), 2.20 (s, 3H), 1.26 (t, J=8.0 Hz, 3H).

Example 210

3-(4-((3-(4-ethylphenyl)-5-methylthiophen-2-yl)methoxy)-2,3-difluorophenyl)propanoic Acid, Cpd 26

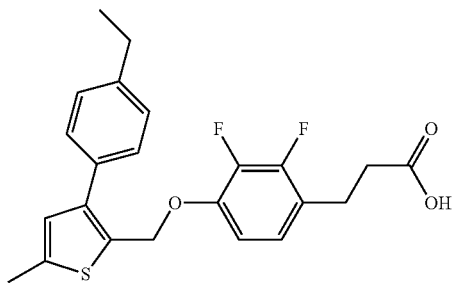 [SMILES: CCc1ccc(-c2cc(C)sc2COc2ccc(CCC(=O)O)c(F)c2F)cc1]

The title compound was prepared according to the procedure described in Example 208 by coupling of (3-(4-ethylphenyl)-5-methylthiophen-2-yl)methanol and ethyl 3-(4-hydroxy-2,3-difluoro phenyl)propanoate followed by hydrolysis of ethyl 3-(4-((3-(4-ethylphenyl)-5-methylthiophen-2-yl)methoxy)-2,3-difluorophenyl)propanoate to afford the desired product as an off-white solid. $^1$H NMR (400 MHz, CDCl$_3$) δ 7.55 (d, J=7.9 Hz, 2H), 7.30 (s, 1H), 7.25 (d, J=7.5 Hz, 2H), 7.02 (d, J=7.8 Hz, 1H), 6.68 (d, J=7.5 Hz, 1H), 5.10 (s, 2H), 2.98 (t, J=7.5 Hz, 2H), 2.71 (m, J=7.8 Hz, 2H), 2.68 (t, J=6.5 Hz, 2H), 2.55 (s, 3H), 1.36 (t, J=8.5 Hz, 3H).

Example 211

3-(4-((2-(4-ethylphenyl)thiophen-3-yl)methoxy)-2,3-difluorophenyl)propanoic Acid, Cpd 48

Step 1: 2-(4-ethylphenyl)thiophene-3-carboxylic Acid

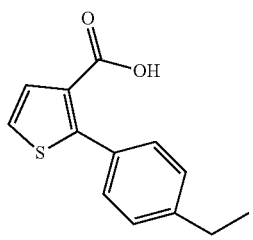 [SMILES: CCc1ccc(-c2sccc2C(=O)O)cc1]

Into a 50-mL sealed tube (1 atm) purged and maintained with an inert atmosphere of nitrogen, was placed 2-bromo-3-thiophenecarboxylic acid (3 g, 14.1 mmol), (4-ethylphenyl)boronic acid (2.28 g, 15.2 mmol), K$_2$CO$_3$ aqueous solution (35 mL, 2M, 70.2 mmol), Pd(PPh$_3$)$_4$ (496 mg, 0.429 mmol), IPA (30 mL) and toluene (30 mL). The resulting solution was stirred overnight at 80° C. in an oil bath. The reaction progress was monitored by TLC/LCMS (ethyl acetate/petroleum ether=1:6). The solids were filtered out and washed by 20 mL ethyl acetate. Collected the organic phases and concentrated under vacuum. The residue was applied onto a silica gel column with ethyl acetate/petroleum ether (1:10). This resulted in 2.33 g (71%) of 2-(4-ethylphenyl)thiophene-3-carboxylic acid as light yellow oil.

Step 2: (2-(4-ethylphenyl)thiophen-3-yl)methanol

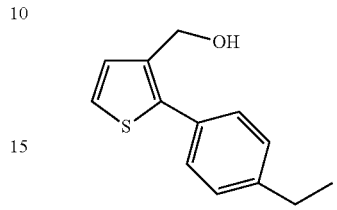

Into a 100-mL 3-necked round-bottom flask (1 atm) purged and maintained with an inert atmosphere of nitrogen, was placed 2-(4-ethylphenyl)thiophene-3-carboxylic acid (0.46 g, 1.98 mmol), anhydrous ether (18 mL). This was followed by the addition of a solution of LiAlH$_4$ (1 M in THF, 2.7 mL, 2.7 mmol) in tetrahydrofuran dropwise with stirring at 0° C. The resulting solution was stirred for 2.0 h at 25° C. The reaction progress was monitored by LCMS/TLC (ethyl acetate/petroleum ether=1:6). The reaction was then quenched by the addition of 10 mL of water and 5 mL of 2N HCl. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:4). This resulted in 0.46 g (100%) of (2-(4-ethylphenyl)thiophen-3-yl)methanol as a white oil.

Step 3: 3-(4-((2-(4-ethylphenyl)thiophen-3-yl)methoxy)-2,3-difluorophenyl)propanoic Acid

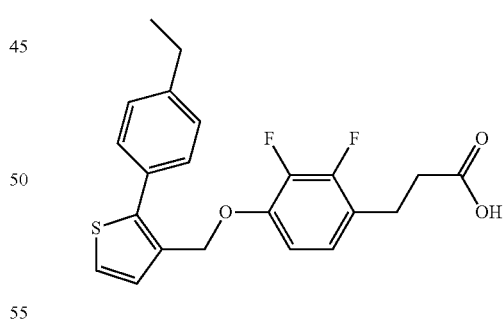

The title compound was prepared according to the procedure described in Example 208 by coupling of (2-(4-ethylphenyl)thiophen-3-yl)methanol and ethyl 3-(4-hydroxy-2,3-difluoro phenyl)propanoate followed by hydrolysis of ethyl 3-(4-((2-(4-ethylphenyl)thiophen-3-yl)methoxy)-2,3-difluorophenyl)propanoate to afford the desired product as an off-white solid. $^1$H NMR (400 MHz, CDCl$_3$) δ 7.40 (d, J=7.1 Hz, 2H), 7.25 (m, 4H), 6.82 (t, J=6.5 Hz, 1H), 6.66 (t, J=6.5 Hz, 1H), 5.10 (s, 2H), 2.95 (t, J=7.5 Hz, 2H), 2.65 (t, J=7.0 Hz, 2H), 1.31 (t, J=9.5 Hz, 3H). LCMS (ESI, M/Z) for C$_{22}$H$_{20}$F$_2$O$_3$S: 403.1 (MH$^+$).

Example 212

3-(4-((2-(4-ethylphenyl)thiophen-3-yl)methoxy)-3,5-difluorophenyl)propanoic Acid, Cpd 52

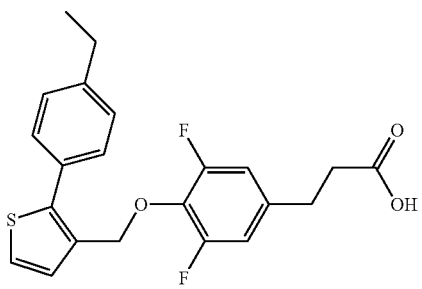 [SMILES: CCc1ccc(-c2sccc2COc2c(F)cc(CCC(=O)O)cc2F)cc1]

The title compound was prepared according to the procedure described in Example 207 by coupling of (2-(4-ethylphenyl)thiophen-3-yl)methanol and ethyl 3-(4-hydroxy-3,5-difluoro phenyl)propanoate followed by hydrolysis of ethyl 3-(4-((2-(4-ethylphenyl)thiophen-3-yl)methoxy)-3,5-difluorophenyl)propanoate to afford the desired product as an off-white solid. $^1$H NMR (400 MHz, CDCl$_3$) δ 7.49 (d, J=6.5 Hz, 2H), 7.28 (m, 3H), 7.20 (m, 1H), 6.76 (d, J=6.5 Hz, 2H), 5.05 (s, 2H), 2.88 (t, J=6.0 Hz, 2H), 2.70 (m, 2H), 2.62 (t, J=6.0 Hz, 2H), 1.25 (t, J=7.5 Hz, 3H).

Example 213

3-(4-((2-(4-ethylphenyl)thiophen-3-yl)methoxy)-2,3-dimethylphenyl)propanoic Acid, Cpd 49

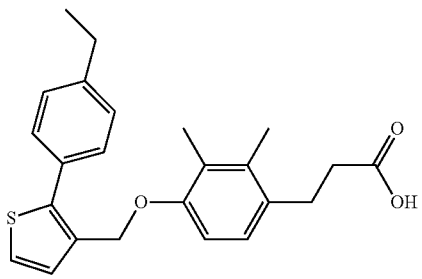 [SMILES: CCc1ccc(-c2sccc2COc2ccc(CCC(=O)O)c(C)c2C)cc1]

The title compound was prepared according to the procedure described in Example 207 by coupling of (2-(4-ethylphenyl)thiophen-3-yl)methanol and ethyl 3-(4-hydroxy-2,3-dimethyl phenyl)propanoate followed by hydrolysis of ethyl 3-(4-((2-(4-ethylphenyl)thiophen-3-yl)methoxy)-2,3-dimethylphenyl)propanoate to afford the desired product as an off-white solid. $^1$H NMR (400 MHz, CDCl$_3$) δ 7.42 (d, J=7.5 Hz, 2H), 7.24 (m, 4H), 6.95 (d, J=6.5 Hz, 1H), 6.65 (d, J=6.5 Hz, 1H), 4.98 (s, 2H), 2.96 (t, J=5.0 Hz, 2H), 2.70 (q, J=5.1 Hz, 2H), 2.62 (t, J=5.2 Hz, 2H), 2.28 (s, 3H), 2.22 (s, 3H), 1.26 (t, J=7.0 Hz, 3H).

Example 214

3-(4-((3-(4-ethylphenyl)-5-(trifluoromethyl)thiophen-2-yl)methoxy)-2,3-difluorophenyl)propanoic Acid, Cpd 21

Step 1: (3-(4-ethylphenyl)-5-(trifluoromethyl)thiophen-2-yl)methanol

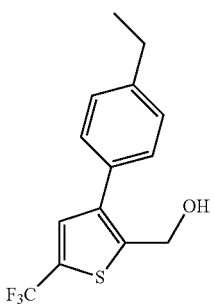 [SMILES: CCc1ccc(-c2cc(C(F)(F)F)sc2CO)cc1]

The title compound was prepared according to the procedure described in Example 208 starting from methyl 3-hydroxy-5-(trifluoromethyl)thiophene-2-carboxylate and by coupling of methyl 5-(trifluoromethyl)-3-(((trifluoromethyl)sulfonyl)oxy)thiophene-2-carboxylate and 4-ethylphenyl boronic acid followed by LAH reduction to afford the desired product as an off-white oil.

Step 2: 3-(4-((3-(4-ethylphenyl)-5-(trifluoromethyl)thiophen-2-yl)methoxy)-2,3-difluorophenyl)propanoic Acid

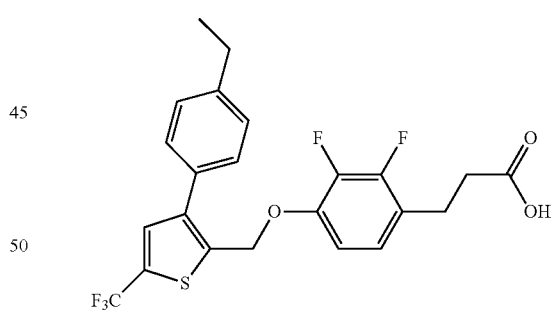

The title compound was prepared according to the procedure described in Example 207 by coupling of (3-(4-ethylphenyl)-5-(trifluoromethyl)thiophen-2-yl)methanol and ethyl 3-(4-hydroxy-2,3-difluoro phenyl)propanoate followed by hydrolysis of ethyl 3-(4-((3-(4-ethylphenyl)-5-(trifluoromethyl)thiophen-2-yl)methoxy)-2,3-difluorophenyl)propanoate to afford the desired product as an off-white solid.

$^1$H NMR (400 MHz, CDCl$_3$) δ 7.45 (s, 1H), 7.30 (m, 4H), 6.85 (t, J=5.6 Hz, 1H), 6.62 (t, J=5.5 Hz, 1H), 5.22 (s, 2H), 2.95 (t, J=6.5 Hz, 2H), 2.68 (m, 4H), 1.25 (t, J=7.5 Hz, 3H).

Example 215

3-(4-((3-(4-ethylphenyl)-5-(trifluoromethyl)thiophen-2-yl)methoxy)-2,3-dimethylphenyl)propanoic Acid, Cpd 246

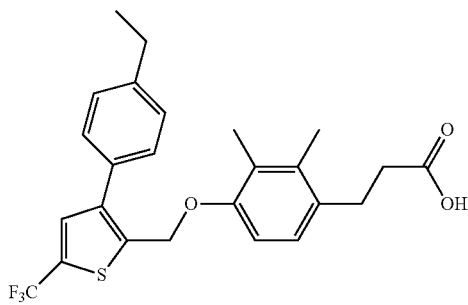 [SMILES: CCc1ccc(-c2cc(C(F)(F)F)sc2COc2ccc(CCC(=O)O)c(C)c2C)cc1]

The title compound was prepared according to the procedure described in Example 208 by coupling of (3-(4-ethylphenyl)-5-(trifluoromethyl)thiophen-2-yl)methanol and ethyl 3-(4-hydroxy-2,3-dimethyl phenyl)propanoate followed by hydrolysis of ethyl 3-(4-((3-(4-ethylphenyl)-5-(trifluoromethyl)thiophen-2-yl)methoxy)-2,3-dimethylphenyl)propanoate to afford the desired product as an off-white solid. $^1$H NMR (400 MHz, CDCl$_3$) δ 7.46 (s, 1H), 7.35 (d, J=6.0 Hz, 2H), 7.28 (d, J=6.0 Hz, 2H), 6.95 (d, J=5.3 Hz, 1H), 6.65 (d, J=5.3 Hz, 1H), 5.15 (s, 2H), 2.96 (t, J=5.5 Hz, 2H), 2.68 (q, J=5.5 Hz, 2H), 2.60 (t, J=6.0 Hz, 2H), 2.25 (s, 3H), 2.18 (s, 3H), 1.28 (t, J=7.0 Hz, 3H).

Example 216

3-(4-((3-(4-ethylphenyl)-5-(trifluoromethyl)thiophen-2-yl)methoxy)-3,5-difluorophenyl)propanoic Acid, Cpd 22

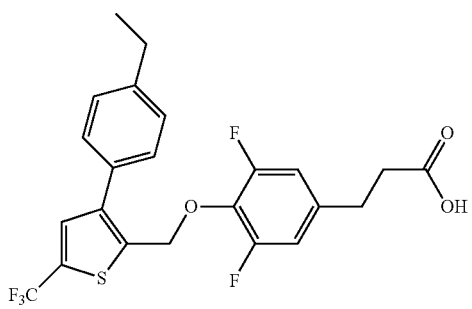 [SMILES: CCc1ccc(-c2cc(C(F)(F)F)sc2COc2c(F)cc(CCC(=O)O)cc2F)cc1]

The title compound was prepared according to the procedure described in Example 208 by coupling of (3-(4-ethylphenyl)-5-(trifluoromethyl)thiophen-2-yl)methanol and ethyl 3-(4-hydroxy-3,5-difluoro phenyl)propanoate followed by hydrolysis of ethyl 3-(4-((3-(4-ethylphenyl)-5-(trifluoromethyl)thiophen-2-yl)methoxy)-3,5-difluorophenyl)propanoate to afford the desired product as an off-white solid. $^1$H NMR (400 MHz, CDCl$_3$) δ 7.48 (s, 1H), 7.45 (d, J=7.5 Hz, 2H), 7.28 (d, J=7.6 Hz, 2H), 6.78 (d, J=7.9 Hz, 2H), 5.21 (s, 2H), 2.92 (t, J=5.1 Hz, 2H), 2.70 (m, 4H), 1.28 (t, J=8.2 Hz, 3H).

Example 217

3-(4-((4-(4-ethylphenyl)thiophen-3-yl)methoxy)-2,3-dimethylphenyl)propanoic Acid, Cpd 41

Step 1: 4-(4-ethylphenyl)thiophene-3-carbaldehyde

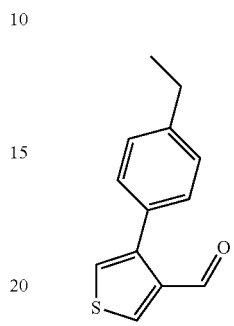

A mixture of 3-bromo-4-formylthiophene (0.62 g, 3.18 mmol) and 4-ethylphenylboronic acid (0.95 g, 6.36 mmol) in toluene (12 mL), EtOH (12 mL) and aqueous Na$_2$CO$_3$ solution (2 M, 3.18 mL, 6.36 mmol) in a seal tube was deoxygenated under reduced pressure and flushed with argon for 3 times, followed by addition of Pd(PPh$_3$)$_4$ (184 mg, 0.16 mmol) and deoxygenated again. The resulting solution was stirred at 128° C. in an oil bath for 5 hour. The reaction progress was monitored by TLC/LCMS (ethyl acetate/petroleum ether=1:6). The reaction was partitioned between ethyl acetate and water. Collected the organic phases and concentrated under vacuum. The residue was applied onto a silica gel column with ethyl acetate/petroleum ether (1:10). This resulted in 440 mg (64%) of 4-(4-ethylphenyl)thiophene-3-carbaldehyde as light yellow oil.

Step 2: (4-(4-ethylphenyl)thiophen-3-yl)methanol

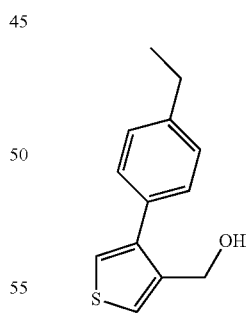

To a solution of 4-(4-ethylphenyl)thiophene-3-carbaldehyde (0.44 g, 2.03 mmol) in MeOH (5 mL) was added sodium borohydride (144 mg, 3.812 mmol) under argon at 0° C. The resulting mixture was stirred at room temperature for 2 h. The residue was extracted with EtOAc, dried over Na$_2$SO$_4$ and purification was conducted using CombiFlash (eluent: 10% EtOAc in heptane to 20% to 40) to afford the title product as a white solid (0.43 g, 97% yield).

Step 3: 3-(4-((4-(4-ethylphenyl)thiophen-3-yl)methoxy)-2,3-dimethylphenyl)propanoic Acid

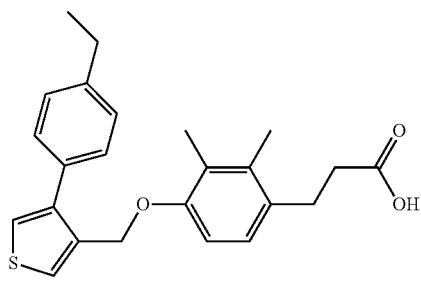 [SMILES: CCc1ccc(-c2cscc2COc2ccc(CCC(=O)O)c(C)c2C)cc1]

The title compound was prepared according to the procedure described in Example 208 step 6 and 7 by coupling of (4-(4-ethylphenyl)thiophen-3-yl)methanol and ethyl 3-(4-hydroxy-2,3-dimethyl phenyl) propanoate followed by hydrolysis of ethyl 3-(4-((3-(4-ethylphenyl)-5-(trifluoromethyl)thiophen-2-yl)methoxy)-2,3-dimethylphenyl)propanoate to afford the desired product as an off-white solid. $^1$H NMR (400 MHz, CDCl$_3$) δ 7.48 (m, 1H), 7.36 (d, J=7.0 Hz, 2H), 7.28 (s, 1H), 7.22 (d, J=7.0 Hz, 2H), 6.95 (d, J=6.5 Hz, 1H), 6.67 (d, J=6.5 Hz, 1H), 4.98 (s, 2H0, 2.94 (t, J=7.0 Hz, 2H), 2.70 (m, 2H), 2.60 (t, J=7.0 Hz, 2H), 2.24 (s, 3H), 2.20 (s, 3H), 1.28 (t, J=6.5 Hz, 3H).

Example 218

3-(4-((4-(4-ethylphenyl)thiophen-3-yl)methoxy)-2,3-difluorophenyl)propanoic Acid, Cpd 43

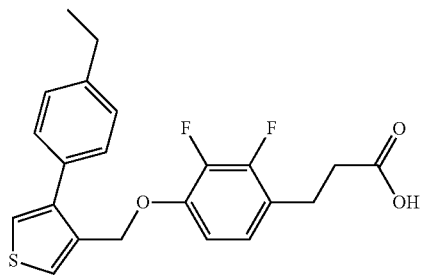 [SMILES: CCc1ccc(-c2cscc2COc2ccc(CCC(=O)O)c(F)c2F)cc1]

The title compound was prepared according to the procedure described in Example 216 by coupling of (4-(4-ethylphenyl)thiophen-3-yl)methanol and ethyl 3-(4-hydroxy-2,3-difluoro phenyl) propanoate followed by hydrolysis of ethyl 3-(4-((3-(4-ethylphenyl)-5-(trifluoromethyl)thiophen-2-yl)methoxy)-2,3-difluorophenyl)propanoate to afford the desired product as an off-white solid. $^1$H NMR (400 MHz, CDCl$_3$) δ 7.52 (s, 1H), 7.42 (m, 2H), 7.28 (m, 3H), 6.80 (m, 1H), 6.62 (m, 1H), 5.02 (s, 2H), 2.95 (t, J=5.5 Hz, 2H), 2.68 (m, 4H), 1.25 (t, J=6.5 Hz, 3H).

Example 219

3-(4-((4-(4-ethylphenyl)thiophen-3-yl)methoxy)-3,5-difluorophenyl)propanoic Acid, Cpd 53

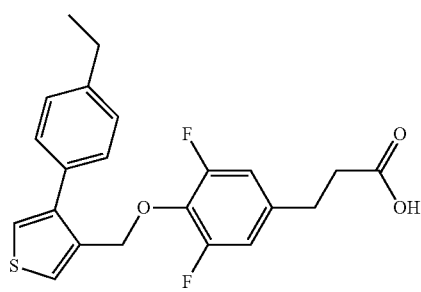 [SMILES: CCc1ccc(-c2cscc2COc2c(F)cc(CCC(=O)O)cc2F)cc1]

The title compound was prepared according to the procedure described in Example 217 by coupling of (4-(4-ethylphenyl)thiophen-3-yl)methanol and ethyl 3-(4-hydroxy-3,5-difluoro phenyl) propanoate followed by hydrolysis of ethyl 3-(4-((3-(4-ethylphenyl)-5-(trifluoromethyl)thiophen-2-yl)methoxy)-3,5-difluorophenyl)propanoate to afford the desired product as an off-white solid. $^1$H NMR (400 MHz, CDCl$_3$) δ 7.48 (m, 3H), 7.25 (d, J=7.0 Hz, 2H), 6.72 (d, J=6.5 Hz, 2H), 5.08 (s, 2H), 2.88 (t, J=5.5 Hz, 2H), 2.70 (m, 4H), 1.30 (t, J=6.8 Hz, 3H).

Example 220

3-(4-[[2-(4-ethylphenyl)-5-methyl-4-(trifluoromethyl)thiophen-3-yl]methoxy]-2,3-dimethylphenyl)propanoic Acid, Cpd 40

Step 1: 3-(acetylsulfanyl)-1,1,1-trifluorobutan-2-one

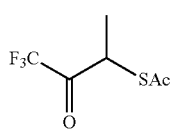

Into a 100-mL round-bottom flask, was placed 3-bromo-1, 1, 1-trifluorobutan-2-one (1 g, 4.88 mmol, 1.00 equiv), N,N-dimethylformamide (10 mL). This was followed by the addition of AcSK (0.55 g) in several batches at 0° C. The resulting solution was stirred overnight at 25° C. The resulting solution was diluted with 20 mL of H$_2$O. The resulting solution was extracted with 3×20 mL of ethyl acetate and the organic layers combined and washed by brine. Then it was dried over anhydrous Na$_2$SO$_4$, concentrated under vacuum. This resulted in 800 mg (crude) of 3-(acetylsulfanyl)-1, 1, 1-trifluorobutan-2-one as colorless oil. This resulted in 1 g (crude) of 3-(acetylsulfanyl)-1, 1, 1-trifluorobutan-2-one as colorless oil.

Step 2: Ethyl 2-amino-4-hydroxy-5-methyl-4-(trifluoromethyl)-4,5-dihydrothiophene-3-carboxylate

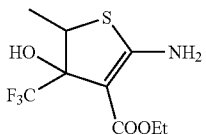 [SMILES: CCOC(=O)C1=C(N)SC(C)C1(O)C(F)(F)F]

Into a 100-mL round-bottom flask, was placed 3-(acetylsulfanyl)-1,1,1-trifluorobutan-2-one (5.8 g, 28.97 mmol, 1.00 equiv), N,N-dimethylformamide (10 mL). This was followed by the addition of TEA (3 g, 29.65 mmol, 1.02 equiv) and ethyl 2-cyanoacetate (3.27 g, 28.91 mmol, 1.00 equiv) dropwise with stirring at 0° C. The resulting solution was stirred overnight at 25° C. Then it was diluted with 20 mL of EA. The organic phase was separated and washed with 3×20 mL of H$_2$O. The mixture was dried over anhydrous sodium sulfate. The solids were filtered out. The resulting mixture was concentrated under vacuum. The residue was applied onto a silica gel column with ethyl acetate/petroleum ether (30/70). The collected fractions were combined and concentrated under vacuum. This resulted in 6.5 g (79%) of ethyl 2-amino-4-hydroxy-5-methyl-4-(trifluoromethyl)-4,5-dihydrothiophene-3-carboxylate as a dark red liquid.

Step 3: Ethyl 2-amino-5-methyl-4-(trifluoromethyl)thiophene-3-carboxylate

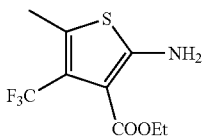 [SMILES: CCOC(=O)c1c(N)sc(C)c1C(F)(F)F]

Into a 100-mL round-bottom flask, was placed ethyl 2-amino-4-hydroxy-5-methyl-4-(trifluoromethyl)-4,5-dihydrothiophene-3-carboxylate (5.7 g, 21.01 mmol, 1.00 equiv), dichloromethane (20 mL), 4-methylbenzene-1-sulfonic acid (3.6 g, 20.91 mmol, 0.99 equiv). The resulting solution was stirred overnight at 25° C. The solids were filtered out. The filtrate was concentrated under vacuum. The residue was applied onto a silica gel column with ethyl acetate/petroleum ether (40/60). The collected fractions were combined and concentrated under vacuum. This resulted in 3.95 g (71%) of ethyl 2-amino-5-methyl-4-(trifluoromethyl)thiophene-3-carboxylate as yellow oil.

Step 4: Ethyl 2-bromo-5-methyl-4-(trifluoromethyl)thiophene-3-carboxylate

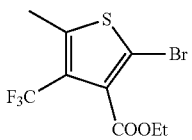 [SMILES: CCOC(=O)c1c(Br)sc(C)c1C(F)(F)F]

Into a 100-mL round-bottom flask, was placed ethyl 2-amino-5-methyl-4-(trifluoromethyl)thiophene-3-carboxylate (3.95 g, 15.60 mmol, 1.00 equiv), CuBr (8.85 g), BuONO (8.2 g), MeCN (20 mL). The resulting solution was stirred overnight at 25° C. The solids were filtered out. The filtrate was concentrated under vacuum. The residue was applied onto a silica gel column with ethyl acetate/petroleum ether (10/90). The collected fractions were combined and concentrated under vacuum. This resulted in 930 mg (18%) of ethyl 2-bromo-5-methyl-4-(trifluoromethyl)thiophene-3-carboxylate as light yellow oil.

Step 5: Ethyl 2-(4-chlorophenyl)-5-methyl-4-(trifluoromethyl)thiophene-3-carboxylate

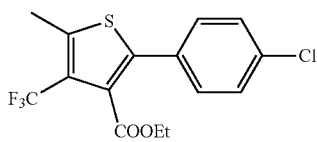 [SMILES: CCOC(=O)c1c(-c2ccc(Cl)cc2)sc(C)c1C(F)(F)F]

Into a 100-mL round-bottom flask purged and maintained with an inert atmosphere of nitrogen, was placed ethyl 2-bromo-5-methyl-4-(trifluoromethyl)thiophene-3-carboxylate (250 mg, 0.79 mmol, 1.00 equiv), (4-chlorophenyl)boronic acid (185 mg, 1.18 mmol, 1.50 equiv), K$_3$PO$_4$ (620 mg, 2.92 mmol, 3.71 equiv), Pd(PPh$_3$)$_4$ (73 mg, 0.06 mmol, 0.08 equiv), dioxane (20 mL). The resulting solution was stirred overnight at 90° C. The solids were filtered out. The filtrate was concentrated under vacuum. The residue was applied onto a silica gel column with ethyl acetate/petroleum ether (1/5). The collected fractions were combined and concentrated under vacuum. This resulted in 200 mg (69%) of ethyl 2-(4-chlorophenyl)-5-methyl-4-(trifluoromethyl)thiophene-3-carboxylate as colorless oil.

Step 6: (2-(4-chlorophenyl)-5-methyl-4-(trifluoromethyl)thiophen-3-yl)methanol

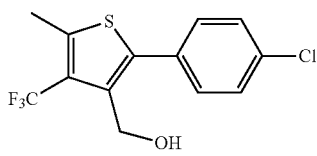 [SMILES: Cc1sc(-c2ccc(Cl)cc2)c(CO)c1C(F)(F)F]

Into a 100-mL round-bottom flask, was placed ethyl 2-(4-chlorophenyl)-5-methyl-4-(trifluoromethyl) thiophene-3-carboxylate (200 mg, 0.57 mmol, 1.00 equiv), tetrahydrofuran (20 mL). This was followed by the addition of LAH (44 mg, 1.16 mmol, 2.02 equiv) in several batches at 0° C. The resulting solution was stirred for 2 h at 25° C. The reaction was then quenched by the addition of 1 g of Na$_2$SO$_4$.10H$_2$O. The solids were filtered out. The resulting mixture was concentrated under vacuum. The residue was applied onto a silica gel column with ethyl acetate/petroleum ether (1/5). The collected fractions were combined and concentrated under vacuum. This resulted in 80 mg (43%) of (5-methyl-2-phenyl-4-(trifluoromethyl)thiophen-3-yl)methanol as light yellow oil.

Step 7: Ethyl 3-(4-((2-(4-chlorophenyl)-5-methyl-4-(trifluoromethyl)thiophen-3-yl)methoxy)-3,5-difluorophenyl)propanoate

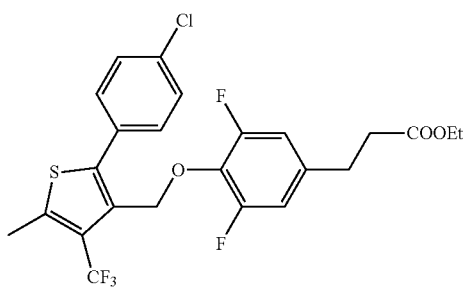 [SMILES: CCOC(=O)CCc1cc(F)c(OCc2c(-c3ccc(Cl)cc3)sc(C)c2C(F)(F)F)c(F)c1]

Into a 100-mL round-bottom flask purged and maintained with an inert atmosphere of nitrogen, was placed (5-methyl-2-phenyl-4-(trifluoromethyl)thiophen-3-yl)methanol (40 mg, 0.13 mmol, 1.00 equiv), ethyl 3-(4-hydroxy-3,5-difluorophenyl)propanoate (35 mg, 0.16 mmol, 1.21 equiv), Bu$_3$P (66 mg), ADDP (69 mg, 0.28 mmol, 2.11 equiv), toluene (30 mL). The resulting solution was stirred overnight at 60° C. Then it was concentrated under vacuum. The residue was diluted with 30 mL of ether. The solids were filtered out. The filtrate was concentrated under vacuum. The residue was applied onto a silica gel column with ethyl acetate/petroleum ether (1/10). This resulted in 40 mg (57%) of ethyl 3-(3,5-difluoro-4-((5-methyl-2-phenyl-4-(trifluoromethyl) thiophen-3-yl)methoxy)phenyl)propanoate as colorless oil.

Step 8: 3-(4-[[2-(4-chlorophenyl)-5-methyl-4-(trifluoromethyl)thiophen-3-yl]methoxy]-3,5-difluorophenyl)propanoic Acid

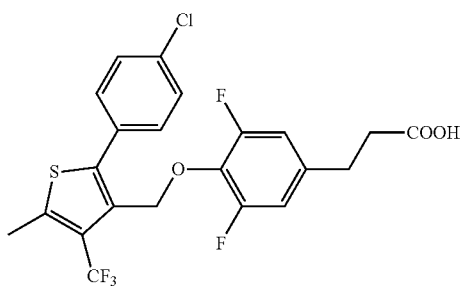 [SMILES: Cc1sc(-c2ccc(Cl)cc2)c(COc2c(F)cc(CCC(=O)O)cc2F)c1C(F)(F)F]

The title compound was prepared according to the procedure described in Example 217 step 7 by hydrolysis of ethyl 3-(4-((2-(4-chlorophenyl)-5-methyl-4-(trifluoromethyl)thiophen-3-yl) methoxy)-3,5-difluorophenyl)propanoate to afford the desired product as an off-white solid. $^1$H NMR (300 MHz, CDCl$_3$) δ: 7.51 (d, J=3.3 Hz, 2H), 7.40 (d, J=6.3 Hz, 2H), 6.76 (d, J=9.9 Hz, 2H), 4.99 (s, 2H), 2.91 (t, J=5.7 Hz, 2H), 2.69 (t, J=6.0 Hz, 2H), 2.63 (s, 3H). Mass spectrum (ESI, m/z): Calcd. for C$_{22}$H$_{16}$ClF$_5$O$_3$S, 489.0 [M−H], found 489.0.

Example 221

3-(4-[[2-(4-ethylphenyl)-5-methyl-4-(trifluoromethyl)thiophen-3-yl]methoxy]-2,3-dimethylphenyl) Propanoic Acid, Cpd 61

Step 1: [2-(4-ethylphenyl)-5-methyl-4-(trifluoromethyl)thiophen-3-yl]methanol

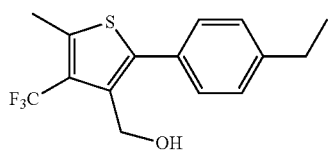 [SMILES: CCc1ccc(-c2sc(C)c(C(F)(F)F)c2CO)cc1]

The title compound was prepared according to the procedure described in Example 220 by Suzuki coupling of ethyl 2-bromo-5-methyl-4-(trifluoromethyl)thiophene-3-carboxylate and 4-ethyl-phenylboronic acid followed by synthetic steps to afford the desired product as a yellow oil.

Step 2: 3-(4-[[2-(4-ethylphenyl)-5-methyl-4-(trifluoromethyl)thiophen-3-yl]methoxy]-2,3-dimethylphenyl) Propanoic Acid

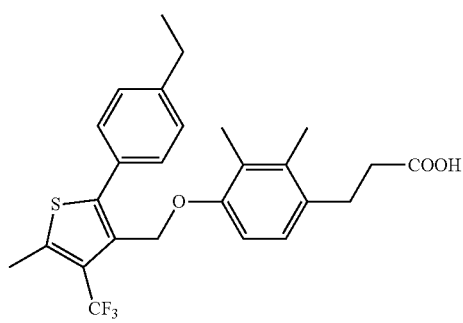 [SMILES: CCc1ccc(-c2sc(C)c(C(F)(F)F)c2COc2ccc(CCC(=O)O)c(C)c2C)cc1]

The title compound was prepared according to the procedure described in Example 220 by coupling of [2-(4-ethylphenyl)-5-methyl-4-(trifluoromethyl)thiophen-3-yl] methanol and ethyl 3-(4-hydroxy-2,3-dimethylphenyl)propanoate followed by hydrolysis of ethyl 3-(4-((2-(4-ethyl phenyl)-5-methyl-4-(trifluoromethyl)thiophen-3-yl) methoxy)-2,3-dimethylphenyl)propanoate to afford the desired product as an off-white solid. $^1$H NMR (300 MHz, CDCl$_3$) δ: 7.43 (d, J=4.2 Hz, 2H), 7.24 (d, J=6.0 Hz, 2H), 6.97 (d, J=6.3 Hz, 2H), 6.67 (d, J=6.3 Hz, 2H), 4.86 (s, 2H), 2.97 (t, J=6.0 Hz, 2H), 2.61-2.73 (m, 7H) 2.23 (s, 3H), 2.18 (s, 3H), 1.27 (t, J=5.7 Hz, 2H). Mass spectrum (ESI, m/z): Calcd. for C$_{26}$H$_{27}$F$_3$O$_3$S, 475.2[M−H], found 475.2.

Example 222

3-(4-[[2-(4-ethylphenyl)-5-methyl-4-(trifluoromethyl)thiophen-3-yl]methoxy]-2,3-dimethylphenyl) propanoic Acid, Cpd 39

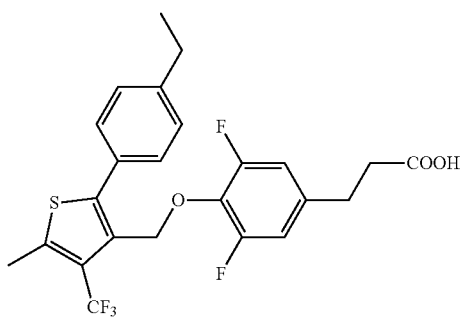 [SMILES: CCc1ccc(-c2sc(C)c(C(F)(F)F)c2COc2c(F)cc(CCC(=O)O)cc2F)cc1]

The title compound was prepared according to the procedure described in Example 220 by coupling of [2-(4-ethylphenyl)-5-methyl-4-(trifluoromethyl)thiophen-3-yl]methanol and ethyl 3-(4-hydroxy-2,3-dimethylphenyl)propanoate followed by hydrolysis of ethyl 3-(4-((2-(4-ethylphenyl)-5-methyl-4-(trifluoromethyl)thiophen-3-yl)methoxy)-3,5-difluorophenyl)propanoate to afford the desired product as an off-white solid.
$^1$H NMR (300 MHz, DMSO) δ:7.29 (s, 4H), 6.96 (d, J=6.9 Hz, 2H), 4.96 (s, 2H), 2.76 (t, J=5.7 Hz, 2H), 2.62-2.68 (m, 2H) 2.59 (s, 3H), 2.50 (d, J=2.4 Hz, 2H), 1.21 (t, J=5.7 Hz, 3H). Mass spectrum (ESI, m/z): Calcd. for $C_{24}H_{21}F_5O_3S$, 483.1[M–H], found 483.1.

Example 223

3-(4-[[4-(4-chlorophenyl)-2-(trifluoromethyl)thiophen-3-yl]methoxy]-3,5-difluorophenyl)propan-1-ol, Cpd 46

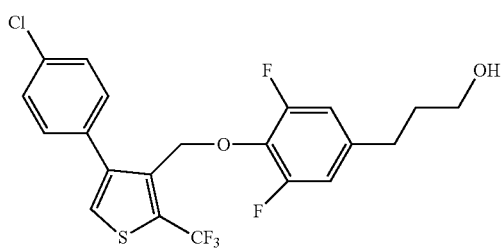 [SMILES: OCCCc1cc(F)c(OCc2c(-c3ccc(Cl)cc3)csc2C(F)(F)F)c(F)c1]

Into a 25-mL 2-necked round-bottom flask (1 atm) purged and maintained with an inert atmosphere of nitrogen, was placed ethyl 3-(4-[[4-(4-chlorophenyl)-2-(trifluoromethyl)thiophen-3-yl]methoxy]-3,5-difluorophenyl)propanoate (60 mg, 0.12 mmol, 1.00 equiv), tetrahydrofuran (3.0 mL). This was followed by the addition of a solution of LiAlH$_4$ (11.3 mg, 0.30 mmol, 2.51 equiv) in tetrahydrofuran (3.0 mL) dropwise with stirring at 0° C. The resulting solution was stirred for 2 h at 25° C. The reaction progress was monitored by LCMS/TLC (ethyl acetate/petroleum ether=1:6). The reaction was then quenched by the addition of 5 mL of water and 2 mL 2N HCl. The resulting solution was extracted with 3×10 mL of ethyl acetate and the organic layers combined and dried over anhydrous sodium sulfate and concentrated under vacuum. The residue was applied onto a TLC-Plate with ethyl acetate/petroleum ether (1:1.5). This resulted in 0.041 g (75%) of 3-(4-[[4-(4-chlorophenyl)-2-(trifluoromethyl)thiophen-3-yl]methoxy]-3,5-difluorophenyl)propan-1-ol as a white solid. $^1$H NMR (CD$_3$OD, 300 Hz): 7.70 (s, 1H), 7.49 (d, J=8.6 Hz, 2H), 7.43 (d, J=8.7 Hz, 2H), 6.80 (d, J=9.3 Hz, 2H), 5.09 (s, 2H), 3.57 (t, J=6.3 Hz, 2H), 2.65 (t, J=7.5 Hz, 2H), 1.76-1.86 (m, 2H). Mass spectrum (ESI, m/z): Calcd. for $C_{21}H_{16}ClF_5O_2S$, 485.0 (M+Na), found 485.2.

Example 224

3-(4-((4-(4-chlorophenyl)-2-(trifluoromethyl)thiophen-3-yl)methoxy)-2,3,5-trifluorophenyl)propan-1-ol, Cpd 56

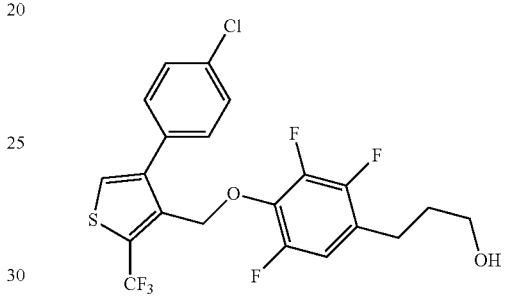

The title compound was prepared according to the procedure described in Example 223 by LAH reduction of ethyl 3-(4-((4-(4-chlorophenyl)-2-(trifluoromethyl)thiophen-3-yl)methoxy)-2,3,5-trifluorophenyl)propanoate to give the desired product as off-white oil. $^1$H NMR (400 MHz, CDCl$_3$) δ 7.50 (d, J=7.5 Hz, 2H), 7.45 (s, 1H), 7.42 (d, J=8.0 Hz, 2H), 6.72 (m, 1H), 5.06 (s, 2H), 3.70 (t, J=9.0 Hz, 2H), 2.72 (t, J=9.1 Hz, 2H), 1.86 (m, 2H), 1.60 (s, 1H).

Example 225

3-(3,5-difluoro-4-((4-(4-methoxyphenyl)-2-(trifluoromethyl)thiophen-3-yl)methoxy)phenyl)propan-1-ol, Cpd 45

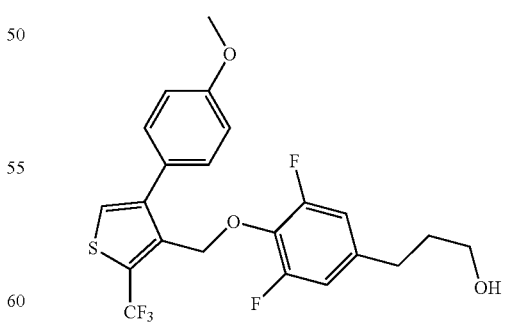

The title compound was prepared according to the procedure described in Example 223 by LAH reduction of ethyl 3-(4-((4-(4-methoxyphenyl)-2-(trifluoromethyl)thiophen-3-yl)methoxy)-3,5-trifluorophenyl)propanoate to give the desired product as off-white oil. $^1$H NMR (400 MHz, CDCl$_3$) δ 7.48 (d, J=8.1 Hz, 2H), 7.35 (s, 1H), 6.97 (d, J=8.0 Hz, 2H), 6.72 (d, J=8.5 Hz, 2H), 5.05 (s, 2H), 3.85 (s, 3H), 3.77 (t, J=7.0 Hz, 2H), 2.68 (t, J=7.1 Hz, 2H), 1.87 (m, 2H), 1.50 (br, s, 1H).

Example 226

3-(4-((4-(benzo[d][1,3]dioxol-5-yl)-2-(trifluoromethyl)thiophen-3-yl)methoxy)-3,5-difluorophenyl)propan-1-ol, Cpd 37

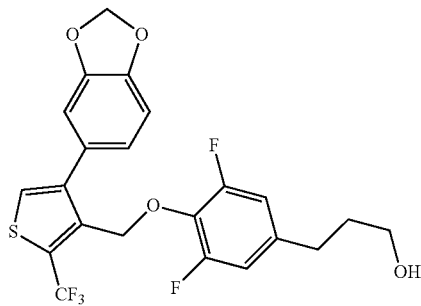 [SMILES: OCCCc1cc(F)c(OCc2c(-c3ccc4c(c3)OCO4)csc2C(F)(F)F)c(F)c1]

The title compound was prepared according to the procedure described in Example 223 by LAH reduction of ethyl 3-(4-((4-(benzo[d][1,3]dioxol-5-yl)-2-(trifluoromethyl)thiophen-3-yl) methoxy)-3,5-difluorophenyl)propanoate to give the desired product as off-white oil. $^1$H NMR (400 MHz, CDCl$_3$) δ 7.35 (s, 1H), 7.08 (s, 1H), 7.02 (d, J=8.1 Hz, 1H), 6.87 (d, J=8.1 Hz, 1H), 6.75 (d, J=8.5 Hz, 2H), 6.02 9s, 2H), 5.11 (s, 2H), 3.67 (d, J=7.5 Hz, 2H), 2.66 (t, J=8.0 Hz, 2H), 1.86 (m, 2H), 1.55 (br, s, 1H).

Example 227

3-(4-((4-(2,3-dihydrobenzofuran-5-yl)-2-(trifluoromethyl)thiophen-3-yl)methoxy)-3,5-difluorophenyl)propan-1-ol, Cpd 55

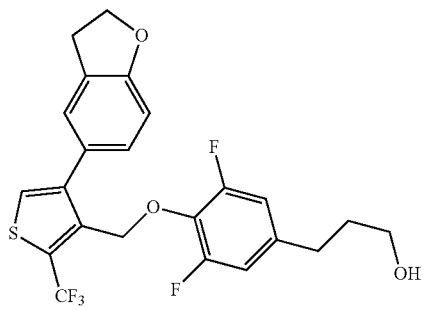 [SMILES: OCCCc1cc(F)c(OCc2c(-c3ccc4c(c3)CCO4)csc2C(F)(F)F)c(F)c1]

The title compound was prepared according to the procedure described in Example 223 by LAH reduction of ethyl 3-(4-((4-(2,3-dihydrobenzofuran-5-yl)-2-(trifluoromethyl) thiophen-3-yl)methoxy)-3,5-difluorophenyl)propanoate to give the desired product as off-white oil. $^1$H NMR (400 MHz, CDCl$_3$) δ 7.42 (s, 1H), 7.3 (s, 1H), 7.26 (m, 1H), 6.82 (d, J=8.6 Hz, 1H), 6.72 (d, J=9.5 Hz, 2H), 5.04 (s, 2H), 4.62 (t, J=10.5 Hz, 2H), 3.68 (t, J=7.5 Hz, 2H), 3.25 (t, J=10.2 Hz, 2H), 2.65 (t, J=7.2 Hz, 2H), 1.84 (m, 2H), 1.55 (br, s, 1H).

Example 228

3-(3,5-difluoro-4-((4-(6-methylpyridin-3-yl)-2-(trifluoromethyl)thiophen-3-yl)methoxy)phenyl)propan-1-ol, Cpd 36

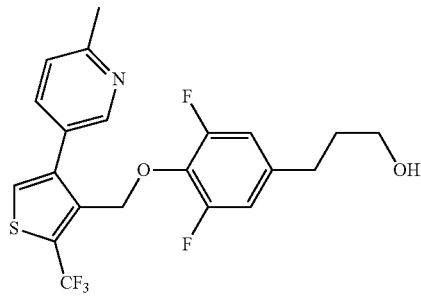 [SMILES: Cc1ccc(-c2csc(C(F)(F)F)c2COc2c(F)cc(CCCO)cc2F)cn1]

The title compound was prepared according to the procedure described in Example 223 by LAH reduction of ethyl 3-(3,5-difluoro-4-((4-(6-methylpyridin-3-yl)-2-(trifluoromethyl)thiophen-3-yl)methoxy)phenyl)propanoate to give the desired product as off-white oil. $^1$H NMR (400 MHz, CDCl$_3$) δ 8.52 (s, 1H), 7.85 (d, J=7.8 Hz, 1H), 7.42 (s, 1H), 7.25 (d, J=7.5 Hz, 1H), 6.70 (d, J=7.5 Hz, 2H), 5.10 (s, 2H), 3.65 (t, J=7.5 Hz, 2H), 2.68 (t, J=7.6 Hz, 2H), 2.65 (s, 3H), 1.85 (t, J=7.5 Hz, 3H), 1.75 (br, s, 1H).

Example 229

3-(3,5-difluoro-4-((4-(6-methoxypyridin-3-yl)-2-(trifluoromethyl)thiophen-3-yl)methoxy)phenyl)propan-1-ol, Cpd 38

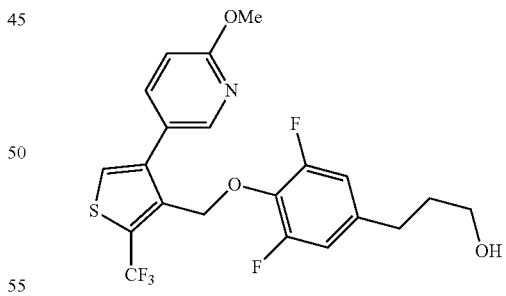

The title compound was prepared according to the procedure described in Example 223 by LAH reduction of ethyl 3-(3,5-difluoro-4-((4-(6-methoxypyridin-3-yl)-2-(trifluoromethyl)thiophen-3-yl)methoxy)phenyl)propanoate to give the desired product as off-white oil. $^1$H NMR (400 MHz, Methanol-d$_4$) δ 8.25 (s, 1H), 7.88 (d, J=7.5 Hz, 2H), 6.90 (d, J=7.5 Hz, 2H), 6.80 (d, J=7.0 Hz, 2H), 5.10 (s, 2H), 3.90 (s, 3H), 3.62 (m, 2H), 2.65 (m, J=6.0 Hz, 2H), 1.80 (m, J=6.8 Hz, 2H). LCMS (ESI, M/Z) for C$_{21}$H$_{18}$F$_5$NO$_3$S: 460.1 (MH$^+$).

Example 230

3-(4-[[5-chloro-3-(4-ethylphenyl)thiophen-2-yl]methoxy]-2,3-difluorophenyl)propan-1-ol, Cpd 14

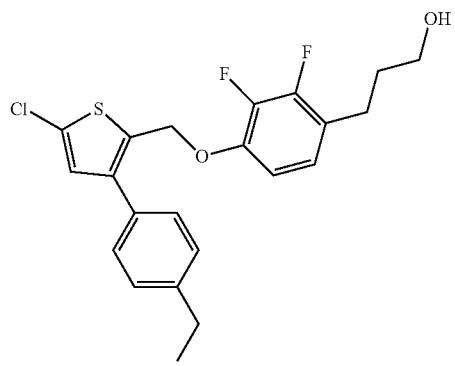 [SMILES: CCc1ccc(-c2cc(Cl)sc2COc2ccc(CCCO)c(F)c2F)cc1]

The title compound was prepared according to the procedure described in Example 223 by LAH reduction of ethyl 3-(4-((3-(4-ethylphenyl)-5-chlorothiophen-2-yl)methoxy)-2,3-difluorophenyl) propanoate to give the desired product as off-white oil. $^1$H-NMR (300 MHz, CD$_3$OD) δ 7.33 (d, J=8.4 Hz, 2H), 7.27 (d, J=8.4 Hz, 2H), 7.04 (s, 1H), 6.89 (t, J=8.4 Hz, 2H), 6.73 (t, J=8.4 Hz, 2H), 5.16 (s, 2H), 3.57 (t, J=6.6 Hz, 2H), 2.65-2.71 (m, 4H), 1.75-1.85 (m, 2H), 1.26 (t, J=7.8 Hz, 3H). Mass spectrum (ESI, m/z): Calcd. for C$_{22}$H$_{21}$C$_1$F$_2$O$_2$S, 235.0 (M-C$_9$H$_9$F$_2$O$_2$), found 235.0.

Example 231

3-(4-[[5-chloro-3-(4-ethylphenyl)thiophen-2-yl]methoxy]-3,5-difluorophenyl)propan-1-ol, Cpd 9

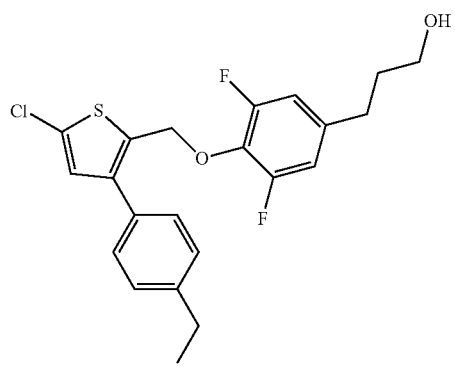 [SMILES: CCc1ccc(-c2cc(Cl)sc2COc2c(F)cc(CCCO)cc2F)cc1]

The title compound was prepared according to the procedure described in Example 223 by LAH reduction of ethyl 3-(4-((5-chloro-3-(4-ethylphenyl)thiophen-2-yl)methoxy)-3,5-difluoro phenyl)propanoate to give the desired product as off-white oil. $^1$H-NMR (300 MHz, CD$_3$OD) δ 7.27 (d, J=8.4 Hz, 2H), 7.17 (d, J=8.4 Hz, 2H), 6.92 (s, 1H), 6.72 (t, J=8.4 Hz, 2H), 5.01 (s, 2H), 3.29 (t, J=6.6 Hz, 2H), 2.54-2.64 (m, 4H), 1.68-1.78 (m, 2H), 1.18 (t, J=7.8 Hz, 3H). Mass spectrum (ESI, m/z): Calcd. for C$_{22}$H$_{21}$C$_1$F$_2$O$_2$S, 235.0 (M-C$_9$H$_9$F$_2$O$_2$), found 235.0.

Example 232

3-(4-[[5-chloro-3-(4-chlorophenyl)thiophen-2-yl]methoxy]-3,5-difluorophenyl)propan-1-ol, Cpd 19

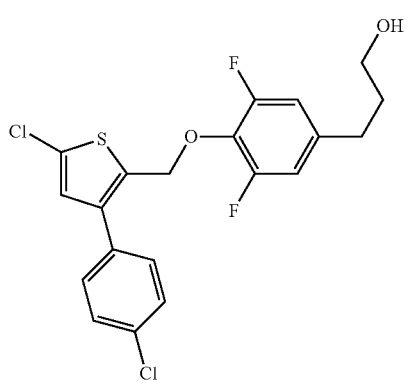 [SMILES: OCCCc1cc(F)c(OCc2sc(Cl)cc2-c2ccc(Cl)cc2)c(F)c1]

The title compound was prepared according to the procedure described in Example 222 by LAH reduction of ethyl 3-(4-((5-chloro-3-(4-chlorophenyl)thiophen-2-yl)methoxy)-3,5-difluoro phenyl)propanoate to give the desired product as off-white oil. $^1$H NMR (300 MHz, CD3OD) δ 7.42-7.52 (m, 4H), 7.07 (s, 1H), 6.85 (d, J=9.6 Hz, 2H), 5.11 (s, 2H), 3.58 (t, J=7.8 Hz, 2H), 2.66 (t, J=6.0 Hz, 2H), 1.79-1.86 (m, 2H).

Example 233

3-(4-[[5-chloro-3-(4-chlorophenyl)thiophen-2-yl]methoxy]-2,3-difluorophenyl)propan-1-ol, Cpd 29

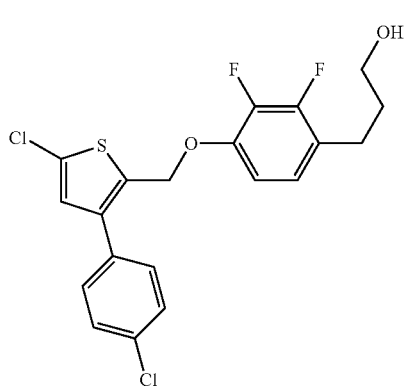 [SMILES: OCCCc1ccc(OCc2sc(Cl)cc2-c2ccc(Cl)cc2)c(F)c1F]

The title compound was prepared according to the procedure described in Example 223 by LAH reduction of ethyl 3-(4-((3-(4-chlorophenyl)-5-chlorothiophen-2-yl)methoxy)-2,3-difluoro phenyl)propanoate to give the desired product as off-white oil. $^1$H NMR (300 MHz, CD3OD) δ: 7.44 (s, 4H), 7.00 (s, 1H), 6.90-6.93 (m, 1H), 6.77-6.80 (m, 1H), 5.16 (s, 2H) 3.58 (t, J=6.3 Hz, 2H), 2.70 (t, J=6.9 Hz, 2H), 1.78-1.83 (m, 2H). Mass spectrum (ESI, m/z): Calcd. for C$_{20}$H$_{16}$Cl$_2$F$_2$O$_2$S, 393.1 (M-Cl), found 393.1.

Example 234

3-(4-[[5-chloro-3-(4-chlorophenyl)thiophen-2-yl]methoxy]-2,3-dimethylphenyl)propan-1-ol, Cpd 15

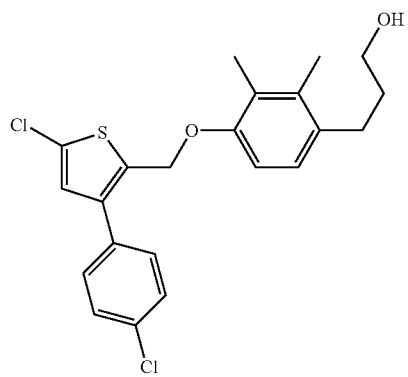 [SMILES: Cc1c(CCCO)ccc(OCc2sc(Cl)cc2-c2ccc(Cl)cc2)c1C]

The title compound was prepared according to the procedure described in Example 223 by LAH reduction of ethyl 3-(4-((3-(4-chlorophenyl)-5-chlorothiophen-2-yl)methoxy)-2,3-dimethyl phenyl)propanoate to give the desired product as off-white oil. $^1$H NMR (300 MHz, CD$_3$OD) δ 7.38 (s, 4H), 7.06 (s, 1H), 6.89 (d, J=8.4 Hz, 1H), 6.62 (d, J=8.4 Hz, 1H), 5.05 (s, 2H), 3.58 (t, J=6.3 Hz, 2H), 2.64 (t, J=7.5 Hz, 2H), 2.21 (s, 3H), 2.14 (s, 3H), 1.76 (t, J=7.5 Hz, 2H). Mass spectrum (ESI, m/z): Calcd. for C$_{22}$H$_{22}$Cl$_2$O$_2$S, 385.1 (M-Cl), found 385.1.

Example 235

3-(4-[[3-(4-ethylphenyl)-5-fluorothiophen-2-yl]methoxy]-2,3-difluorophenyl)propan-1-ol, Cpd 17

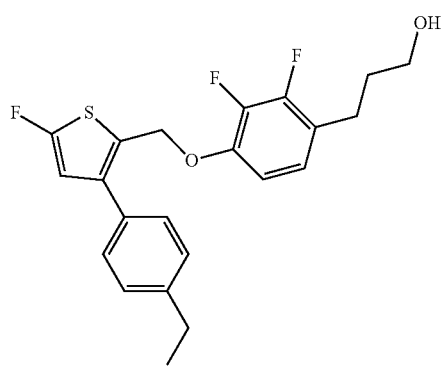 [SMILES: CCc1ccc(-c2cc(F)sc2COc2ccc(CCCO)c(F)c2F)cc1]

The title compound was prepared according to the procedure described in Example 223 by LAH reduction of ethyl 3-(4-((3-(4-ethylphenyl)-5-fluorothiophen-2-yl)methoxy)-2,3-difluoro phenyl)propanoate to give the desired product as off-white oil. $^1$HNMR (300 MHz, CD$_3$OD) δ 7.25-7.42 (m, 4H), 6.93 (t, J=8.4 Hz, 1H), 6.73 (t, J=8.4 Hz, 1H), 6.70 (s, 2H), 5.12 (s, 2H), 3.58 (t, J=7.5 Hz, 2H), 2.65-2.78 (m, 4H), 1.76-1.86 (m, 2H), 1.32 (t, J=7.8 Hz, 3H). Mass spectrum (ESI, m/z): Calcd. for C$_{22}$H$_{21}$F$_3$O$_2$S, 405.1 (M–H), found 405.1.

Example 236

3-(4-[[3-(4-ethylphenyl)-5-fluorothiophen-2-yl]methoxy]-3,5-difluorophenyl)propan-1-ol, Cpd 27

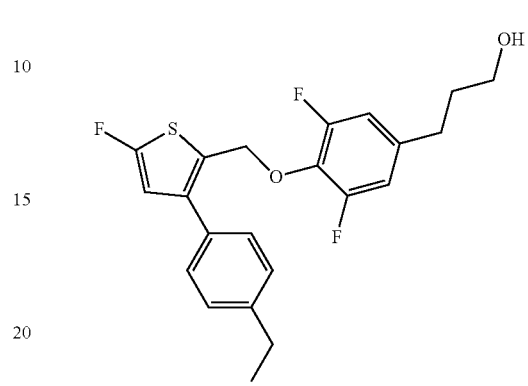

The title compound was prepared according to the procedure described in Example 223 by LAH reduction of ethyl 3-(4-((3-(4-ethylphenyl)-5-fluorothiophen-2-yl)methoxy)-3,5-difluoro phenyl)propanoate to give the desired product as off-white oil. $^1$HNMR (300 MHz, CD$_3$OD) δ 7.37 (d, J=8.1 Hz, 2H), 7.26 (d, J=8.1 Hz, 2H), 6.81 (t, J=9.3 Hz, 1H), 6.63 (s, 2H), 5.01 (s, 2H), 3.58 (t, J=6.0 Hz, 2H), 2.63-2.74 (m, 4H), 1.77-1.87 (m, 2H), 1.28 (t, J=7.8 Hz, 3H). Mass spectrum (ESI, m/z): Calcd. for C$_{22}$H$_{21}$F$_3$O$_2$S, 219.1 [M-C$_9$H$_9$F$_2$O$_2$], found 219.1.

Example 237

3-(4-[[3-(4-chlorophenyl)-5-fluorothiophen-2-yl]methoxy]-3,5-difluorophenyl)propan-1-ol, Cpd 18

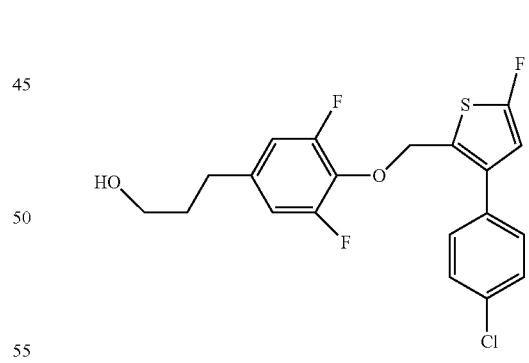

The title compound was prepared according to the procedure described in Example 223 by LAH reduction of ethyl 3-(4-((3-(4-chlorophenyl)-5-fluorothiophen-2-yl)methoxy)-3,5-difluoro phenyl)propanoate to give the desired product as off-white oil. $^1$H NMR (300 MHz, CD$_3$OD) δ7.40-7.52 (m, 4H), 6.83 (d, J=9.6 Hz, 2H), 6.67 (s, 1H), 5.08 (s, 2H), 3.57 (t, J=6.6 Hz, 2H), 2.659 (t, J=7.5 Hz, 2H), 1.77-1.86 (m, 2H). Mass spectrum (ESI, m/z): Calcd. for: C$_{20}$H$_{16}$ClF$_3$O$_2$S, 225.0 (M-C$_9$H$_9$F$_2$O$_2$), found 224.9.

Example 238

3-(4-[[3-(4-chlorophenyl)-5-fluorothiophen-2-yl]methoxy]-2,3-dimethylphenyl)propan-1-ol, Cpd 30

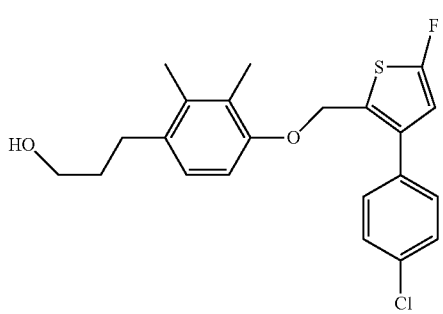 [SMILES: Cc1c(CCCO)ccc(OCc2sc(F)cc2-c2ccc(Cl)cc2)c1C]

The title compound was prepared according to the procedure described in Example 223 by LAH reduction of ethyl 3-(4-((3-(4-chlorophenyl)-5-fluorothiophen-2-yl)methoxy)-2,3-dimethyl phenyl)propanoate to give the desired product as off-white oil. $^1$H NMR (300 MHz, CD3OD) δ: 7.36-7.39 (m, 4H), 6.85 (d, J=8.4 Hz, 1H), 6.63 (s, 1H), 6.58 (d, J=8.1 Hz, 1H), 4.98 (s, 2H), 3.54 (t, J=6.3 Hz, 2H), 2.58-2.63 (m, 2H), 2.17 (s, 3H), 2.10 (s, 3H), 1.64-1.74 (m, 2H). Mass spectrum (ESI, m/z): Calcd. for $C_{22}H_{22}ClFO_2S$, 403.1 (M–H), found 403.0.

Example 239

3-(4-[[2-(4-ethylphenyl)-5-methyl-4-(trifluoromethyl)thiophen-3-yl]methoxy]-3,5-difluorophenyl)propan-1-ol, Cpd 32

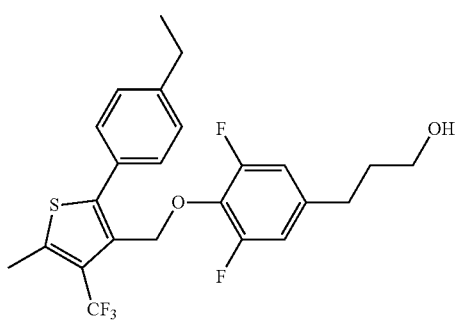 [SMILES: CCc1ccc(-c2sc(C)c(C(F)(F)F)c2COc2c(F)cc(CCCO)cc2F)cc1]

The title compound was prepared according to the procedure described in Example 223 by LAH reduction of ethyl 3-(4-[[2-(4-ethylphenyl)-5-methyl-4-(trifluoromethyl)thiophen-3-yl]methoxy]-3,5-difluorophenyl)propanoate to give the desired product as off-white oil. $^1$H NMR (300 MHz, CDCl$_3$) δ: 7.47 (d, J=8.1 Hz, 2H), 7.24 (s, 2H), 6.74 (d, J=9.3 Hz, 2H), 5.02 (s, 2H), 3.66-3.72 (m, 2H), 2.68-2.74 (m, 2H), 2.60 (s, 3H), 1.81-1.88 (m, 2H), 1.27 (t, J=3.9 Hz, 3H). Mass spectrum (ESI, m/z): Calcd. for $C_{24}H_{23}F_5O_2S$, 283.1 [M-$C_9H_9F_2O_2$], found 283.1.

Example 240

3-(4-[[3-(4-ethylphenyl)thiophen-2-yl]methoxy]-2,3-difluorophenyl)propan-1-ol, Cpd 4

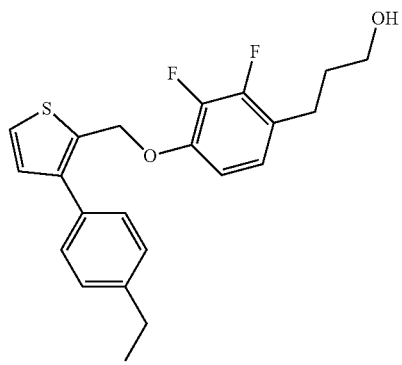 [SMILES: CCc1ccc(-c2ccsc2COc2ccc(CCCO)c(F)c2F)cc1]

The title compound was prepared according to the procedure described in Example 223 by LAH reduction of ethyl 3-(4-[[5-chloro-3-(4-ethylphenyl)thiophen-2-yl]methoxy]-2,3-difluoro phenyl)propanoate to give the desired product as off-white oil. $^1$H NMR (300 MHz, CD$_3$OD) δ7.41 (d, J=5.1 Hz, 1H), 7.30 (d, J=8.4 Hz, 2H), 7.20 (d, J=8.4 Hz, 2H), 7.08 (d, J=5.1 Hz, 1H), 6.82 (t, J=8.7 Hz, 1H), 6.68 (t, J=8.7 Hz, 1H), 5.14 (s, 2H), 3.53 (t, J=6.3 Hz, 2H), 2.59-2.66 (m, 4H), 1.70-1.80 (m, 2H), 1.23 (t, J=7.8 Hz, 3H). Mass spectrum (ESI, m/z): Calcd. for $C_{22}H_{22}F_2O_2S$, 201.1 [M-$C_9H_9F_2O_2$], found 201.1.

Example 241

3-(4-[[3-(4-ethylphenyl)thiophen-2-yl]methoxy]-3,5-difluorophenyl)propan-1-ol, Cpd 20

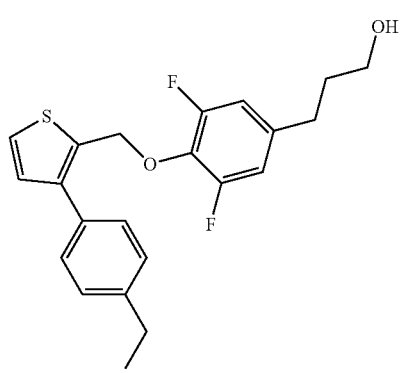 [SMILES: CCc1ccc(-c2ccsc2COc2c(F)cc(CCCO)cc2F)cc1]

The title compound was prepared according to the procedure described in Example 223 by LAH reduction of ethyl 3-(4-[[5-chloro-3-(4-ethylphenyl)thiophen-2-yl]methoxy]-3,5-difluoro phenyl)propanoate to give the desired product as off-white oil. $^1$H NMR (300 MHz, CD$_3$OD) δ 7.36-7.42 (m, 3H), 7.21 (d, J=7.8 Hz, 2H), 7.08 (d, J=8.1 Hz, 1H), 6.70-6.80 (m, 2H), 5.13 (s, 2H), 3.51 (t, J=7.2 Hz, 2H), 2.525-2.69 (m, 4H), 1.72-1.81 (m, 2H), 1.23 (t, J=7.5 Hz, 3H). Mass spectrum (ESI, m/z): Calcd. for $C_{22}H_{22}F_2O_2S$, 201.1 [M-$C_9H_9F_2O_2$], found 201.1.

Example 242

3-(4-((3-(4-ethylphenyl)-5-methylthiophen-2-yl)methoxy)-2,3-difluorophenyl)propan-1-ol, Cpd 23

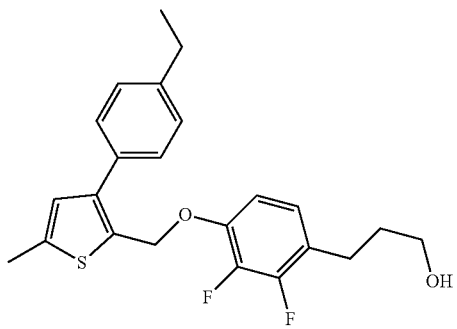 [SMILES: CCc1ccc(-c2cc(C)sc2COc2ccc(CCCO)c(F)c2F)cc1]

The title compound was prepared according to the procedure described in Example 223 by LAH reduction of ethyl 3-(4-((3-(4-ethylphenyl)-5-methylthiophen-2-yl)methoxy)-2,3-difluoro phenyl)propanoate to give the desired product as off-white oil. $^1$H NMR (400 MHz, CDCl$_3$) δ 7.35 (d, J=7.0 Hz, 2H), 7.24 (d, J=7.1 Hz, 2H), 6.78 (s, 1H), 6.72 (m, J=5.8 Hz, 1H), 6.62 (m, J=7.2 Hz, 1H), 5.11 (s, 2H), 3.72 (t, J=8.1 Hz, 2H), 2.72 (m, J=5.2 Hz, 2H), 2.65 (m, J=7.5 Hz, 2H), 2.49 (s, 3H), 1.82 (m, J=5.8 Hz, 2H), 1.70 (br, s, 1H), 1.28 (t, J=7.2 Hz, 3H).

Example 243

3-(4-((3-(4-ethylphenyl)-5-methylthiophen-2-yl)methoxy)-3,5-difluorophenyl)propan-1-ol, Cpd 24

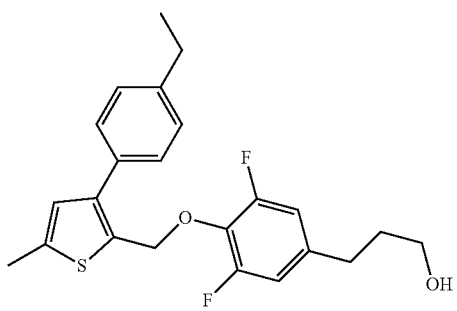 [SMILES: CCc1ccc(-c2cc(C)sc2COc2c(F)cc(CCCO)cc2F)cc1]

The title compound was prepared according to the procedure described in Example 223 by LAH reduction of ethyl 3-(4-((3-(4-ethylphenyl)-5-methylthiophen-2-yl)methoxy)-3,5-difluoro phenyl)propanoate to give the desired product as off-white oil. $^1$H NMR (400 MHz, CDCl$_3$) δ 7.35 (d, J=7.0 Hz, 2H), 7.24 (d, J=7.1 Hz, 2H), 6.78 (s, 1H), 6.72 (d, J=7.8 Hz, 2H), 5.11 (s, 2H), 3.72 (t, J=8.1 Hz, 2H), 2.72 (m, J=5.2 Hz, 2H), 2.65 (m, J=7.5 Hz, 2H), 2.49 (s, 3H), 1.82 (m, J=5.8 Hz, 2H), 1.70 (br, s, 1H), 1.28 (t, J=7.2 Hz, 3H).

Example 244

2-(5-[[3-(4-ethylphenyl)-5-(trifluoromethyl)-1,2-thiazol-4-yl]methoxy]-2,3-dihydro-1H-inden-1-yl) acetic Acid, Cpd 176

Step 1: Ethyl 2-[(1E)-5-methoxy-2, 3-dihydro-1H-inden-1-ylidene]acetate

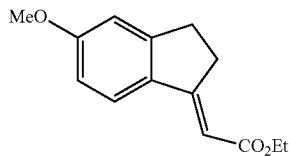 [SMILES: CCOC(=O)/C=C1\CCc2cc(OC)ccc21]

Into a 250-mL 3-necked round-bottom flask purged and maintained with an inert atmosphere of nitrogen, was placed sodium hydride (1 g, 46.00 mmol, 2.50 equiv), toluene (150 mL), ethyl 2-(diethoxyphosphoryl)acetate (7 g, 31.22 mmol, 1.69 equiv). This was followed by the addition of 5-methoxy-2,3-dihydro-1H-inden-1-one (3 g, 18.50 mmol, 1.00 equiv) at 30° C. The resulting solution was stirred overnight at 100° C. in an oil bath. The resulting solution was diluted with 10 mL of water. The resulting solution was extracted with 3×100 mL of toluene and the organic layers combined. The resulting mixture was washed with 2×20 mL of sodium chloride. The resulting mixture was concentrated under vacuum. The residue was applied onto a silica gel column with ethyl acetate/petroleum ether (30:70). This resulted in 2 g (47%) of ethyl 2-[(1E)-5-methoxy-2,3-dihydro-1H-inden-1-ylidene]acetate as yellow oil.

Step 2: Ethyl 2-(5-methoxy-2,3-dihydro-1H-inden-1-yl)acetate

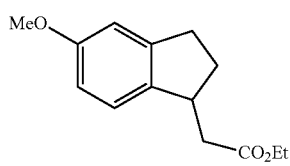

Into a 50-mL round-bottom flask, was placed ethyl 2-(5-methoxy-2,3-dihydro-1H-inden-1-ylidene)acetate (500 mg, 2.15 mmol, 1.00 equiv), methanol (3 mL), Palladium carbon (500 mg). To the mixture hydrogen was introduced in. The resulting solution was stirred overnight at room temperature. The solids were filtered out. The mixture was dried over anhydrous sodium sulfate. The solids were filtered out. The resulting mixture was concentrated under vacuum. The residue was applied onto a silica gel column with ethyl acetate/petroleum ether (15:85). This resulted in 300 mg (59%) of ethyl 2-(5-methoxy-2,3-dihydro-1H-inden-1-yl) acetate as colorless oil.

Step 3: Ethyl 2-(5-hydroxy-2, 3-dihydro-1H-inden-1-yl)acetate

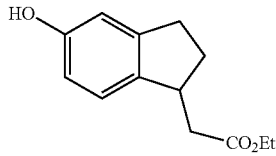 [SMILES: CCOC(=O)CC1CCc2cc(O)ccc21]

Into a 100-mL 3-necked round-bottom flask purged and maintained with an inert atmosphere of nitrogen, was placed ethyl 2-(5-methoxy-2,3-dihydro-1H-inden-1-yl)acetate (200 mg, 0.85 mmol, 1.00 equiv), dichloromethane (5 mL). This was followed by the addition of BBr₃ (1 mL) at −78° C. The resulting solution was stirred for 15 min at 30° C. The reaction was then quenched by the addition of 5 mL of water/ice. The resulting solution was extracted with 3×10 mL of ethyl acetate and the organic layers combined and dried over anhydrous sodium sulfate. The resulting mixture was concentrated under vacuum. The residue was applied onto a silica gel column with ethyl acetate/petroleum ether (30:70). This resulted in 150 mg (74%) of ethyl 2-(5-hydroxy-2,3-dihydro-1H-inden-1-yl)acetate as colorless oil.

Step 4: Ethyl 2-(5-[[3-(4-ethylphenyl)-5-(trifluoromethyl)-1,2-thiazol-4-yl]methoxy]-2,3-dihydro-1H-inden-1-yl)acetate

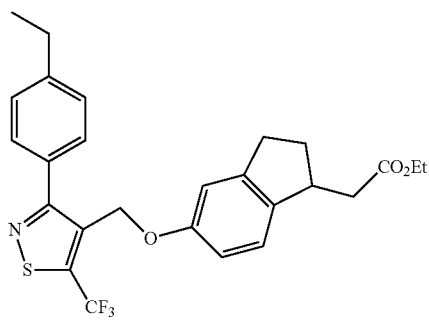 [SMILES: CCOC(=O)CC1CCc2cc(OCc3c(-c4ccc(CC)cc4)nsc3C(F)(F)F)ccc21]

Into a 50-mL round-bottom flask, was placed [3-(4-ethylphenyl)-5-(trifluoromethyl)-1,2-thiazol-4-yl]methyl methanesulfonate (160 mg, 0.44 mmol, 1.00 equiv), ethyl 2-(5-hydroxy-2,3-dihydro-1H-inden-1-yl)acetate (97 mg, 0.44 mmol, 1.01 equiv), potassium carbonate (183 mg, 1.32 mmol, 3.02 equiv), N,N-dimethylformamide (3 mL). The resulting solution was stirred overnight at 30° C. The resulting solution was diluted with 20 mL of H₂O. The resulting mixture was washed with 3×20 mL of sodium chloride. The mixture was dried over anhydrous sodium sulfate. The resulting mixture was concentrated under vacuum. The residue was applied onto a silica gel column with ethyl acetate/petroleum ether (15:85). This resulted in 200 mg (93%) of ethyl 2-(5-[[3-(4-ethylphenyl)-5-(trifluoromethyl)-1,2-thiazol-4-yl]methoxy]-2,3-dihydro-1H-inden-1-yl)acetate as colorless oil.

Step 5: 2-(5-[[3-(4-ethylphenyl)-5-(trifluoromethyl)-1,2-thiazol-4-yl]methoxy]-2,3-dihydro-1H-inden-1-yl)acetic Acid

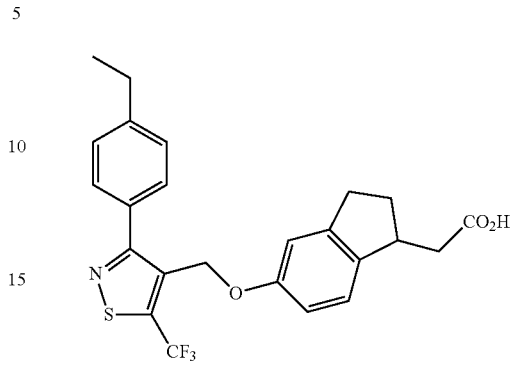

Into a 50-mL round-bottom flask, was placed ethyl 2-(5-[[3-(4-ethylphenyl)-5-(trifluoromethyl)-1,2-thiazol-4-yl]methoxy]-2,3-dihydro-1H-inden-1-yl)acetate (220 mg, 0.45 mmol, 1.00 equiv), tetrahydrofuran (5 mL), water (4 mL), LiOH (97 mg, 4.05 mmol, 9.01 equiv). The resulting solution was stirred overnight at 30° C. The pH value of the solution was adjusted to 2 with hydrogen chloride (1 mol/L). The resulting solution was extracted with 3×3 mL of ethyl acetate and the organic layers combined and concentrated under vacuum. The crude product was purified by Prep-HPLC with the following conditions (waters 2767-16): Column, SunFire Prep C18,19*150 mm 5 umH PrepC-001 (T)18600256819513816414 04; mobile phase, PhaseA:water with 0.05% NH₄HCO₃, PhaseB:CH₃CN (50% CH₃CN up to 100% in 10 min, hold 100% in 1.9 min, down to 50% in 0.1 min, hold 50% in 1.9 min); Detector, UV220&254 nm. This resulted in 18 mg (19%) of 2-(5-[[3-(4-ethylphenyl)-5-(trifluoromethyl)-1,2-thiazol-4-yl]methoxy]-2,3-dihydro-1H-inden-1-yl)acetic acid as light yellow oil. ¹H NMR: (CDCl₃, 400 MHz): δ 7.65 (d, J=8.0 Hz, 2H), 7.30 (d, J=4.8 Hz, 2H), 7.17 (d, J=8.0 Hz, 1H), 6.79-6.85 (m, 2H), 5.05 (s, 2H), 3.58-3.61 (m, 1H), 2.82-2.98 (m, 3H), 2.69-2.75 (m, 2H), 2.44-2.54 (m, 2H), 1.79-1.88 (m, 1H), 1.28 (t, J=7.5 Hz, 3H). Mass spectrum (ESI, m/z): Calcd. for C₂₄H₂₂F₃NO₃S, 460.1 (M−H), found 460.1.

Example 245

2-(6-[[3-(4-ethylphenyl)-5-(trifluoromethyl)-5H-1 [3],2-thiazol-4-yl]methoxy]-2,3-dihydro-1-benzofuran-3-yl)ethan-1-ol, Cpd 220

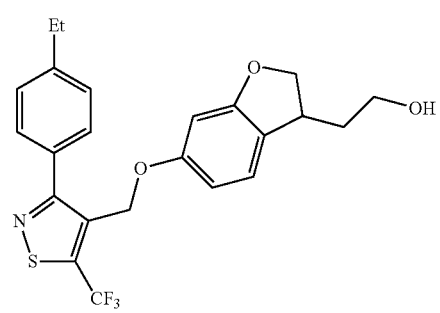 [SMILES: CCc1ccc(-c2nsc(C(F)(F)F)c2COc2ccc3c(c2)OCC3CCO)cc1]

Into a 50-mL round-bottom flask purged and maintained with an inert atmosphere of nitrogen, was placed methyl 2-(6-[[3-(4-ethylphenyl)-5-(trifluoromethyl)-5H-1^[3],2-thiazol-4-yl]methoxy]-2,3-dihydro-1-benzofuran-3-yl)acetate (60 mg, 0.13 mmol, 1.00 equiv), tetrahydrofuran (15 mL), LiAlH$_4$ (5.5 mg, 0.14 mmol, 1.16 equiv) was added at 0° C. The resulting solution was stirred for 2 h at 25° C. The reaction was then quenched by the addition of Na$_2$SO$_4$.10H$_2$O. The solids were filtered out. The resulting mixture was concentrated under vacuum. The crude product (45 mg) was purified by Prep-HPLC with the following conditions (1# waters 2767-5): Column, SunFire Prep C18, 19*150 mm 5 umH PrepC-001(T) 1860025681951381641404; mobile phase, PhaseA: water with 0.05% NH$_4$HCO$_3$ PhaseB: CH$_3$CN (20% CH$_3$CN up to 80% in 10 min, up to 100% in 0.1 min), Detector, UV220&254 nm. This resulted in 28 mg (49%) of 2-(6-[[3-(4-ethylphenyl)-5-(trifluoromethyl)-5H-1 [3],2-thiazol-4-yl] methoxy]-2,3-dihydro-1-benzofuran-3-yl)ethan-1-ol as colorless oil. $^1$H NMR (300 MHz, DMSO) δ:7.61 (d, J=6.0 Hz, 2H), 7.37 (d, J=6.0 Hz, 2H), 7.12 (d, J=5.7 Hz, 1H), 6.46 (d, J=6.9 Hz, 2H), 5.06 (s, 2H), 4.63 (t, J=6.6 Hz, 2H), 4.22 (t, J=5.1 Hz, 1H), 3.41-3.53 (m, 3H), 2.68 (t, J=6.0 Hz, 2H), 1.84-1.89 (m, 1H), 1.59-1.67 (m, 1H), 1.27 (t, J=5.4 Hz, 3H). Mass spectrum (ESI, m/z): Calcd. for C$_{23}$H$_{22}$F$_3$NO$_3$S, 472.1[M+23], found 472.1.

Example 246

3-(4-[[3-(4-chlorophenyl)-5-(trifluoromethyl)-1,2-thiazol-4-yl]methoxy]-3,5-difluorophenyl)prop-2-yn-1-ol, Cpd 213

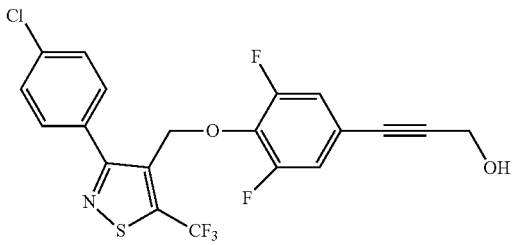 [SMILES: OCC#Cc1cc(F)c(OCc2c(-c3ccc(Cl)cc3)nsc2C(F)(F)F)c(F)c1]

Into a 50-mL 3-necked round-bottom flask (1 atm) purged and maintained with an inert atmosphere of nitrogen, was placed 3-(4-chlorophenyl)-4-(2,6-difluoro-4-iodophenoxymethyl)-5-(trifluoromethyl)-1,2-thiazole (240 mg, 0.45 mmol, 1.00 equiv), Pd(dppf)$_2$Cl$_2$ (15 mg, 0.02 mmol, 0.04 equiv), CuI (3.4 mg, 0.02 mmol, 0.04 equiv), Cs$_2$CO$_3$ (295 mg, 0.91 mmol, 2.01 equiv), trimethyl(prop-2-yn-1-yloxy) silane (116 mg, 0.90 mmol, 2.00 equiv), tetrahydrofuran (5.0 mL). The resulting solution was stirred overnight at 35° C. in an oil bath. The solvent was removed. The residue was applied onto a TLC-Plate with ethyl acetate/petroleum ether (1/6). 200 mg 3-(4-chlorophenyl)-4-((2, 6-difluoro-4-(3-(trimethylsilyloxy)prop-1-ynyl)phenoxy)methyl)-5-(trifluoromethyl)isothiazole was got. Dichloromethane (3.0 mL) and TBAF (THF solution 1.0 mL) were added to the mixture. The result solution was stirred for another 3 h at 35 degree C. The resulting mixture was concentrated under vacuum. The residue was applied onto a silica gel column with ethyl acetate/petroleum ether (1/4). This resulted in 25 mg (12%) of 3-(4-[[3-(4-chlorophenyl)-5-(trifluoromethyl)-1,2-thiazol-4-yl]methoxy]-3,5-difluorophenyl)prop-2-yn-1-ol as a light yellow solid. $^1$H NMR (300 MHz, CD$_3$OD) δ 7.73 (d, J=8.4 Hz, 2H), 7.49 (d, J=8.7 Hz, 2H), 7.01 (d, J=9.0 Hz, 2H), 5.23 (s, 2H), 4.35 (s, 2H). Mass spectrum (ESI, m/z): Calcd. for C$_{20}$H$_{11}$ClF$_5$NO$_2$S, 460.0 (M+H), found 460.0.

BIOLOGICAL EXAMPLES

In Vitro Assays

Biological Example 1

Human GPR120 DiscoveRx PathHunter Beta-Arrestin Assay

Assay Principle:
The binding of an agonist (medium/long chain fatty acids or small molecule agonists) to the G-protein-coupled receptor GPR120 activates phospholipase C, leading to release of intracellular Ca$^{+2}$ through the generation of inositol 1,4,5-trisphosphate (InsP3 or IP3). GPR120 activation can also trigger intracellular signaling via recruitment of Beta-Arrestin. In the present method, agonist-induced activation of the human GPR120 receptor is monitored through the use of PathHunter CHO-K1 GPR120 Beta-Arrestin Cell Line engineered by DiscoveRx, as detailed below. The cell lines are designed to co-express both the ProLink/Enzyme Donor (PK)-tagged GPCR and the Enzyme Activator (EA)-tagged Beta-Arrestin fusion proteins. Upon GPR120 receptor stimulation/activation, the EA-tagged Beta-Arrestin portion is translocated to the tagged receptor, where the two enzyme fragments are brought within close proximity. Under these conditions, these fragments can interact and form an active Beta-gal enzyme complex through Enzyme Fragment Complementation (EFC). This active Beta-gal complex can enzymatically hydrolyse the substrate to produce a detectable light signal; therefore, activation as a function of agonist concentration can be expressed as an EC$_{50}$ value to determine relative compound activities. This in vitro assay therefore serves to assess compound agonist activity of the GPR120.

Procedure β-Arrestin A:
In Procedure β-arrestin A, the cell used were PathHunter CHO-K1 GPR120 β-Arrestin Cell Line, expressing the long form of human GPR120 (Genbank accession number NM_181745), with 3000 cells per well.

Procedure β-Arrestin B:
In Procedure β-arrestin B the cells used were PathHunter CHO-K1 GPR120S β-Arrestin Cell Line, expressing the short form of the GPR120 receptor (Accession # NM_181745), with 5000 cells/well.

Assay Procedure:
The selected CHO-K1 GPR120 β-Arrestin cells were cultured in Ham's F12 media supplemented with 10% fetal bovine serum (FBS), 1% Glutamine, 1×p/s, 800 µg/mL G418 and 300 µg/mL Hygromycin B (for selection). Cell stocks were maintained and grown in a sub-confluent state using standard cell culture procedures. The day before the experiment, the cells were harvested with non-enzymatic cell dissociation buffer and re-suspended in complete growth media at the desired concentration. A Corning 384-plate was then seeded with the proper number of cells in a volume of 25 µL, per well. The seeded plates were incubated overnight at 37° C.

On the day of the experiment, the Assay Buffer containing (a) HBSS with Ca$^{++}$ and Mg$^{++}$, (b) 20 mM HEPES, and (c) 0.1% BSA stabilizer (pH 7.4) was prepared. The growth medium was gently removed from the cell plates and 20 μL of Assay Buffer added to each well. The plate was then incubated at 37° C. for 60 min. Test compounds were serially diluted in Assay Buffer to desired concentrations (more particularly to one or more of the following μM concentrations: 25, 12.5, 6.25, 3.125, 1.5625, 0.78125, 0.390625, 0.1953125, 0.09765625, 0.048828125, 0.024414063, 0.012207031). Five μL of compound dilution was then added to each well and the plate incubated at 37° C. for 90 min. The detection reagents were prepared according to the manufacture's instruction. Twelve μL of the detection reagents were added to each well and the plate incubated at room temperature for 60 min.

The plates were read on an EnVision instrument, using Protocol name: Luminescence, Plate type: 384 Costar, Measurement height: 3 mm, Measurement time: 1 s, Aperture: 384 Plate aperture. The % activity relative to the positive control was calculated using the following equation:

$$\% \text{ Activity} = \frac{Count_{compound} - Count_{vehicle}}{Count_{postivite\ control} - Count_{vehicle}} \times 100\%$$

The % Activity values were plotted versus the concentration of test compound and fitted to a sigmoidal dose-response curve with a Hill slope=1 (fixed value) using nonlinear regression with GraphPad Prism 5.0 to calculate the $EC_{50}$ values. The Fitting Equation was: $Y=Bottom+(Top-Bottom)/(1+10^{((Log\ EC_{50}-X)*HillSlope)})$, where X is the log of the concentration and Y is the response. Resultant data is shown in Table 1.

Biological Example 2

In Vitro Assay: Human GPR120 in Calcium Flux Assay

Assay Principle

This in vitro assay serves to assess test compound agonist activity against the short splice variant (SVS with Accession number NM_001195755.1 confirmed by sequencing data) of the GPR120 receptor. The Human Short splice variant #2 (NM_001195755.1) is missing an in-frame coding exon compared to variant 1 (the Human Long splice variant NM_181745.3), resulting in a shorter isoform (GPR120-S) lacking a 16 aa protein segment compared to isoform GPR120-L. The assay platform utilizes HEK-293 cells stably transfected to express the Human GPR120 short form. These cells are first loaded with the $Ca^{+2}$ sensitive dye, Fluo-4 NW. Upon stimulation, intracellular released $Ca^{+2}$ can bind to the dye and alter its fluorescence intensity. This increase in fluorescence signal, and thus the flux in intracellular $[Ca^{2+}]$, is detected and quantitated by fluorescence imaging using a FLIPR reader. The effect of the agonist is measured as a function of concentration and used to calculate an $EC_{50}$ based upon a response curve.

Procedure Calcium A:
In this procedure 2500 cells/well were employed.
Procedure Calcium B:
In this procedure 4200 cells/well were employed.
Assay Procedure:
A Human GPR120 clone (Genbank accession number NM_001195755.1) was placed into the pcDNA3.1 mammalian expression vector carrying the neomycin resistance gene. A stable mammalian cell was generated by placing the above clone into a HEK293 background. Clonal cells responding to long chain fatty acids had expression levels of GPR120 confirmed by RT-qPCR. Human HEK-GPR120 cells were cultured in Dulbecco's Modified Eagle's Medium (DMEM)/F12 medium supplemented with 10% fetal bovine serum (FBS), 1% L-Glutamine and 1% penicillin/streptomycin and 0.5 mg/ml G-418. Cells were split 2 times a week to keep the cells in the log-phase growth.

In preparation for the assay, HEK cells stably transfected with Human GPR120 (2.5K cells per well in 25 uL growth medium) were seeded into 384-well plates and then incubated overnight (37° C., 5% $CO_2$). The next day, the media was changed to 20 μL assay buffer and the cell starved for 1 h at 37° C. The dye loading solution (2× dye) was prepared using 10 mL assay buffer, 100 μL of 250 mM probenecid, 1 bottle of Component A, and 20 μl of dye in DMSO. Twenty L of the 2× dye loading buffer was then added to each well. The plates were incubated at 37° C. for 30 min, then at room temperature for an additional 15 minutes, before performing the assay on FLIPR. Test compounds were prepared in assay buffer (2 uL of cpd+198 uL assay buffer, final DMSO in assay plate is 0.2%) at the desired concentration, more particularly at 100, 50, 25, 12.5, 6.25, 3.125, 1.562, 0.781, 0.391, 0.195, 0.098, 0.049, 0.024 and 0.012 μM.

The assay was performed on a FLIPR plate reader using the following parameters. Baseline was read for 10 seconds at 1 sec intervals. The program was set to transfer 10 μL of ligand from compound plate to cell plate after baseline reading. Aspiration was executed at: 10 μL/sec speed, 4.6 μL height; Dispensing was executed at: 30 μL/sec speed, 45 μL height. After compound addition, each well was read for 300 sec, with measurements collected at 1 sec intervals.

The kinetic data from the FLIPR was based upon a 5 minute window for data collection. The fluorescence of each sample well was used for individual calculations of a normalized RFU value, which was defined as maximum response minus the minimum response. The normalized fluorescence reading (RFU) was calculated as follows:

RFU=Fmax−Fmin

The data were fitted to a sigmoidal dose-response curve with a variable Hill slope (<2) using nonlinear regression with GraphPad Prism 5.0 to calculate the $EC_{50}$ values. The Fitting Equation was: $Y=Bottom+(Top-Bottom)/(1+10^{((Log\ EC_{50}-X)*HillSlope)})$, where X is the log of the concentration and Y is the response. Resultant data is shown in Table 1.

TABLE 1

| Cpd | hGPR120 β-arrestin A EC50 (μM) | hGPR120 β-arrestin B EC50 (μM) | GPR120 $Ca^{2+}$ Assay A EC50 (μM) | GPR120 $Ca^{2+}$ Assay B EC50 (μM) |
|---|---|---|---|---|
| 1 | 0.218 | 0.205 | 0.024 | |
| 2 | 0.097 | 0.068 | 0.030 | |
| 3 | | 0.083 | 0.049 | |
| 4 | 0.261 | | 0.059 | |
| 5 | 0.191 | | 0.061 | |
| 6 | | | 0.090 | |
| 7 | 0.209 | | 0.101 | |
| 8 | 0.167 | | 0.114 | |
| 9 | 0.203 | | 0.117 | |
| 10 | | | 0.123 | |
| 11 | 0.222 | | 0.126 | |
| 12 | 0.125 | | 0.135 | |
| 13 | 0.498 | | 0.163 | |
| 14 | 0.265 | | 0.163 | |
| 15 | | | 0.266 | |
| 16 | | 1.513 | 0.382 | |
| 17 | | | 0.406 | |

TABLE 1-continued

| Cpd | hGPR120 β-arrestin A EC50 (μM) | hGPR120 β-arrestin B EC50 (μM) | GPR120 Ca²⁺ Assay A EC50 (μM) | GPR120 Ca²⁺ Assay B EC50 (μM) |
|---|---|---|---|---|
| 18 | | | 0.518 | |
| 19 | 0.108 | | 0.634 | |
| 20 | 0.168 | | 0.657 | |
| 21 | | | 0.788 | |
| 22 | | | 0.924 | |
| 28 | 0.186 | | | |
| 29 | 0.243 | | | |
| 31 | 0.503 | | 0.046 | |
| 32 | 0.031 | | 0.048 | |
| 33 | 0.431 | 0.322 | 0.050 | |
| 34 | 0.208 | | 0.065 | |
| 35 | 0.270 | | 0.070 | |
| 36 | | | 0.090 | |
| 37 | 0.057 | 0.022 | 0.094 | |
| 38 | 0.071 | | 0.101 | |
| 39 | | | 0.128 | |
| 40 | 0.650 | | 0.129 | |
| 41 | 0.711 | | 0.142 | |
| 42 | 0.445 | | 0.143 | |
| 43 | 0.591 | | 0.147 | |
| 44 | 0.456 | | 0.152 | |
| 45 | 0.123 | | 0.154 | |
| 46 | 0.125 | | 0.165 | |
| 47 | | | 0.166 | |
| 48 | 0.236 | | 0.168 | |
| 49 | 0.304 | | 0.170 | |
| 50 | 0.100 | | 0.171 | |
| 51 | 0.213 | | 0.172 | |
| 52 | 0.344 | | 0.181 | |
| 53 | 0.668 | | 0.191 | |
| 54 | | | 0.199 | |
| 55 | 0.176 | | 0.231 | |
| 56 | 0.108 | | 0.237 | |
| 57 | | | 0.278 | |
| 58 | 0.639 | | 0.293 | |
| 59 | | | 0.348 | |
| 60 | | | 0.510 | |
| 61 | | | 0.564 | |
| 62 | | | 0.747 | |
| 63 | | 0.122 | | 0.200 |
| 64 | | | | 0.923 |
| 65 | 0.168 | 0.126 | 0.013 | |
| 66 | 0.108 | | 0.019 | |
| 67 | 0.086 | 0.043 | 0.025 | |
| 68 | | | 0.028 | |
| 69 | 0.083 | | 0.031 | |
| 70 | 0.098 | | 0.034 | |
| 71 | 0.278 | 0.139 | 0.037 | |
| 72 | 0.103 | | 0.039 | |
| 73 | 0.134 | | 0.041 | |
| 74 | 0.143 | 0.063 | 0.042 | |
| 75 | 0.141 | | 0.042 | |
| 76 | | 0.179 | 0.042 | |
| 77 | 0.191 | | 0.045 | |
| 78 | 0.028 | 0.031 | 0.050 | |
| 79 | 0.071 | 0.062 | 0.051 | |
| 80 | 0.246 | | 0.051 | |
| 81 | 0.094 | | 0.051 | |
| 82 | 0.172 | | 0.054 | |
| 83 | 0.054 | | 0.056 | |
| 84 | 0.119 | | 0.056 | |
| 85 | 0.166 | | 0.056 | |
| 86 | 0.085 | | 0.057 | |
| 87 | 0.088 | | 0.062 | |
| 88 | 0.081 | | 0.067 | |
| 89 | | 0.416 | 0.067 | |
| 90 | | 0.154 | 0.067 | |
| 91 | | 0.031 | 0.069 | |
| 92 | | | 0.070 | |
| 93 | 0.038 | 0.027 | 0.071 | |
| 94 | | 0.104 | 0.071 | |
| 95 | | 0.116 | 0.072 | |
| 96 | 0.287 | | 0.073 | |
| 97 | 0.338 | | 0.073 | |
| 98 | 0.185 | | 0.074 | |
| 99 | 0.091 | | 0.075 | |
| 100 | 0.097 | | 0.076 | |
| 101 | 0.189 | | 0.076 | |
| 102 | 0.040 | | 0.078 | |
| 103 | | | 0.080 | |
| 104 | 0.399 | | 0.083 | |
| 105 | 0.217 | | 0.086 | |
| 106 | 0.098 | | 0.086 | |
| 107 | | 0.118 | 0.089 | |
| 108 | 0.261 | 0.162 | 0.089 | |
| 109 | | 0.075 | 0.089 | |
| 110 | | 0.105 | 0.094 | |
| 111 | 0.244 | | 0.098 | |
| 112 | | | 0.099 | |
| 113 | 0.071 | | 0.099 | |
| 114 | 0.295 | | 0.100 | |
| 115 | 0.070 | | 0.104 | |
| 116 | 0.112 | 0.088 | 0.104 | |
| 117 | 0.254 | | 0.104 | |
| 118 | 0.257 | | 0.105 | |
| 119 | 0.128 | | 0.106 | |
| 120 | | 0.310 | 0.107 | |
| 121 | | 0.051 | 0.108 | |
| 122 | 1.286 | | 0.109 | |
| 123 | 0.303 | | 0.111 | |
| 124 | | | 0.114 | |
| 125 | | | 0.121 | |
| 126 | | 0.223 | 0.121 | |
| 127 | 0.178 | | 0.122 | |
| 128 | | 0.059 | 0.124 | |
| 129 | | 0.116 | 0.125 | |
| 130 | | | 0.125 | |
| 131 | | | 0.129 | |
| 132 | 0.122 | | 0.130 | |
| 133 | 0.539 | | 0.131 | |
| 134 | 0.252 | 0.409 | 0.133 | |
| 135 | 0.058 | | 0.134 | |
| 136 | | 0.526 | 0.135 | |
| 137 | | 0.413 | 0.137 | |
| 138 | 0.114 | 0.161 | 0.137 | |
| 139 | 0.077 | | 0.138 | |
| 140 | 0.067 | | 0.139 | |
| 141 | 0.105 | | 0.148 | |
| 142 | 0.141 | 0.100 | 0.155 | |
| 143 | | 0.374 | 0.156 | |
| 144 | | | 0.160 | |
| 145 | | 0.132 | 0.160 | |
| 146 | | | 0.165 | |
| 147 | | 0.390 | 0.165 | |
| 148 | 0.242 | | 0.165 | |
| 149 | | | 0.167 | |
| 150 | 0.240 | | 0.167 | |
| 151 | | 0.085 | 0.169 | |
| 152 | 0.183 | 0.183 | 0.173 | |
| 153 | 0.189 | 0.104 | 0.175 | |
| 154 | 0.431 | | 0.178 | |
| 155 | | 0.719 | 0.182 | |
| 156 | 0.368 | | 0.185 | |
| 157 | | | 0.188 | |
| 158 | | | 0.191 | |
| 159 | | 0.415 | 0.198 | |
| 160 | 0.116 | | 0.200 | |
| 161 | | | 0.202 | |
| 162 | 0.156 | 0.054 | 0.202 | |
| 163 | | | 0.203 | |
| 164 | | 0.427 | 0.210 | |
| 165 | | 0.435 | 0.215 | |
| 166 | 1.342 | | 0.217 | |
| 167 | | 0.352 | 0.222 | |
| 168 | 0.325 | | 0.223 | |
| 169 | 0.486 | | 0.225 | |
| 170 | 0.813 | | 0.225 | |
| 171 | | 1.214 | 0.226 | |
| 172 | | 0.147 | 0.229 | |
| 173 | | 0.421 | 0.236 | |
| 174 | | 0.085 | 0.246 | |
| 175 | | 0.230 | 0.247 | |

TABLE 1-continued

| Cpd | hGPR120 β-arrestin A EC50 (μM) | hGPR120 β-arrestin B EC50 (μM) | GPR120 Ca$^{2+}$ Assay A EC50 (μM) | GPR120 Ca$^{2+}$ Assay B EC50 (μM) |
|---|---|---|---|---|
| 176 | | | 0.261 | |
| 177 | | | 0.263 | |
| 178 | | | 0.263 | |
| 179 | 0.490 | | 0.268 | |
| 180 | 0.568 | 0.294 | 0.270 | |
| 181 | | 0.819 | 0.274 | |
| 182 | | | 0.281 | |
| 183 | 0.052 | | 0.300 | |
| 184 | | 0.997 | 0.300 | |
| 185 | 0.324 | | 0.301 | |
| 186 | | | 0.303 | |
| 187 | 0.889 | | 0.305 | |
| 188 | | 0.153 | 0.306 | |
| 189 | 0.612 | | 0.310 | |
| 190 | 0.379 | | 0.314 | |
| 191 | | | 0.323 | |
| 192 | | | 0.332 | |
| 193 | 0.322 | 0.990 | 0.344 | |
| 194 | | 0.040 | 0.362 | |
| 195 | | 0.307 | 0.366 | |
| 196 | | 0.195 | 0.370 | |
| 197 | | 0.224 | 0.392 | |
| 198 | | 1.941 | 0.405 | |
| 199 | | 0.622 | 0.423 | |
| 200 | | | 0.453 | |
| 201 | 0.341 | | 0.453 | |
| 202 | | | 0.468 | |
| 203 | | 1.481 | 0.478 | |
| 204 | | | 0.496 | |
| 205 | | 0.741 | 0.530 | |
| 206 | 0.540 | | 0.551 | |
| 207 | | | 0.566 | |
| 208 | | 0.554 | 0.578 | |
| 209 | 0.229 | | 0.579 | |
| 210 | | 1.052 | 0.580 | |
| 211 | | | 0.597 | |
| 212 | | 0.074 | 0.600 | |
| 213 | 0.059 | 0.087 | 0.603 | |
| 214 | | | 0.606 | |
| 215 | | 2.144 | 0.648 | |
| 216 | 0.466 | | 0.674 | |
| 217 | | | 0.677 | |
| 218 | | | 0.688 | |
| 219 | 0.210 | | 0.690 | |
| 220 | | | 0.702 | |
| 221 | | 0.731 | 0.756 | |
| 222 | | 1.946 | 0.757 | |
| 223 | 0.182 | | 0.770 | |
| 224 | | 0.229 | 0.831 | |
| 225 | | 0.227 | 0.840 | |
| 226 | | | 0.849 | |
| 227 | | 3.783 | 0.867 | |
| 228 | | | 0.923 | |
| 229 | | 1.805 | 0.936 | |
| 230 | 0.474 | | 1.020 | |
| 231 | 0.961 | | 1.021 | |
| 232 | | | 1.088 | |
| 233 | | | 1.102 | |
| 234 | 0.145 | | | |
| 235 | 0.302 | | | |
| 237 | | 0.096 | | |
| 238 | 0.090 | | 0.521 | |
| 239 | 0.203 | | | |
| 240 | | | | |
| 241 | | | | 0.45 |
| 242 | | | | 1.29 |
| 244 | | | | >5 |
| 246 | | | | 2.35 |
| 250 | | | | 3.23 |
| 251 | | | | >5 |

In Vivo Assays

Biological Example 3

GPR120 DIO Mice OGTT Screening 18-22 week old, C57Bl6 mice on a high fat diet (60% HFD) for 12-16 weeks (ave. body weight ~37-41 g) were fasted for 6 hr, with removal of food occurring at 7 am on the morning of the study. The animals were sorted into treatment groups the day before the study by body weight. Animals outside the bounds of ~30-50 g were left out of the study. The animals had been handled and shammed a total of 5-8 days (1-3 days immediately prior to the study). Glucose (in 1 mL syringes) was drawn up the morning of the study. Test compounds were kept spinning and were only drawn into 1 ml syringes prior to study commencement. Animals were bled via tail snip to determine basal glucose levels prior to dosing of treatments. An Ascensia BREEZE Blood Glucose Monitoring System by Bayer was used for determining glucose levels.

Animals were moved into the testing room at ~9-11 am, to yield them time to acclimate. The bleeds and dosing started at approximately 1 pm in 30-second intervals per animal. All groups were dosed 30 minutes prior to glucose administration at a dose volume of 10 ml/kg (the dose volume was calculated separately for each individual animal). Test compounds were administered at one or more of the following dosages: 0.1 mg/kg, 0.3 mg/kg, 1 mg/kg, 3 mg/kg and 10 mg/kg.

Thirty minutes after the first dose (with test compound) animals were bled again for a second baseline, or T=0, and immediately dosed with glucose (20% solution; TEKNOVA, 250 ml sterile bottle w/catalogue number G0525) via a PO injection. The exact dose volume for glucose was also calculated separately for each individual animal.

Blood glucose was measured at 15, 30, 45, 60, and 90 minutes post-glucose administration via the snipped tail. If an animal reached a value of "HI", the upper limit of the glucometer (600 mg/dl) was substituted as the blood glucose value and the study was analyzed as normal with no exclusions. If 50% or more of any treatment group reaches a "HI" value at least once, the study was considered invalid and repeated. Glucose values were typed into an EXCEL spreadsheet where they were used to calculate glucose AUC and delta AUC post-compound and post-glucose. The glucose excursion curves and the different versions of the AUC's were graphed in GraphPad Prism 5.

Statistical Methods:

Note: All statistics completed in this study were completed using the statistical software package GraphPad Prism 5. Standard procedures for analyzing data sets from screening GPR120 compounds in DIO mouse OGTT's were as listed here below. In addition to the statistics that were run using GraphPad Prism 5, Microsoft Excel was used to calculate the percent changes in AUC from vehicle groups as detailed below.

Change from −30 to 0 BSLN Glucose, Raw Glucose AUC −30 to 90 min, Delta Glucose AUC −30 to 90 min, Raw Glucose AUC 0 to 90 min, Delta Glucose AUC 0 to 90 min were analyzed using Column Statistics Analysis, with mean values used to calculate % change from the vehicle mean group, as well as mean, SEM and/or % change from vehicle, where appropriate; and using One-Way ANOVA w/a Tukey Post-Test (Comparing All Pairs of Columns) with each treatment group examined to see if it was statistically significant compared to vehicle (*=P<0.05, =P<0.01, *=P<0.001).

Representative compounds of the present invention were tested according to the procedure as described in Biological Example 3, with results as listed in Table 2, below. Where a compound was tested more than once, each result is listed individually.

TABLE 2

GPR120 DIO OGTT Results

| Cpd No. | DIO Lowering Glucose AUC (−30 to 90) @ 10 mg/kg |
|---|---|
| 1 | −0.26 |
| 2 | −0.5 |
| 3 | −0.49 |
| 65 | −0.61 |
| 67 | −0.78 |
| 71 | −0.52 |
| 73 | −0.51 |
| 74 | −0.71 |
| 76 | −0.8 |

Biological Example 4

A: GPR120 C57bl6 Mouse IPGTT

Male, C57bl/6J Mice were ordered in at 8 weeks of age from Jackson Labs. Individual mice weighed anywhere in the range of 25-30 grams on study day. The mice were fasted, with removal of food occurring at 7 am on the morning of the study. Animals were moved into the room at 10:00 am, to give them time to acclimate. Glucose (insulin syringes) was drawn up either the night before or the morning of the study. Glucose was dosed (IP) at 1.5 g/kg at 7.5 ml/kg (20% glucose straight TEKNOVA, 250 ml sterile bottle w/ catalogue number G0525). Test compounds were kept spinning and were only drawn into the syringes prior to study commencement. Animals were bled via tail snip to determine basal glucose levels prior to dosing of treatments. An Ascensia BREEZE Blood Glucose Monitoring System by Bayer (using unique 10-test disks) was used for determining glucose levels. The bleeds started at approximately 12:45 pm and dosing started, at 1-minute intervals, immediately after. All groups were dosed 30 minutes prior to glucose administration at a dose volume of 10 ml/kg (the dose volume was calculated separately for each individual animal). Thirty minutes after the first dose animals were bled again for a second baseline, or T=0, and immediately dosed with glucose via an i.p. injection. The exact dose volume for glucose was also calculated separately for each individual animal. Glucose measurements were taken at −30 min prior to compound dose, at t=0 (immediately prior to glucose dose), and at 15, 30, 45, 60, 90 min post glucose dose.

Glucose values were entered into an Excel sheet and graphed in GraphPad Prism. The following were calculated from Prism: Change from −30 to 0 BSLN Glucose, Raw Glucose AUC −30 to 90 min, Delta Glucose AUC −30 to 90 min, Raw Glucose AUC 0 to 90 min, Delta Glucose AUC 0 to 90 min.

In Vivo Assay: B: C57bl6 Mouse OGTT:
The assay design is the same as that described above for the C57bl6 mouse IPGTT. The difference is that glucose was dosed PO at 3 g/kg, 7.5 ml/kg of 40% glucose.

Representative compounds of the present invention were tested according to the procedures as described in Biological Example 4, above with results as listed in Table 3, below. In the results presented below, the designation "nd" indicates that no numbers were reported (results were not different from vehicle). Where a compound was tested more than once, each result is listed individually.

TABLE 3

GPR120 C57bl6 Mouse IPGTT OGTT Results

| Cpd No. | C57 IPGTT | | | | C57 OGTT |
|---|---|---|---|---|---|
| | 1 mg/kg | 3 mg/kg | 10 mg/kg | 30 mg/kg | 3 mg/kg |
| 38 | | −9 | | | −44 |
| 42 | | −14 | | | −44 |
| 46 | | | | −83 | −49 |
| 46 | | −26 | −75 | −61 | |
| 70 | | | | −88 | |
| 71 | | −14 | | | −37 |
| 78 | | | −41 | | −39 |
| 79 | | | −60 | | |
| 85 | | | | −69 | −49 |
| 85 | | −29 | −48 | −57 | |
| 100 | | | −42 | | −39 |
| 102 | | | −50 | | −32 |
| 102 | | | −27 | | |
| 106 | | | −34 | | |
| 142 | | | | −64 | −49 |
| 142 | | −34 | −61 | −53 | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (I)

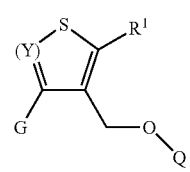

Formula (I)

wherein
Y is N;
R¹ is selected from the group consisting of hydrogen, $C_{1-4}$alkyl, fluoro, chloro, cyclopropyl, 1,1-difluoroethyl, perfluoroethyl, trifluoromethyl, and phenyl; wherein phenyl is optionally independently substituted with one or two substituents that are $C_{1-2}$alkyl, methoxy, chloro, fluoro, or trifluoromethyl;
Q is selected from the group consisting of q2 to q6

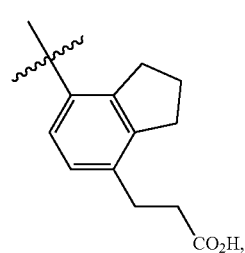

q2

-continued q3
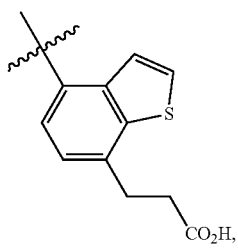

q4
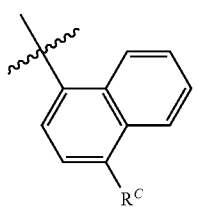

q5
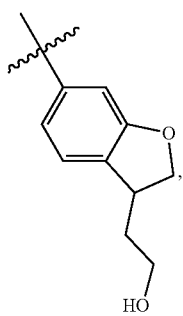

q6
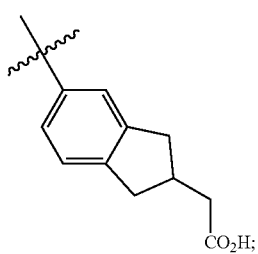

$R^C$ is

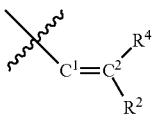

i)
wherein the bond between $C^1$ and $C^2$ is a single bond or double bond;
$R^2$ is hydroxymethyl or carboxy;
$R^4$ is hydrogen or methyl;
G is
4-($R^A$)phenyl, wherein $R^A$ is $C_{1-3}$alkyl;
or an enantiomer, diastereomer, or pharmaceutically acceptable salt form thereof.

2. The compound of claim 1 wherein $R^1$ is selected from the group consisting of hydrogen, $C_{1-2}$alkyl, fluoro, chloro, cyclopropyl, perfluoroethyl, trifluoromethyl, and phenyl; wherein phenyl is optionally independently substituted with one or two substituents that are $C_{1-2}$alkyl, methoxy, chloro, or fluoro.

3. The compound of claim 2 wherein $R^1$ is selected from the group consisting of hydrogen, methyl, trifluoromethyl, and phenyl; wherein phenyl is optionally independently substituted with one or two substituents that are methyl, methoxy, chloro, or fluoro.

4. The compound of claim 1 wherein Q is selected from the group consisting of q2 to q4

$R^C$ is i)
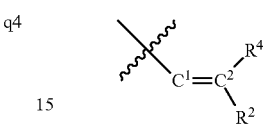

wherein the bond between $C^1$ and $C^2$ is a single bond or double bond;
$R^2$ is hydroxymethyl or carboxy;
$R^4$ is hydrogen or methyl.

5. The compound of claim 1 wherein G is 4-($R^A$)phenyl, wherein $R^A$ is $C_{1-2}$alkyl.

6. A compound of Formula (I)

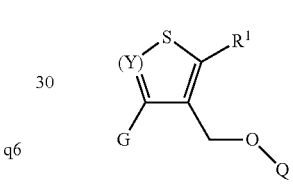

Formula (I)

wherein
Y is N;
$R^1$ is selected from the group consisting of hydrogen, $C_{1-2}$alkyl, fluoro, chloro, cyclopropyl, perfluoroethyl, trifluoromethyl, and phenyl; wherein phenyl is optionally independently substituted with one or two substituents that are $C_{1-2}$alkyl, methoxy, chloro, or fluoro;
Q is selected from the group consisting of q1 to q4 q2
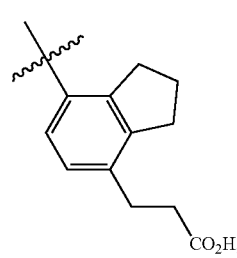

q3
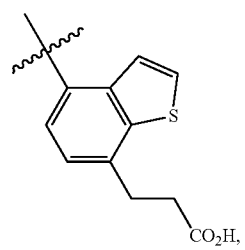

-continued

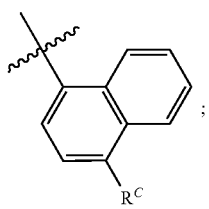
q4 wherein
R<sup>C</sup> is
i)

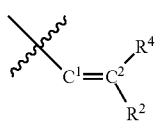

wherein the bond between $C^1$ and $C^2$ is a single bond or double bond;
$R^2$ is hydroxymethyl or carboxy;
$R^4$ is hydrogen or methyl;
G is
4-($R^A$)phenyl, wherein $R^A$ is $C_{1-2}$alkyl;
or an enantiomer, diastereomer, or pharmaceutically acceptable salt form thereof.

7. A compound of Formula (I)

Formula (I)

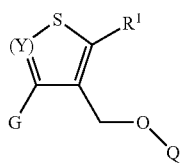

wherein
Y is N;
$R^1$ is selected from the group consisting of hydrogen, methyl, trifluoromethyl, and phenyl; wherein phenyl is optionally independently substituted with one or two substituents that are methyl, methoxy, chloro, or fluoro;
Q is selected from the group consisting of q1 to q4 q2

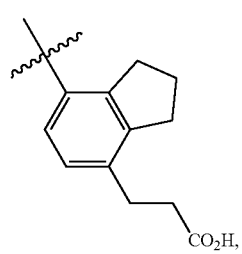

-continued

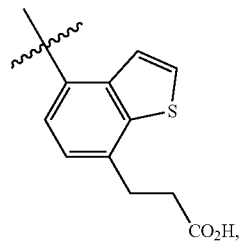
q3

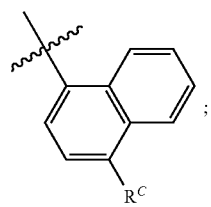
q4 wherein
R<sup>C</sup> is

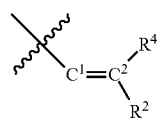

wherein the bond between $C^1$ and $C^2$ is a single bond;
$R^2$ is hydroxymethyl or carboxy;
$R^4$ is hydrogen or methyl;
G is
4-($R^A$)phenyl, wherein $R^A$ is
or an enantiomer, diastereomer, or pharmaceutically acceptable salt form thereof.

8. A compound selected from the group consisting of
Cpd 92, 3-(4-{[3-(4-Ethylphenyl)-5-(trifluoromethyl)isothiazol-4-yl]methoxy}-1-benzothiophen-7-yl)propanoic acid;
Cpd 103, 3-(7-{[3-(4-Ethylphenyl)-5-(trifluoromethyl)isothiazol-4-yl]methoxy}-2,3-dihydro-1H-inden-4-yl)propanoic acid;
Cpd 130, 3-(4-{[3-(4-Ethylphenyl)-5-(trifluoromethyl)isothiazol-4-yl]methoxy}naphthalen-1-yl)propanoic acid;
Cpd 176, (5-{[3-(4-Ethylphenyl)-5-(trifluoromethyl)isothiazol-4-yl]methoxy}-2,3-dihydro-1H-inden-1-yl)acetic acid;
Cpd 220, 2-(6-{[3-(4-Ethylphenyl)-5-(trifluoromethyl)isothiazol-4-yl]methoxy}-2,3-dihydro-1-benzofuran-3-yl)ethanol;
or a pharmaceutically acceptable salt form thereof.

9. A pharmaceutical composition comprising a compound of claim 1 and at least one of a pharmaceutically acceptable carrier, a pharmaceutically acceptable excipient, and a pharmaceutically acceptable diluent.

10. The pharmaceutical composition of claim 9, wherein the composition is a solid oral dosage form.

11. The pharmaceutical composition of claim 9, wherein the composition is a syrup, an elixir or a suspension.

12. A method of treating Type II diabetes mellitus comprising administering to a subject in need thereof a therapeutically effective amount of the composition of claim 9.

13. A method of treating Type II diabetes mellitus comprising administering to a subject in need thereof, a therapeutically effective amount of a compound of claim 1.

\* \* \* \* \*